United States Patent
Lunyak et al.

(10) Patent No.: US 12,138,282 B2
(45) Date of Patent: Nov. 12, 2024

(54) TREATMENT WITH AN IL-2 BASED THERAPY

(71) Applicant: Aelan Cell Technologies, Inc., San Francisco, CA (US)

(72) Inventors: Victoria Lunyak, San Anselmo, CA (US); Meenakshi Gaur, San Francisco, CA (US)

(73) Assignee: AELAN CELL TECHNOLOGIES, INC., Greenbrae, CA (US)

( * ) Notice: Subject to any disclaimer, the term of this patent is extended or adjusted under 35 U.S.C. 154(b) by 0 days.

(21) Appl. No.: 15/579,186

(22) PCT Filed: Jun. 2, 2016

(86) PCT No.: PCT/US2016/035472
§ 371 (c)(1),
(2) Date: Sep. 5, 2018

(87) PCT Pub. No.: WO2016/196765
PCT Pub. Date: Dec. 8, 2016

(65) Prior Publication Data
US 2018/0136209 A1    May 17, 2018

Related U.S. Application Data

(60) Provisional application No. 62/175,203, filed on Jun. 12, 2015, provisional application No. 62/170,604, filed on Jun. 3, 2015, provisional application No. 62/170,619, filed on Jun. 3, 2015.

(51) Int. Cl.
| | |
|---|---|
| A61K 35/28 | (2015.01) |
| A61K 38/20 | (2006.01) |
| A61K 38/43 | (2006.01) |
| A61P 35/00 | (2006.01) |
| C07K 16/24 | (2006.01) |
| C12N 5/00 | (2006.01) |
| C12N 5/0775 | (2010.01) |
| C12Q 1/6886 | (2018.01) |
| G01N 33/574 | (2006.01) |

(52) U.S. Cl.
CPC .......... *A61K 35/28* (2013.01); *A61K 38/2013* (2013.01); *A61K 38/43* (2013.01); *A61P 35/00* (2018.01); *C07K 16/246* (2013.01); *C12N 5/0018* (2013.01); *C12N 5/0663* (2013.01); *C12N 5/0667* (2013.01); *C12Q 1/6886* (2013.01); *G01N 33/574* (2013.01); *C12N 2501/2302* (2013.01); *C12N 2501/65* (2013.01); *C12Q 2600/158* (2013.01); *G01N 2333/4703* (2013.01); *G01N 2333/475* (2013.01); *G01N 2333/495* (2013.01); *G01N 2333/55* (2013.01); *G01N 2333/705* (2013.01); *G01N 2333/91205* (2013.01); *G01N 2333/96466* (2013.01); *G01N 2333/96486* (2013.01)

(58) Field of Classification Search
CPC ........................... A61K 35/28; A61K 38/2013
See application file for complete search history.

(56) References Cited

U.S. PATENT DOCUMENTS

| | | | |
|---|---|---|---|
| 4,929,354 A | 5/1990 | Meyering et al. | |
| 5,270,192 A | 12/1993 | Li et al. | |
| 5,541,064 A | 7/1996 | Bacus et al. | |
| 5,595,756 A * | 1/1997 | Bally ................... | A61K 9/1272 264/4.1 |
| 6,582,955 B2 | 6/2003 | Martinez et al. | |
| 6,759,245 B1 | 7/2004 | Toner et al. | |
| 6,858,146 B1 | 2/2005 | Myers et al. | |
| 7,160,719 B2 | 1/2007 | Nyberg | |
| 7,970,769 B2 | 6/2011 | Kang et al. | |
| 8,172,784 B2 | 5/2012 | Yarmush et al. | |
| 8,981,066 B2 | 3/2015 | Lunyak | |
| 9,074,172 B2 | 7/2015 | Johnson | |
| 10,921,324 B2 | 2/2021 | Lunyak et al. | |
| 11,291,689 B2 | 4/2022 | Lunyak et al. | |
| 2002/0086356 A1 | 7/2002 | Tuschl et al. | |
| 2003/0215936 A1 | 11/2003 | Kallioniemi et al. | |
| 2004/0033589 A1 | 2/2004 | O'Brien | |
| 2006/0160187 A1 | 7/2006 | Denis-Mize et al. | |
| 2011/0003008 A1 | 1/2011 | Lim | |
| 2011/0111435 A1 | 5/2011 | Dobson et al. | |
| 2012/0165216 A1 | 6/2012 | Samper Rodriguez et al. | |
| 2013/0095065 A1 | 4/2013 | Peters et al. | |
| 2013/0251670 A1 | 9/2013 | Riordan et al. | |
| 2013/0252821 A1 | 9/2013 | Sukhatme et al. | |
| 2013/0344603 A1 | 12/2013 | Lunyak | |
| 2014/0024548 A1 | 1/2014 | Singh et al. | |

(Continued)

FOREIGN PATENT DOCUMENTS

| | | |
|---|---|---|
| CN | 101855553 A | 10/2010 |
| CN | 104039351 A | 9/2014 |

(Continued)

OTHER PUBLICATIONS

Panelli et al. Forecasting the cytokine storm following systemic interleukin (IL)-2 administration. Journal of Translational Medicine, 2004; 2(17):1-14 (Year: 2004).*

(Continued)

*Primary Examiner* — Vanessa L. Ford
*Assistant Examiner* — Sandra Dillahunt
(74) *Attorney, Agent, or Firm* — Cooley LLP

(57) ABSTRACT

Described herein are companion methods and kits useful for IL-2-based therapies and for mesenchymal stem cell-based therapies.

12 Claims, 98 Drawing Sheets
Specification includes a Sequence Listing.

(56) References Cited

U.S. PATENT DOCUMENTS

| | | |
|---|---|---|
| 2014/0205563 A1 | 7/2014 | Maguire et al. |
| 2019/0234948 A1 | 8/2019 | Lunyak et al. |
| 2019/0241958 A1 | 8/2019 | Lunyak et al. |
| 2021/0302429 A1 | 9/2021 | Lunyak et al. |
| 2022/0370503 A1 | 11/2022 | Lunyak et al. |

FOREIGN PATENT DOCUMENTS

| | | |
|---|---|---|
| CN | 104427992 A | 3/2015 |
| JP | 2004-520270 | 7/2004 |
| JP | 2005-503131 | 2/2005 |
| JP | 2007-527242 A | 9/2007 |
| JP | 2013-526705 | 6/2013 |
| JP | 2014-503821 A | 2/2014 |
| WO | WO-92/16235 A1 | 10/1992 |
| WO | WO-0218418 A1 | 3/2002 |
| WO | WO-200218418 A1 | 3/2002 |
| WO | WO-2002092002 A2 | 11/2002 |
| WO | WO-2009006439 A1 | 1/2009 |
| WO | WO-2011048222 A1 | 4/2011 |
| WO | WO-2011142952 A1 | 11/2011 |
| WO | WO-2012058097 A1 | 5/2012 |
| WO | WO-2013056240 A1 | 4/2013 |
| WO | WO-2013063155 A2 | 5/2013 |
| WO | WO-2013078392 A1 | 5/2013 |
| WO | WO-2013112942 A1 | 8/2013 |
| WO | WO-2013126565 A1 | 8/2013 |
| WO | WO-2014054004 A1 | 4/2014 |
| WO | WO-2014128634 A1 | 8/2014 |
| WO | WO-2015153011 A1 | 10/2015 |
| WO | WO-2016196765 A1 | 12/2016 |
| WO | WO-2016196774 A1 | 12/2016 |
| WO | WO-2017/160880 A1 | 9/2017 |
| WO | WO-2017/184873 A2 | 10/2017 |
| WO | WO-2017/184895 A2 | 10/2017 |

OTHER PUBLICATIONS

Panelli et al. Journal of Translational medicine, 2004; 2(17): 1-14 (Year: 2004).*
Tartour et al. Br. J. Cancer (1994), 69, 1130-1135 (Year: 1994).*
Sabatino et al. Journal of Clinical Oncology, 2009; 27(16): 2645-2652 (Year: 2009).*
Sim et al. Clin Invest. 2014;124(1):99-110 (Year: 2014).*
Jiang et al. Oncoimmunology 2016, vol. 5, No. 6, e1163462, 1-10 (Year: 2016).*
Sporn et al. Chemoprevention of Cancer, Carcinogenesis, vol. 21 (2000), 525-530 (Year: 2000).*
Auerbach et al. Cancer and Metastasis Reviews, 2000, 19: 167-172 (Year: 2000).*
Gura T. Science, 1997, 278(5340): 1041-1042 (Year: 1997).*
Jain RK. Scientific American, Jul. 1994,58-65 (Year: 1994).*
Hait. Nature Reviews/Drug Discovery, 2010, 9, pp. 253-254 (Year: 2010).*
Gravanis et al. Chin Clin Oncol, 2014, 3, pp. 1-5 (Year: 2014).*
Bean. PNAS 2018; 115(50): 12539-12543 (Year: 2018).*
Deenick, E. K. et al. "Stochastic model of T cell proliferation: a calculus revealing IL-2 regulation of precursor frequencies, cell cycle time, and survival", J. Immunol May 15, 2003; 170(10):4963-72.
Extended European Search Report issued Oct. 24, 2018 for EP Application No. 16804415.4, 9 pages.
Feng, J. et al. "GFOLD: a generalized fold change for ranking differentially expressed genes from RNA-seq data", Bioinformatics. Nov. 1, 2012 [retrieved from the Internet Jun. 27, 2019]; 28(21):2782-8. Epub Aug. 24, 2012.
International Search Report issued Dec. 5, 2016 for PCT Application No. PCT/US2016/035472 filed Jun. 2, 2016, 6 pages.
Kang, S. G. et al. "Cytotoxicity of human umbilical cord blood-derived mesenchymal stem cells against human malignant glioma cells", Childs Nerv Syst. Mar. 2008; 24(3):293-302. Epub Oct. 30, 2007.

Panelli, M. C. et al. "Forecasting the cytokine storm following systemic interleukin (IL)-2 administration", J Transl Med. 2004; 2:17. Published online Jun. 2, 2004.
U.S. Appl. No. 16/164,676, filed Oct. 18, 2018, for Lunyak et al.
U.S. Appl. No. 16/164,701, filed Oct. 18, 2018, for Lunyak et al.
Written Opinion issued Dec. 5, 2016 for PCT Application No. PCT/US2016/035472 filed Jun. 2, 2016, 6 pages.
Aggarwal, S. et al., "Human mesenchymal stem cells modulate allogenic immune cell responses," Blood, 2005; vol. 105: 4, pp. 1815-1822.
Akhurst, et al., TGF-B signaling in cancer—a double-edged sword, Trends in Cell Biology, Nov. 2001, pp. S44-S51.
Anonymous, "Agilent Whole Human Genome Oligo Microarray Kit with SurePrint Technology Whole Human Genome Oligo Microarray Kit", Jan. 1, 2004; 1- 4,XP055514859, Retrieved from the Internet: URL : http://www.swisslabs.eu/uploads/files/Whole_Human Genome_Oligo_Microarray_Kit.pdf [retrieved on Oct. 12, 2018]; 4 pages.
Aravindhan, Mesenchymal stem cells and cancer therapy: insights into targeting the tumour vasculature, Cancer Cell Int., 2021, 16 pages.
Beane, O. S. et al., "Impact of Aging on the Regenerative Properties of Bone Marrow-, Muscle-, and Adipose-Derived Mesenchymal Stem/Stromal Cells", PLOS One, Dec. 26, 2014; 9(12): 1-22.
Blaber et al., "Analysis of in vitro secretion profiles from adipose-derived cell populations," Journal of Translational Medicine 2012, 10:172, 16 pages.
Brummelkamp, et al., A System for Stable Expression of Short Interfering RNAs in Mammalian Cells, Science, Mar. 21, 2002, pp. 550-553, vol. 296, Issue 5567.
Choudhry, et al., Prospects of IL-2 in Cancer Immunotherapy, Review article, BioMed Research International, Oct. 2018, 7 pages.
Corcoran, et al., Mesenchymal Stem Cells in Early Entry of Breast Cancer into Bone Marrow, PLoS One, 2008, 10 pages.
Cuiffo, et al., Mesenchymal stem cells in tumor development Emerging roles and concepts, Cell Adhesion & Migration, May/Jun. 2012, pp. 220-230.
Deenick, E. K. et al. "Stochastic model of T cell proliferation: a calculus revealing IL-2 regulation of precursor frequencies, cell cycle time, and survival", J. Immunol. May 15, 2003 [Retrieved from the Internet Jun. 27, 2019]; 170(10):4963-72.
Dixit, V. et al. "The bioartificial liver: state-of-the-art", Eur. J. Surg. Suppl. 1998; 582:71-6.
Dominici, M. et al. "Minimal criteria for defining multipotent mesenchymal stromal cells. The International Society for Cellular Therapy position statement", Cytotherapy. 2006; 8(4): 315-7.
Dornburg, Reticuloendotheliosis viruses and derived vectors, Gene Therapy, Jul. 1, 1995, pp. 301-310.
Duda, et al., Malignant cells facilitate lung metastasis by bringing their own soil, PNAS, Dec. 14, 2010, pp. 21677-21682.
Eglitis, et al., Retroviral vectors for introduction of genes into mammalian cells, Biotechniques, Jul.-Aug. 1988, pp. 608-614, vol. 6, No. 7.
Ewald, et al., Therapy-Induced Senescence in Cancer, J Natl Cancer Inst., 2010, pp. 1536-1546.
Extended European Search Report issued Oct. 25, 2018 for EP Application No. 16804422.0, 11 pages.
Extended European Search Report for EP Application No. 21207206.0, mailed May 25, 2022, 13 pages.
Fan, H.et al. "Comparative study of regulatory T cells expanded ex vivo from cord blood and adult peripheral blood", Immunology. Jun. 2012; 136(2): 218-30.
Glenn J. D. et al. "Mesenchymal stem cells: Emerging mechanisms of immunomodulation and therapy", World J Stem Cells. Nov. 26, 2014; 6(5): 526-39. Published online Nov. 26, 2014.
International Search Report issued Nov. 7, 2016 for PCT Application No. PCT/US2016/035487 filed Jun. 2, 2016, 6 pages.
Jin, H. J. et al. "Comparative analysis of human mesenchymal stem cells from bone marrow, adipose tissue, and umbilical cord blood as sources of cell therapy", Int. J. Mol. Sci. Sep. 3, 2013; 14(9):17986-8001.

(56) References Cited

OTHER PUBLICATIONS

Lee, et al., Expression of small interfering RNAs targeted against HIV-1 rev transcripts in human cells, Nature Biotechnology, 2002, pp. 500-505, vol. 20.

Legallais, C. et al. "Bioartifical livers (BAL): current technological aspects and future developments", J. Membr. Sci. 2001; 181:81-95.

Li, X. et al. "Comprehensive characterization of four different populations of human mesenchymal stem cells as regards their immune properties, proliferation and differentiation", Int J Mol Med. Sep. 2014; 34(3):695-704. Epub Jun. 25, 2014.

Massagué, J., "TGFβ in Cancer," Cell, Jul. 2008 134, 215-230.

Miyagishi, et al., U6 promoter-driven siRNAs with four uridine 3' overhangs efficiently suppress targeted gene expression in mammalian cells, Nature biotechnology, 2002, pp. 497-500.

Nabha, et al., Bone marrow stromal cells enhance prostate cancer cell invasion through type I collagen in an MMP-12 dependent manner, Int. J. Cancer, 2008, pp. 2482-2490.

Nardella, et al., Pro-senescence therapy for cancer treatment, Nature Reviews, Cancer, Jul. 2011, pp. 503-511.

Neel, et al., The Dual Role of TGF in Human Cancer: From Tumor Suppression to Cancer Metastasis, Review Article, Molecular Biology, Oct. 2012, 30 pages.

Niu, D. G. et al. "Morphine promotes cancer stem cell properties, contributing to chemoresistance in breast cancer", Oncotarget. Feb. 28, 2015; 6(6):3963-76.

Niu, P. et al., "Transcriptional profiling of interleukin-2-primed human adipose derived mesenchymal stem cells revealed dramatic changes in stem cells response imposed by replicative senescence", Oncotarget. Jul. 14, 2015; 6(20): 17938-57.

Non-Final Office Action mailed on Jul. 12, 2021 for U.S. Appl. No. 15/579,184, filed on Oct. 9, 2018, 9 pages.

Notice of Allowance issued for U.S. Appl. No. 15/579,184, mailed Nov. 19, 2021, 7 pages.

Oskarsson, et al., Metastatic Stem Cells: Sources, Niches, and Vital Pathways, Cell Stem Cell, Mar. 6, 2014, pp. 306-321.

Overwijk, et al., Engineering IL-2 to Give New Life to T Cell Immunotherapy, Annual Review of Medicine, Oct. 29, 2020, pp. 30.1-30.31.

Paddison, et al., Short hairpin RNAs (shRNAs) induce sequence-specific silencing in mammalian cells, Genes & Development, 2002, pp. 948-958, vol. 16.

Paul, et al., Effective expression of small interfering RNA in human cells, Nature Biotechnology, 2002, pp. 505-508, vol. 20.

Perez, L. M. et al. "Obese-derived ASCs show impaired migration and angiogenesis properties", Arch Physiol Biochem. Dec. 11, 2013; 119(5):195-201. Epub May 14, 2013.

Prasanna, et al., Therapy-Induced Senescence: Opportunities to Improve Anticancer Therapy, JNCI J Natl Cancer Inst, 2021, pp. 1285-1298.

Restriction Requirement issued for U.S. Appl. No. 15/579,184, mailed Dec. 14, 2020, 8 pages.

Rumman, et al., Concise Review: Quiescence in Adult Stem Cells: Biological Significance and Relevance to Tissue Regeneration, Stem Cells, 2015, pp. 2903-2912.

Schmitt, et al., A Senescence Program Controlled by p53 and p16INK4s Contributes to the Outcome of Cancer Therapy, Cell, May 3, 2002, pp. 335-346, vol. 109.

Shao, et al., Hematopoietic stem cell senescence and cancer therapy-induced long-term bone marrow injury, Transl Cancer Res., Oct. 2013, pp. 397-411.

Smigiel, K. S. et al. "Regulatory T-cell homeostasis: steady-state maintenance and modulation during inflammation", Immunol Rev. May 2014; 259(1):40-59.

Tollervey, J. et al. "Epigenetics: Judge, jury and executioner of stem cell fate", Epigenetics. Aug. 1, 2012; 7(8): 823-840.

Uccelli, et al., Mesenchymal stem cells in health and disease, Nature, Sep. 2008, pp. 726-736.

Wang, J. et al., "Inhibition of activated pericentromeric SINE/Alu repeat transcription in senescent human adult stem cells reinstates self-renewal", Cell Cycle. Sep. 1, 2011; 10(17):3016-30. Epub Sep. 1, 2011.

Wang J. et al. "Primate-specific endogenous retrovirus-driven transcription defines naive-like stem cells", Nature. Dec. 18, 2014; 516(7531):405-9. Epub Oct. 15, 2014.

Watson et al., "Comparison of Markers and Function Attributes of Human Adipose-Derived Stem Cells and Dedifferentiated Adipocyte Cells from Subcutaneous Fat of an Obese Diabetic Donor," Advances in Wound Care 3(3): 219-228, 2014.

Written Opinion issued Nov. 7, 2016 for PCT Application No. PCT/US2016/035487 filed Jun. 2, 2016, 10 pages.

Zhou et al., "Comparison of mesenchymal stromal cells from human bone marrow and adipose tissue for the treatment of spinal cord injury," Cytotherapy, 15: 434-448, 2013.

Ivanova-Todorova et al., "Conditioned medium from adipose tissue-derived mesenchymal stem cells induces CD4+FOXP3+ cells and increases IL-10 secretion" J Biomed Biotechnol. (2012) 2012:295167, 8 pages.

\* cited by examiner

FIGS. 2A-2B
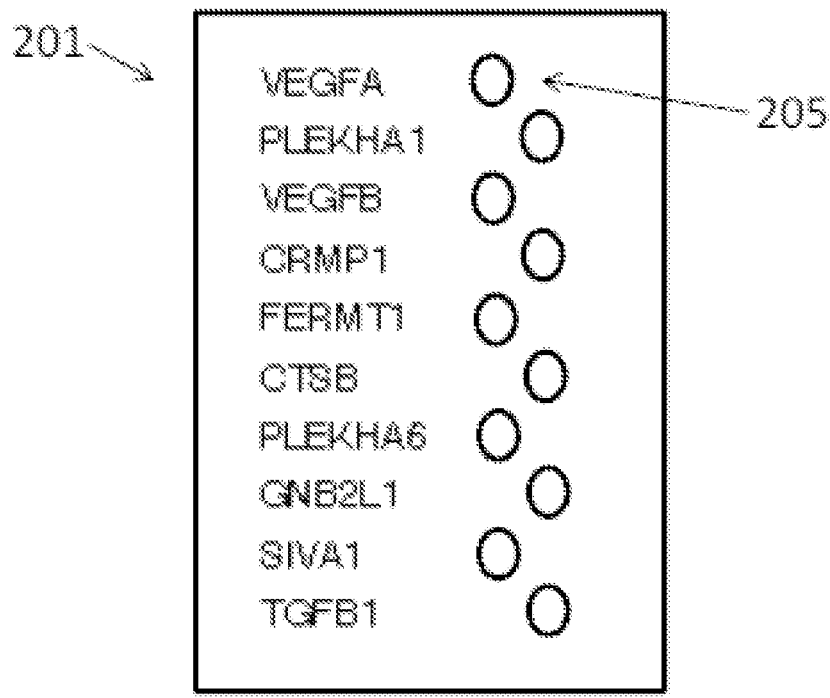
FIG. 2A
FIG. 2B

FIGS. 3A-D
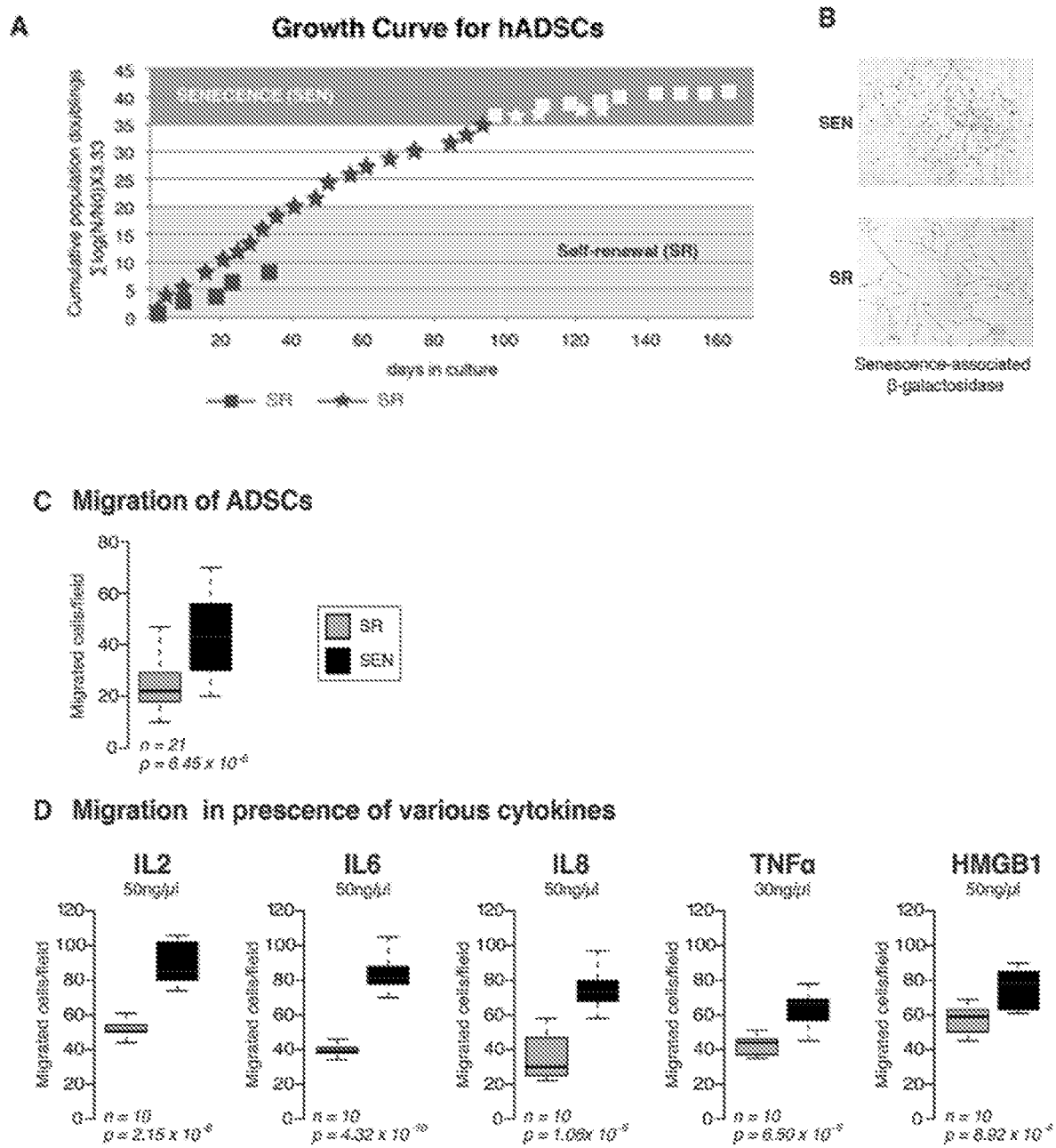

FIGS. 4A-C
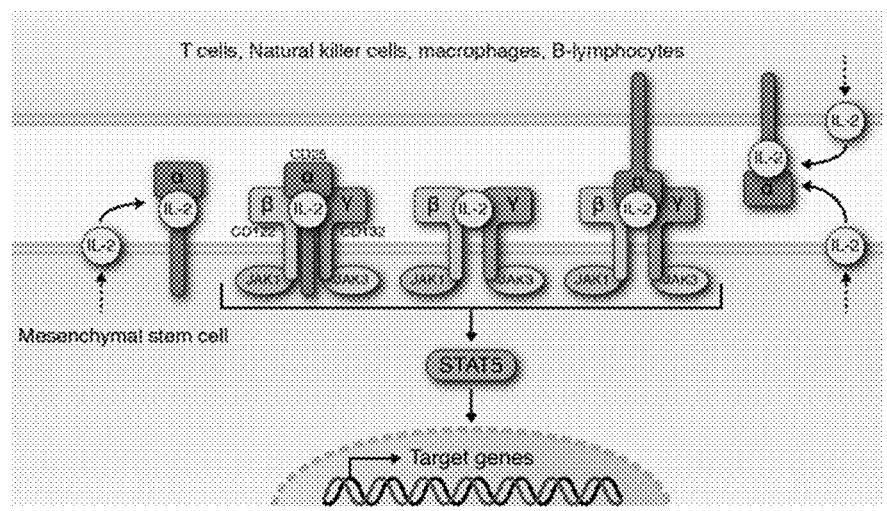
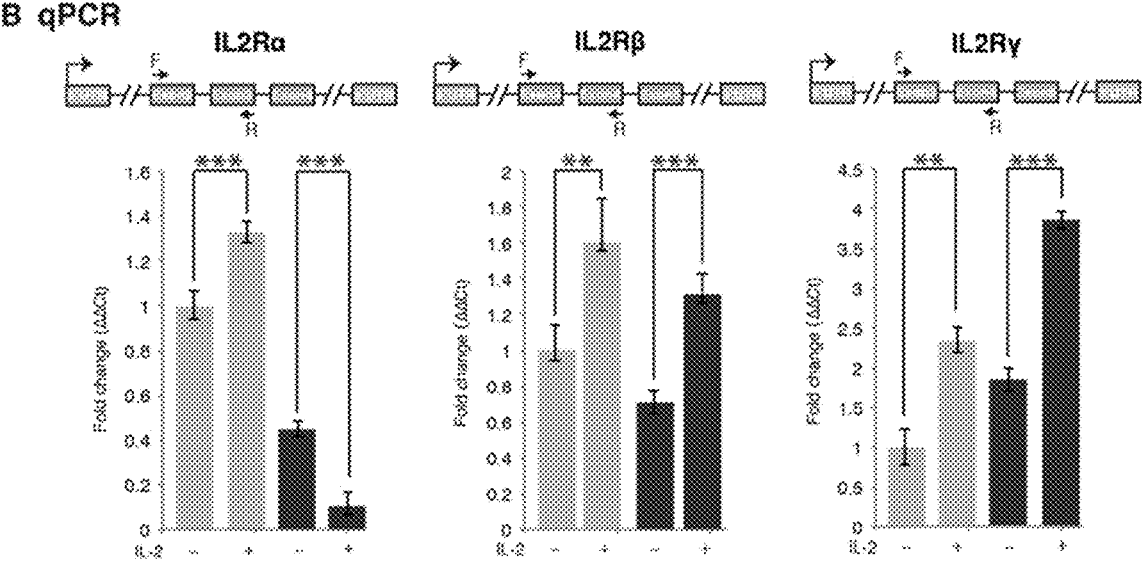
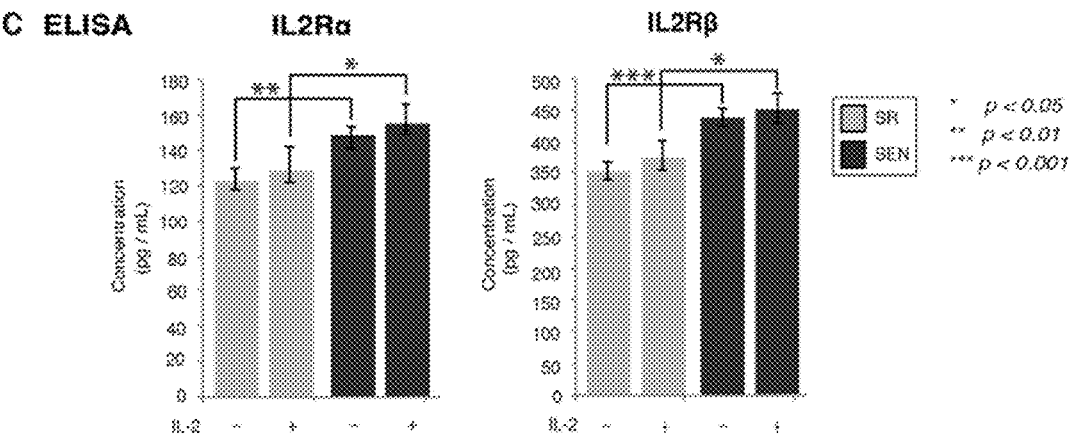

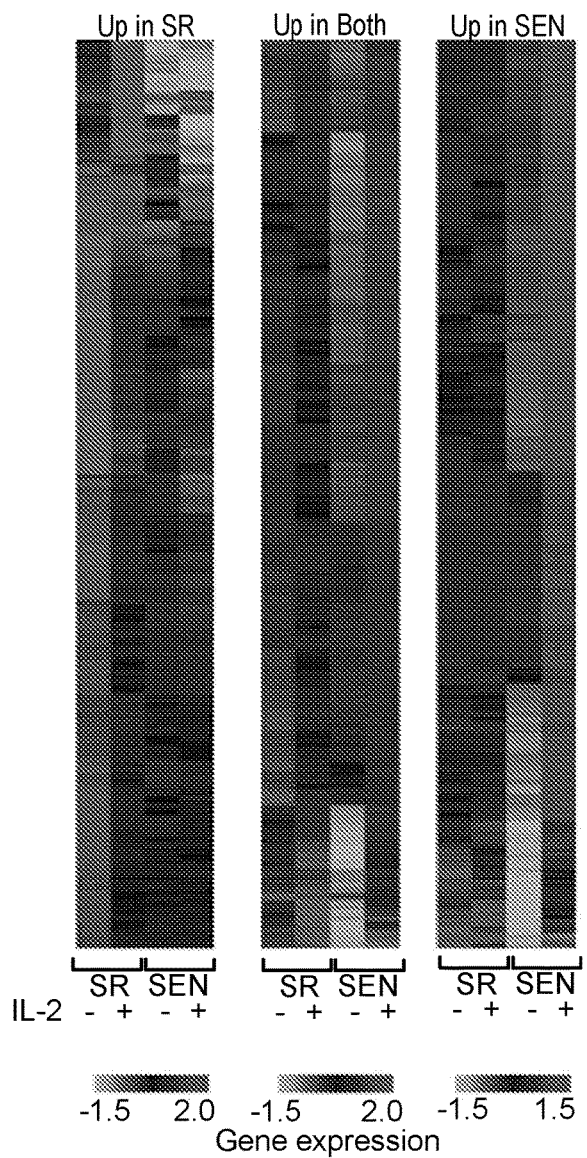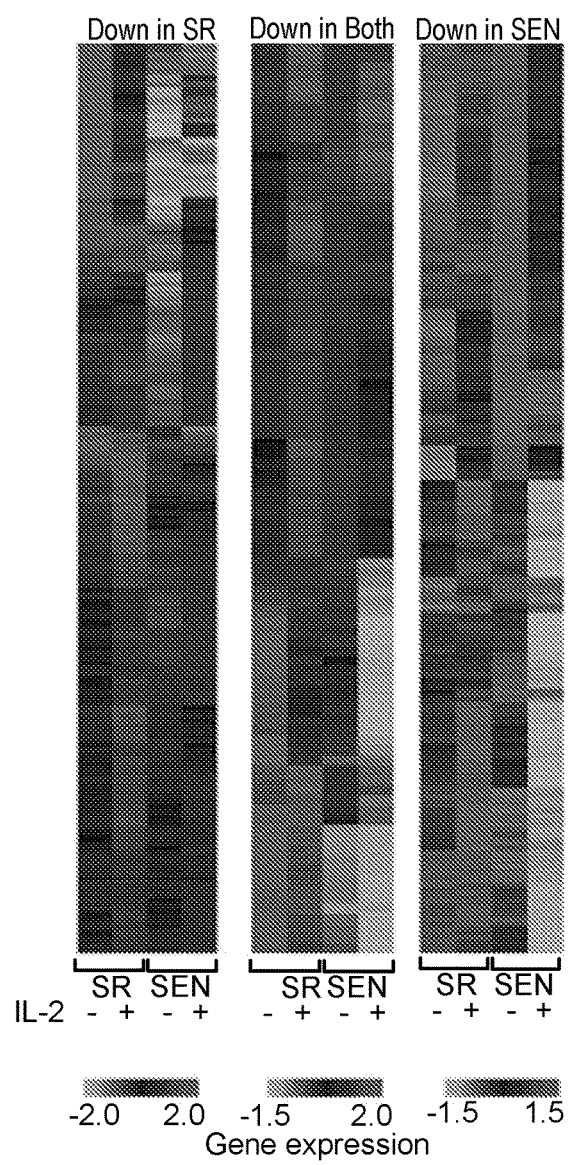

Trophic factors

Anti-inflammatory and immunomodulatory

Anti-appoptotic and metastasis promoting

FIG. 10A BIOLOGICAL PATHWAYS UPREGULATED UPON IL-2 TREATMENT
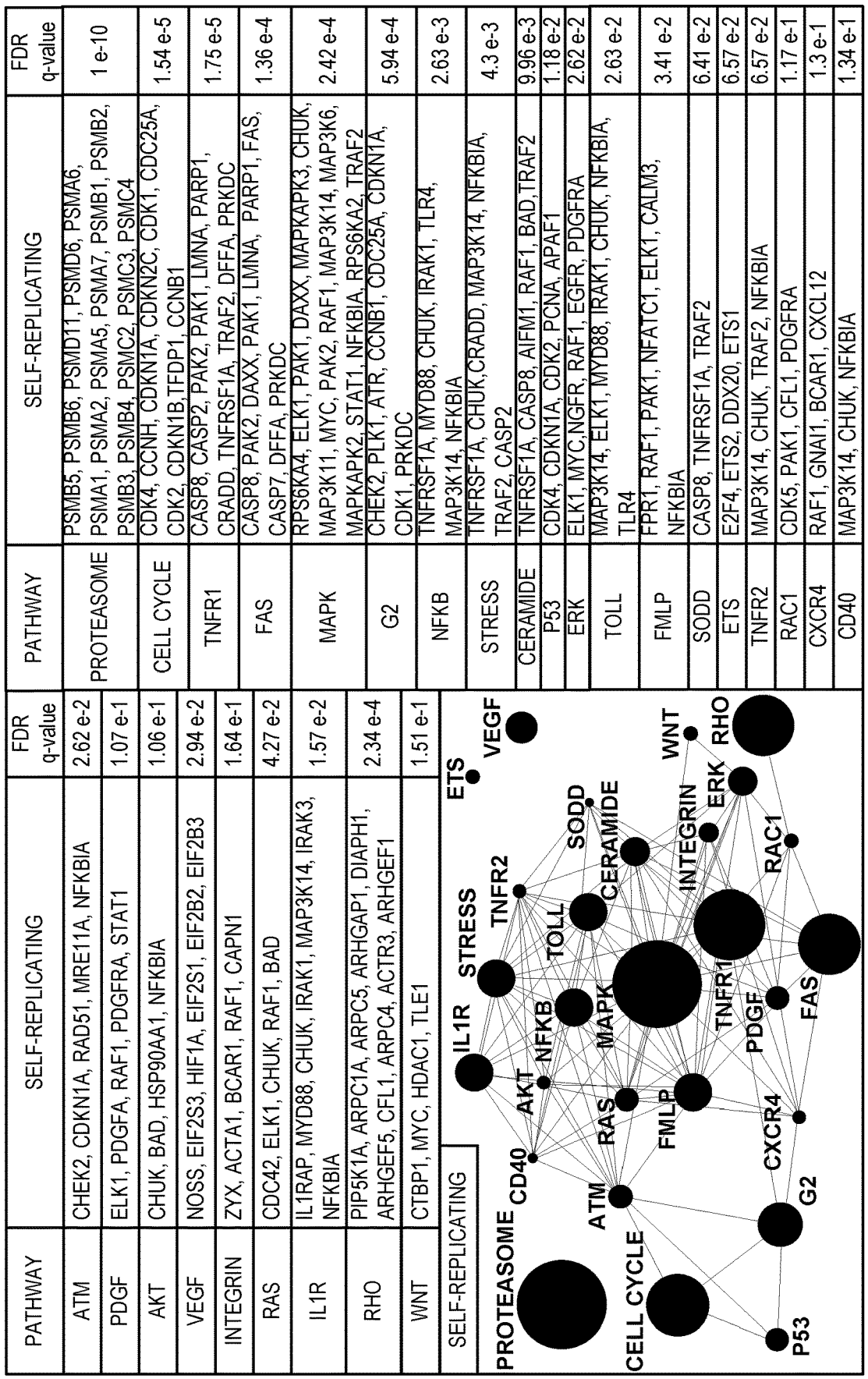

FIG. 10A (Continued)

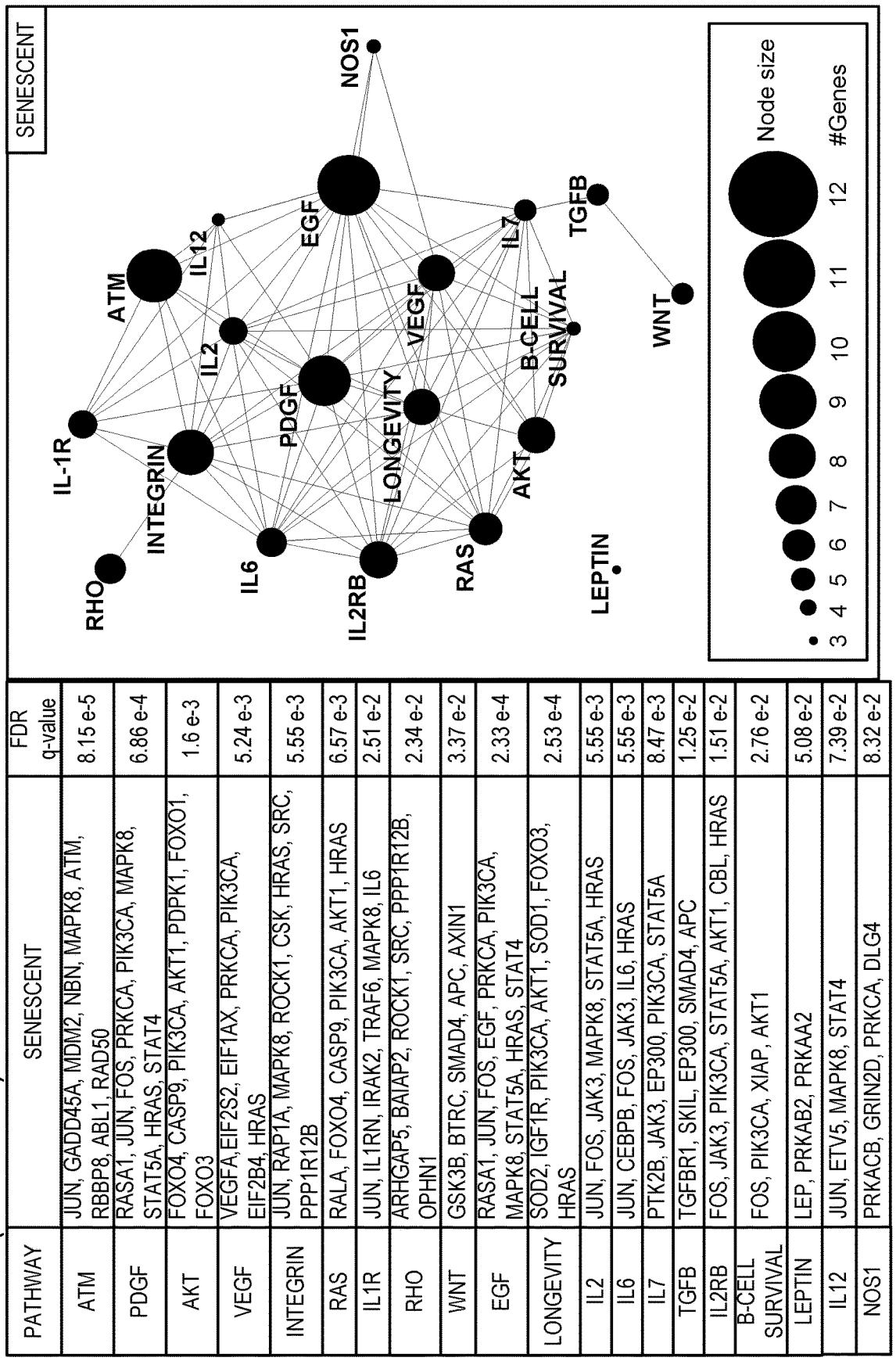

| PATHWAY | SENESCENT | FDR q-value |
|---|---|---|
| ATM | JUN, GADD45A, MDM2, NBN, MAPK8, ATM, RBBP8, ABL1, RAD50 | 8.15 e-5 |
| PDGF | RASA1, JUN, FOS, PRKCA, PIK3CA, MAPK8, STAT5A, HRAS, STAT4 | 6.86 e-4 |
| AKT | FOXO4, CASP9, PIK3CA, AKT1, PDPK1, FOXO1, FOXO3 | 1.6 e-3 |
| VEGF | VEGFA, EIF2S2, EIF1AX, PRKCA, PIK3CA, EIF2B4, HRAS | 5.24 e-3 |
| INTEGRIN | JUN, RAP1A, MAPK8, ROCK1, CSK, HRAS, SRC, PPP1R12B | 5.55 e-3 |
| RAS | RALA, FOXO4, CASP9, PIK3CA, AKT1, HRAS | 6.57 e-3 |
| IL1R | JUN, IL1RN, IRAK2, TRAF6, MAPK8, IL6 | 2.51 e-2 |
| RHO | ARHGAP5, BAIAP2, ROCK1, SRC, PPP1R12B, OPHN1 | 2.34 e-2 |
| WNT | GSK3B, BTRC, SMAD4, APC, AXIN1 | 3.37 e-2 |
| EGF | RASA1, JUN, FOS, EGF, PRKCA, PIK3CA, MAPK8, STAT5A, HRAS, STAT4 | 2.33 e-4 |
| LONGEVITY | SOD2, IGF1R, PIK3CA, AKT1, SOD1, FOXO3, HRAS | 2.53 e-4 |
| IL2 | JUN, FOS, JAK3, MAPK8, STAT5A, HRAS | 5.55 e-3 |
| IL6 | JUN, CEBPB, FOS, JAK3, IL6, HRAS | 5.55 e-3 |
| IL7 | PTK2B, JAK3, EP300, PIK3CA, STAT5A | 8.47 e-3 |
| TGFB | TGFBR1, SKIL, EP300, SMAD4, APC | 1.25 e-2 |
| IL2RB | FOS, JAK3, PIK3CA, STAT5A, AKT1, CBL, HRAS | 1.51 e-2 |
| B-CELL SURVIVAL | FOS, PIK3CA, XIAP, AKT1 | 2.76 e-2 |
| LEPTIN | LEP, PRKAB2, PRKAA2 | 5.08 e-2 |
| IL12 | JUN, ETV5, MAPK8, STAT4 | 7.39 e-2 |
| NOS1 | PRKACB, GRIN2D, PRKCA, DLG4 | 8.32 e-2 |

FIG. 10B  BIOLOGICAL PATHWAYS DOWNREGULATED UPON IL-2 TREATMENT

| PATHWAY | SELF-REPLICATING | FDR q-value |
|---|---|---|
| G2 | GADD45A, CDKN2D | 5.35 e-1 |
| P53 | GADD45A, BAX | 5.35 e-1 |
| MTOR | EIF3A, FKBP1A | 5.35 e-1 |
| ETS | NCOR2, CSF1R | 5.35 e-1 |

FIG. 10B
(Continued)

| PATHWAY | SENESCENT | FDR q-value | PATHWAY | SENESCENT | FDR q-value |
|---|---|---|---|---|---|
| G2 | PRKDC, CDK1, CDKN1A, CCNB1, CHEK1, CDC25C, CDC25B, PLK1 | 3.06 e-5 | PDGF | MAP3K1, STAT1, SRF, PDGFRA, PDGFA | 3.28 e-2 |
|  |  |  | CERAMIDE | CASP8, MAP3K1, TRAF2, CYCS | 3.92 e-2 |
| P53 | CDK2, CDKN1A, CDK4, PCNA | 1.86 e-2 | NFKB | MAP3K1, MAP3K14, TNFRSF1B, IL1R1 | 4.25 e-2 |
|  |  |  | RAC1 | MAP3K1, PDGFRA, CFL1, CHN1 | 4.25 e-2 |
|  |  |  | CD40 | IKBKAP, MAP3K1, MAP3K14 | 6.79 e-2 |
| MTOR | EIF4A1, PRS6, TSC1 | 1.59 e-1 | B-CELL SURVIVAL | BIRC5, CCT4, ITGA1 | 7.61 e-2 |
| MCM | CDK2, KITLG, ORC6, ORC3, MCM2, MCM3, MCM4, MCM5, MCM7, CDT1 | 1.62 e-8 | CDC42RAC | ARPC4, CDC42, PDGFRA | 7.61 e-2 |
| PROTEA-SOME | PSMA7, PSMA5, PSMA6, PSMB3, PSMB5, PSMB6, PSMB7, PSMC2, PSMC3 | 2.17 e-5 | IL-10 | BLVRA, BLVRB, STAT1 | 8.64 e-2 |
|  |  |  | EGF | EGFR, MAP3K1, SRF, STAT1 | 9.19 e-2 |
| HIV-I NEF | PRKDC, CASP8, LMNA, PARP1, LMNB1, LMNB2, MAP3K1, TRAF2, CYCS, MAP3K14, TNFRSF1B, ACTG1 | 2.52 e-5 | RHO | ARHGAP1, ARPC4, CFL1, PIP5K1A | 1 e-1 |
|  |  |  | IL-1R | IL1R1, IRAK3, MAP3K1, MAP3K14 | 1.09 e-1 |
| CELL CYCLE | CDK2, CDK1, CDKN1A, CCNB1, CDK4, TFDP1, CDKN2C, CCND3 | 2.52 e-5 | mCALPAIN | ACTA1, EGFR, ITGA1 | 1.79 e-1 |
|  |  |  | STRESS | MAP3K1, MAP3K14, TRAF2 | 1.79 e-1 |
| RB | CDK2, CDK1, CDK4, CHEK1, CDC25C, CDC25B | 6.97 e-5 | TALL1 | MAP3K14, TRAF2 | 2.81 e-1 |
|  |  |  | NO1 | ACTA1, CALM3, FLT1 | 2.97 e-1 |
| TNFR1 | PRKDC, CASP8, LMNA, PARP1, LMNB1, LMNB2, MAP3K1, TRAF2 | 1.02 e-4 | 4-1BB | MAP3K1, TRAF2 | 3.21 e-1 |
| FAS | PRKDC, CASP8, LMNA, PARP1, LMNB1, LMNB2, MAP3K1, TRAF2 | 1.1 e-3 | LAIR | C5, ITGA4 | 3.21 e-1 |
|  |  |  | ETS | E2F4, ETS1 | 3.4 e-1 |
| TNFR2 | MAP3K1, TRAF2, MAP3K14, TNFRSF1B, IKBKAP | 4.02 e-3 | FMLP | CALM3, CAMK1G, MAP3K1 | 3.8 e-1 |
| NFAT | ACTA1, MEF2C, CALM3, CAMK1G, CTF1, FGF2, HAND2 | 2.9 e-2 | CCR5 | CALM3, CCL2 | 3.8 e-1 |
|  |  |  | ERK | EGFR, PDGFRA | 5.82 e-1 |
| SODD | CASP8, TRAF2, TNFRSF1B | 3.24 e-2 | TOLL | MAP3K1, MAP3K14 | 8.06 e-1 |
| ATM | CDKN1A, CHEK1, MRE11A, RAD51 | 3.28 e-2 | INTEGRIN | ACTA1, ITGA1 | 8.25 e-1 |

SR-MSCs
No IL-2 Stimulation

SR-MSCs
No IL-2 Stimulation

SR-MSCs
No IL-2 Stimulation

SR-MSCs
No IL-2 Stimulation

SR-MSCs
No IL-2 Stimulation

SR-MSCs
No IL-2 Stimulation

SR-MSCs
+ IL-2 Stimulation

SR-MSCs
+ IL-2 Stimulation

FIG. 47
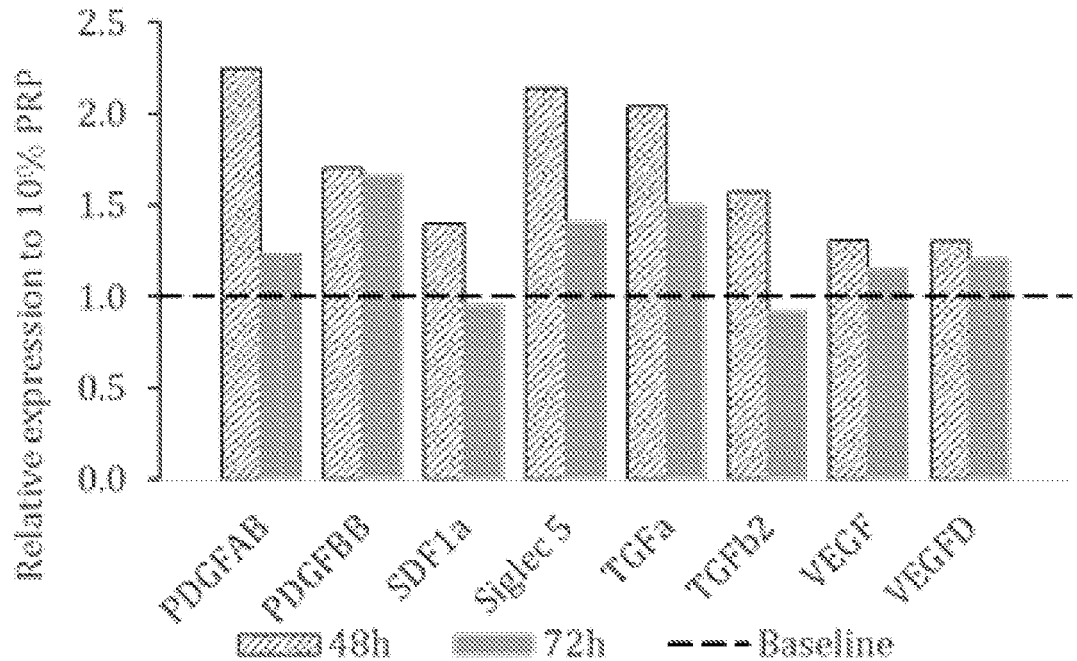
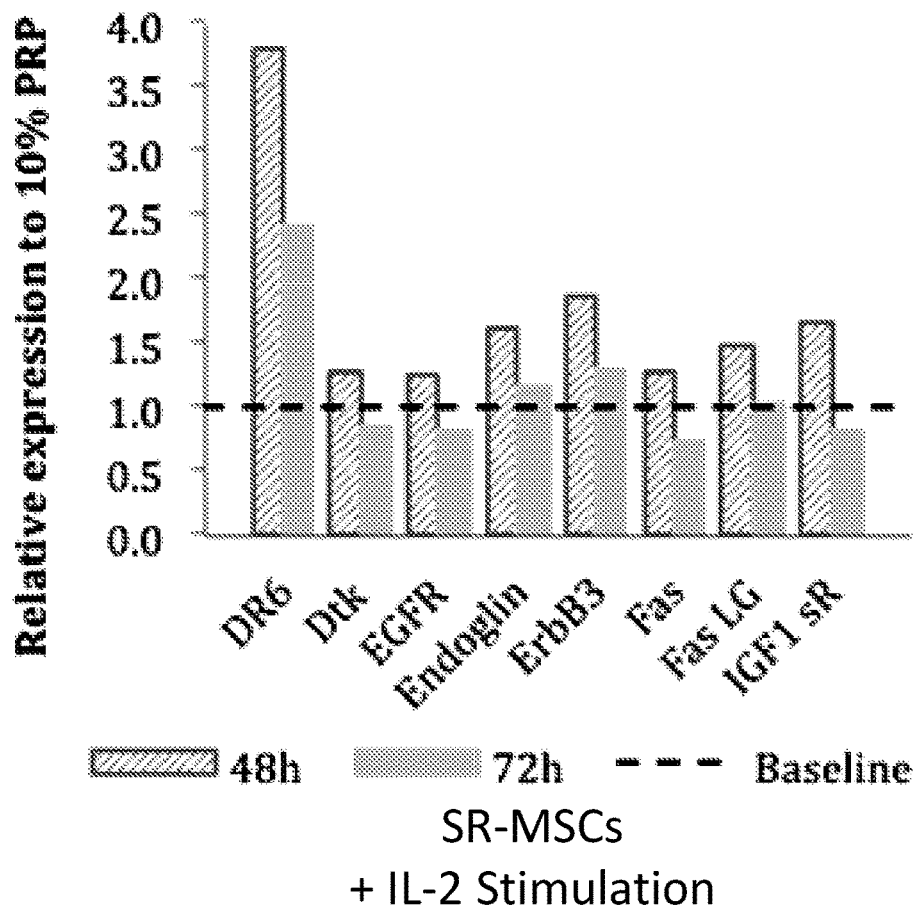
SR-MSCs
+ IL-2 Stimulation

SR-MSCs
+ IL-2 Stimulation

FIG. 54
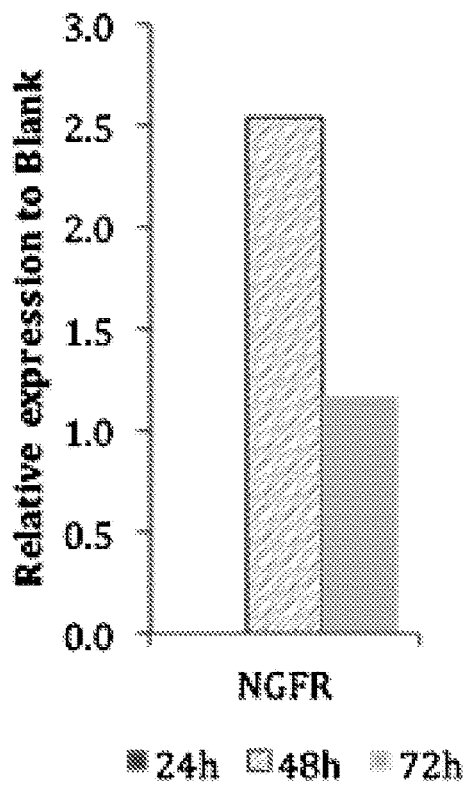
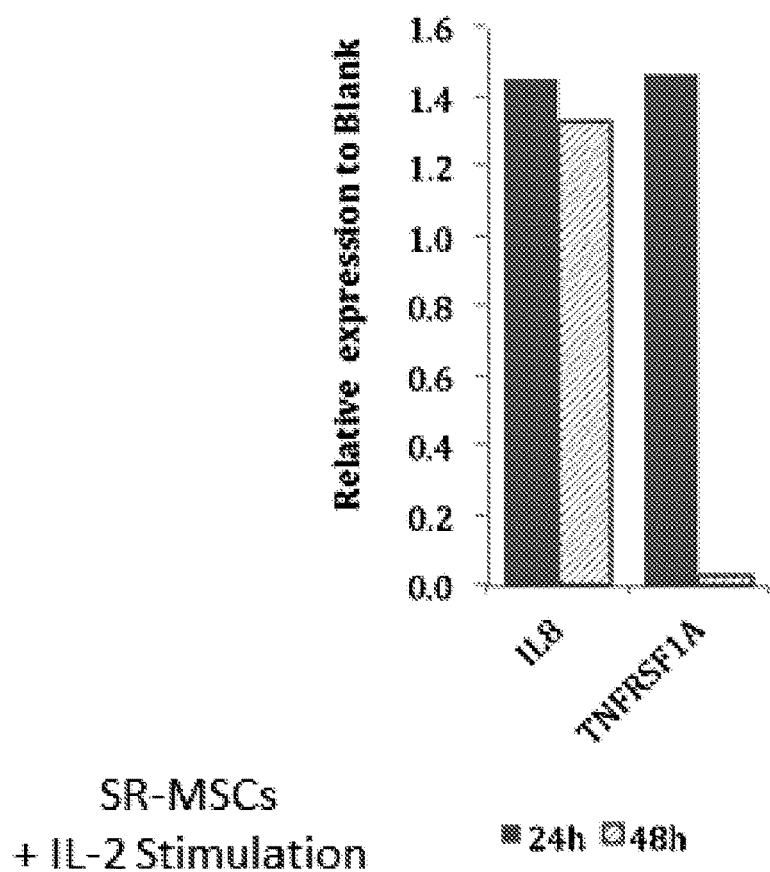
SR-MSCs
+ IL-2 Stimulation

SR-MSCs
+ IL-2 Stimulation

SR-MSCs
+ IL-2 Stimulation

SR-MSCs
+ IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
No IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

SEN-MSCs
+ IL-2 Stimulation

TREATMENT WITH AN IL-2 BASED THERAPY

CROSS REFERENCE TO RELATED APPLICATIONS

This application claims priority to U.S. Provisional Application Ser. No. 62/170,604, filed Jun. 3, 2015, U.S. Provisional Application Ser. No. 62/170,619, filed Jun. 3, 2015, and U.S. Provisional Application Ser. No. 62/175,203, filed Jun. 12, 2015, each of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALNC_003_01US_SeqList_ST25.txt, date recorded: Sep. 4, 2018, file size 3 kilobytes).

BACKGROUND OF THE INVENTION

Interleukin 2 (IL-2) is a type of cytokine signaling molecule in the immune system and is used therapeutically. IL-2 is manufactured using recombinant DNA technology and is marketed as a protein therapeutic called aldesleukin (branded as Proleukin®). IL-2 is approved in several countries for the treatment of cancers (metastatic melanoma and renal cell carcinoma) and HIV.

IL-2 has been approved as a chemotherapeutic agent for cancer treatment with a high-dose regimen, but it may also be administered in a low-dose form. The high-dose regimen involves giving the drug intravenously, every eight hours, as tolerated, for up to 15 doses. High-dose IL-2 therapy produces overall response rates of only about 15% to 20%; moreover, it is associated with significant toxicities that affect essentially every organ system. Because of the severity of these side effects, patients are hospitalized and sometimes need intensive care unit support while the drug is being given; in severe cases, IL-2 treatment is discontinued.

Human mesenchymal stem cells (MSCs) are currently one of the primary sources of stem cells for transplantation to treat a variety of conditions (Kucerova, *Cancer Res* Jul. 1, 2007 67; 6304). Such transplanted stem cells in the presence of a pro-inflammatory or otherwise inhospitable environment in vivo may produce unwanted adverse events. Little is known regarding the extent to which the beneficial properties of MSCs are affected by their local environment.

Taken together, to date, little is known in how to determine potential adverse events associated with the administration of an IL-2 therapy, and the potential adverse effects of the environment on transplanted MSCs. Thus there exists a need for companion methods and kits for improving the treatment of patients who are treated with IL-2, and for patients receiving MSC-based therapies. Described herein are methods and kits for these purposes.

SUMMARY OF THE INVENTION

Described herein are companion methods and kits for determining whether an individual eligible to receive an IL-2-based therapy or whether an individual already receiving an IL-2-based therapy will potentially experience adverse events associated with that IL-2-based therapy. If it is determined that the individual may experience adverse events, such as an increased risk of tumorigenesis or metastasis, rather than the eradication of the underlying disease such as cancer, a treatment decision can be taken to not undergo any further IL-2-based therapy. Likewise, if it is determined that it is likely that the individual may not experience adverse events associated with the IL-2 based therapy, a decision can be made to commence or continue the administration of the IL-2 based therapy.

Also described herein are companion methods and kits for determining whether an individual eligible to receive a MSC-based therapy will potentially experience adverse events associated with the therapy.

Thus, in one aspect of the invention, provided herein are methods for determining whether an individual eligible to receive an IL-2-based therapy may experience an adverse event associated with the IL-2-based therapy, the method comprising: (a) measuring the expression levels of at least two biomarkers selected from a panel of biomarkers in a sample from the individual, wherein either (1) the individual has received at least one dose of an IL-2-based therapy or (2) the sample is combined with IL-2 in vitro, and wherein the panel of biomarkers comprises TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1; and (b) comparing the levels of the biomarkers to reference levels, wherein an increase in the levels above the reference levels indicates that the individual may experience an adverse event associated with the IL-2-based therapy, and wherein a decrease or no change in the levels compared to the references levels indicates that the individual may not experience an adverse event associated with the IL-2-based therapy. In one variation of the invention, the individual has received (e.g. has been administered) at least one dose of an IL-2-based therapy; in some variations, the individual has received the IL-2-based therapy for the treatment of a cancer. In some variations, the sample has been obtained from the individual 24, 48, or 72 hours after having received the IL-2-based therapy. In another variation, the sample from the individual is combined with IL-2 in vitro for further analysis; in some variations, the sample can be combined for a period of about 24 hours, after which the biomarkers are measured 24, 48, or 72 hours following removal of the IL-2. As contemplated herein, the sample can be any biological sample; in one variation, the sample is a blood, plasma, or serum sample. In particular variation, the method comprises measuring the expression levels of at least three biomarkers from the panel of biomarkers, at least four biomarkers from the panel of biomarkers, or at least five biomarkers from the panel of biomarkers. In some variations, the method comprises measuring the expression levels of TIE-1, TIE-2, TIMP-4, VEGFA, PLEKHA1, VEGFB, CRMP1, FERMT1, CTSB, PLEKHA6, GNB2L1, and TGFβ1. In some variations, the method may further comprise measuring additional biomarkers. In one particular variation, the method further comprises measuring the expression level of SIVA1, and querying for decreased expression of this biomarker. As contemplated herein, either the RNA or protein expression levels can be measured. Accordingly, in one variation, the method comprises measuring protein levels of the biomarkers, for example with an ELISA assay, an antibody proteomic array, immunohistochemistry, or mass spectrometry. In another variation, the method comprises measuring RNA levels of the biomarkers, for example with a Q-PCR assay or RNA-seq. In some variations, the method comprises obtaining the sample from the individual as a part of the method. Upon determination of the results of the expression, the method may comprise further comprising administering an effective amount of the IL-2-based therapy to the individual if it is determined in step (b) that the individual may not experience an adverse event associated with the IL-2-based therapy. The method may even further comprise administering a rejuvenation therapy to the individual if it is determined in step (b) that the individual may experience an adverse event associated with the IL-2-based therapy.

In another aspect, the invention provides a method of treating an individual for cancer with an IL-2-based therapy. In one variation, the method of treating an individual for cancer with an IL-2-based therapy comprises (a) measuring the expression levels of at least two biomarkers selected from a panel of biomarkers in a sample from the individual, wherein either (1) the individual has received at least one dose of an IL-2-based therapy or (2) the sample is combined with IL-2 in vitro, and wherein the panel of biomarkers comprises TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1B, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1; (b) comparing the levels of the biomarkers to reference levels, wherein no change or a decrease in the levels below the reference levels indicates that the individual may not experience an adverse event associated with the IL-2-based therapy; and (c) administering an effective amount of the IL-2-based therapy to the individual if it determined in step (b) that the individual may not experience an adverse event associated with the IL-2-based therapy. In another variation, the method of treating an individual for cancer with an IL-2-based therapy comprises administering an effective amount of the IL-2-based therapy to the individual when the expression levels of at least two biomarkers is decreased or exhibits no change, in comparison to reference levels in a sample from the individual wherein either (1) the individual has received at least one dose of an IL-2-based therapy or (2) the sample is combined with IL-2 in vitro, and wherein the panel of biomarkers comprises TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1B, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1. In one variation of the invention, the individual has received (e.g. has been administered) at least one dose of an IL-2-based therapy. In some variations, the sample has been obtained from the individual 24, 48, or 72 hours after having received the IL-2-based therapy. In another variation, the sample from the individual is combined with IL-2 in vitro for further analysis; in some variations, the sample can be combined for a period of about 24 hours, after which the biomarkers are measured 24, 48, or 72 hours following removal of the IL-2. As contemplated herein, the sample can be any biological sample; in one variation, the sample is a blood, plasma, or serum sample. In particular variation, the method comprises measuring the expression levels of at least three biomarkers from the panel of biomarkers, at least four biomarkers from the panel of biomarkers, or at least five biomarkers from the panel of biomarkers. In some variations, the method comprises measuring the expression levels of TIE-1, TIE-2, TIMP-4, VEGFA, PLEKHA1, VEGFB, CRMP1, FERMT1, CTSB, PLEKHA6, GNB2L1, and TGFβ1. In some variations, the method may further comprise measuring additional biomarkers. In one particular variation, the method further comprises measuring the expression level of SIVA1, and querying for decreased expression of this biomarker. As contemplated herein, either the RNA or protein expression levels can be measured. Accordingly, in one variation, the method comprises measuring protein levels of the biomarkers, for example with an ELISA assay, an antibody proteomic array, immunohistochemistry, or mass spectrometry. In another variation, the method comprises measuring RNA levels of the biomarkers, for example with a Q-PCR assay or RNA-seq. In some variations, the method comprises obtaining the sample from the individual as a part of the method. The method may even further comprise administering a rejuvenation therapy to the individual if it is determined that the individual may experience an adverse event associated with the IL-2-based therapy.

In another aspect, the invention provides a method of determining whether a population of mesenchymal stem cells (MSCs) is suitable for administration into an individual for a MSC-based therapy, comprising: (a) incubating IL-2 with the population of MSCs; (b) measuring the expression levels in the MSCs of at least two biomarkers selected from a panel of biomarkers, wherein the panel of biomarkers comprises TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1B, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1; and (c) comparing the levels of the biomarkers to reference levels, wherein an increase in the levels above the reference levels indicates that the MSCs are not suitable for administration into an individual and no change or a decrease in the levels below the reference levels indicates that the MSCs are suitable for administration into an individual. In some variations, the method comprises measuring the expression levels of at least three biomarkers from the panel of biomarkers, measuring the expression levels of at least four biomarkers from the panel of biomarkers, or measuring the expression levels of at least five biomarkers from the panel of biomarkers. In some variations, the method comprises measuring the expression levels of TIE-1, TIE-2, TIMP-4, VEGFA, PLEKHA1, VEGFB, CRMP1, FERMT1, CTSB, PLEKHA6, GNB2L1, and TGFβ1. In some variations, the method may further comprise measuring additional biomarkers. In one particular variation, the method further comprises measuring the expression level of SIVA1, and querying for decreased expression of this biomarker. As contemplated herein, either the RNA or protein expression levels can be measured. Accordingly, in one variation, the method comprises measuring protein levels of the biomarkers, for example with an ELISA assay, an antibody proteomic array, immunohistochemistry, or mass spectrometry. In another variation, the method comprises measuring RNA levels of the biomarkers, for example with a Q-PCR assay or RNA-seq. In some variations, the incubation period is for about 24 hours. In some variations, the measuring is carried out 24, 48, or 72 hours following the incubation period with IL-2. In some variations, the method further comprises administering the population of cells to the individual. The method may further comprise rejuvenating the cells prior to administering the cells to the individual.

In another aspect of the invention, provided herein are kits for assessing the suitability of a population of MSCs for transplant or for determining whether an IL-2-based therapy should be administered comprising reagents for measuring the expression level of at least two biomarkers selected from a panel of biomarkers in a sample, wherein the panel of biomarkers comprises TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1. In some variations, the kit comprises reagents for measuring the expression level of at least three biomarkers in the sample, for measuring the expression level of at least four biomarkers in the sample, or for measuring the expression level of at least five biomarkers in the sample. In some variations, the kit comprises reagents for measuring TIE-1, TIE-2, TIMP-4, VEGFA, PLEKHA1, VEGFB, CRMP1, FERMT1, CTSB, PLEKHA6, GNB2L1, and TGFβ1. In some variations, the kit comprises IL-2.

It is to be understood that one, some, or all of the properties of the various variations described herein may be combined to form other variations of the present invention. These and other aspects of the invention will become apparent to one of skill in the art.

BRIEF DESCRIPTION OF THE DRAWINGS

FIG. 2A is a schematic of an exemplary assay for determining if an IL-2-based therapy should be administered. FIG. 2B illustrates example screening results using the assay shown in FIG. 2A. In FIG. 2B the result is positive, with the expression of several markers increased, indicating that potential adverse events could be associated with the administration of IL-2.

FIGS. 3A-3D illustrate how replicative senescence (SEN) impairs the migratory properties of the human adipose derived mesenchymal stem cells (hADSCs, also referred to herein interchangeably hADSCs). FIG. 3A shows a growth curve of hADSCs and is represented as cumulative population doubling over day in culture. FIG. 3B shows detection of senescence-associated β-galactosidase. FIG. 3C shows ex vivo migration assays for SR (left) and SEN (right) hADSCs. FIG. 3D shows the migration of SR-hADSCs (left) and SEN-hADSCs (right).

FIGS. 4A-4C illustrate the gene expression of IL-2 receptor isoforms and their association with membrane in SR-hADSCs and SEN-hADSCs induced with IL-2. FIG. 4A shows a schematic representation of IL-2 receptor composition. FIG. 4B shows IL-2 receptors α, β, and γ assessed by quantitative PCR (Q-PCR) SR and SEN hADSC, either, in the presence or absence of IL-2. FIG. 4C shows the cellular membrane-associated protein levels of IL-2Rα and IL-2Rβ.

FIGS. 6A-6D show a comparison of gene expression levels between SR and SEN cells upon IL-2 treatment.

FIG. 8A provides a schematic representation of the RNA-seq analysis design. FIG. 8B shows the distributions of the gene-specific RNA-seq read counts for each condition prior to ACTB normalization. FIG. 8C shows the condition-specific RNA-seq read counts for ACTB that were used for normalization. FIG. 8D shows distributions of the gene specific RNA-seq read counts for each condition after ACTB normalization.

FIGS. 10A-10B represent tables of the genes differentially expressed upon IL-2 treatment in SEN and SR hAMCS. FIG. 10A shows biological pathways enriched for genes up-regulated upon IL-2 treatment in SR and SEN hADSCs. FIG. 10B shows biological pathways enriched for genes down-regulated upon IL-2 treatment in SR and SEN hADSCs.

DETAILED DESCRIPTION OF THE INVENTION

I. Methods

1. Introduction

Figure 1A:
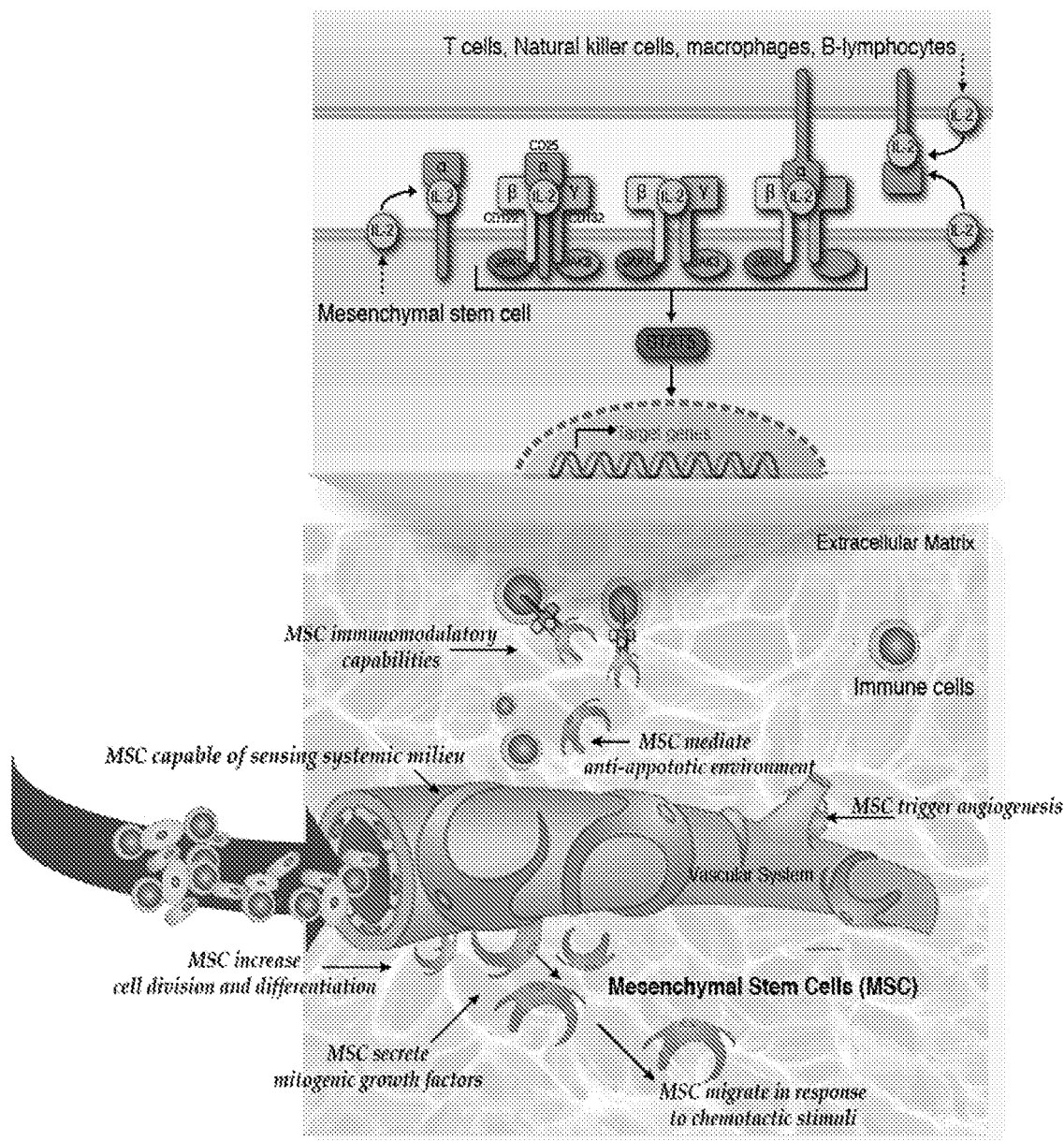
FIG. 1A is schematic illustrating the positioning of MSCs in vivo on blood vessels, rendering them capable of sensing and responding to an inflammatory environment, and treatment with cytokines.

Provided herein are companion methods and kits useful for IL-2-based therapies and for mesenchymal stem cell-based therapies.

Specifically, in one variation of the invention, provided herein are methods for determining whether an individual eligible to receive an IL-2-based therapy, for treatment of a condition such as cancer or HIV, may experience an adverse event associated with that IL-2-based therapy. The method involves measuring an increase in the expression levels of certain biomarkers in a sample from the individual upon exposure to IL-2, such biomarkers indicative of the cellular senescence of MSCs in the sample. The expression of such biomarkers would indicate that the individual could experience an adverse event (such as tumorigenesis or metastasis) if the IL-2-based therapy were to be administered or continued. Treatment decisions can be made based on the practice of this method and use of the kits described herein.

In another variation of the invention, provided here are methods for determining the suitability of a population of MSCs for administration (e.g. transplant) into an individual for an MSC-based therapy. The method involves measuring a change in the expression levels of certain biomarkers in the MSCs upon exposure to IL-2, such biomarkers associated with cellular senescence of the MSCs. If an increase in the biomarkers is observed, it would indicate that if the cells were administered to an individual, the individual may experience adverse events associated with the transplantation, such as metastatic transformation and invasive growth. Conversely if no change or a decrease in the expression levels of biomarkers is observed, it could indicate the suitability of the population of cells for administration. Treatment decisions regarding MSC transplantation can be made based on the practice of this method and use of the kits described herein.

These are discussed in further detail herein.

2. SEN-MSCs and SR-MSCs

Provided herein are methods for measuring the expression levels of biomarkers upon exposing a sample comprising MSCs to IL-2, wherein the biomarkers are indicative of cellular senescence. As used herein SEN MSCs are cells that are replicatively senescent. Replicative senescence is characterized by growth arrest, apoptosis resistance, high levels of metabolic activities, morphological and cell-size changes, high levels of expression of the tumor suppressors P16, P21, P53 and/or RB, increased activity of senescence associated beta galactosidase (SA-β-gal) and the loss of the ability to synthesize and repair DNA. The replicative aging of MSCs can influence their biological properties.

SR-MSCs, on the other hand, are associated with being productive: express a set of coding or non-coding RNAs indicative of quality; are self-renewing; are not senescent; are not nearing senescence; have been passaged 6 times or less; exhibit high growth potential; produce proteins of interest; allow for long-term tissue regeneration; induce long-term correction of a disease; exhibit no or only a low chance of immortalization; exhibit no or low tumorigenic potential; and contain few or no pro-viral integrations. In an exemplary variation, productive stem cells are self-renewing. In some variations, productive stem cells exhibit at least two, three, four, five, or more of the features associated with being productive.

3. Detection of the Biomarkers of Interest

The companion methods described herein are dependent on measuring expression levels of at least two biomarkers from a panel of biomarkers associated with cellular senescence, for example the panel may comprise biomarkers that are anti-apoptotic, angiogenic, tumorigenic, lead to vascular development, responsible for invasive growth, metastasis, cell motility, migration and the like. Generally, the methods provide measurement of the markers to make a determination if use of an IL-2 therapy, or transplantation of MSCs, could lead to adverse events. As used herein, adverse events following an IL-2 therapy or MSC transplantation include, but are not limited to an increase in tumorigenesis, anti-apoptotic activity, angiogenesis, vascular development, invasive growth, metastasis, cell motility, and migration.

As provided herein, biomarkers associated with cellular senescence that are upregulated in response to IL-2 can include those listed in Tables 1-4, Table 5B, and FIGS. 7A-7D.

In some variations the method comprises measuring RNA levels of the biomarkers. Such methods are known to those in the art, and include, but are not limited to the use of an Q-PCR, array-based technologies, RNA-seq, transcriptome analysis, single-cell transcriptomic analysis, and in situ-hybridization.

In some variations the method comprises measuring protein levels of the biomarkers. Such methods are known to those in the art, and include, but are not limited to the use of an ELISA assay, proteomic array, immunohistochemistry, Western Blot, mass spectrometry (MS), an antibody array, or a chemiluminescence assay.

In some variations the method comprises measuring both the RNA and protein levels of the biomarkers.

The biomarkers are measured, and compared to a reference level. As contemplated herein, a reference level can comprise a sample from the same individual before IL-2 treatment; can comprise a sample from a healthy individual who has not received any IL-2; or can comprise a collection of samples representing a heterogeneous group of individuals who have not received IL-2 treatment.

In particular variations, it is determined that the RNA expression levels of a biomarker is increased if it displays at least 1.1, at least 1.2, at least 1.3, at least 1.4, at least 1.5, at least 2, at least 3, at least 4, at least 5, at least 6, at least 7, at least 8, at least 9, at least 10, at least 15, at least 20, at least 25, at least 50, at least 75, or even at least 100-fold higher expression than the reference level of the biomarker. Fold can generally refer to raw fold values, GFOLD values, or fold values calculated using algorithms known to a skilled artisan.

RNA-dependent differences in the gene expression can be measured using a GFOLD calculation method (Feng et al, *Bioinformatics*. 2012), for estimating fold changes that takes into account the uncertainty of gene expression measurement by RNA-seq. In these variations, the use of GFOLD allows for the relative difference of gene expression and facilitates the comparison of genes with different expression levels or of different lengths.

In particular variations, it is determined that the protein expression levels of a biomarker is increased if it displays at least 1.1, at least 1.2, at least 1.3, at least 1.4, at least 1.5, at least 2, at least 3, at least 4, at least 5, at least 6, at least 7, at least 8, at least 9, at least 10, at least 15, at least 20, at least 25, at least 50, at least 75, or even at least 100 fold higher expression fold higher expression than the reference level of the biomarker.

4. Identity of the Biomarkers of Interest

As referred to herein, by "biomarker" it is meant any biological molecule (or fragment thereof) of interest, e.g. a biomarker which is present on the cell cytoplasm, surface, or secreted out. Such biomarkers include, but are not limited to, biomolecules comprising polypeptides, proteins, carbohydrates, lipids, glycoproteins, ribonucleoproteins, lipoproteins, glycolipids and fragments thereof. Where the biomarker comprises a protein, the protein can be a secreted protein, an intracellular protein, or a membrane protein. Biomarker proteins include, but are not limited to, peptides, polypeptides, glycoproteins, lipoproteins, cytokines, growth factors, antibodies, and other immunogenic molecules. The biomarker also may be a transmembrane protein or may be bound to a transmembrane protein or membrane lipid, for example.

As provided herein, biomarkers associated with cellular senescence that are upregulated in response to IL-2 are those listed in Tables 1-4, Table 5B, and FIGS. 7A-7D.

In some variations, the methods comprise measuring the expression levels of at least 3, at least 4, at least 5, at least 6, at least 7, at least 8, at least 9, at least 10, at least 11, at least 12, at least 13, at least 14, at least 15, at least 16, at least 17, at least 18, at least 19, or even at least 20 biomarkers from the panel of biomarkers for determination of potential adverse events associated with IL-2-based therapeutics and/or for the determination of the suitability of a population of MSCs for transplantation.

In some variations, the expression levels of at least two biomarkers selected from any of the biomarkers presented in Tables 1-4 are measured. In some variations, the expression levels of at least two biomarkers presented in FIGS. 7A-7D are measured. In some variations, the expression levels of at least two biomarkers presented in Table 5B are measured In one variation, the expression levels of at least two biomarkers are measured, wherein the first biomarker is TIE-1 and the second biomarker is selected from the group consisting of TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TIE-2 and the second biomarker is selected from the group consisting of TIE-1, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1. In one variation, the expression levels of at least two biomarkers are measured, wherein the first biomarker is TIE-1 and the second biomarker is selected from the group consisting of TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TIMP-4 and the second biomarker is selected from the group consisting of TIE-1, TIE-2, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is FGF1 and the second biomarker is selected from the group consisting of TIE-1, TIE-2, TIMP-4, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is LIF and the second biomarker is selected from the group consisting of TIE-1, TIE-2, TIMP-4, FGF1, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TGFBR2 and the second biomarker is selected from the group consisting of TIE-1, TIE-2, TIMP-4, FGF1, LIF, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is CSF1 and the second biomarker is selected from the group consisting of TIE-1, TIE-2, TIMP-4, FGF1, LIF, TGFBR2, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TGFα and the second biomarker is selected from the group consisting of TIE-1, TIE-2, TIMP-4, FGF1, LIF, TGFBR2, CSF1, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TGFβ1 and the second biomarker is selected from the group consisting of TIE-2, TIMP-4, FGF1, LIF, TGFBR2, CSF1, TGFα, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL17D and the second biomarker is selected from the group consisting of TIE-1, TIMP-4, FGF1, LIF, TGFBR2, CSF1, TGFα, TGFβ1, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is SDF2 and the second biomarker is selected from the group consisting of TIE-1, TIE-2, TIMP-4, FGF1, LIF, TGFBR2, CSF1, TGFα, TGFβ1, IL17D, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TGFBRAP1 and the second biomarker is selected from the group consisting of TIE-1, TIE-2, FGF1, LIF, TGFBR2, CSF1, TGFα, TGFβ1, IL17D, SDF2, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is FGF11 and the second biomarker is selected from the group consisting of TIE-1, TIE-2, TIMP-4, LIF, TGFBR2, CSF1, TGFα, TGFβ1, IL17D, SDF2, TGFBRAP1, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is TNFSF13B and the second biomarker is selected from the group consisting of TIE-1, TIE-2, TIMP-4, FGF1, TGFBR2, CSF1, TGFα, TGFβ1, IL17D, SDF2, TGFBRAP1, FGF11, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is FGF14 and the second biomarker is selected from the group consisting of TIE-1, TIE-2, TIMP-4, FGF1, LIF, CSF1, TGFα, TGFβ1, IL17D, SDF2, TGFBRAP1, FGF11, TNFSF13B, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL1β and the second biomarker is selected from the group consisting of TIE-1, TIE-2, TIMP-4, FGF1, LIF, TGFBR2, TGFα, TGFβ1, IL17D, SDF2, TGFBRAP1, FGF11, TNFSF13B, FGF14, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL-11, and the second biomarker is selected from the group consisting of TIE-1, TIE-2, TIMP-4, FGF1, LIF, TGFBR2, CSF1, TGFβ1, IL17D, SDF2, TGFBRAP1, FGF11, TNFSF13B, FGF14, IL1β, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL-32 the second biomarker is selected from the group consisting of TIE-2, TIMP-4, FGF1, LIF, TGFBR2, CSF1, TGFα, IL17D, SDF2, TGFBRAP1, FGF11, TNFSF13B, FGF14, IL1β, IL-11, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL-6 and the second biomarker is selected from the group consisting of TIE-1, TIMP-4, FGF1, LIF, TGFBR2, CSF1, TGFα, TGFβ1, SDF2, TGFBRAP1, FGF11, TNFSF13B, FGF14, IL1β, IL-11, IL-32, IL1RN, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL1RN and the second biomarker is selected from the group consisting of TIE-1, TIE-2, TIMP-4, FGF1, LIF, TGFBR2, CSF1, TGFα, TGFβ1, IL17D, TGFBRAP1, FGF11, TNFSF13B, FGF14, IL1β, IL-11, IL-32, IL-6, IL-20RB, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL-20RB and the second biomarker is selected from the group consisting of TIE-1, TIE-2, FGF1, LIF, TGFBR2, CSF1, TGFα, TGFβ1, IL17D, SDF2, FGF11, TNFSF13B, FGF14, IL1β, IL-11, IL-32, IL-6, IL1RN, IL-21R, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is IL-21R and the second biomarker is selected from the group consisting of TIE-1, TIE-2, TIMP-4, LIF, TGFBR2, CSF1, TGFα, TGFβ1, IL17D, SDF2, TGFBRAP1, TNFSF13B, FGF14, IL1β, IL-11, IL-32, IL-6, IL1RN, IL-20RB, PLAU, GNB2L1, PLEKHA6, CTSB, FERMT1, CRMP1, VEGFB, VEGFA, and PLEKHA1.

In one variation, the expression levels of at least two biomarkers are measured, wherein the first biomarker is PLAU and the second biomarker is selected from the group consisting of TIE-1, TIE-2, TIMP-4, FGF1, TGFBR2, CSF1, TGFα, TGFβ1, IL17D, SDF2, TGFBRAP1, FGF11, FGF14, IL1β, IL-11, IL-32, IL-6, IL1RN, IL-20RB, IL-21R, GNB2L1, PLEKHA6, CTSB, FERMT1, CRMP1, VEGFB, VEGFA, and PLEKHA1.

In one variation, the expression levels of at least two biomarkers are measured, wherein the first biomarker is GNB2L1 and the second biomarker is selected from the group consisting of TIE-1, TIE-2, TIMP-4, FGF1, LIF, CSF1, TGFα, TGFβ1, IL17D, SDF2, TGFBRAP1, FGF11, TNFSF13B, IL1β, IL-11, IL-32, IL-6, IL1RN, IL-20RB, IL-21R, PLAU, PLEKHA6, CTSB, FERMT1, CRMP1, VEGFB, VEGFA, and PLEKHA1.

In one variation, the expression levels of at least two biomarkers are measured, wherein the first biomarker is PLEKHA6 and the second biomarker is selected from the group consisting of TIE-1, TIE-2, TIMP-4, FGF1, LIF, TGFBR2, TGFα, TGFβ1, IL17D, SDF2, TGFBRAP1, FGF11, TNFSF13B, FGF14, IL-11, IL-32, IL-6, IL1RN, IL-20RB, IL-21R, PLAU, GNB2L1, CTSB, FERMT1, CRMP1, VEGFB, VEGFA, and PLEKHA1.

In one variation, the expression levels of at least two biomarkers are measured, wherein the first biomarker is CTSB and the second biomarker is selected from the group consisting of TIE-1, TIMP-4, FGF1, LIF, TGFBR2, CSF1, TGFα, TGFβ1, SDF2, TGFBRAP1, FGF11, TNFSF13B, FGF14, IL1β, IL-11, IL-32, IL1RN, IL-20RB, IL-21R, PLAU, GNB2L1, PLEKHA6, FERMT1, CRMP1, VEGFB, VEGFA, and PLEKHA1.

In one variation, the expression levels of at least two biomarkers are measured, wherein the first biomarker is FERMT1 and the second biomarker is selected from the group consisting of TIE-1, TIE-2, TIMP-4, FGF1, LIF, TGFBR2, CSF1, TGFα, TGFβ1, IL17D, TGFBRAP1, FGF11, TNFSF13B, FGF14, IL1β, IL-11, IL-32, IL-6, IL-20RB, IL-21R, PLAU, GNB2L1, PLEKHA6, CTSB, CRMP1, VEGFB, VEGFA, and PLEKHA1.

In one variation, the expression levels of at least two biomarkers are measured, wherein the first biomarker is CRMP1 and the second biomarker is selected from the group consisting of TIE-1, TIE-2, FGF1, LIF, TGFBR2, CSF1, TGFα, TGFβ1, IL17D, SDF2, FGF11, TNFSF13B, FGF14, IL1β, IL-11, IL-32, IL-6, IL1RN, IL-21R, PLAU, GNB2L1, PLEKHA6, CTSB, FERMT1, VEGFB, VEGFA, and PLEKHA1.

In one variation, the expression levels of at least two biomarkers are measured, wherein the first biomarker is VEGFB and the second biomarker is selected from the group consisting of TIE-1, TIE-2, TIMP-4, LIF, TGFBR2, CSF1, TGFα, TGFβ1, IL17D, SDF2, TGFBRAP1, TNFSF13B, FGF14, IL1β, IL-11, IL-32, IL-6, IL1RN, IL-20RB, PLAU, GNB2L1, PLEKHA6, CTSB, FERMT1, CRMP1, VEGFA, and PLEKHA1.

In one variation, the expression levels of at least two biomarkers are measured, wherein the first biomarker is VEGFA and the second biomarker is selected from the group consisting of TIE-1, TIE-2, TIMP-4, FGF1, TGFBR2, CSF1, TGFα, TGFβ1, IL17D, SDF2, TGFBRAP1, FGF11, FGF14, IL1β, IL-11, IL-32, IL-6, IL1RN, IL-20RB, IL-21R, GNB2L1, PLEKHA6, CTSB, FERMT1, CRMP1, VEGFB and PLEKHA1.

In one variation, the expression levels of at least two biomarkers are measured, wherein the first biomarker is PLEKHA1 the second biomarker is selected from the group consisting of TIE-1, TIE-2, TIMP-4, FGF1, LIF, CSF1, TGFα, TGFβ1, IL17D, SDF2, TGFBRAP1, FGF11, TNFSF13B, IL1β, IL-11, IL-32, IL-6, IL1RN, IL-20RB, IL-21R, PLAU, PLEKHA6, CTSB, FERMT1, CRMP1, VEGFB, and VEGFA.

In other variations provided herein, of the at least two biomarkers measured, at least one biomarker is a factor leading to vascular development, including factors involved in vascular development and remodeling related to angiogenesis such as TIE-1, TIE-2, TIMP-4, VEGFA, VEGFB, FBLN5, FBLN7, PGF, ANGPT1, ANGPT2, ANGPTL2, ANGPTL6, TNFSF12, PRKCA, PIK3CA, and ESM1.

In some variations provided herein, of the at least two biomarkers measured, at least one biomarker is an anti-inflammatory or immunomodulatory factor such as CD99, CERCAM, HIVEP1, PTGER1, IL-32, ITFG1, ITGAV, HIVEP2, CSF1R, TNFSF13, IRAK3, MYL9, NOS3, IL12A, TNFRSF21, IRAK1, IL33, LRRC8A, CLEC11A, CCL28, ESM1, CMIP, TNFRSF25, CHST3, CD72, CD320, CD83, IL6, CD68, CD99, IL-16, or ILF3. The method may further comprise determining if KIF 14, CCL2, ILF2, IL7R, PEAR 1, or IL 16 expression levels decrease.

In some variations provided herein, of the at least two biomarkers measured, at least one biomarker is a transforming growth factors (TGFα, TGFβ1 or TGFβ2), transforming growth factor beta receptor TGFBR2, or transforming growth factor beta receptor-associated protein TGFBRAP1.

In some variations provided herein, of the at least two biomarkers measured, at least one biomarker is a cell motility, migration and invasive growth promoting factor such as TIE-1, TIE-2, TIMP-4, CGNL1, CGREF1, CRMP1, FGD6, TNK2, PTGS1, TNFAIP8, CTSB, CTSO, FAP, FERMT1, PLEKHA1, PLEKHA6, ROCK1, or ROCK2.

In some variations provided herein, of the at least two biomarkers measured, at least one biomarker is an anti-apoptotic factor, for example VEGFA, VEGFB, PLEKHA1, PLEKHA6, CRMP1, FERMY1, CTSB, TGFB1, or GNB2L1.

In some variations provided herein, the decrease in expression levels of CHD24, CYR61, ILK, NEDD9, MYL9, PPAP2B, RELN, ICAM 2, ICAM3 and TLN2 are additionally monitored as these are factors that promote cell adhesion.

In some variations, the decrease in expression levels of SIVA1 is additionally measured.

In some variations provided herein, of the at least two biomarkers measured, at least one biomarker is an interleukin, for example IL1b, IL3, IL5, IL6, IL9, IL10, IL12b, IL18-binding protein-α, IL9, IL-11, IL12a, IL12b, IL-4, or IL-16.

In some variations provided herein, of the at least two biomarkers measured, at least one biomarker is an interleukin receptor, for example IL1Rα, IL1R4, IL10Rβ, IL18Rβ, IL1R2, IL-21R, IL-2Rβ, IL-2Rγ, IL5Rα, IL1R1, IL1R2, or IL1R4.

In some variations provided herein, of the at least two biomarkers measured, at least one biomarker is a chemokine, for example CCL8, CCL13, CCL15, CCL17, CCL18, CCL20, CCL22, CCL24, CCL26, CXCL9, CXCL11, CCL2, CCL4, CCL5, CCL23, CCL25, CCL27, CXCL10, CCL23, CXCL16, or CCL27.

In some variations provided herein, of the at least two biomarkers measured, at least one biomarker is a growth factor, hormone or growth factor receptor for example FGF6, IGF1, IGF2, LAP, NT3, PDGFAA, PDGFAB, SCF, TGF2, TGFα, TGFβ1, TGFb3, TNFβ, PDGFRα, PDGFRβ, VEGF, VEGFD, VEGFR, FGF4, FGF9, HGF like, IGFBP 6, PDGFBβ, IFNγ, SDF1A, DR6, ENDOGLIN, ERBB3, FAS LG, GDNF, GITR LG, LEPR, SCFR, SIGLEC 5, TIE-1&2, BDNF, BMP4, FGF7, IGFBP2, DR6, ANG, CNTF, EGF, EOTAXIN 1, NGFR, ACRP30, AGRP, ANGPT2, LEP, NT4, HGF, PRL, SCFR, FAS LG, IGFBP 1, OR IGFBP 2.

In one variation, the at least two biomarkers are selected from a panel of biomarkers comprising TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the method comprises measuring the expression levels of at least 2, least 3, at least 4, at least 5, at least 6, at least 7, at least 8, at least 9, at least 10, at least 11, at least 12, at least 13, at least 14, at least 15, at least 16, at least 17, at least 18, at least 19, or even at least 20 biomarkers selected from TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1.

In one variation, the levels of TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1 are measured.

In one variation, the method comprises measuring the expression levels of at least 2, at least 3, at least 4, at least 5, at least 6, at least 7, or even at least 8 biomarkers selected from VEGFA, PLEKHA1, VEGFB, CRMP1, FERMT1, CTSB, PLEKHA6, GNB2L1, and TGFβ1.

In one variation, the method comprises measuring the expression levels VEGFA, PLEKHA1, VEGFB, CRMP1, FERMT1, CTSB, PLEKHA6, GNB2L1, and TGFβ1.

In some variations, the method further comprises measuring the level of SIVA1. SIVA1 is one of the few biomarkers observed to decrease in SEN-MSCs, when exposed to IL-2.

In some variations, the expression of at least two biomarkers selected from a panel of biomarkers comprising TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1 is measured, and the expression level of SIVA1 is measured. If it is determined that the expression level of the at least two biomarkers is increased, relative to reference levels, and the expression level of SIVA1 is decreased, relative to reference levels, then it is determined that either (1) the individual has an increased likelihood of experiencing adverse events associated with the IL-2-based therapy; or (2) the population of MSCs is not suitable for use in transplantation.

In some variations, the expression of at least two biomarkers selected from a panel of biomarkers comprising TIE-1, TIE-2, TIMP-4, FGF1, LIF, TGFBR2, CSF1, TGFα, TGFβ1, IL17D, SDF2, TGFBRAP1, FGF11, TNFSF13B, FGF14, IL1β, IL-11, IL-32, IL-6, IL1RN, IL-20RB, IL-21R, PLAU, GNB2L1, PLEKHA6, CTSB, FERMT1, CRMP1, VEGFB, VEGFA, and PLEKHA1 is measured, and the expression level of SIVA1 is measured. If it is determined that the expression level of the at least two biomarkers is decreased, or exhibits no change, relative to reference levels, and the expression level of SIVA1 is increased, relative to reference levels, then it is determined that either (1) the individual has an increased likelihood of experiencing adverse events associated with the IL-2-based therapy; or (2) the population of MSCs is not suitable for use in transplantation.

In some variations, the expression of at least two biomarkers selected from a panel of biomarkers comprising VEGFA, PLEKHA1, VEGFB, CRMP1, FERMT1, CTSB, PLEKHA6, GNB2L1, and TGFβ1 is measured, and the expression level of SIVA1 is measured. If it is determined that the expression level of the at least two biomarkers is increased, relative to reference levels, and the expression level of SIVA1 is decreased, relative to reference levels, then it is determined that either (1) the individual has an increased likelihood of experiencing adverse events associated with the IL-2-based therapy; or (2) the population of MSCs is not suitable for use in transplantation.

In some variations, the expression of at least two biomarkers selected from a panel of biomarkers comprising TIE-1, TIE-2, TIMP-4, VEGFA, PLEKHA1, VEGFB, CRMP1, FERMT1, CTSB, PLEKHA6, GNB2L1, and TGFβ1 is measured, and the expression level of SIVA1 is measured. If it is determined that the expression level of the at least two biomarkers is decreased, or exhibits no change, relative to reference levels, and the expression level of SIVA1 is increased, relative to reference levels, then it is determined that either (1) the individual has an increased likelihood of experiencing adverse events associated with the IL-2-based therapy; or (2) the population of MSCs is not suitable for use in transplantation.

In a particular variation of the invention, the RNA expression level of the TGFβ1 biomarker is decreased by about at 0.25-fold in the sample upon IL-2 treatment, as compared to a reference level (sample not treated with IL-2). The fold can be raw fold or a GFOLD value.

In a particular variation of the invention, the RNA expression level of the SIVA1 biomarker is decreased by about at 0.2-fold in the sample upon IL-2 treatment, as compared to a reference level (sample not treated with IL-2). The fold can be raw fold or a GFOLD value.

In a particular variation of the invention, the RNA expression level of the CRMP1 biomarker is increased by about at least 0.22-fold in the sample upon IL-2 treatment, as compared to a reference level (sample not treated with IL-2). The fold can be raw fold or a GFOLD value.

In a particular variation of the invention, the RNA expression level of the VEGFB biomarker is increased by about at least 0.19-fold in the sample upon IL-2 treatment, as compared to a reference level (sample not treated with IL-2). The fold can be raw fold or a GFOLD value.

In a particular variation of the invention, the RNA expression level of the VEGFA biomarker is increased by about at least 1.5-fold or about 1.78-fold in the sample upon IL-2 treatment, as compared to a reference level (sample not treated with IL-2). The fold can be raw fold or a GFOLD value.

In a particular variation of the invention, the RNA expression level of the PLEKHA1 biomarker is increased by about at least 0.46-fold in the sample upon IL-2 treatment, as compared to a reference level (sample not treated with IL-2). The fold can be raw fold or a GFOLD value.

In a particular variation of the invention, the RNA expression level of the CTSB biomarker is increased by about at least 0.25-fold in the sample upon IL-2 treatment, as compared to a reference level (sample not treated with IL-2). The fold can be raw fold or a GFOLD value.

In a particular variation of the invention, the RNA expression level of TGFβ1 is decreased by about −0.25 GFOLD and SIVA1 is decreased by about −0.2 GFOLD upon IL-2 treatment, and the levels of CRMP1 is increased by about 0.22 GFOLD, VEGFB is increased by about 0.19 GFOLD, VEGFA is increased by about 1.78 GFOLD, PLEKHA1 is increased by about 0.459 GFOLD, CTSB is increased by about 0.25 GFOLD under the same conditions.

In a particular variation of the invention, the protein expression level of the TIE-1 biomarker is increased by about at least 2-fold, at least 3-fold, or about 3.73-fold in the sample upon IL-2 treatment, as compared to a reference level (sample not treated with IL-2).

In a particular variation of the invention, the protein expression level of the TIE-2 biomarker is increased by about at least 2-fold, at least 3-fold, at least 4-fold, at least 5-fold or about 5.24-fold in the sample upon IL-2 treatment, as compared to a reference level (sample not treated with IL-2).

In a particular variation of the invention, the protein expression level of the TIMP-4 biomarker is increased by about at least 2-fold, at least 3-fold, at least 4-fold, or about 4.31-fold in the sample upon IL-2 treatment, as compared to a reference level (sample not treated with IL-2).

In a particular variation of the invention, the protein expression level of the IL-11 biomarker is increased by about at least 1.1-fold, at least 1.2-fold, at least 1.3-fold, at least 1.4, or about 1.42-fold in the sample upon IL-2 treatment, as compared to a reference level (sample not treated with IL-2).

In a particular variation of the invention, the protein expression level of the IL1β biomarker is increased by about at least 1.1-fold, or about 1.14-fold in the sample upon IL-2 treatment, as compared to a reference level (sample not treated with IL-2).

In a particular variation of the invention, the protein expression level of the TGFα biomarker is increased by about at least 1.5-fold, at least 2-fold, or about 2.4-fold in the sample upon IL-2 treatment, as compared to a reference level (sample not treated with IL-2).

In a particular variation of the invention, the protein expression level of the TGFβ1 biomarker is increased by about at least 1.1-fold, at least 1.2-fold, a least 1.3 fold, at least 1.4 fold, or about 1.44-fold in the sample upon IL-2 treatment, as compared to a reference level (sample not treated with IL-2).

In a particular variation of the invention, in a sample, the protein expression level of the TIE-1 biomarker is increased by about 3.73-fold, the protein expression level of TIE-2 is increased by about 5.24 times, the protein expression level of TIMP-4 is increased by about 4.31 times, the protein expression level of IL-11 is increased by about 1.42 times, the protein expression level of IL1β is increased by about 1.14 times, the protein expression level of TGFα is increased by about 2.4 times, TGFβ1 is increased by about 1.44 times, as compared to reference levels.

5. Companion Methods for IL-2 Therapeutics

As contemplated herein, administration of IL-2 influences the secretory properties MSCs and IL-2 treatment may lead to potential adverse outcomes in certain individuals. Described herein are diagnostic kits, assays and methods that may be used to determine whether an individual eligible to receive an IL-2-based therapy may experience an adverse event associated with the IL-2-based therapy, based on the characterization of production of certain biomarkers (as described above). Also described herein are methods of treating a patient with IL-2.

As used herein, potential adverse events associated with an IL-2-based therapy are associated with cellular senescence, and include events such as angiogenesis, tumorigenesis, vascular development, invasive growth, metastasis, cell motility, migration, and the like. The invention allows the determination of whether an individual may experience, will experience, or is likely to experience an adverse event associated with an IL-2-based therapy. In one variation, the invention allows determination of an increased likelihood of experiencing an adverse event by about 10%, 20%, 30%, 40%, 50%, 60%, 70%, 80%, 90%, or even about 100%.

In one variation, the individual has received at least one dose of an IL-2-based therapy before the method is carried out on a sample from the individual. In this variation, the method for determining whether an individual eligible to receive an IL-2-based therapy may experience an adverse event associated with the IL-2-based therapy comprises: measuring the expression levels of at least two biomarkers selected from a panel of biomarkers indicative of MSC senescence described herein (the panel of biomarkers are anti-apoptotic, angiogenic, tumorigenic, lead to vascular development, responsible for invasive growth, metastasis, cell motility, migration and the like) in a sample from the individual, wherein the individual has received at least one dose of an IL-2-based therapy; and comparing the levels of the biomarkers to reference levels, wherein an increase in the levels above the reference levels indicates that the individual may experience an adverse event associated with the IL-2-based therapy, and wherein a decrease or no change in the levels compared to the references levels indicates that the individual may not experience an adverse event associated with the IL-2-based therapy.

In another variation, a sample from the individual is obtained, and exposed to (incubated with, combined with, etc) IL-2 in vitro. In this variation, the method for determining whether an individual eligible to receive an IL-2-based therapy may experience an adverse event associated with the IL-2-based therapy comprises: measuring the expression levels of at least two biomarkers selected from a panel of biomarkers indicative of MSC senescence in a sample from the individual, wherein the individual has received at least one dose of an IL-2-based therapy; and comparing the levels of the biomarkers to reference levels, wherein an increase in the levels above the reference levels indicates that the individual may experience an adverse event associated with the IL-2-based therapy, and wherein a decrease or no change in the levels compared to the references levels indicates that the individual may not experience an adverse event associated with the IL-2-based therapy.

In another variation, the method is directed at treating an individual for cancer with an IL-2-based therapy, the method comprising administering an effective amount of the IL-2-based therapy to the individual when the expression levels of at least two biomarkers is increased in comparison to reference levels in a sample from the individual wherein either (1) the individual has received at least one dose of an IL-2-based therapy or (2) the sample is combined with IL-2 in vitro, and wherein the panel of biomarkers comprises biomarkers for cellular senescence.

The biomarkers, if present in elevated levels, are indicative of the presence of SEN MSCs, and indicate a likelihood that further treatment with IL-2 could lead to adverse effects such as the promotion of tumorigenesis, invasion, or metastasis in the individual. Based on this, it can be determined that the individual should not receive an IL-2-based therapy. Alternatively, if upon practice of these methods, it is determined that use of an IL-2-based therapy would likely not lead to adverse effects (e.g. likely to not promote tumorigenesis, invasion, or metastasis), based on the expression of a particular set of biomarkers, then it could be determined that it is acceptable to administer an IL-2-based therapy, and optionally would be administered the IL-2-based therapy.

As used herein, an "IL-2-based therapy" is one that involves administration of IL-2 alone, or IL-2 in combination with another agent. Administration of IL-2 contemplates administration of an active portion of IL-2, either alone or fused to other motifs. An IL-2-based therapy can be administered by any form of injection, including intravenous (IV), intramuscular (IM), or transdermal or subcutaneous (SC) injection; by an oral or nasal route; or by topical administration (cream, droplets, etc.). In a particular variation of the invention, IL-2 is used as a sustained-release formulation, or a formulation that is administered using a sustained release device. Such devices are well known in the art, and include, for example, transdermal patches, and miniature implantable pumps that can provide for drug delivery over time in a continuous, steady-state fashion at a variety of doses to achieve a sustained-release effect. Sublingual or eye drop formulations may also be contemplated.

As provided herein, the sample used for the expression analysis can be any sample, including, but limited to a tissue, biopsy, blood, plasma, serum, urine, saliva, CSF, stool, lymph, semen, and sweat. In particular variations, the sample is a blood, plasma, or serum sample; in an exemplary variation the sample is blood. Without being bound to any theory, because MSCs are positioned in perivascular compartments, the factors produced by MSCs in response to the IL-2 administration may be systemic/circulatory, and could be readily measurable in a blood sample.

In the variations provided herein, the expression levels of the sample can be measured at any time following the administration of the IL-2-based therapy to the individual or at any time following in vitro mixing of the IL-2 (mixing of an active portion of IL-2, either alone or fused to other motifs with the sample), for example, 15 minutes, 30 minutes, 1 hour, 2, 3, 4, 6, 12, 15, 24, 36, 48, 72, or even 96 hours afterwards.

In some variations, an individual is administered multiple doses of the IL-2-based therapy prior to measurement. In some variations the individual is administered a single dose of the IL-2-based therapy prior to measurement. Typically the dose of IL-2 depends on the specific IL-2 product selection. Approximately 0.001 to 0.1 mg/kg of patient body weight can be administered; in some variations, about 0.005, 0.01, 0.05 mg/kg may be administered. In some variations, 600,000 IU/kg is administered (IU can be determined by a lymphocyte proliferation bioassay and is expressed in International Units (IU) as established by the World Health Organization 1st International Standard for human IL-2. In some variations, IL-2 doses ranges from 0.01 MIU/day to 3.0 MIU/day/patient (MIU are millions international unit). IL-2-based therapies can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of IL-2 can include a single treatment or, can include a series of treatments. In one variation, the compositions are administered every 8 hours for five days, followed by a rest period of 2 to 14 days, e.g., 9 days, followed by an additional five days of administration every 8 hours.

The companion methods for IL-2 treatment provided herein may be particularly suited as a companion method for cancer, given the widespread use of IL-2-based therapeutics for cancer treatment. However, the methods described are not limited for cancer therapeutics, and are applicable to any disease for which an IL-2 is an approved or candidate treatment. In some variations, however, the individual has received the IL-2-based therapy for the treatment of a cancer. In some variations the cancer is selected from among renal cell carcinoma, melanoma, breast cancer, pancreatic cancer, ovarian cancer, colon cancer, lung cancer, non-small cell lung cancer, in situ carcinoma (ISC), squamous cell carcinoma (SCC), thyroid cancer, cervical cancer, uterine cancer, prostate cancer, testicular cancer, brain cancer, bladder cancer, stomach cancer, hepatoma, melanoma, glioma, retinoblastoma, mesothelioma, myeloma, lymphoma, and leukemia. In some examples, the cancer is a late-stage cancer, a metastatic cancer, or a relapsed cancer. In other variations, the IL-2 treatment is for any condition associated to or caused by an undesirable immune response, for example for inflammatory, immune-related or autoimmune diseases, including without limitation HCV-related vasculitis, uveitis, myositis, type I diabetes, systemic lupus erythematous, systemic vasculitis, psoriasis, allergy, asthma, Crohn's disease, Multiple Sclerosis, Rheumatoid Arthritis, atherosclerosis, autoimmune thyroid disease, neuro-degenerative diseases, Alzheimer's disease, graft-versus-host disease, spontaneous abortion and allograft rejection.

Where it is determined that the individual is suitable to receive an IL-2-based therapy, the treatment may be altered based on the determined levels of detected biomarkers in the sample, relative to the reference sample. The methods can be used to modify the treatment regimen (e.g. escalating the dosage or dosing schedule), based on the determined levels of biomarkers in the sample relative to the reference sample.

In a particular variation, if it is determined that the individual will likely not (e.g. may not) experience adverse effects from an IL-2-based therapy, and is then administered the IL-2-based therapy, the individual may subsequently be tested again to monitor for adverse effects. Thus, in this variation, an individual is tested for the likelihood of potential adverse effects both before treatment and once treatment has commenced. The dose and schedule of administration can be adjusted accordingly. For example, low-dosage regimens for IL-2 treatments may be clinically implemented. In addition to the companion methods described in this invention, the IL-2 treatment effect can be monitored by additional measurements, for example effects of IL-2-based therapies on the differentiation of T-cells in vivo.

Figure 1B:
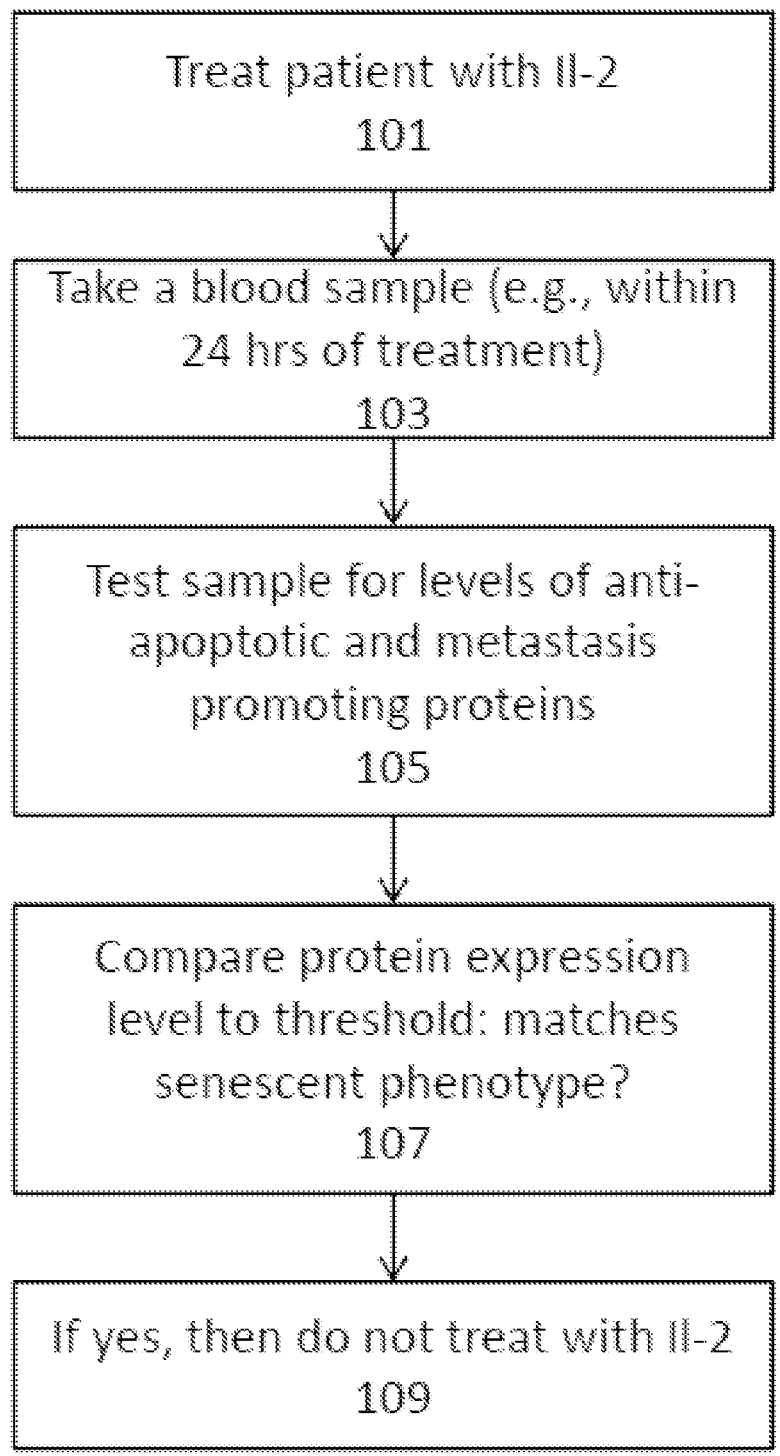
FIG. 1B is a chart illustrating one exemplary method of testing an individual, or a stem cell to determine if an IL-2-based therapy should be initiated or continued.

FIG. 1B illustrates an exemplary method of treating a patient with IL-2 by querying the replicative senescence status of MSC. In this example, the patient is treated with one or more doses of IL-2 101, and within a predetermined period of time (e.g., between a start time of 1 hour, 2 hours, 3 hours, 4 hours, 5 hours, 6 hours, 7 hours, 8 hours, 9 hours, 10 hours, 11 hours, 12 hours, etc., and a stop time of 12 hours, 13 hours, 14 hours, 15 hours, 16 hours, 17 hours, 18 hours, 19 hours, 20 hours, 21 hours, 22 hours, 23 hours, 24 hours, 30 hours, 36 hours, 42 hours, 48 hours, 72 hours, or 96 hours etc.), taking a sample from the patient 103. The sample may be any appropriate fluid or tissue as provided herein (e.g., blood, blood plasma, blood serum, urine, etc.). This sample may then be examined to detect the presence/absence and/or level of a panel of biomarkers 105.

6. Quality Control of MSCs Prior to Use in Cell-Based Therapies

MSCs are administered (transplanted) for a variety of indications. An important aspect of the invention is the determination of which MSCs would be suitable for administration, prior to the administration. Specifically, the methods provided allow for the selection of populations of MSCs suitable for administration, upon testing, in order to avoid or reduce the likelihood of anti-apoptotic, angiogenic, and tumorigenic activities associated with the transplanted MSCs in the in vivo environment that may be proinflammatory or otherwise not conducive.

Thus in another aspect provided herein are methods for assessing the quality and potential of stem cells in a sample. Such methods and kits are useful for helping to ensure the safety and quality of a population of MSCs before it is used in an individual.

In one variation, a method of determining whether a population of MSCs is suitable for administration into an individual for a stem cell-based therapy, comprises (a) incubating the population of MSCs with IL-2 (incubating with an active portion of IL-2, either alone or fused to other motifs); (b) measuring the expression levels in the cells of a panel of biomarkers associated with cellular senescence, wherein the panel of biomarkers are anti-apoptotic, angiogenic, tumorigenic, lead to vascular development, responsible for invasive growth, metastasis, cell motility, migration and the like; (c) comparing the levels of the biomarkers to reference levels, wherein an increase in the levels above the reference levels indicates that the stem cells are not optimal for administration into an individual and could lead to adverse effects if administered. However, no change or a decrease in the levels below the reference levels could indicate that the stem cells are suitable for administration into an individual. Generally by suitable, it is intended to convey that the cells would cause little or no adverse events, such as be tumorigenic, metastasis promoting, anti-apoptotic and the like.

In some variations, the population of cells is intended for autologous use. In other variations, the population of cells is intended for allogeneic use. In some variations, the population of cells comprise cells of a homogenous origin, e.g. from a single individual. In some variations, the populations of cells comprise cells of heterogeneous origin, e.g. composed of cells from a variety of sources.

In the variations provided herein, the expression levels of the sample can be measured at any time following the incubation of the IL-2, for example, 15 minutes, 30 minutes, 1 hour, 2, 3, 4, 6, 12, 15, 24, 36, 48, 72, or even 96 hours after incubation with IL-2.

II. Kits and Articles of Manufacture

The present application also provides kits for measuring the levels of biomarkers in a sample.

In one variation, the kits of the invention are for assessing the suitability of a population of MSCs for transplant.

In another variation, the kits of the invention are for determining whether an IL-2-based therapy should be administered to an individual in need thereof.

In one variation, a kit comprises reagents for measuring the RNA expression level of at least two biomarkers in a sample. For example, the kit may comprise probes or primers, e.g. Q-PCR primers, specific to at least two biomarkers selected from any of the biomarkers described herein.

In a particular variation, the kit comprises at least two reagents specific for measuring a biomarker selected from TIE-1, TIE-2, TIMP-4, FGF1, FGF11, FGF14, LIF, TGFBR2, CSF1, TGFα, TGFβ1, IL17D, SDF2, TGFBRAP1, TNFSF13B, IL1B, IL-11, IL-32, IL-6, IL1RN, IL-20RB, IL-21R, PLAU, GNB2L1, PLEKHA6, PLEKHA1, CTSB, FERMT1, CRMP1, VEGFB, and SIVA1, and VEGFA. In some variations the primer comprises a label, for example a fluorescent label. In some variations, the kit comprises at least 3, at least 4, at least 5, at least 6, at least 7, at least 8, at least 9, at least 10, at least 11, at least 12, at least 13, at least 14, at least 15, at least 16, at least 17, at least 18, at least 19, or even at least 20 reagents, e.g. probes or primers, for measuring the RNA expression level of biomarkers in a sample.

In other variations, a kit comprises reagents for measuring the protein expression level of at least two biomarkers in sample. For example, the kit may comprise antibodies specific to at least two biomarkers selected from TIE-1, TIE-2, TIMP-4, FGF1, FGF11, FGF14, LIF, TGFBR2, CSF1, TGFα, TGFβ1, IL17D, SDF2, TGFBRAP1, TNFSF13B, IL1B, IL-11, IL-32, IL-6, IL1RN, IL-20RB, IL-21R, PLAU, GNB2L1, PLEKHA6, PLEKHA1, CTSB, FERMT1, CRMP1, VEGFB, and SIVA1, and VEGFA. In some variations the antibody comprises a label, for example a fluorescent label. In some variations, the kit comprises an array or ELISA plate comprising at least 3, at least 4, at least 5, at least 6, at least 7, at least 8, at least 9, at least 10, at least 11, at least 12, at least 13, at least 14, at least 15, at least 16, at least 17, at least 18, at least 19, or even at least 20 reagents, e.g. antibodies, for measuring the protein expression level of biomarkers in a sample.

In some variations, the kits further comprise an IL-2 composition (a composition comprising full length-IL-2, or a portion of IL-2, either alone or fused to other motifs with the sample). This IL-2 composition can be used for testing a sample in vitro or for admiration into an individual, to practice the methods of the invention.

In some variations, the kit further comprises a reference standard for use in the assay (a sample to be tested along side to determine the reference levels are generated under the same conditions). In some variations, the kit further comprises a written list of values that serve as reference levels, for example reference levels from a population of healthy individuals, or individuals not treated with IL-2, that provide a reference against which the results of the assay can be checked.

In some variations as contemplated herein, the kits provide multiple assays for the measurement of expression levels of particular biomarkers that can be used in parallel, or in serial. For example a kit may comprise three assay plates, with Q-PCR primers or antibodies, one directed to the detection of growth factor biomarkers, one directed to the detection of anti-apoptotic biomarkers, and one directed to the detection of factors involved in cell motility and migration. In another variation, the kit may comprise three assay plates, useful for assaying the tested sample at three different time points. It is understood that the kit may comprise four, five, or more such plates for the purpose of serial or parallel detection of biomarkers.

The present application also provides articles of manufacture comprising any one of the kits described herein.

It is to be understood that the terminology employed herein is used for the purpose of describing particular variations only and is not intended to be limiting since the scope of the present invention will be limited only by the appended claims and equivalents thereof. The following examples are for illustrative purposes. These are intended to show certain aspects and variations of the present invention but are not intended to limit the invention in any manner.

EXAMPLES

Example 1: Materials and Methods

This example provides exemplary methods of the invention and provides the materials and methods subsequently used in Examples 2-10.

Isolation, Culture and Characterization of MSCs

MSCs used in this research were isolated from human adipose tissues obtained from healthy adult female donors age 32 and 49 undergoing routine liposuction procedures at the UCSD medical center, San Diego, CA. The MSC isolation protocol was approved by the local ethics committee and performed as previously described. Isolated adipose-derived stem cell lines were grown in DMEM/F12 medium (Life Technologies). In accordance with the MSC minimal definition criteria set by the International Society for Cellular Therapy, flow cytometric analysis showed that hADSCs express CD29, CD73, CD90 and CD105 but do not express CD11b, CD14, CD19, CD34, CD45, CD80, CD86 (antibodies from eBiosciense, USA). Morphological analysis showed that the cells present a fibroblast-like morphology, were plastic adherent and capable of adipogenic, chondrogenic and osteogenic differentiation under in vitro conditions using commercially available differentiation mediums (Invitrogen, USA). Cumulative population doublings (PD) were calculated as $PD=\log(N/NO) \times 3.33$ across the multiple passages as a function of the number of days of growth in culture, where NO is the number of cells plated in the flask and N is the number of cells harvested at this passage. hADSCs PD 4 or PD 6 SR populations and PD 41 and 45 for SEN populations were used in all experiments. Treatment with recombinant IL-2 (Peprotech, USA) was performed as described (Deenick E K, Gett A V, Hodgkin P D (2003). J Immunol 170: 4963-4972). 20U/ml of IL-2 was added to the culturing media for 24 hours at 37° C.

Senescence—Associated SA-β Galactosidase Assay

The assay for monitoring the expression of pH-dependent senescence-associated (3-galactosidase activity (SA-(βGal) was performed as described in manufacturer's kit (BioVision) and previously published in Wang J, Geesman G J, Hostikka S L, Atallah M, Blackwell B, et al. (2011) Inhibition of activated pericentromeric SINE/Alu repeat transcription in senescent human adult stem cells reinstates self-renewal. Cell cycle 10: 3016-3030. The cultured hADSCs were washed with PBS for 15 minutes at room temperature, washed with twice with PBS and stained with X-Gal containing supplement overnight at 37° C. The cells were washed twice with PBS, and the images were captured using a microscope (Nikons, TE300, DXM1200 Digital Camera, Japan).

Migration and Invasion Assay

Transwell filters were from Corning Incorporated (Acton, MA., USA) and all the cytokines in use were obtained from Peprotech Inc. (Rocky Hill, NJ, USA). The migration assay was performed as described in Perez L M, Bernal A, San Martin N, Galvez B G (2013), Arch Physiol Biochem 119: 195-201 using 8 mm thick Transwell chambers. For the Transwell migration assay, $1.0 \times 10^4$ cells were suspended in 80 ul of serum-free alpha-MEM and seeded in the upper chamber of 24-well Transwell plates containing 8 mm pore size filters (Corning, Costar, USA). In the lower chamber, 600 ul of DMEM or medium containing cytokines: IL-2, IL-6, IL-8, TNF-α, HMGβ1 was added. The concentrations in used were: 50 ng/ml IL-2, IL-6, IL-8 and HMGβ1; 30 ng/ml TNF-α as described in (Perez et al., 2013, Arch Physiol Biochem 119: 195-201). hADSCs were incubated at 37° C. for 16h. The cells retained in the upper chamber were removed by swab and those that had migrated through the filter were fixed with 4% paraformaldehyde for 20 minutes at room temperature and stained overnight with 5% toluidine blue. The cells were counted at the lower side; in five different randomly selected 10× fields using a bright-field microscope (Nikons, TE300, DXM1200 Digital Camera, Japan). These experiments were done with hADSCs of two donors age 32 and 41, ether SR or SEN populations, with each donor sampled more than three times.

Enzyme-Linked Immunosorbent Assays (ELISA)

hADSCs (SR or SEN) were plated at a density of $10^5$ cells per 10 $cm^2$ dish and treated with 20 U/mL of IL-2 for 24 hour, with untreated controls as previously described in Deenick E K, Gett A V, Hodgkin P D (2003) Stochastic model of T cell proliferation: a calculus revealing IL-2 regulation of precursor frequencies, cell cycle time, and survival. J Immunol 170: 4963-4972. Then, cell membrane-associated protein fractions were prepared using Mem-PER Plus #89842 (ThermoFisher Scientific) following the manufacturer's protocol. Measurements of the concentrations of IL-2 receptors alpha and beta were obtained using human IL-2R alpha and human IL-2R beta ELISA kits #ELH-IL-2Ra and #ELH-IL-2Rb (RayBiotech, Inc) respectively. The optical densities for the standards (recombinant IL-2 receptors alpha and beta) as well as the experimental samples were measured at 450 nm by SPECTRA Max Plus (Molecular Devices) and concentrations were calculated as described in the manufacturer's protocol.

Real-Time Quantitative Polymerase Chain Reaction

Total RNA was isolated from hADSCs using the RNeasy Mini Kit (Qiagen, Germany) cDNA was then synthesized using the RevertAid First Strand cDNA Synthesis Kit (Fermentas, USA). Real-time quantitative polymerase chain reaction (Q-PCR) was performed using TaqMan instrument. The expression levels were calculated as $2^{-\Delta\beta Ct}$, where relative expression was determined by normalization to beta-actin gene expression. All assays were conducted in triplicates and negative control samples without cDNA were used. Primers for the Q-PCR were as follows:

```
IL-2 Receptor Alpha chain (IL-2Rα)
For:
                                   (SEQ ID NO: 1)
5'-CTGCCACTCGGAACACAAC-3'
and Rev:
                                   (SEQ ID NO: 2)
5'-TGGTCCACTGGCTGCATT-3'.

IL-2 Receptor Beta chain (IL-2R.beta.β)
For:
                                   (SEQ ID NO: 3)
5'-ACTCGAGAGCCAACATCTCC-3'
and Rev:
                                   (SEQ ID NO: 4)
5'-TCCGAGGATCAGGTTGCAG-3'.

IL-2 Receptor Gamma 1 chain (IL-2Rγ1)
For:
                                   (SEQ ID NO: 5)
5'-TGGATGGGCAGAAACGCTA-3'
and Rev:
                                   (SEQ ID NO: 6)
5'-GGCTTCCAATGCAAACAGGA-3'.

STAT 5A
     For:
                                   (SEQ ID NO: 7)
     5'-ACGCAGGACACAGAGAATGA-3'
     and Rev:
                                   (SEQ ID NO: 8)
     5'-CTGGGCAAACTGAGCTTGG-3'.

STAT 5B
     For:
                                   (SEQ ID NO: 9)
     5'-ACACAGCTCCAGAACACGT-3'
     and Rev:
                                   (SEQ ID NO: 10)
     5'-TGTTGGCTTCTCGGACCAA-3'.

VEGF A
     For:
                                   (SEQ ID NO: 11)
     5'-GGAGGAGGGCAGAATCATCA-3'
     and Rev:
                                   (SEQ ID NO: 12)
     5'-ATCAGGGGCACACAGGATG-3'.
```

Transcriptomic Analysis

Transcriptomic analysis was performed with IL-2 treated and untreated (control group) SR and SEN hADSCs as previously described in Deenick E K, Gett A V, Hodgkin P D (2003) Stochastic model of T cell proliferation: a calculus revealing IL-2 regulation of precursor frequencies, cell cycle time, and survival. J Immunol 170: 4963-4972. The two genotypes shown in FIG. 3A were used for the analysis of four different conditions: SR or SEN cells, with or without IL-2 stimulation, respectively. The same amount ($10^6$) cells was seeded in DMEM F12 media for each experimental condition, and IL-2 treatment was performed by adding 20U/ml of recombinant IL-2 (Peprotech, USA) directly into the media for 24 hours as previously described in Deernick et al. 2003. Total RNA was isolated from samples using TRIzol reagent (Invitrogen, USA) according to the manufacturer's instructions. Samples from two different patients were combined together for the relevant conditions and RNA concentrations were measured with the Qubit 2.0 fluorimeter using the RNA HS Assay kit (Invitrogen, Life technologies, USA).

100 ng of total RNA of each sample was used to construct the libraries for sequencing on the Ion Proton™ System (Life technologies, USA) following the manufacturer's instructions. Prior to rRNA depletion and RNA-seq library construction, the ERCC RNA Spike-In Control mix (Ambion, Life Technologies) was added to total RNA for quality control analysis. The ERCC RNA Spike-In control mix contains 92 transcripts 250-2000 nt in length that mimic natural eukaryotic mRNAs. According to the protocol provided by manufacturer for 100 ng of total RNA was added to 2 ul of Mix1 in dilution 1:1000 of spike-in. Afterwards, rRNA depletion was performed with the Low Input Ribominus Eukaryote System v2 (Ambion, Life technologies, USA). cDNA libraries were constructed with Ion total RNA-seq kit v2 (Ambion, Life technologies, USA), and barcoded with Ion Xpress RNA-seq barcode (Ambion, Life technologies). The size distribution and quantification of the libraries were performed on a Bioanalyzer 2100 (Agilent technologies, USA). Library sequencing was performed on the Ion Proton™ System with P1 chip, and each library was sequenced 3 times.

RNA-Seq Data Analysis

RNA-seq reads from individual Ion Proton™ System sequencing runs were combined for each of the four conditions. Sequence reads were mapped to the reference human genome assembly hg19 (GRCh37) using the Torrent Mapping Alignment Program (TMAP, Life technologies). The quality of the four condition-specific combined RNA-seq runs was evaluated by comparing the expected counts of ERCC spike-in RNA sequences, obtained from the manufacturer's website, against the observed counts of RNA-seq tags that map to the same sequences. Initial gene expression levels were taken as the sum of exon-mapped reads for individual NCBI RefSeq gene models (c), and lowly expressed genes (read counts per million<1) were removed from subsequent analyses. For each library, individual gene expression levels were normalized using the beta-actin (ACTB) expression levels ($c_{ACTB}$) and the total exon length 1 of each gene. For library j, the beta-acting normalization factor $s_j$ was calculated as $$\frac{\frac{1}{n}\sum_{k=1}^{n} c_{ACTB,k}}{c_{ACTB,j}}$$

and the final normalized expression value for gene i in library j was calculated as $$e_{i,j} = \frac{c_{i,j} * s_j}{l_i}.$$

Differential gene expression analysis between pairs of libraries was performed using the program GFOLD v1.1.3, Feng J, Meyer C A, Wang Q, Liu J S, Shirley Liu X, et al. (2012) GFOLD: a generalized fold change for ranking differentially expressed genes from RNA-seq data. Bioinformatics 28: 2782-2788. GFOLD was chosen based on its demonstrated superior performance in characterizing differentially expressed genes in the absence of replicate data sets. GFOLD analysis yields a score that measures the extent of differential gene expression between conditions; the recommended GFOLD score cut-off of ±0.01 was used to define differentially expressed genes here. Functional enrichment analysis for differentially expressed genes between pairs of libraries was performed using the program GSEA v2.1.0. Specifically, individual pathways containing multiple genes that are up-regulated or down-regulated upon IL-2 treatment in SR, SEN or both were identified in this way. Individual pathways for specific sets of differentially regulated genes (IL-2+ up-regulated in SR and/or SEN and IL-2+ down-regulated in SR and/or SEN) were related using networks where the nodes correspond to pathways and the edges correspond to the presence of shared genes between pathways.

Figure 9:
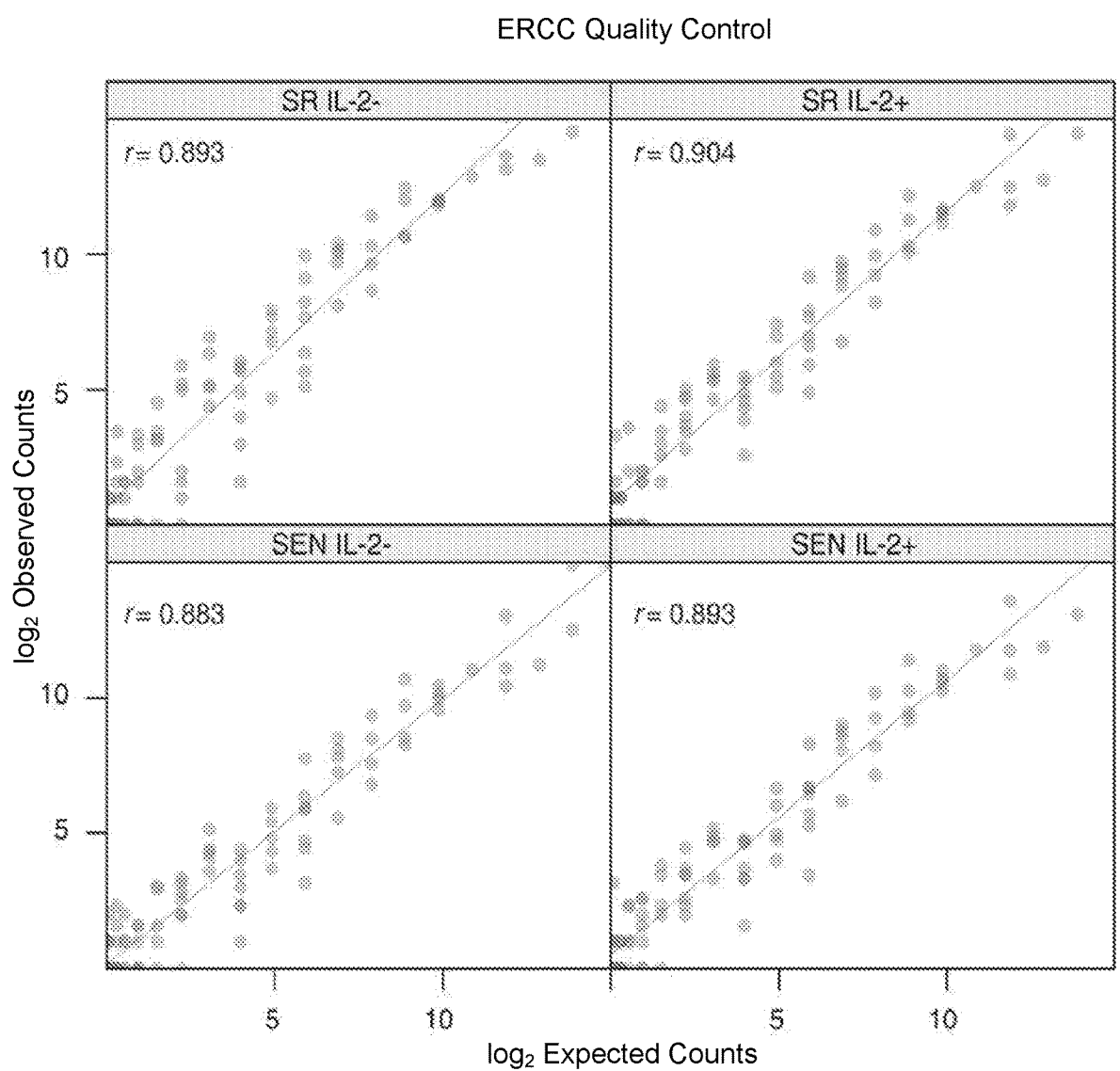
FIG. 9 shows External RNA Controls Consortium (ERCC, a common set of external RNA controls) dose response used for quality control of RNA-seq experiments.

FIG. 9 shows External RNA Controls Consortium (ERCC, a common set of external RNA controls) dose response used for quality control of RNA-seq experiments. For each of the four condition-specific RNA-seq pools, the expected counts of ERCC spike-in RNA sequences were regressed against the observed counts of RNA-seq tags that map to the same sequences. Observed versus expected counts were highly correlated, as indicated by the shape of the regression and the Pearson correlation r-values, consistent with high quality RNA-seq results.

Example 2: Characterization of the MSC Senescent Phenotype

Described in this example is a study that was conducted to evaluate the impact of replicative senescence on the transcriptional activity of human adipose-derived MSCs (hADSCs) in response to IL-2 signaling.

IL-2 signals via specific receptors, with three classes of cell surface receptors formed by various combinations of three IL-2R subunits: IL-2Rα (CD25), IL-2Rβ (CD 122) and IL-2Rg (CD 132). The experimental results indicate that hADSCs transcriptionally express all three receptors, however protein expression of the IL-2Rα (IL-2Rα) in hADSCs is lower than seen for IL-2Rβ. These observations indicate that an IL-2 receptor composition consisting of IL-2Rβ and IL-2Rγ isoforms might mediate the predominant form of IL-2 cytokine recognition by hADSCs. The receptor composition changes only slightly upon replicative aging of the hADSCs, indicating that responsiveness of hADSCs to IL-2 does not change upon their senescence.

hADSCs were isolated and cultured as described above. Ex vivo replicative senescence led to decreased proliferation, accumulation of DNA damage and morphological changes: hADSCs became much larger with an irregular and flat shape, and nuclei became more circumscribed in phase contrast microscopy with the granular cytoplasm appearance of many inclusions and aggradations. The growth curve of hADSCs obtained from two different patients are shown in FIG. 3A. Typical staining for senescence-associated SA-β galactosidase activity for either hADSCs in linear growth rate, SR, or when cell lines cease their proliferation, SEN, is shown in FIG. 3B.

Example 3: SEN-MSCs Demonstrate a Higher Propensity for Migration

This examples shows that replicative senescence affects the migratory potential of hADSCs. Migration assays were performed, using a set of cytokines and growth factors using the Transwell system as described in the Materials and Methods section, below. It was observed that adipose-derived MSCs undergoing replicative senescence demonstrated a higher propensity for migration. It was observed that SEN hADSCs showed significantly higher basal migration capacity then their SR counterparts (FIG. 3C). FIG. 3C shows ex vivo migration assays for self-renewing (SR, on left) and senescent (SEN, on right) hADSCs. The black lines indicate the median values, and the whiskers indicate the range of values. Statistical differences were evaluated by a T-test with the p-value (p) as depicted.

In addition, the response of SEN hADSCs to different cytokine chemo-attractants was measured. It was observed that hADSCs have an increased ability to migrate for late passages in comparison to early passages (FIG. 3D), indicating that replicative senescence increases the migratory properties of hADSCs in response to the tested chemo-attractants. IL-2 was the most potent chemo-taxis stimulant on SEN-MSCs, whereas the TNF-α was less potent among the tested chemo-attractants in these experiments (FIG. 3D). FIG. 3D shows the migration of self-renewing SR (on left) and senescence SEN (right) hADSCs. hADSCs were induced to migrate in the presence of different cytokines (50 ng/ml IL-2, IL-6, IL-8, HMGB1; 30 ng/ml TNF). The graphic represents the mean of ten independent experiments (n=10). P-values (p) related to experimental measurements are listed under the graphs.

These data indicated that replicative senescence modifies the migratory properties of hADSCs and may influence the response of MSCs to the inflammatory environment and influence their immunomodulation output.

Example 4: Differential Response to Il-2 Stimulation in Human Adipose-Derived MSCs Upon Replicative Senescence Assessment of the IL-2 receptor isoforms expression, by Q-PCR, demonstrated significant changes in expression of the IL-2Rα isoform in comparison to IL-2Rγ and IL-2Rβ upon replicative senescence ex vivo (FIG. 4B). FIG. 4B shows IL-2 receptors α, β, and γ assessed by quantitative PCR (Q-PCR) in un-stimulated (IL-2-)SR cells (first bar) and SEN cells (third bar) and upon stimulation with 20 ug/ml of recombinant IL-2 (IL-2+) (SR cells, second bar;

SEN cells, fourth bar). Data shown as fold change (ΔΔCT). Mean±SD from three independent experiments is shown. Notably, the increased accumulation of the IL-2Rβ and IL-2Ra transcripts was recorded after IL-2 treatment in both SR and SEN hADSCs, whereas IL-2Ra expression was abrogated when senescent cells were subjected to similar treatments (FIG. 4B).

However, the data indicated that protein level expression of the cellular membrane associated IL-2Rα receptor showed the opposite pattern (FIG. 4C). FIG. 4C shows the cellular membrane-associated levels of IL-2Ra and IL-2Rβ. The levels were quantified by ELISA in un-stimulated (IL-2-) SEN (third bar) and SR (first bar) hADSCs and upon stimulation with 20 ug/ml of recombinant IL-2 (IL-2+) SEN (fourth bar) and SR (second bar). Data are expressed as pictogram per milliliter. Results are the mean of three independent experiments (mean±SD). Statistical significance was estimated by a t-test, where *$p<0.001$, $p<0.01$, *$p<0.05$.

Although the transcriptional status of IL-2 receptor isoforms does vary between the two different cell states (SR and SEN), it does not seem to be dependent upon IL-2 exposure (induction) as measured by the ELISA assay (described in the Materials and Methods, above). The data also demonstrated that protein encoding IL-2α receptor chain is less abundant than the IL-2Rβ isoform (compare 120 pg/ml of IL-2Rα to 350 pg/ml IL-2Rβ to 150 pg/ml of IL-2Rα and 440 pg/ml IL-2Rβ upon replicative senescence ex vivo) as shown in FIG. 4C. These data indicate that hADSCs response to IL-2 stimulation occurs through the intermediate-affinity receptor dimer composed of IL-2Rβ (CD 122) and the common IL-2Rγ (CD 132).

Figure 5:
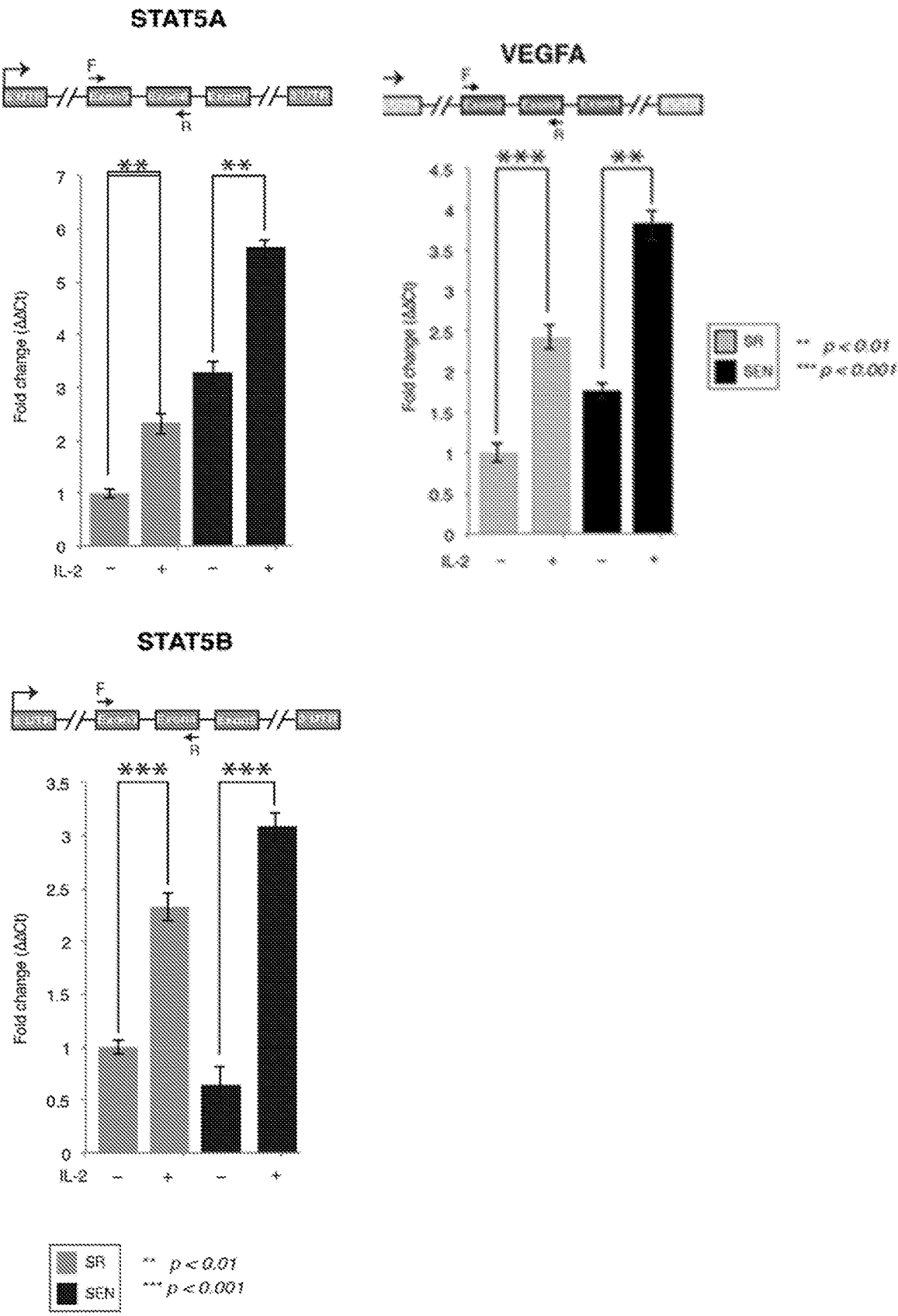
FIG. 5 illustrates the effect of stimulation of the SR and SEN hADSCs with IL-2. STAT5A, STAT5B and VEGFA mRNA expression was assessed by quantitative RT-PCR.
Figure 7A:
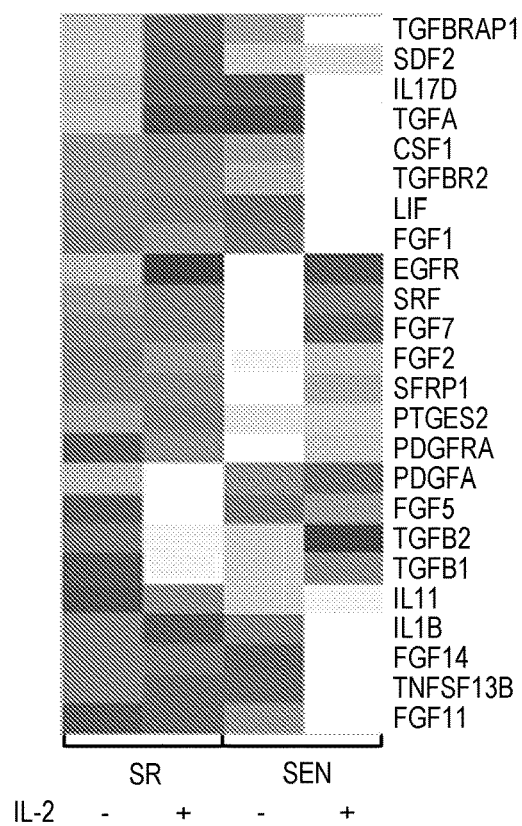
FIGS. 7A-7D illustrate gene expression levels for SR and SEN cells upon IL-2 treatment among functionally coherent sets of genes.
Figure 7B:
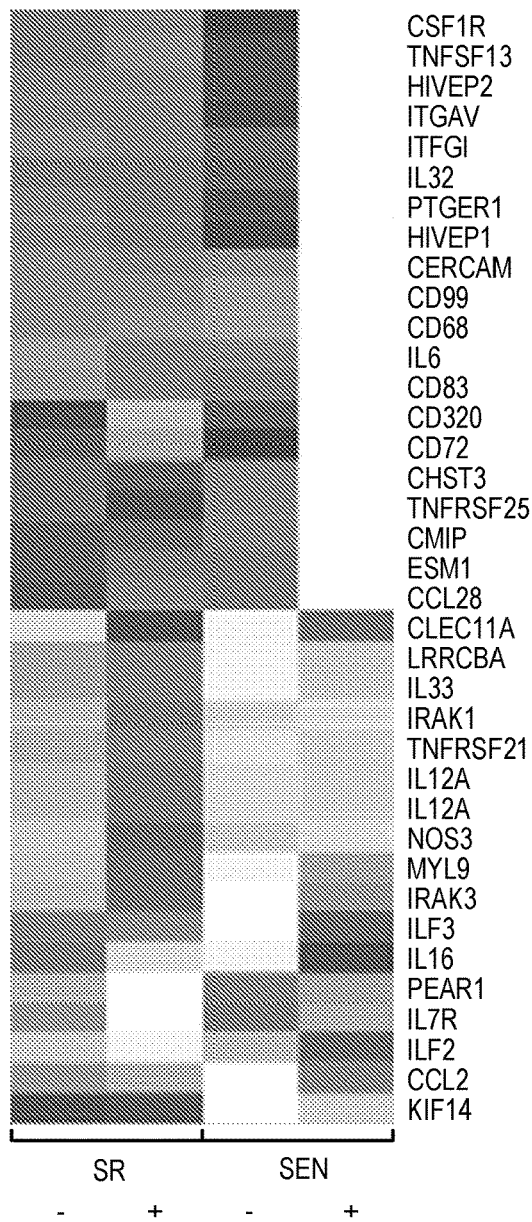

IL-2 signals via JAM and JAK3 to activate STAT5A and STAT5B, and additionally uses Ras-MAP kinase and phosphoinositol 3-kinase dependent signaling pathways. The expression of downstream target of IL-2, STAT5, is shown in FIGS. 5, 7A and 7B and the table of FIGS. 10A and 10B. In hADSCs, both STAT5A and STAT5B gene transcription follows the IL-2/STAT5 signaling axis.

FIG. 5 illustrates the effect of stimulation of the SR and SEN hADSCs with IL-2. IL-2 upregulates mRNA of a mediator of IL-2 signaling STAT5 gene. STAT5A and STAT5B mRNA expression was assessed by quantitative RT-PCR in un-stimulated (IL-2-) SR (first bar) and SEN cells (third bar) and upon stimulation with 20 ug/ml of recombinant IL-2 (IL-2+) (SR+IL-2, second bar; SEN+IL-2, third bar). Data are shown as fold change (MCT). Mean±SD from three independent experiments is shown. The position of the Q-PCR primers is depicted graphically. Statistical significance was estimated by the t-test, where *$p<0.001$, $p<0.01$.

It was next investigated how IL-2 and its downstream target STAT5 affects transcriptional outcomes in hADSCs upon their replicative senescence ex vivo.

Figure 8A:
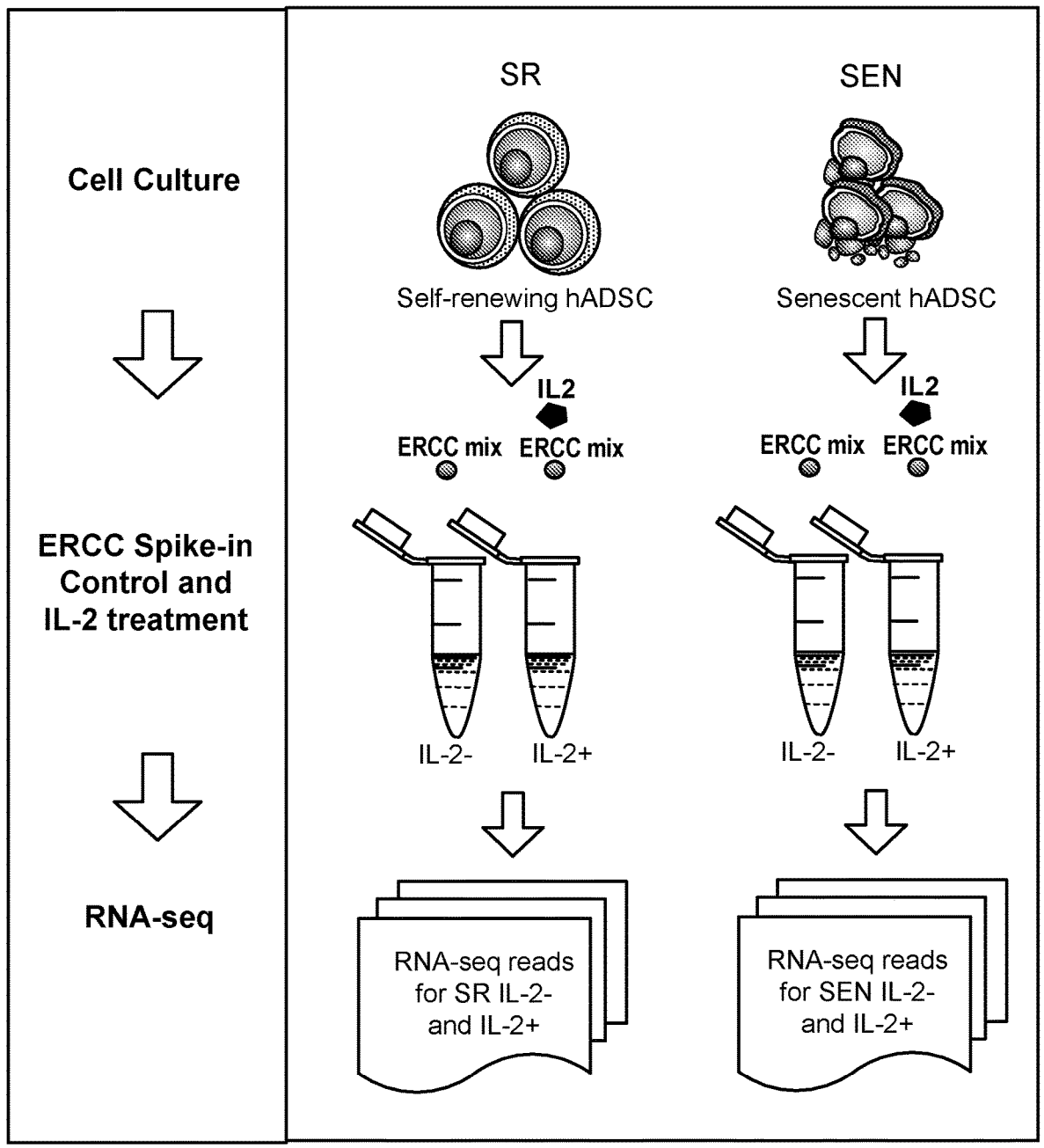
FIGS. 8A-8D illustrate the analysis for RNA-seq profiling of SR and SEN hADSCs subjected to IL-2 treatment.
Figure 8B:
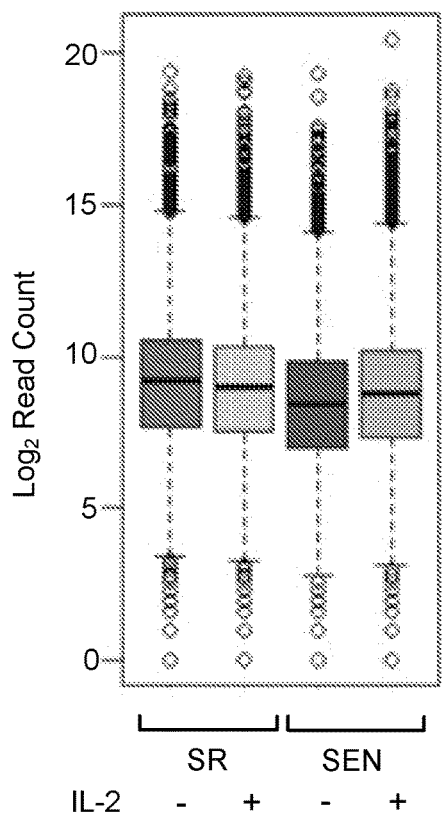
Figure 8C:
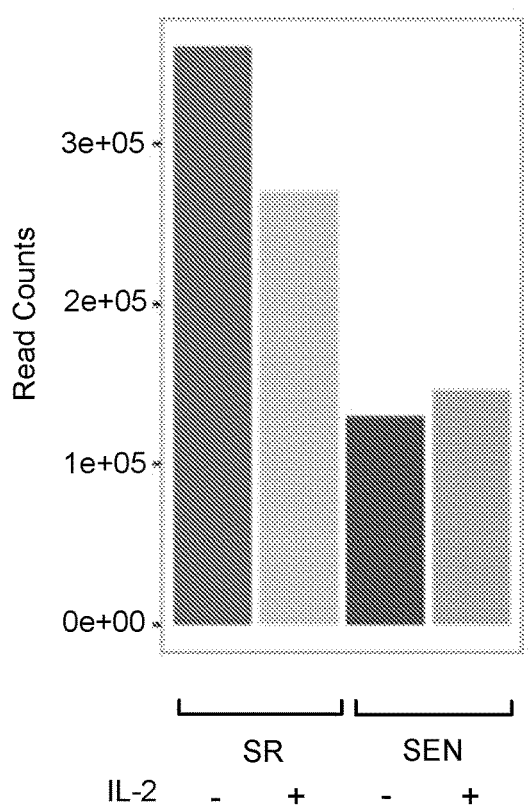

Exposure to IL-2 resulted in altered gene expression in human MCSs upon replicative senescence. To address how the transcriptional response to the IL-2/STAT5 axis changes upon replicative aging of hADSCs ex vivo, a RNA-seq transcriptome analysis was performed, using the Ion Proton™ System as described in Example 1 and shown in FIG. 8A. The gene expression levels in hADSCs across four conditions (libraries) was compared: self-renewal upon normal ex vivo culture (SR IL-2-), self-renewal upon 24 hrs recombinant IL-2 stimulation (SR IL-2+), replicative senescence upon normal ex vivo culture (SEN IL-2-), and replicative senescence upon 24 hrs recombinant IL-2 stimulation (SEN IL-2+). Distributions of the total read counts for the four conditions representing each condition are shown in FIG. 8B.

Figure 6A:
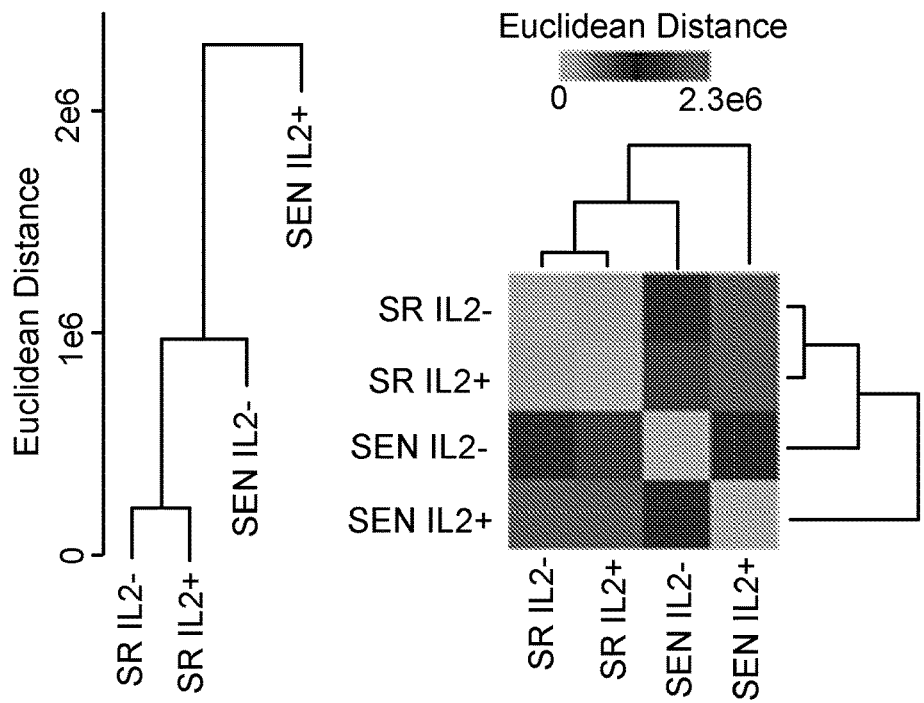
Figure 8D:
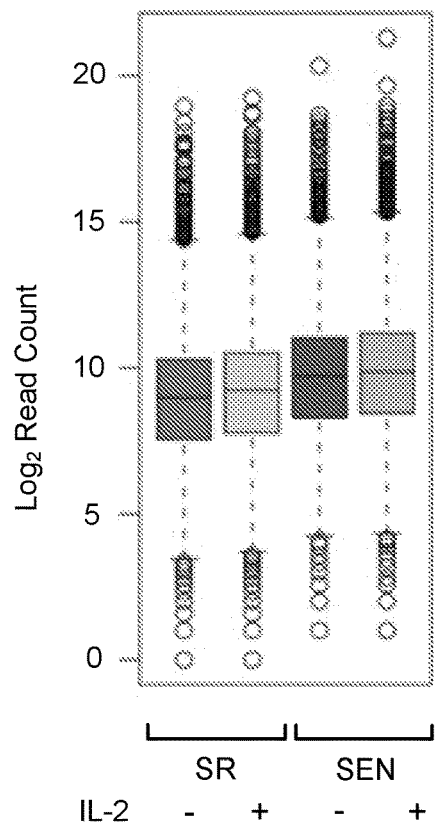

Beta-actin expression levels were used to normalize gene expression levels between conditions (as described in Example 1). This approach was taken to allow for the fact that overall gene expression levels may change upon IL-2 treatment. Beta-actin normalized gene expression distributions reveal overall up-regulation of gene expression upon IL-2 treatment in both SR and SEN states (FIG. 8D). However, comparison of individual gene expression levels among the four conditions indicates that IL-2 treatment more significantly affects SEN-compared to SR-hADSCs (FIG. 6A). FIG. 6A shows a hierarchical clustering showing the pairwise distance between conditions based on comparison of condition-specific gene expression profiles. The SR IL-2- and SR IL-2+ conditions group closely together when individual gene expression levels are compared followed by the SEN IL-2- condition. The SEN IL-2+ condition is an outlier amongst the four conditions showing a substantially divergent pattern of individual gene expression levels. This indicates that that the biological response to IL-2 treatment in hADSCs upon senescence may significantly impede MSC function via global transcriptional de-regulation in response to IL-2.

Figure 6B:
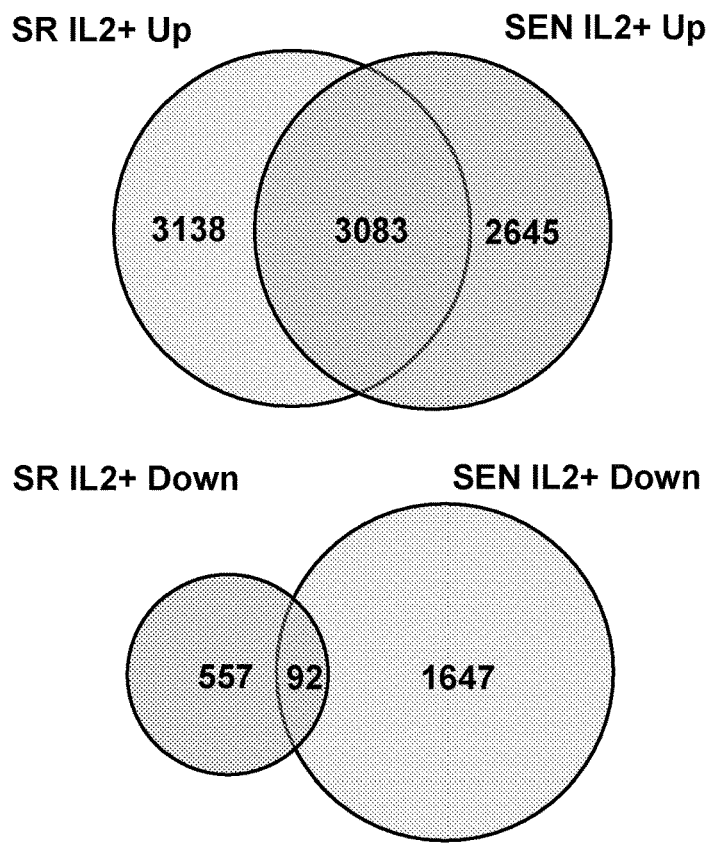

Expression levels were further compared between conditions in order to identify individual genes that are differentially expressed, up- and down-regulated, in response to IL-2 treatment in both SR and SEN states (FIG. 6B). FIG. 6B is a Venn diagram showing the numbers of genes, which are up-regulated and downregulated upon IL-2 treatment. There are several more genes that are up-regulated (8,866) compared to down-regulated (2,296) upon IL-2 treatment in both SR and SEN hADSCs. There is also a substantially higher proportion of genes that are up-regulated in both SR and SEN hADSCs (35%) compared to genes that are down-regulated in both states (4%). The greatest asymmetry is seen for genes that are down regulated in SEN hADSCs upon IL-2 treatment (1,739); there are many more such genes than seen for the SR IL-2+ condition (649). This difference indicates that the overall divergence of the SEN IL-2+ condition is largely attributed to genes that are down-regulated upon IL-2 treatment, which is an unexpected result given the overall up-regulation across both SR and SEN upon IL-2 treatment (FIG. 6B and FIG. 8D).

FIGS. 6C-6D shows heat maps showing the expression levels of genes that are up-regulated (FIG. 6C) and down-regulated (FIG. 6D) upon IL-2 treatment. Normalized gene expression levels are shown as heat maps in grayscale. Groups correspond to genes that are up- or down-regulated in SR-only, SEN-only or both conditions.

Taken together, these data indicate that SEN hADSCs have lost the ability to generate coordinated regulatory changes in response to IL-2 treatment to the same extent that exists for actively proliferating SR cells. The greater number of up-regulated genes seen for SR IL-2+, compared to SEN IL-2-, is consistent with this interpretation.

Provided herein are pathways enriched upon IL-treatment. FIG. 10A shows a table (FIG. 10A) indicating biological pathways enriched for genes up-regulated upon IL-2 treatment in SR and SEN hADSCs. In FIG. 10A, enriched pathways are shown along with the individual IL-2+ up-regulated genes belonging to the pathway and the pathway enrichment significance levels. Pathways with gene members up-regulated in SR are shown in the left column, and pathways with gene members up-regulated in SEN are shown in the right column. Pathways with gene members up-regulated in both SR and SEN are shown in the top row followed by pathways with gene members up-regulated only in SEN, and finally pathways with gene members up-regulated only in SR. Networks are shown relating pathways that are up-regulated in SR (left column) and pathways that are up-regulated in SEN (right column). The network nodes represent pathways, and the sizes of the nodes correspond to the number of up-regulated genes in that pathway. Pathway nodes are connected by edges if the pathways share up-regulated genes, and edge-weights correspond to the number of up-regulated genes shared between the pathways.

Figure 10B:
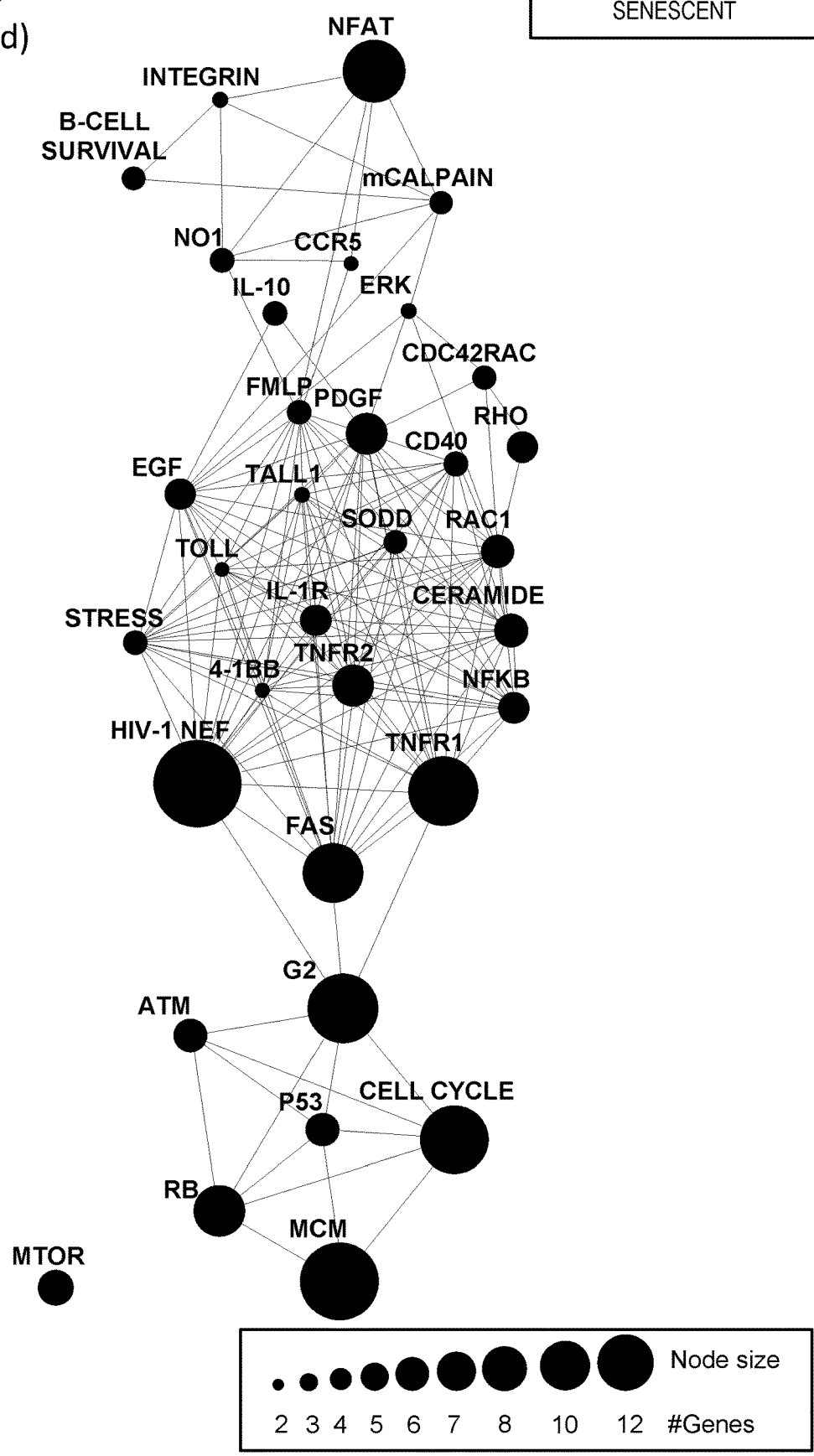

FIG. 10B is a table (FIG. 10B) illustrating biological pathways enriched for genes down-regulated upon IL-2 treatment in SR and SEN hADSCs. Enriched pathways are shown along with the individual IL-2+ down-regulated genes belonging to the pathway and the pathway enrichment significance levels. Pathways with gene members down-regulated in SR are shown in the left column, and pathways with gene members down-regulated in SEN are shown in the right column. Pathways with gene members down-regulated in both SR and SEN are shown in the top row followed by pathways with gene members down-regulated only in SEN, and finally pathways with gene members down-regulated only in SR. A network is shown relating pathways that are down-regulated in SEN (left column). The network nodes represent pathways, and the sizes of the nodes correspond to the number of SEN down-regulated genes in that pathway. Pathway nodes are connected by edges if the pathways share SEN down-regulated genes, and edge-weights correspond to the number of down-regulated genes shared between the pathways.

Figure 7C:
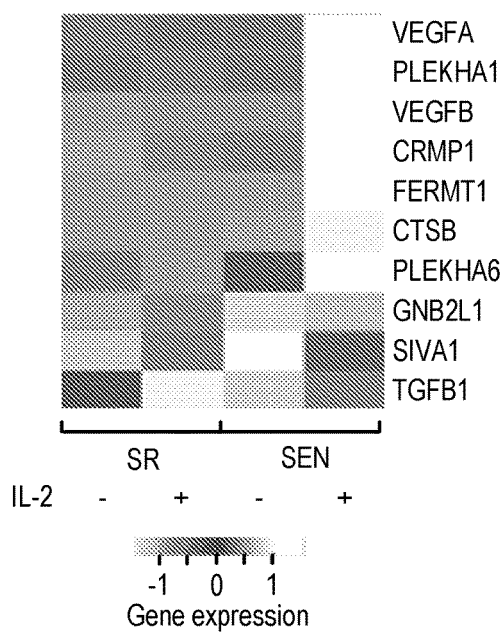
Figure 7D:
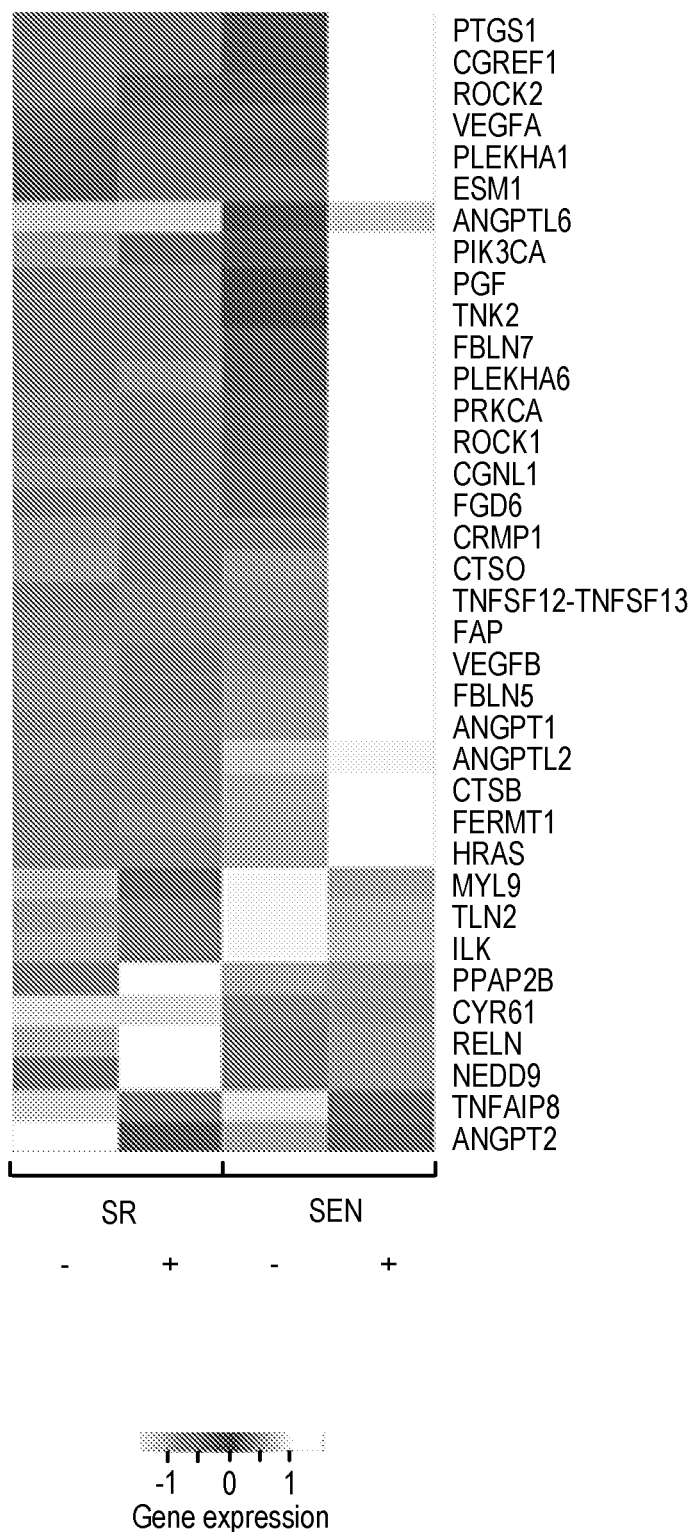

Example 5: Trophic Properties of the hADSCs after IL-2 Stimulation are Susceptible to Replicative Aging Ex-Vivo FIGS. 7A-7D illustrate gene expression levels for SR and SEN cells upon IL-2 treatment among functionally coherent sets of genes. Expression levels are shown for sets of genes characterized as (in FIG. 7 A) trophic factors, (in FIG. 7B) anti-inflammatory and immunomodulatory, (as shown in FIG. 7C) anti-apoptotic and metastasis promoting, and (as shown in FIG. 7D) migration and angiogenesis promoting. Normalized gene expression levels are shown as heat maps in grayscale.

The trophic properties of the MSCs after IL-2 exposure are susceptible to replicative aging ex vivo (e.g., FIG. 7A, Table 1). The secretion of a broad range of bioactive molecules is believed to be the main mechanism by which MSCs achieve their therapeutic effects. MSCs secrete an array of growth factors and anti-inflammatory proteins with complex feedback mechanisms among the many types of immune cells.

Table 1 shows the differential expression of trophic factors upon IL-2 treatment in SEN and SR cells. The SR GFOLD values represent the fold difference in SR cells treated with IL-2, relative to SR cells not treated with IL-2; the SEN GFOLD values represent the fold difference in SEN cells treated with IL-2, relative to SEN cells not treated with IL-2.

TABLE 1

Differential Expression of Trophic Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| TGFBRAP1 | NM_001142621 | 941 | 1475 | 2242 | 2601 | 0.51 | 0.12 |
| SDF2 | NM_006923 | 685 | 992 | 1466 | 1516 | 0.37 | 0.00 |
| IL17D | NM_138284 | 9 | 49 | 69 | 124 | 0.97 | 0.34 |
| TGFα | NM_001099691 | 147 | 295 | 316 | 484 | 0.67 | 0.37 |
| CSF1 | NM_000757 | 1466 | 1691 | 3953 | 4906 | 0.09 | 0.24 |
| TGFBR2 | NM_001024847 | 3416 | 4028 | 20586 | 25244 | 0.16 | 0.26 |
| LIF | NM_002309 | 163 | 227 | 942 | 1652 | 0.13 | 0.67 |
| FGF1 | NM_001144892 | 287 | 237 | 524 | 741 | 0.00 | 0.31 |
| EGFR | NM_005228 | 4980 | 5431 | 5971 | 5368 | 0.06 | −0.09 |
| SRF | NM_003131 | 1689 | 1742 | 2132 | 1957 | 0.00 | −0.02 |
| FGF7 | NM_002009 | 756 | 766 | 1131 | 946 | 0.00 | −0.11 |
| FGF2 | NM_002006 | 5573 | 5301 | 8776 | 8185 | −0.01 | −0.05 |
| SFRP1 | NM_003012 | 1351 | 1346 | 4190 | 3575 | 0.00 | −0.15 |
| PTGES2 | NM_025072 | 521 | 746 | 1778 | 1699 | 0.33 | 0.00 |
| PDGFRA | NM_006206 | 3877 | 4533 | 5085 | 3109 | 0.15 | −0.63 |
| PDGFA | NM_002607 | 612 | 866 | 790 | 682 | 0.32 | −0.04 |
| FGF5 | NM_004464 | 4322 | 5738 | 3329 | 2895 | 0.34 | −0.12 |
| TGFB2 | NM_001135599 | 352 | 422 | 166 | 314 | 0.02 | 0.60 |
| TGFβ1 | NM_000660 | 4834 | 6297 | 3413 | 5582 | 0.32 | 0.64 |
| IL-11 | NM_000641 | 583 | 758 | 152 | 950 | 0.19 | 2.35 |
| IL1B | NM_000576 | 73 | 108 | 75 | 229 | 0.06 | 1.17 |
| FGF14 | NM_004115 | 61 | 69 | 89 | 255 | 0.00 | 1.11 |
| TNFSF13B | NM_001145645 | 0 | 12 | 10 | 104 | 0.65 | 2.12 |
| FGF11 | NM_004112 | 67 | 48 | 10 | 198 | 0.00 | 3.09 |

The data indicated that the expression of growth factors in hADSCs upon stimulation with IL-2 is subjected to significant changes upon replicative senescence ex vivo. While the exposure of actively proliferating (SR) hADSCs to IL-2 resulted in increased expression of mitogenic proteins such as stromal cell-derived factor 2 (SDF2) and SDFL2, and prostaglandin E synthetase 2 (PTGES2), both SR and SEN hADSCs are marked by significant increases of transforming growth factors alpha and beta (TGFα, TGFβ1 and TGFβ2), transforming growth factor beta receptor TGFBR2 and transforming growth factor beta receptor-associated protein TGFBRAP1, as well as transforming growth factor beta-induced (TGFBI), which are known to increase fibroblast, epithelial and endothelial cell division when secreted in systemic milieu (FIG. 7A and Tables 5A-5D).

In addition, both SR and SEN IL-2 stimulated hADSCs were marked by up-regulation of colony stimulating factor 1 (CSF-1), LIF, IL-11, IL-17D, IL-1β and tumor necrosis factor (ligand) superfamily TNFSF13B, a cytokine encoding gene that stimulates B- and T-cell function (FIGS. 7A, 7B and FIGS. 10A-10B).

Taking into account that paracrine IL-17D induces expression of IL-6, IL-8, and GM-CSF genes in endothelial cells, and IL-1β stimulates fibroblast growth factor activity (TGFα, TGFβ1 and TGFβ2 genes are notably up-regulated in IL-2-exposed hADSCs) in autocrine and paracrine fashion, along with thymocyte and B-cell proliferation and maturation by inducing release of IL-2 from these cells, the data indicate that the transcriptional status of both SR and SEN hADSCs may point to enhanced immunomodulatory properties of these cells after IL-2 exposure via a complex regulatory feed-back loop.

Both SR and SEN hADSCs exposed to IL-2 are marked by significant increases in expression of transforming growth factors alpha and beta (TGFα, TGFβ1 and TGFβ2), transforming growth factor beta receptor TGFBR2 and transforming growth factor beta receptor-associated protein TGFBRAP1, as well as transforming growth factor beta-induced (TGFBI) genes (FIG. 7A).

Provided herein is a TGFβ biomarker. TGFβ is believed to be important in regulation of the immune system by promoting differentiation of CD+4 T-cells and inhibiting immune-surveillance, thereby imposing immunosuppression. However, the higher level of TGFβ expression in adipose-derived human MSCs after exposure to IL-2 might promote carcinogenesis. In addition, differences in the IL-2 dependent expression of growth factors upon senescence of hADSCs that have not been observed in SR cells were also noted. This includes up-regulation of a subset of fibroblast growth factor family members (FGF 1, FGF 11, FGF 14) accompanied by down-regulation of other members, such as FGF2, FGF 5, FGF7, (FIG. 7A, Table 1, and Tables 5A-5D).

IL-2 exposed SEN hADSCs are marked by EGF mRNA up-regulation, but down-regulation of mRNA to its receptor EGFR, together a decrease in expression of the serum response factor SRF and the secreted modulator of WNT signaling SFRP1. Interestingly, the expression of both a potent mitogen for cells of mesenchymal origin that promotes wound healing, PDGFA, and its receptor, PDGFRA, is significantly suppressed in SEN hADSCs in comparison to SR cells subjected to IL-2 exposure (FIG. 7A, FIG. 10A, Table 1, and Tables 5A-5D).

These data indicate senescence-related differences in the nature of IL-2 mediated transcriptional response in hADSCs that might impede these cells immunomodulatory properties ex vivo and, ultimately, in vivo.

A panel of anti-inflammatory and immunomodulatory markers for IL-2 treatment, IL-2 in combination with other drugs and IL-2 exposed human MSCs is shown (Table 2).

The invention also contemplates the determination of which pathways are regulated in response to IL-2 treatment. Genes designated as up- or down-regulated in IL-2 treated SR and SEN hADSCs were analyzed, using an integrated gene-set enrichment and pathway network approach to capture the biological reality of coordinated cellular responses to IL-2 stimulation. To do this, pathways that were statistically enriched for up- or down-regulated genes were identified, and then chosen based on the differentially expressed genes that they have in common (FIGS. 10A-10B). The pathway network representation was weighted based on the numbers of differentially expressed genes in each pathway and the extent to which different pathways share sets of differentially expressed genes. This approach allowed identification of a highly connected network structure with numerous functionally related pathways as well as functionally relevant network substructures.

Upon senescence of hADSCs, IL-2 is less stimulatory for the gene pathways promoting proliferation (cell cycle pathway, q-value=1.54 e-5), imposing G2 checkpoint (G2 pathway, q-value=5.94e-4), p53 pathway (q-value=1.18e-2), major signal transduction MAPK pathway (MAPK, q-value=2.42e-4) and its major subgroup ERK pathway (ERK, q-value=2.62e-2), which regulate important cellular function such as survival, migration and proliferation.

The data also provide information regarding the functionality of MSCs in carcinogenic settings. Both SR and SEN hADSCs exposed to IL-2 are marked by significant increases in expression of transforming growth factors alpha and beta (TGFα, TGFβ1 and TGFβ2), transforming growth factor beta receptor TGFBR2 and transforming growth factor beta receptor-associated protein TGFBRAP1, as well as transforming growth factor beta-induced (TGFBI) genes (FIG. 7A).

IL-2 treated SEN hADSCs show that prominent up-regulated genes are enriched for pathways associated with inflammation (IL-6 pathway, q-value=5.55e-3) and EGF signaling (q-value=2.33e-4) that have been proven to provide a survival advantages to MSCs. The SEN hADSCs exposed to IL-2 are also marked by increased expression of IL-1 R·IL-6 and IL-12 (FIG. 7B).

The observed connection to the angiogenic VEGF pathway (q-value=5.24e-3) (FIG. 10A, right side and FIG. 7D) and the enhanced capacity of SEN hADSC to migration (FIGS. 3A, 3B) may indicate that IL-2 exposed SEN-MSCs could acquire properties necessary to support a tumorigenic environment and metastasis. In addition, up-regulation of the genes included in nitric oxide synthase pathway (iNOS) NOS1 pathway (q-value=8.32e-2) in hADSC upon replicative senescence once again support that MSCs undergoing senescence can acquire metastasis-promoting properties via immunosuppression.

Pathways important for support of proliferation and DNA repair are down-regulated in hADCSs upon senescence: Cell Cycle pathway (q-value=2.52e-5), MCM pathway (q-value=1.62e-8), RB pathway (q-value=6.97e-5) ATM pathway (q-value=3.28e-2), p53 pathway (q-value=1.86 e-2) shown in FIG. 10B. Overall, the data indicated that there are more biological pathways subjected to IL-2 triggered down-regulation in senescence then in self-renewal and these biological pathways are interconnected (FIG. 10B), further linking together a physiological impairment of IL-2 response upon replicative aging of hADSCs, thus indicating that such impairment might be an integral to adipose-derived stem cell deviated function in vivo and upon clinical applications.

The data provide a list of molecular marker targets critical for assessment of immunomodulatory and anti-inflammatory events and making informative decision for prioritizing autologous or allogeneic MSCs usage for clinical applications, and/or used as a companionship diagnostics of monitoring cancer treatment with an IL-2 agent and/or IL-2 with cell therapies in clinical settings (Table 2).

Table 2 shows the differential expression of anti-inflammatory and immunomodulatory factors upon IL-2 treatment in SEN and SR cells. The SR GFOLD values represent the fold difference in SR cells treated with IL-2, relative to SR cells not treated with IL-2; the SEN GFOLD values represent the fold difference in SEN cells treated with IL-2, relative to SEN cells not treated with IL-2.

TABLE 2

Differential Expression of Anti-Inflammatory and Immunomodulatory Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| CSF1R | NM_005211 | 80 | 43 | 189 | 455 | −0.27 | 0.98 |
| TNFSF13 | NM_003808 | 69 | 55 | 104 | 172 | 0.00 | 0.31 |
| HIVEP2 | NM_006734 | 2739 | 2790 | 3876 | 5495 | 0.00 | 0.43 |
| ITGAV | NM_002210 | 6797 | 7110 | 10656 | 17227 | 0.01 | 0.65 |
| ITFG1 | NM_030790 | 1067 | 1164 | 2398 | 3793 | 0.00 | 0.57 |
| IL-32 | NM_001012631 | 404 | 422 | 526 | 1397 | 0.00 | 1.24 |
| PTGER1 | NM_000955 | 9 | 19 | 37 | 104 | 0.00 | 0.86 |
| HIVEP1 | NM_002114 | 1142 | 1217 | 1447 | 2046 | 0.00 | 0.38 |
| CERCAM | NM_016174 | 6943 | 7119 | 12879 | 16369 | 0.00 | 0.31 |
| CD99 | NM_001277710 | 6948 | 7069 | 13830 | 16928 | 0.00 | 0.25 |
| CD68 | NM_001251 | 3830 | 3590 | 9144 | 11331 | −0.02 | 0.26 |
| IL6 | NM_000600 | 434 | 502 | 782 | 996 | 0.00 | 0.19 |
| CD83 | NM_001040280 | 19 | 27 | 69 | 107 | 0.00 | 0.12 |
| CD320 | NM_016579 | 1068 | 782 | 990 | 1360 | −0.29 | 0.32 |
| CD72 | NM_001782 | 61 | 36 | 73 | 122 | −0.06 | 0.25 |
| CHST3 | NM_004273 | 2867 | 2935 | 2766 | 3706 | 0.00 | 0.34 |
| TNFRSF25 | NM_003790 | 61 | 68 | 56 | 98 | 0.00 | 0.25 |
| CMIP | NM_198390 | 1503 | 1435 | 1289 | 2460 | 0.00 | 0.82 |
| ESM1 | NM_007036 | 2562 | 1887 | 1863 | 7612 | −0.34 | 1.94 |
| CCL28 | NM_148672 | 68 | 37 | 44 | 170 | −0.20 | 1.39 |
| CLEC11A | NM_002975 | 1071 | 1403 | 1601 | 1449 | 0.25 | −0.02 |
| LRRC8A | NM_001127244 | 3710 | 4256 | 6709 | 6370 | 0.12 | −0.02 |
| IL33 | NM_033439 | 55 | 84 | 220 | 198 | 0.03 | 0.00 |
| IRAK1 | NM_001569 | 5587 | 6539 | 9009 | 9094 | 0.17 | 0.00 |
| TNFRSF21 | NM_014452 | 244 | 331 | 636 | 616 | 0.16 | 0.00 |
| IL12A | NM_000882 | 14 | 36 | 94 | 91 | 0.29 | 0.00 |
| NOS3 | NM_000603 | 48 | 83 | 137 | 142 | 0.19 | 0.00 |
| MYL9 | NM_006097 | 10584 | 19391 | 38407 | 32665 | 0.83 | −0.21 |
| IRAK3 | NM_007199 | 181 | 304 | 613 | 488 | 0.43 | −0.13 |
| ILF3 | NM_012218 | 5977 | 5913 | 6830 | 6368 | 0.00 | −0.04 |
| IL-16 | NM_001172128 | 129 | 72 | 150 | 120 | −0.35 | 0.00 |
| PEAR1 | NM_001080471 | 1926 | 2387 | 510 | 187 | 0.21 | −1.16 |
| IL7R | NM_002185 | 831 | 954 | 634 | 545 | 0.04 | −0.02 |
| ILF2 | NM_001267809 | 1344 | 1961 | 1878 | 1580 | 0.43 | −0.13 |
| CCL2 | NM_002982 | 98 | 147 | 160 | 102 | 0.15 | −0.23 |
| KIF14 | NM_014875 | 329 | 331 | 381 | 251 | 0.00 | −0.33 |

Example 6: Anti-Inflammatory and Immunomodulatory Properties of IL-2 Exposed Human MSCs Next, it was investigated how exposure to the IL-2 pro-inflammatory environment, when imposed on replicative aging, affects the expression of the genes assigned to provide immunomodulatory properties of hADSCs (e.g., the anti-inflammatory and immunomodulatory properties of IL-2 exposed human MSC). The data demonstrated that the capacity for immunomodulation is affected by replicative aging of the human adipose-derived MCS during ex vivo passaging (FIG. 7B and Table 2).

IL-2 exposure in SR hADSCs activates distinct set of genes attributed to T cell regulation. IL-2 exposure of self-renewing hADSCs results in up-regulation of genes, such as TNFRSF21 (involved in T cells differentiation), IL12A (T-cell activator), ILF2 (potent regulator of transcription of the IL-2 gene during T-cell activation), IL33 (paracrine inducer of T-helper type 2 associated cytokines) and down-regulation of CCL28 (chemotactic factor for CD+4, CD+8 T-cells), CD320 (receptor molecule with autocrine and paracrine function to augment the proliferation of plasma cells) shown in FIG. 7B, Table 2, and Tables 5A-5D).

Contrary to that, IL-2 exposed SEN hADSCs were characterized by significant transcriptional up-regulation of CD320, a number of integrins which could be involved in modulation of T-cell function (ITG 11, ITGA V, ITFG 1), and genes encoding important regulatory molecules such as: the T-cell adhesion receptor (CD99), a factor attributed to the maintenance of naïve T-cells (CHST3), T-cell activators (HIVEP1 and HIVEP2), a gene involved in T-cell signaling pathway (CMIP) and an autocrine/paracrine factor, PTGER1, involved in inhibition of CD+ cell proliferation (FIG. 7B, Table 2, and Tables 5A-5D).

The data also demonstrated that SR hADSCs exposed to IL-2 trigger down-regulation of transcriptional activities of the genes encoding surface receptors that play a role in B-cell proliferation and differentiation (CD72) and horning macrophages (CD68). Both of these genes are significantly transcriptionally up-regulated in senescent cells upon similar treatment (FIG. 7B, Table 2, Tables 5A-5D). In addition, IL-2 treated SEN hADSCs are set apart from similarly treated SR cells by transcriptional down-regulation of the genes required for pro-B to pre-B transitioning, the LRRC8A and PEAR1 genes, that regulate a number of non-adherent myeloid progenitors. In contrast, the genes involved in lymphocyte activation and homeostasis (CD83 and TNFRSF25) as well as leukocyte transmigration (CERCAM), and the genes responsible for endothelial cell-leukocyte interaction (ESM1), and a gene important for control monocytes/macrophage mediated immunological process (TNFSF 13), are up-regulated in SEN hADSCs (FIG. 7B, Table 2, and Tables 5A-5D).

IL-2 exposure results in the differential expression of a number of cytokines and factors critical for chemotaxis (shown in FIG. 7B and Table 2).

SR hADSCs are marked by up-regulation of IL-33, IL-12A, IL10RB, IL1RAP, IL7R, ILF2 and NOS3 genes, while IL-16 and CSF1R genes are down-regulated in these cells.

In SEN hADSCs treated under similar conditions with IL-2, the genes encoding cytokines IL-32, IL-6, IL1RN, IL-20RB, IL-21R and inducers of inflammation TNFSF13 and TNFSF12, as well as the gene encoding extracellular matrix remodeler PLAU are up-regulated.

At the same time, several factors essential for cytokinesis such as MYL9, KIF14, IRAC3, as well as the genes encoding chemotactic factor that attracts monocytes and basophils (CCL2) and the CLEC11A gene regulating proliferation and differentiation of hematopoietic precursor cells, are down-regulated (FIG. 7B).

Similar down-regulation is also found for several interleukin receptor encoding genes IL7R, IL1R1, IL15RA, and interleukin enhancer binding factors ILF2 and ILF3.

These observations, together with IL-2 dependent differential transcriptional expression of cytokines in SEN hADSCs (up-regulation of IL-32, IL-6, PLAU genes; down-regulation of CCL2, CLEC11A, ILF3, IRAK3, KIF14, MYL9 genes) and in SR hADSCs (up-regulation of IL12A, IL7R, IRAK1, NOS3 genes; down-regulation of IL-16, CSF1R genes), indicate that the immunomodulatory properties of hADSCs are susceptible to senescence imposed changes.

The observed connection to the angiogenic VEGF pathway (q-value=5.24e-3) (FIG. 10A, right side and FIG. 7D) and the enhanced capacity of SEN hADSC to migration (FIGS. 4A,B) indicates that IL-2 exposed SEN-MSCs could acquire properties necessary to support a tumorigenic environment and metastasis. In addition, up-regulation of the genes included in nitric oxide synthase pathway (iNOS) NOS1 pathway (q-value=8.32e-2) in hADSC upon replicative senescence also indicate that MSCs undergoing senescence can acquire metastasis-promoting properties via immunosuppression.

Example 7: Anti-Apoptotic and Metastasis Promoting Properties of IL-2-Stimulated hADSCs Upon Replicative Senescence These experiments were also used to examine the anti-apoptotic and metastasis promoting properties of IL-2 exposed MSC upon replicative senescence.

The panel of anti-apoptotic and metastasis promoting markers for IL-2 treatment, IL-2 in combination with other drugs, or IL-2 in combination with MSC is shown in Table 3. The data provide a list of molecular marker targets important for assessment of anti-apoptotic and metastasis promoting events and making informative decision for prioritizing autologous or allogeneic MSCs usage for clinical applications, and/or used as a companion diagnostics of monitoring cancer treatment with an IL-2 agent and/or IL-2 with cell therapies in clinical settings (Table 3).

Table 3 shows the differential expression of anti-apoptotic and metastasis factors upon IL-2 treatment in SEN and SR cells. The SR GFOLD values represent the fold difference in SR cells treated with IL-2, relative to SR cells not treated with IL-2; the SEN GFOLD values represent the fold difference in SEN cells treated with IL-2, relative to SEN cells not treated with IL-2.

TABLE 3

Differential Expression of Anti-Apoptotic and Metastasis Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| VEGFA | NM_001025366 | 5690 | 5914 | 5781 | 20606 | 0.00 | 1.78 |
| PLEKHA1 | NM_001195608 | 716 | 676 | 713 | 1096 | 0.00 | 0.46 |
| VEGFB | NM_003377 | 989 | 1070 | 1832 | 2253 | 0.00 | 0.19 |
| CRMP1 | NM_001288661 | 168 | 209 | 401 | 547 | 0.00 | 0.23 |
| FERMT1 | NM_017671 | 76 | 70 | 264 | 325 | 0.00 | 0.02 |
| CTSB | NM_147780 | 28365 | 28109 | 115877 | 138711 | 0.00 | 0.25 |
| PLEKHA6 | NM_014935 | 78 | 57 | 150 | 251 | 0.00 | 0.40 |
| GNB2L1 | NM_006098 | 16273 | 18409 | 33137 | 32212 | 0.14 | −0.01 |
| SIVA1 | NM_006427 | 410 | 591 | 674 | 512 | 0.31 | −0.20 |
| TGFβ1 | NM_000660 | 4834 | 6297 | 3413 | 5582 | 0.32 | 0.64 |

For example, MSCs have been proven to assist reversal of apoptosis in cardiomyoblasts after ischemia, as well as damaged neurons and lung fibroblasts. Stanniocalcin 1 (STC 1) has been identified as an essential factor capable of potent apoptotic reversal in fibroblasts damaged by UV and acidity.

The data indicate that IL-2 exposure transcriptionally upregulates both STC1 and STC2 genes, and such activation is not dependent on the replicative aging of hADSCs, at least ex vivo (Tables 5A-5D). In addition, paracrine effectors such as VEGF and TGFB1 have been implicated in the reversal of apoptosis in endothelial cells. The expression of genes encoding both of these factors is up-regulated in SR and SEN hADSCs upon IL-2 treatment (FIG. 7C, FIG. 5, Table 3, and Tables 5A-5D).

The third graph of FIG. 5 shows that IL-2 upregulates transcription of the VEGFA gene upon replicative senescence of hADSCs. VEGFA gene expression was assessed by quantitative Q-PCR in unstimulated (IL-2-) senescent (dark) and self-renewing (light) hADSCs and upon stimulation with 20 ug/ml of recombinant IL-2 (IL-2+). Data shown as fold change ΔΔCT Mean±SD from three independent experiments is shown. The position of the q-PCR primers are depicted graphically. Statistical significance was estimated by t-test, where *$p<0.001$, $p<0.01$.

However, transcriptional activity of VEGFA is notably higher in senescence than in actively proliferating cells as further verified by Q-PCR analysis shown in FIG. 7C. Notably, the SIVA1 gene encoding a pro-apoptotic factor and a potent inducer of T lymphocytes apoptosis is significantly down-regulated in senescent cells upon IL-2 treatment in comparison to proliferating hADSCs (FIG. 7C, Table 3, and Tables 5A-5D). SIVA1 is not a strictly pro-apoptotic factor, but also a potent suppressor of tumor metastasis. Importantly, a number of the factors responsible for invasive growth and metastasis are significantly up-regulated in SEN hADSCs exposed to IL-2 in comparison with similarly treated SR cells (FIG. 7C and Table 3). This includes RACK1, PLEKHA1, PLEKHA6, CTSB, CRMP1, FERMT1 genes. These data indicated that pretreatment/exposure of hADSCs with IL-2 may enhance the antiapoptotic properties of these cells in general, and that such enhancement is effected by replicative senescence, at least in culture.

It was demonstrated that in IL-2 treated SEN hADSCs, prominent up-regulated genes are enriched for pathways associated with inflammation (IL-6 pathway, q-value=5.55e-3) and EGF signaling (q-value=2.3 3 e-4) that have been proven to provide a survival advantages to MSCs. The SEN hADSCs exposed to IL-2 are also marked by increased expression of IL-1β, IL-6 and IL-12 (FIG. 7B), cytokines known to stimulate IL-17 from lymphocytes.

The data also indicated that lymphocytes are the only source of IL-17 production, and those MSCs, particularly upon their senescence, display high transcriptional activity of IL-17 when subjected to a pro-inflammatory environment (FIG. 7A). The MCS-derived IL-17 together with MCS-derived CSF-1 may induce systemic neutrophil expansion and macrophages infiltration similar to studies indicating a critical role for these factors in promoting cancer progression and metastasis as well as in a number of inflammatory diseases including psoriasis.

Example 8: Transcriptional Profiling Indicates Gene Targets Regulating Enhanced Migration and Angiogenesis in IL-2 Stimulated hADSCs Upon Replicative Senescence The panel of the markers indicating enhanced migration and angiogenesis in IL-2 treatments upon aging is shown (Table 4)

The list of molecular marker targets critical for assessment of migration and angiogenesis promoting events can assist in making informative decisions for prioritizing autologous or allogeneic MSCs usage for clinical applications, and/or used as a companion diagnostics of monitoring cancer treatment with an IL-2 agent and/or IL-2 with cell therapies in clinical settings (Table 4). Transcriptional profiling indicates gene targets regulating enhanced migration and angiogenesis in IL-2 stimulated ADS Cs upon replicative senescence. Further analysis of the transcriptional response indicates that IL-2 stimulation of SEN hADSCs s enhances the expression of genes involved in vascular development and remodeling related to angiogenesis. It was observed significant up-regulation of the VEGFA, VEGFB, FBLNS, FBLN7, PGF, ANGPT1, ANGPT2, ANGPTL2, ANGPTL6, TNFSF12, PRKCA, PIK3CA, HRAS genes as well as a gene encoding a potent modulator of endothelial cell-leukocyte adhesion, ESM1 (FIG. 7D, FIGS. 10A-10B, Table 4, and Tables 5A-5D).

Table 4 shows the differential expression of migration and angiogenesis factors upon IL-2 treatment in SEN and SR cells. The SR GFOLD values represent the fold difference in SR cells treated with IL-2, relative to SR cells not treated with IL-2; the SEN GFOLD values represent the fold difference in SEN cells treated with IL-2, relative to SEN cells not treated with IL-2.

TABLE 4

Differential Expression of Migration and Angiogenesis Promoting Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| PTGS1 | NM_000962 | 1202 | 1233 | 2595 | 8456 | 0.00 | 1.63 |
| CGREF1 | NM_001166239 | 60 | 77 | 137 | 384 | 0.00 | 1.15 |
| ROCK2 | NM_004850 | 2014 | 2149 | 2171 | 2737 | 0.00 | 0.24 |
| VEGFA | NM_001025366 | 5690 | 5914 | 5781 | 20606 | 0.00 | 1.78 |
| PLEKHA1 | NM_001195608 | 716 | 676 | 713 | 1096 | 0.00 | 0.46 |
| ESM1 | NM_007036 | 2562 | 1887 | 1863 | 7612 | −0.34 | 1.94 |
| ANGPTL6 | NM_031917 | 339 | 195 | 279 | 342 | −0.50 | 0.02 |
| PIK3CA | NM_006218 | 519 | 597 | 720 | 939 | 0.00 | 0.22 |
| PGF | NM_002632 | 471 | 471 | 842 | 1503 | 0.00 | 0.69 |
| TNK2 | NM_005781 | 582 | 624 | 813 | 1176 | 0.00 | 0.38 |
| FBLN7 | NM_153214 | 201 | 195 | 268 | 353 | 0.00 | 0.13 |
| PLEKHA6 | NM_014935 | 78 | 57 | 150 | 251 | 0.00 | 0.40 |
| PRKCA | NM_002737 | 3139 | 3258 | 4215 | 5298 | 0.00 | 0.26 |
| ROCK1 | NM_005406 | 2280 | 2326 | 2662 | 3068 | 0.00 | 0.12 |
| CGNL1 | NM_001252335 | 11 | 22 | 67 | 115 | 0.00 | 0.27 |
| FGD6 | NM_018351 | 419 | 411 | 749 | 1055 | 0.00 | 0.33 |
| CRMP1 | NM_001288661 | 168 | 209 | 401 | 547 | 0.00 | 0.23 |
| CTSO | NM_001334 | 222 | 275 | 499 | 617 | 0.01 | 0.10 |
| TNFSF12-TNFSF13 | NM_172089 | 268 | 259 | 464 | 577 | 0.00 | 0.11 |
| FAP | NM_004460 | 1810 | 1767 | 4594 | 6279 | 0.00 | 0.39 |
| VEGFB | NM_003377 | 989 | 1070 | 1832 | 2253 | 0.00 | 0.19 |
| FBLN5 | NM_006329 | 5879 | 6117 | 8801 | 10137 | 0.00 | 0.15 |
| ANGPT1 | NM_001146 | 386 | 406 | 1069 | 1346 | 0.00 | 0.20 |
| ANGPTL2 | NM_012098 | 1241 | 1362 | 4927 | 5560 | 0.00 | 0.11 |
| CTSB | NM_147780 | 28365 | 28109 | 115877 | 138711 | 0.00 | 0.25 |
| FERMT1 | NM_017671 | 76 | 70 | 264 | 325 | 0.00 | 0.02 |
| HRAS | NM_176795 | 604 | 604 | 996 | 1124 | 0.00 | 0.03 |

TABLE 4-continued

Differential Expression of Migration and Angiogenesis Promoting Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| MYL9 | NM_006097 | 10584 | 19391 | 38407 | 32665 | 0.83 | −0.21 |
| TLN2 | NM_015059 | 2058 | 2352 | 4839 | 4309 | 0.09 | −0.10 |
| ILK | NM_001014795 | 5437 | 6108 | 8647 | 8164 | 0.11 | −0.03 |
| PPAP2B | NM_003713 | 1703 | 2546 | 2327 | 1579 | 0.48 | −0.45 |
| CYR61 | NM_001554 | 31391 | 30861 | 12856 | 12074 | 0.00 | −0.05 |
| RELN | NM_005045 | 2490 | 2989 | 925 | 671 | 0.17 | −0.29 |
| NEDD9 | NM_006403 | 2617 | 3093 | 2123 | 1956 | 0.15 | −0.01 |
| TNFAIP8 | NM_001077654 | 109 | 101 | 67 | 100 | 0.00 | 0.05 |
| ANGPT2 | NM_001118897 | 430 | 259 | 89 | 179 | −0.47 | 0.58 |

The vascular endothelial growth factor, VEGF, released by MCSs, enables recruitment of endothelial lineage cells and initiation of vascularization as was previously reported. It is further demonstrated that up-regulation of VEGFA gene expression in SEN hADSCs can be detected by quantitative RT-PCR analysis and IL-2 exposure results in a statistically significant increase of VEGFA gene transcription in SR and SEN hADSCs (FIG. 7D and Table 4).

In response to IL-2, a group of genes responsible for cell motility, migration and invasive growth are significantly up-regulated only in the hADSCs undergoing replicative senescence: CGNL1, CGREF 1, CRMP1, FGD6, TNK2, PTGS1, TNFAIP8, CTSB, CTSO, FAP, FERMT1, PLEKHA1, PLEKHA6, ROCK1, ROCK2. A set of genes promoting cell adhesion, such as CHD24, CYR61, ILK, NEDD9, MYL9, PPAP2B, RELN and TLN2 were down-regulated (FIG. 7D, Table 4, and Tables 5A-5D). These data further the support experimental evidence for the enhanced migration capacity of SEN hADSCs shown in FIG. 3B.

Example 9: Proteomic Antibody Array Data

Table 6 provides the raw values for all proteomic array data.

MSCs from a 38 year old patient in 10% PRP containing StemPro MSC SFM Xeno-free medium plated on a substrate. SR or SEN hADSC determined as described in Example 1 were plated at a density of 2500 cells/cm2 in 700 ul/cm2 of 10% PRP containing StemPro MSC SFM Xeno-free medium. SEN and SR hADSCs were stimulated with IL-2 for 24 hrs or remained without stimulation with IL-2 (IL-2-), after which media was exchanged to the 10% PRP containing StemPro MSC SFM Xeno-free medium. Cells were kept at 37° C. and 5% CO2 for 24, 48, and 72 hrs after which media was collected and analyzed. Equal volumes of medium were analyzed on RayBio C-Series Human Cytokine Antibody Array AAH-CYT-2000 (RayBiotech, Inc). C-Series Human Cytokine Antibody Array AAH-CYT-2000 is based on chemiluminescence assay principle and contains antibodies to 174 proteins of interest. Data were extracted from the membranes using LI-COR Biosciences densitometry software (Li-COR). The raw data were normalized by taking the ratio between Average Intensity of the given protein signal/to Average Intensity Negative Control, to account for differences in exposure and array to array variation. Data are presented in FIGS. 11-90 and Table 6 demonstrate protein factors secreted upon IL-2 exposure. These proteins include, but not limited to factors indicated in the tables in FIGS. 7A-7D and secretory profiles recapitulate transcriptional data.

Figure 11:
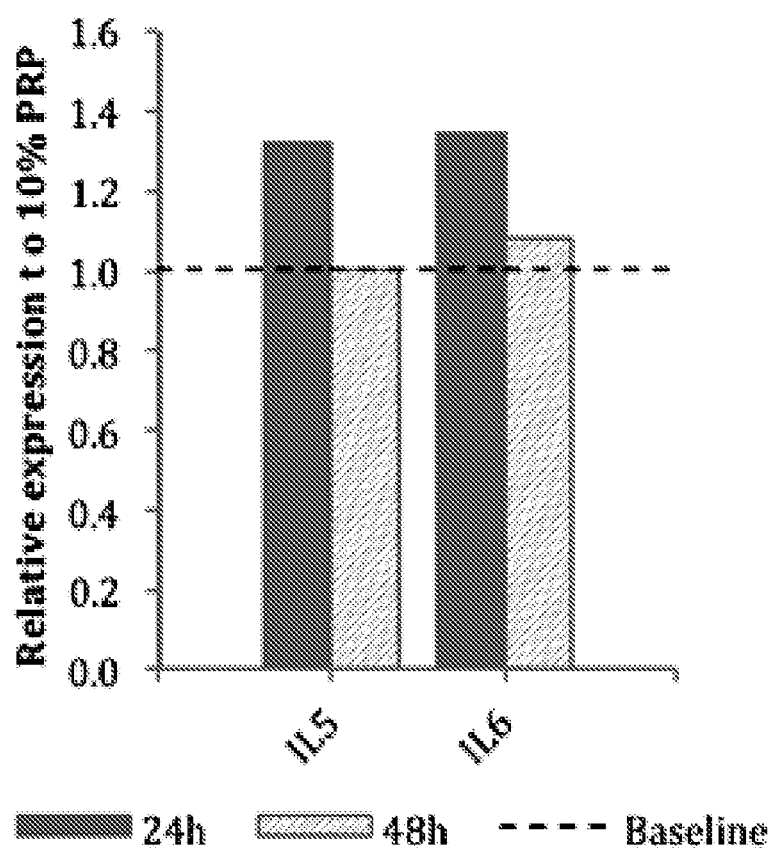
FIGS. 11-90 illustrate the increase in secretion of the named proteins (factors) from SR-hADSCs or SEN-hADSCs, following incubation with media alone (no IL-2 stimulation) or following stimulation with IL-2.
Figure 12:
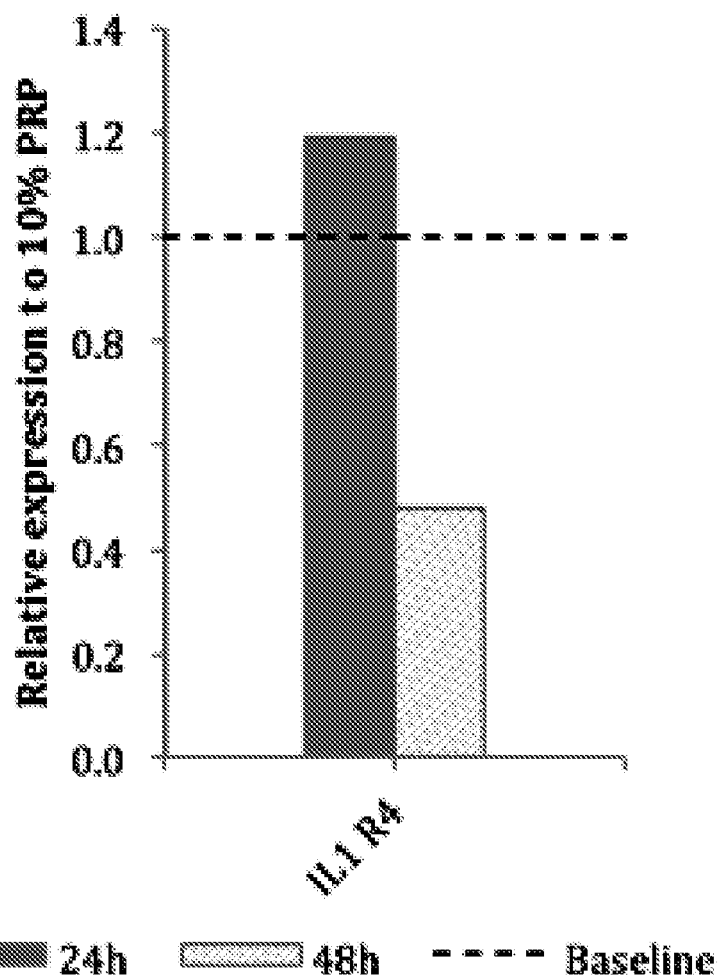
Figure 13:
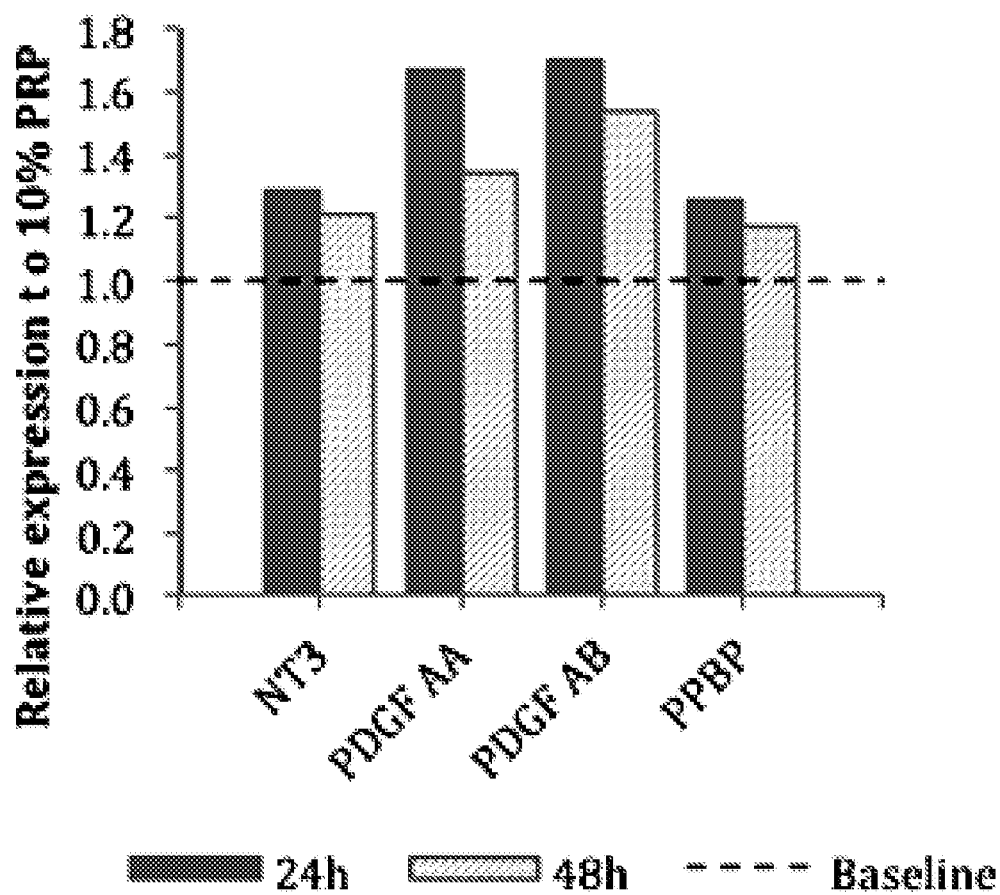
Figure 14:
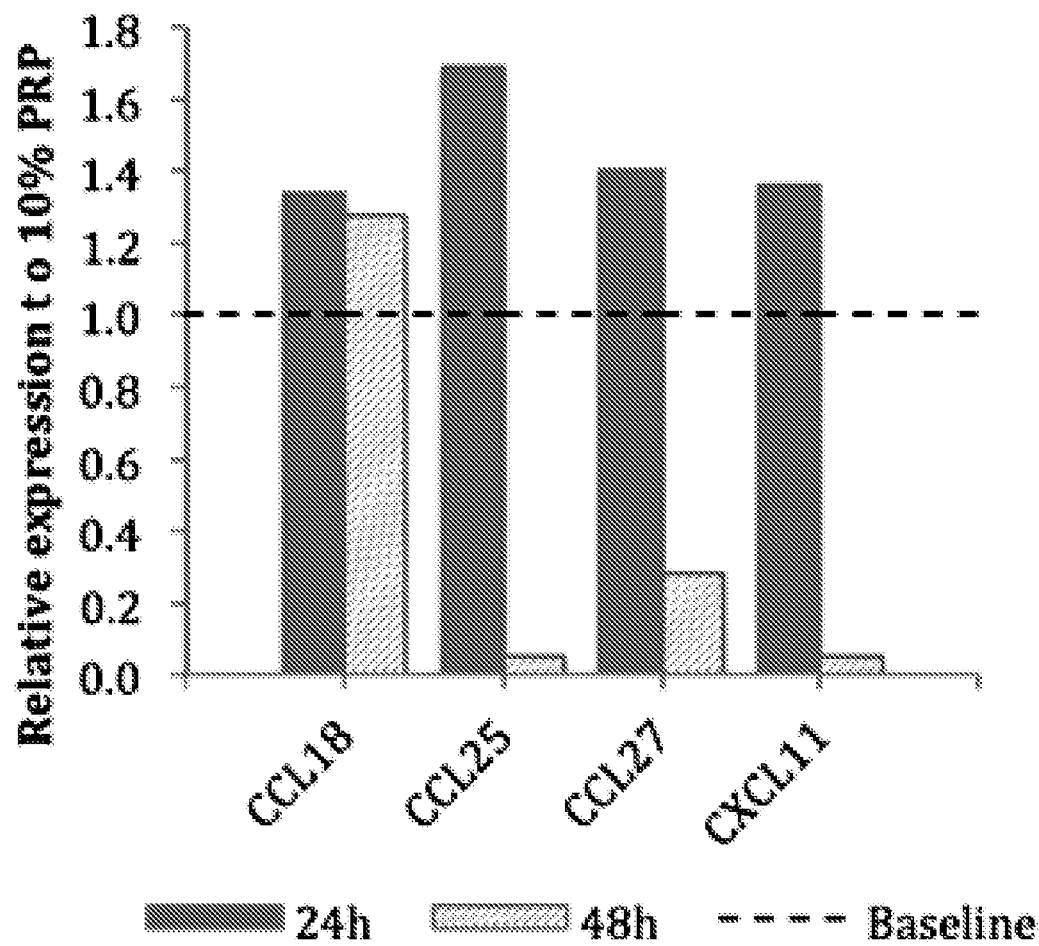
Figure 15:
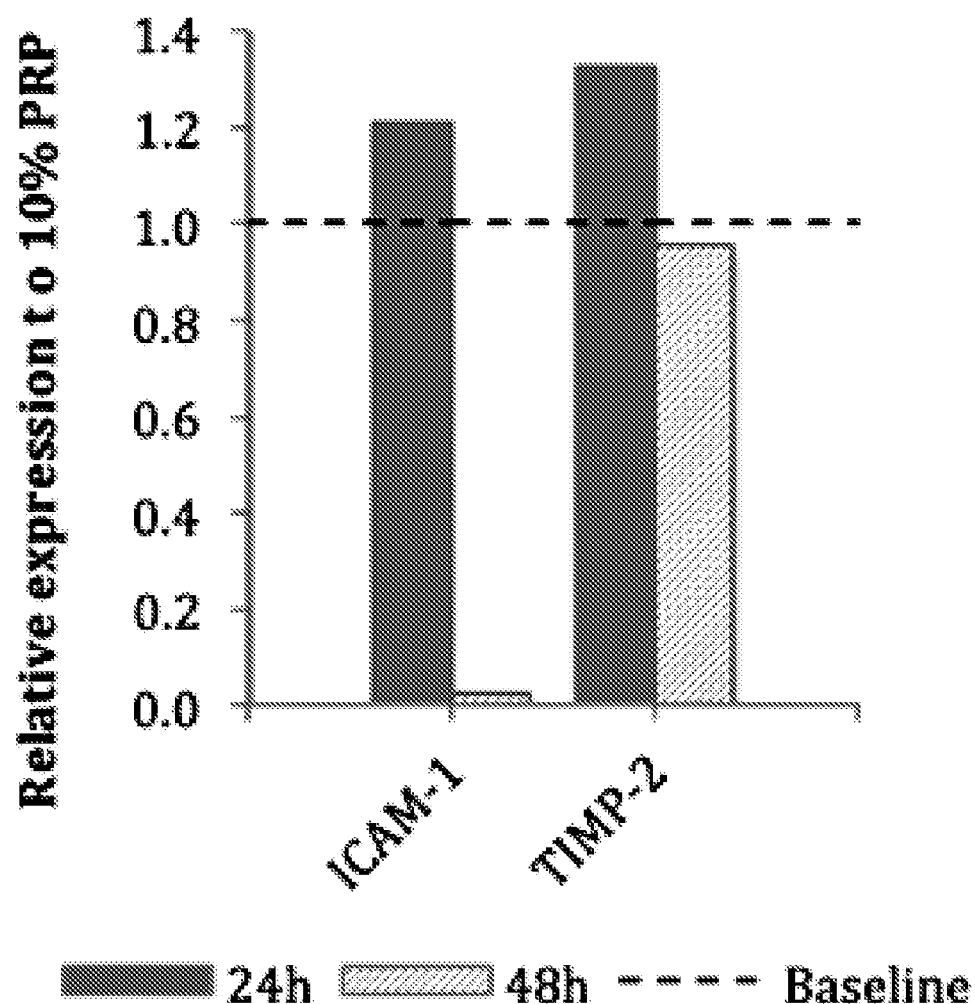
Figure 16:
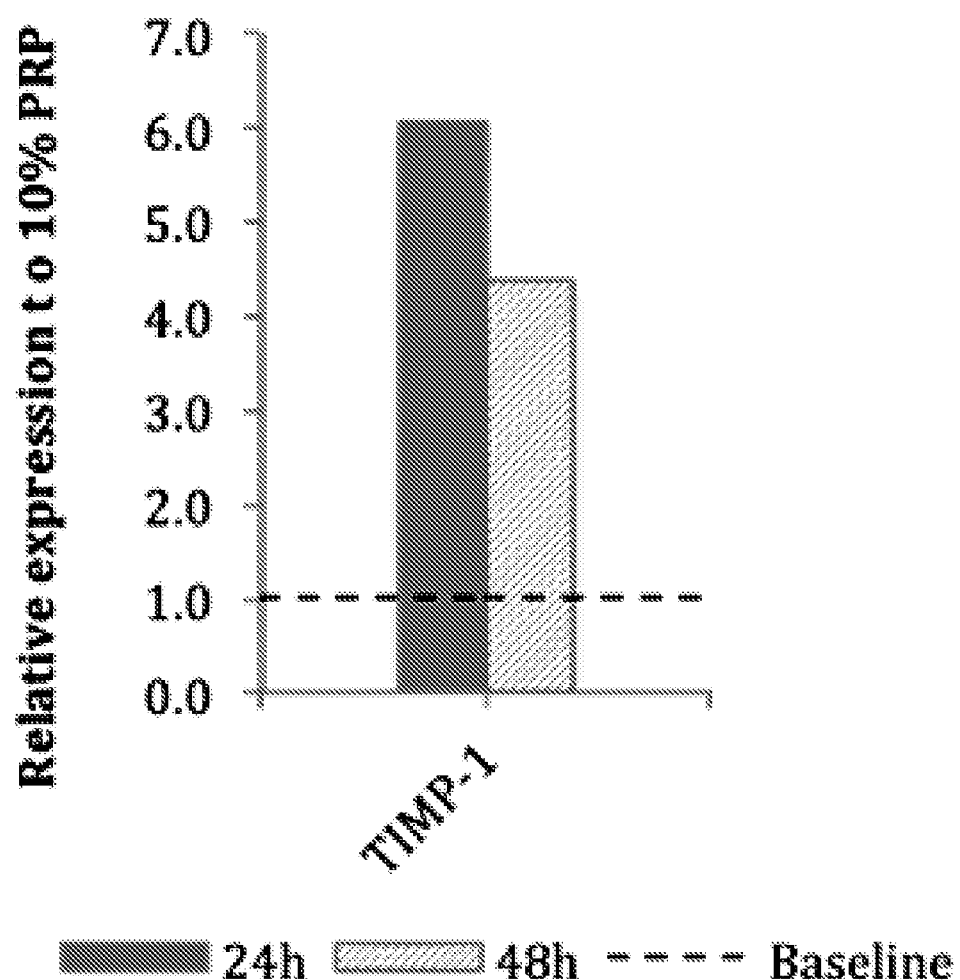
Figure 17:
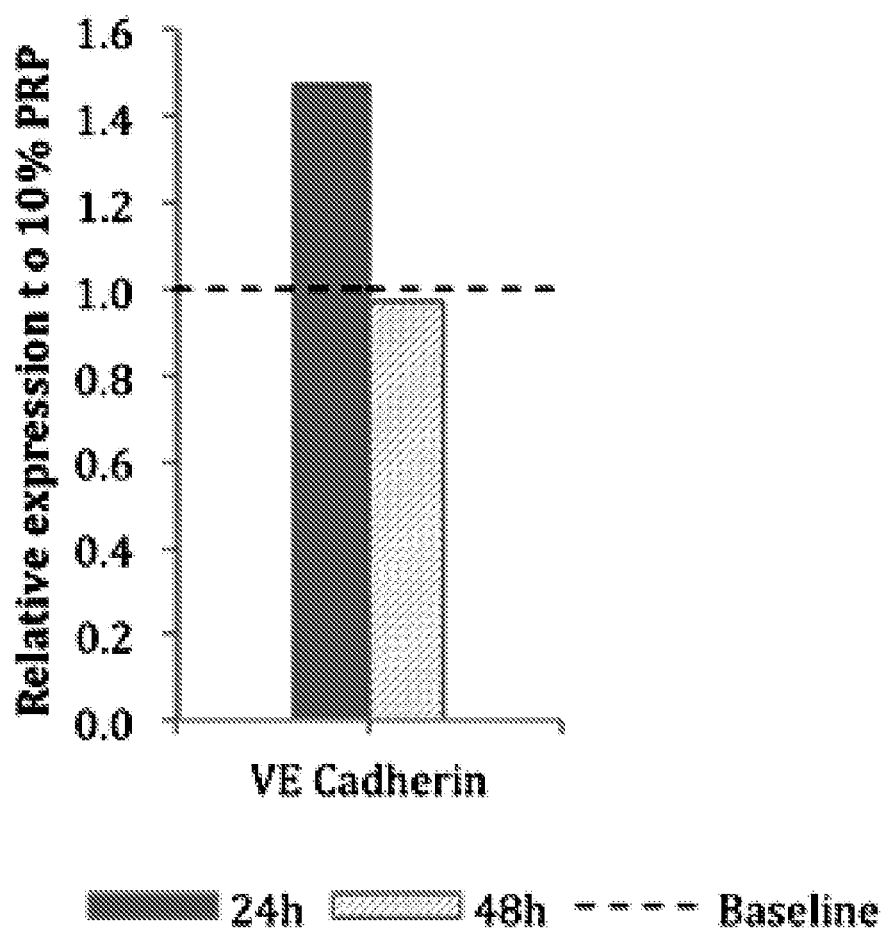

FIGS. 11-17 show the increase in secretion of the below named proteins (factors) from SR-hADSCs, 24 hours post incubation with media containing 10% PRP (platelet-rich plasma) alone (no IL-2 stimulation). Secretion levels are shown relative to the amount of the corresponding protein present at basal levels in the 10% PRP containing media, used for hADSC support. FIG. 11 shows the increase in secretion of Interleukin 5 (IL5) and Interleukin 6 (IL6). FIG. 12 shows the increase in secretion of Interleukin 1 receptor 4 (IL1R4). FIG. 13 shows the increase in secretion of Neurotrophin 3 (NT3), platelet derived growth factor A alpha (PDGF AA), platelet derived growth factor A beta (PDGF AB), and pro-platelet basic protein (PPBP). FIG. 14 shows the increase in secretion of Chemokine (C—C motif) ligand 18 (CCL18), Chemokine (C—Cmotif) ligand 25 (CCL25), Chemokine (C—C motif) ligand 27 (CCL27), and CXC chemokine ligand 11 (CXCL11). FIG. 15 shows the increase in secretion of Intercellular Adhesion Molecule 1 (ICAM-1) and Metalloproteinase inhibitor 2 (TIMP-2). FIG. 16 shows the increase in secretion of Metalloproteinase inhibitor 1 (TIMP-1). FIG. 17 shows the increase in secretion of vascular epithelium (VE) Cadherin (calcium dependent cell adhesion protein).

Figure 18:
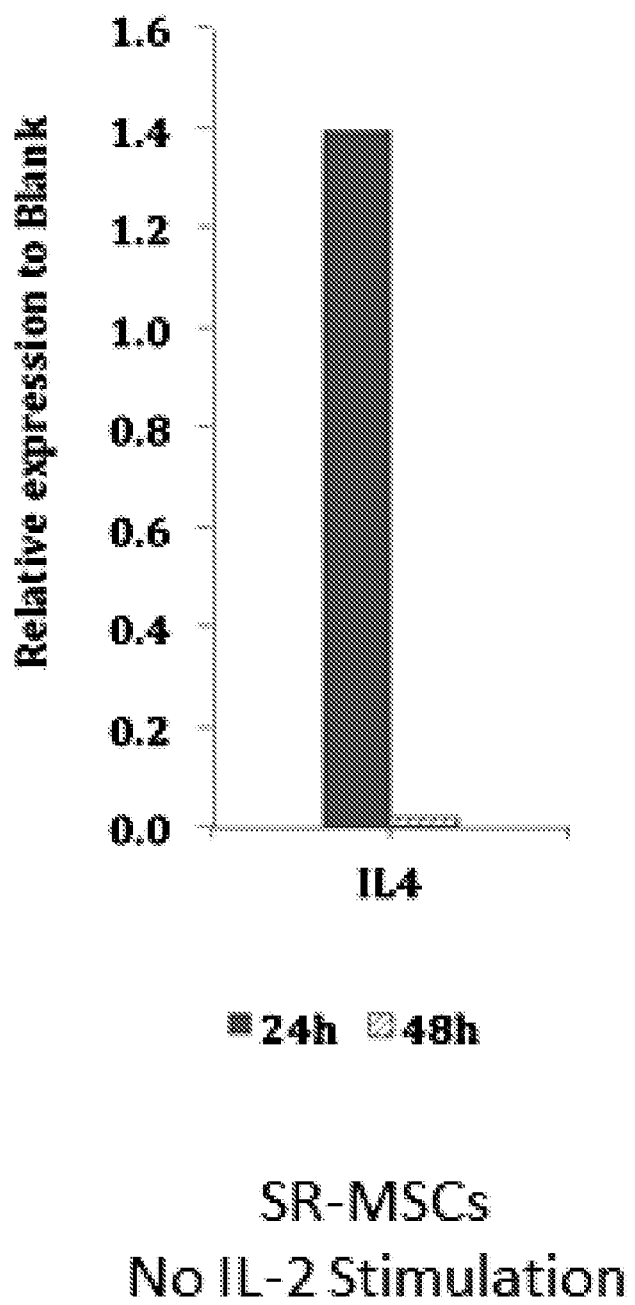
Figure 19:
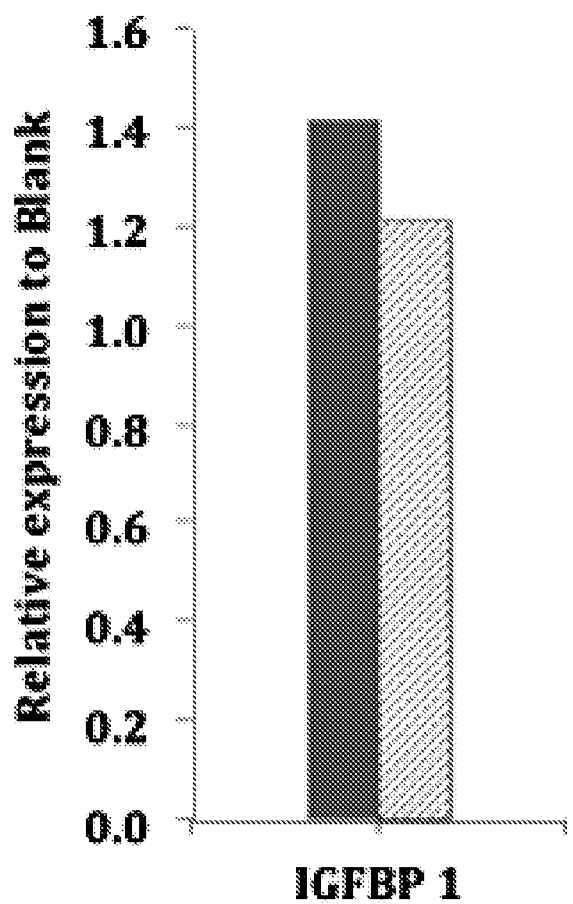

FIGS. 18-19 show the increase in secretion of the below named proteins (factors) from SR-hADSCs, 24 hours post incubation with 10% PRP alone (no IL-2 stimulation). These proteins were found to not be present in PRP. FIG. 18 shows the increase in secretion of Interleukin 4 (IL4). FIG. 19 shows the increase in secretion of insulin-like growth factor-binding protein-1 (IGFBP1).

Figure 20:
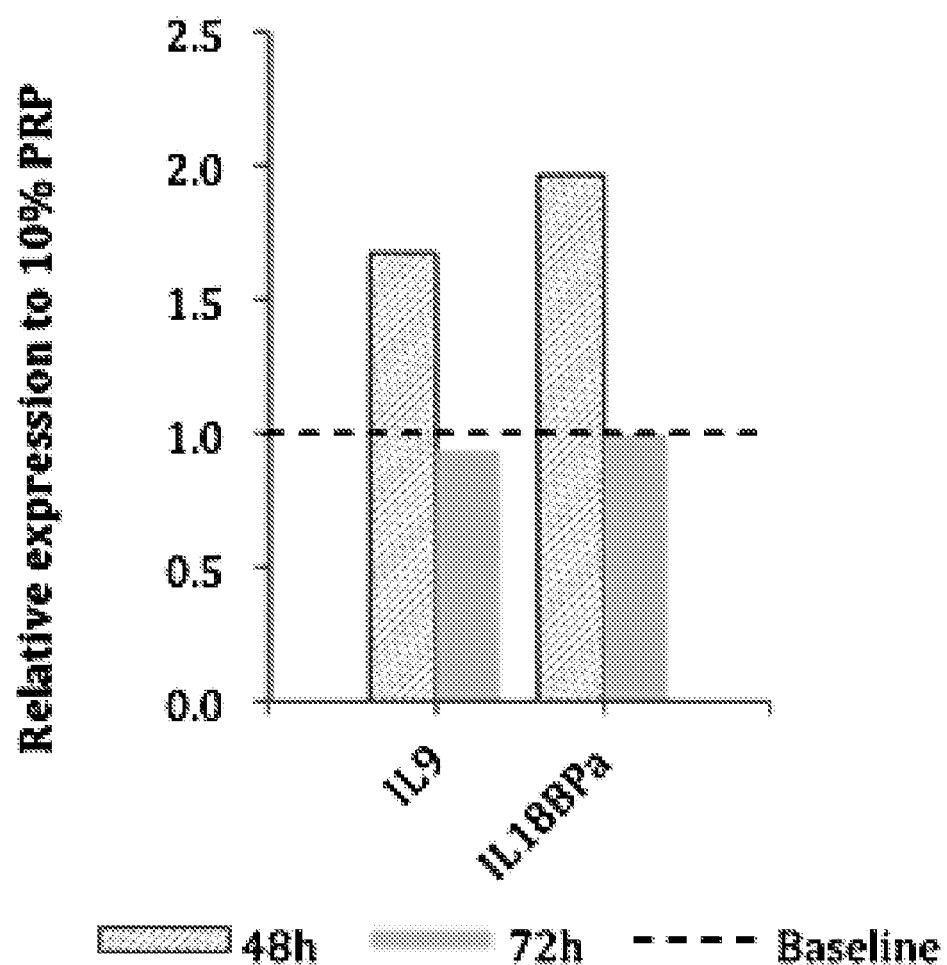
Figure 21:
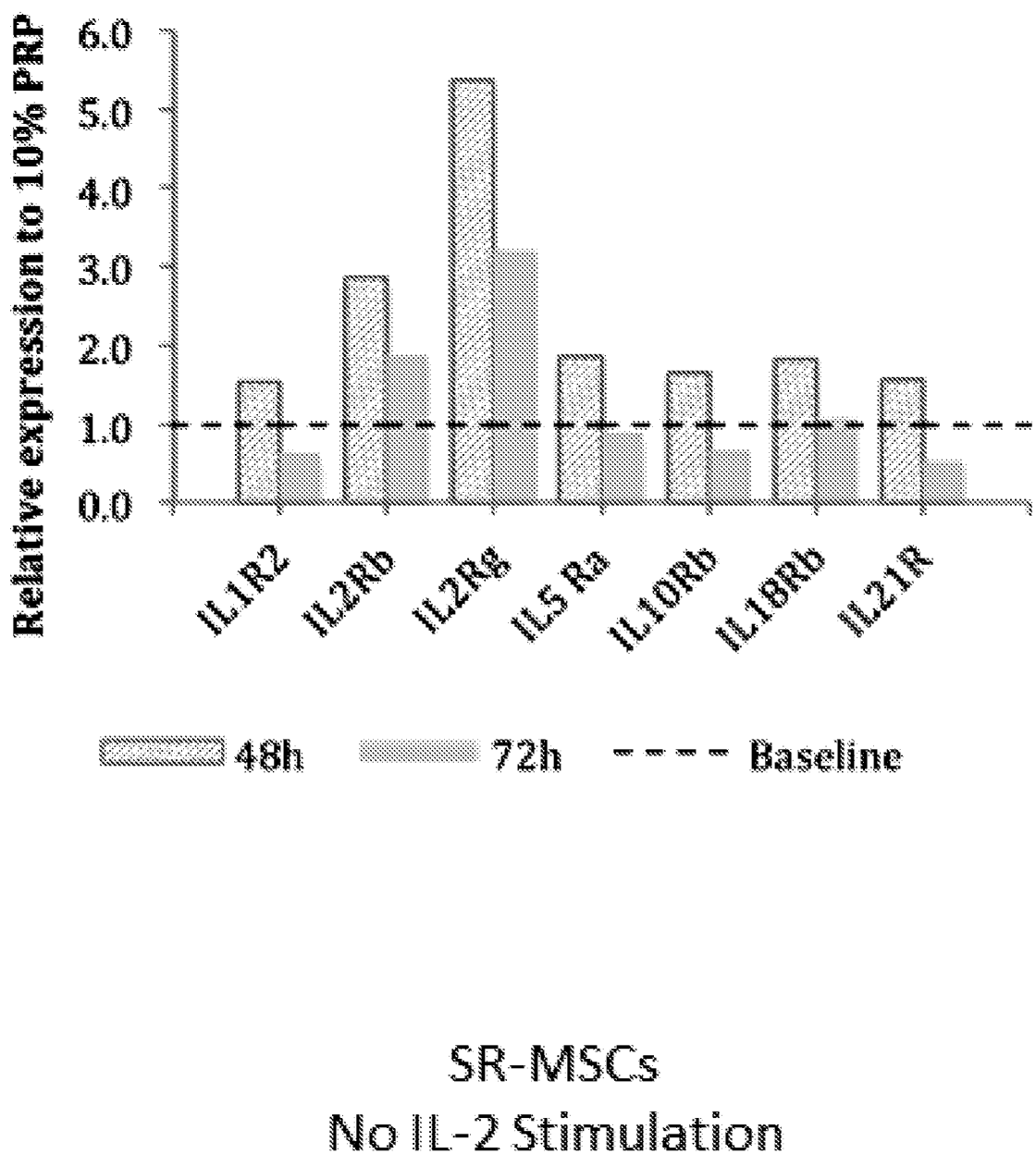
Figure 22:
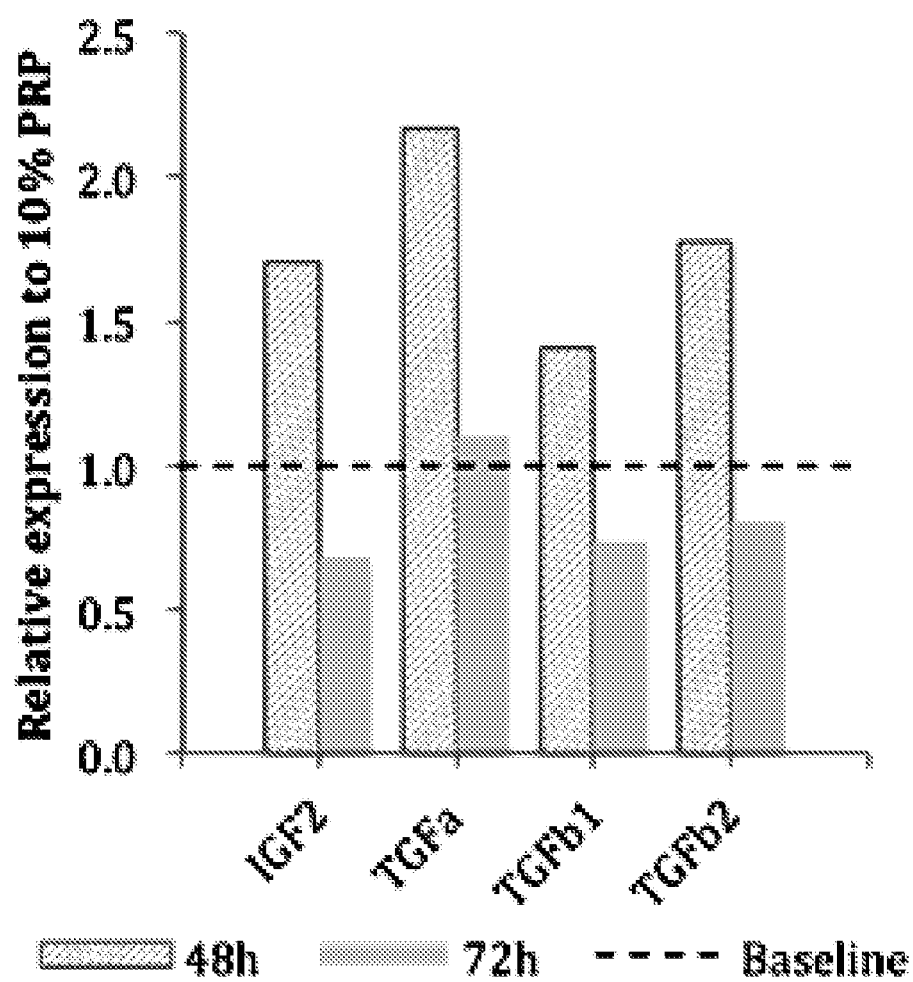
Figure 23:
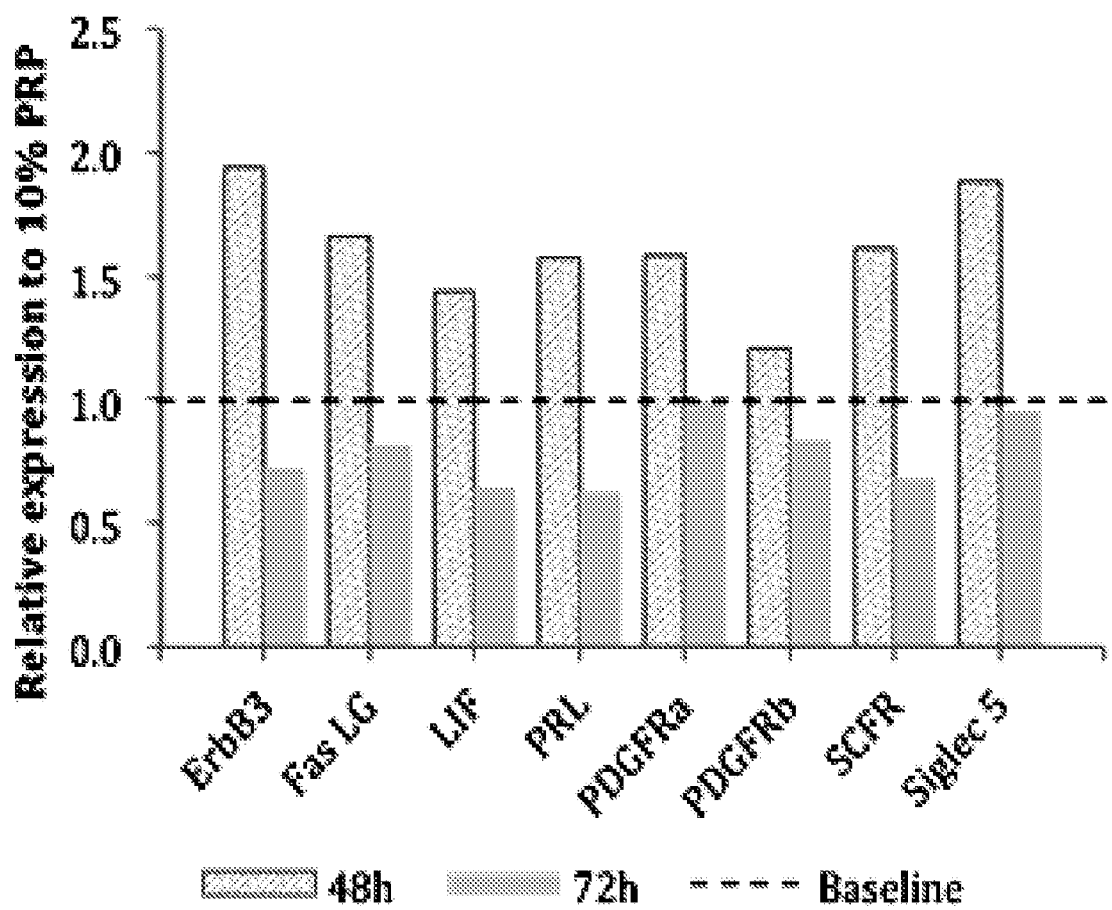
Figure 24:
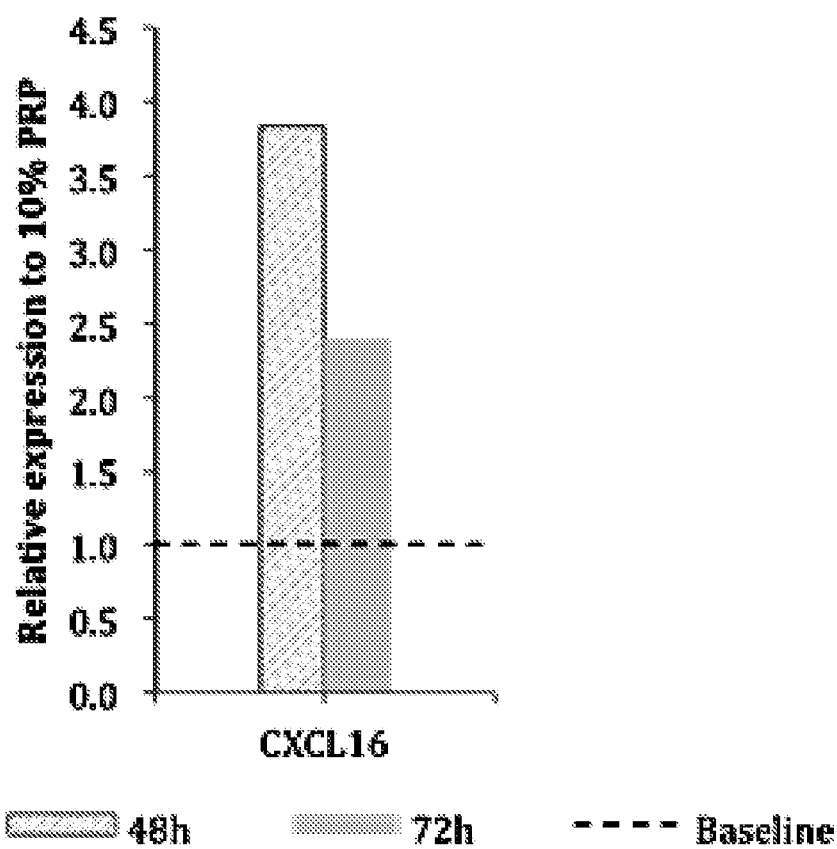
Figure 25:
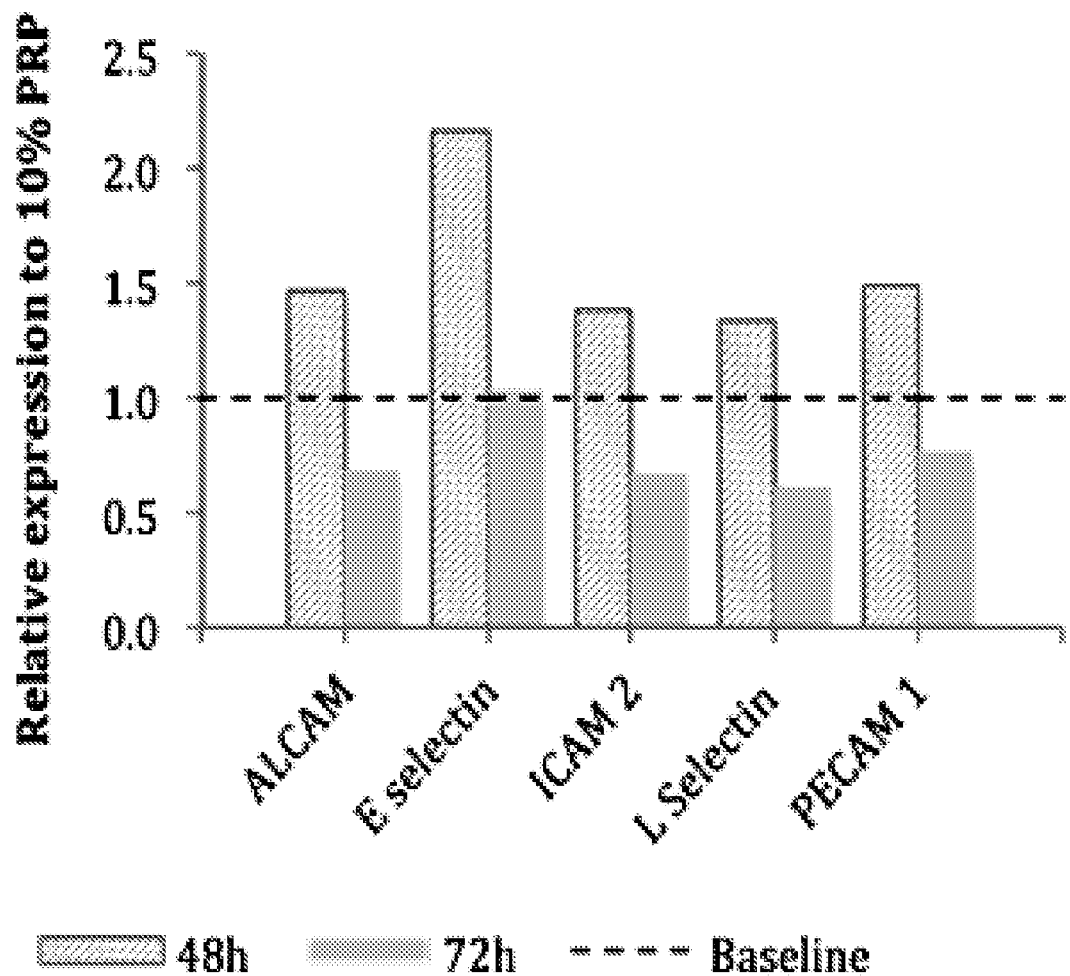
Figure 26:
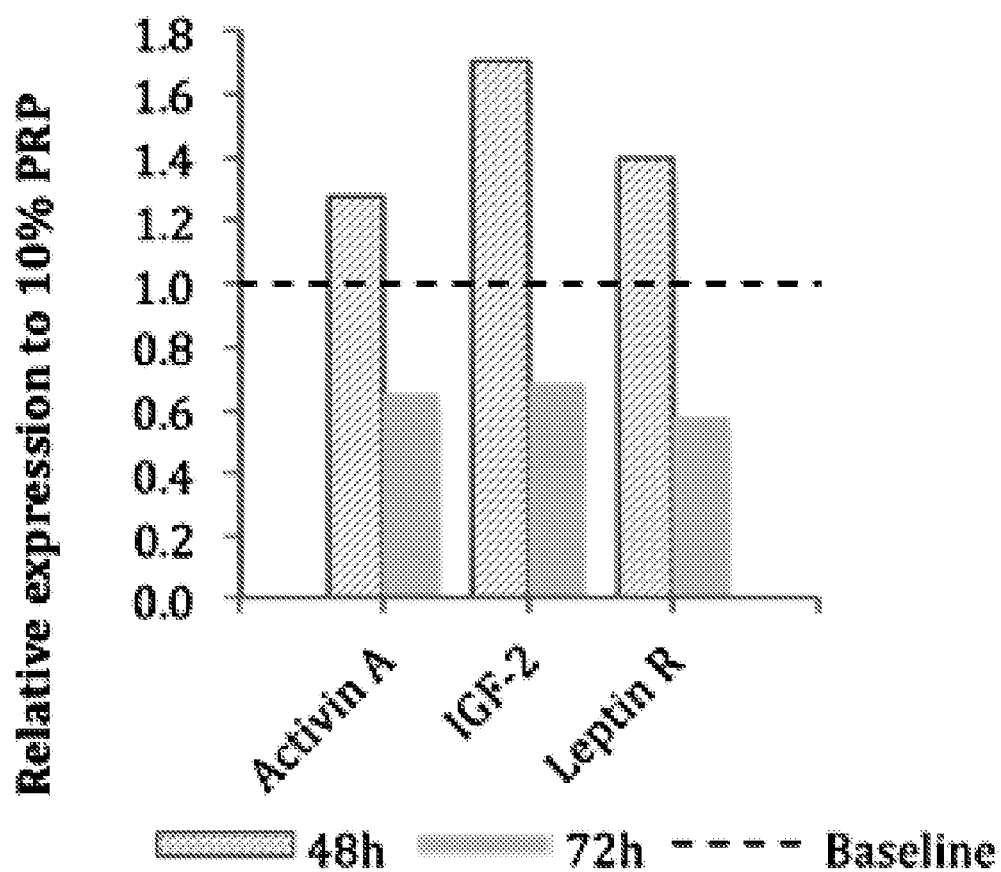
Figure 27:
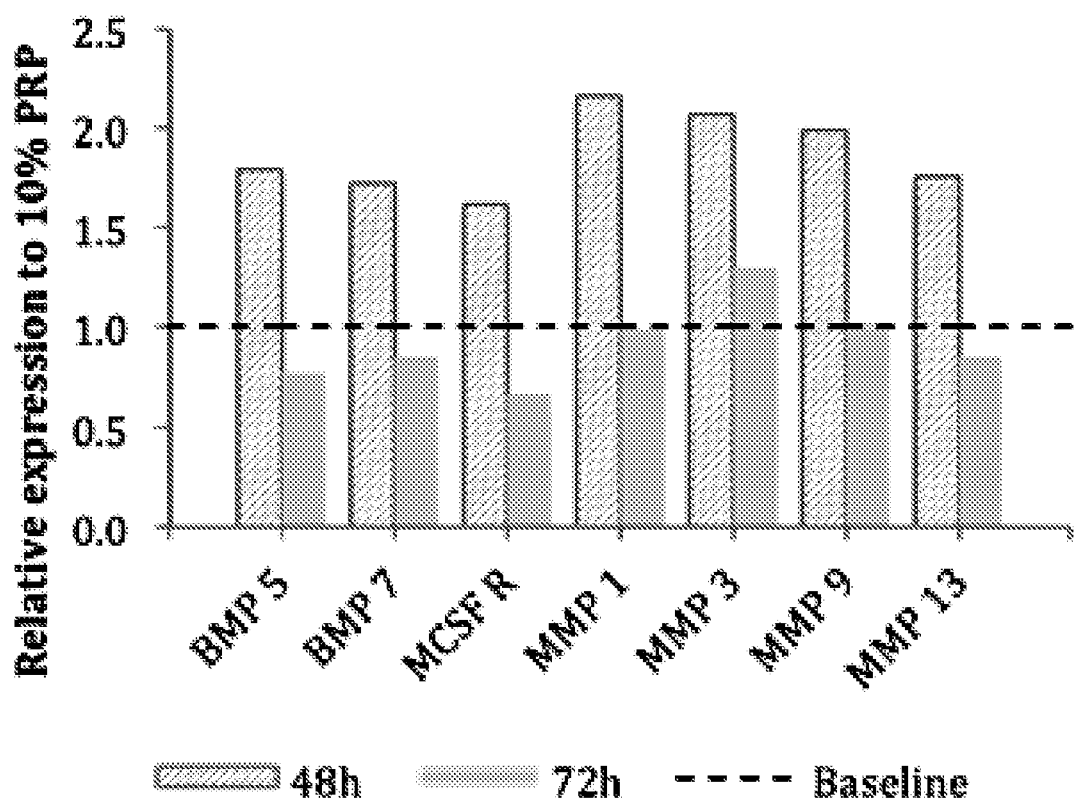
Figure 28:
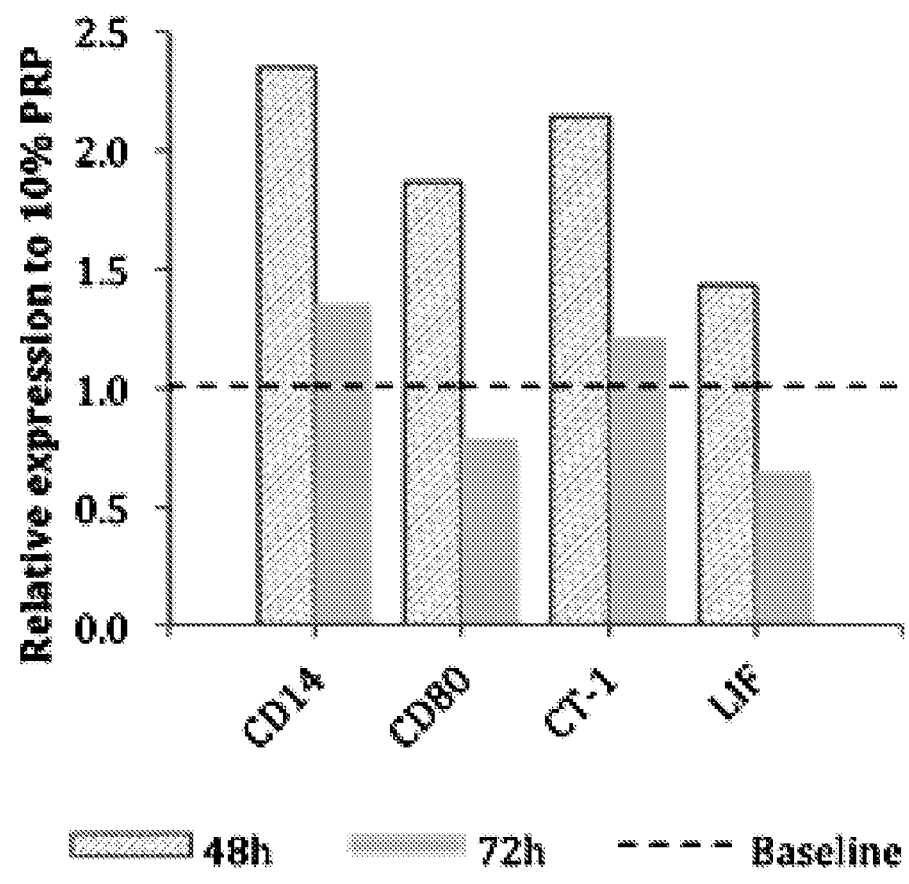
Figure 29:
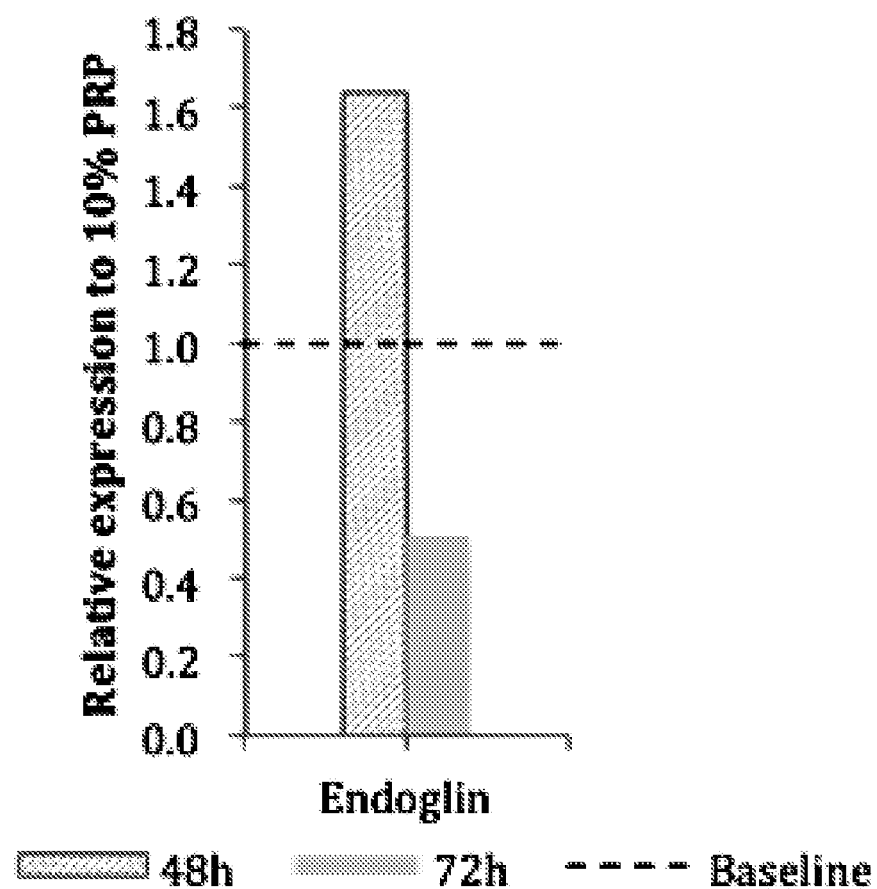
Figure 30:
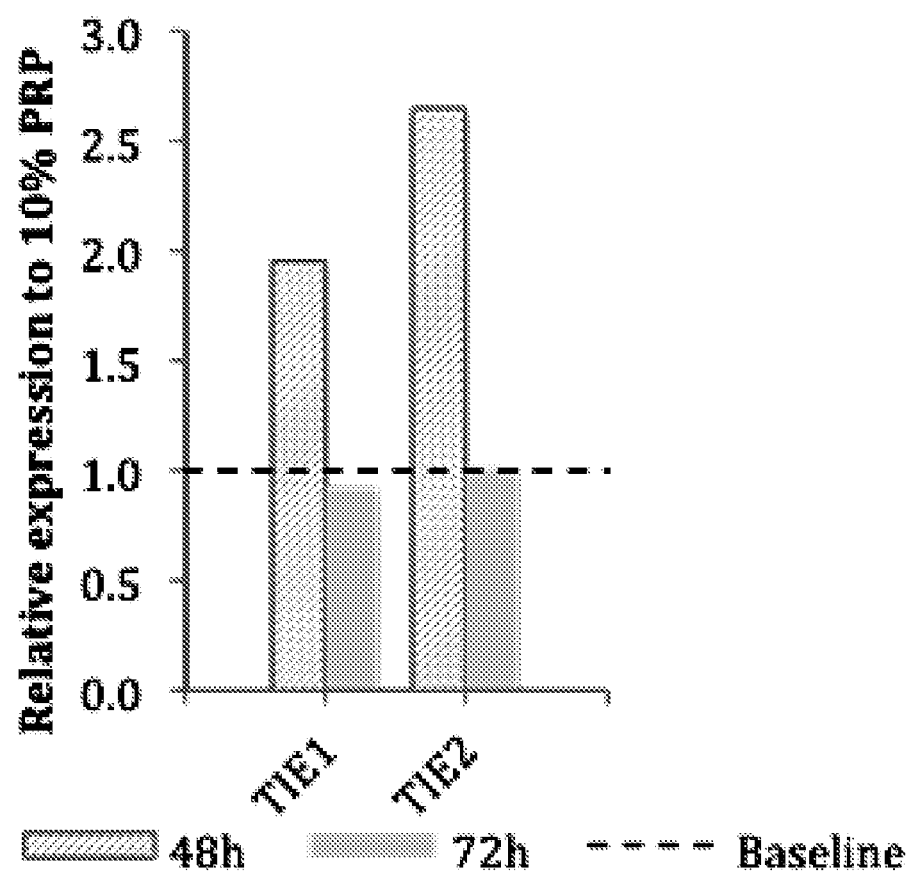
Figure 31:
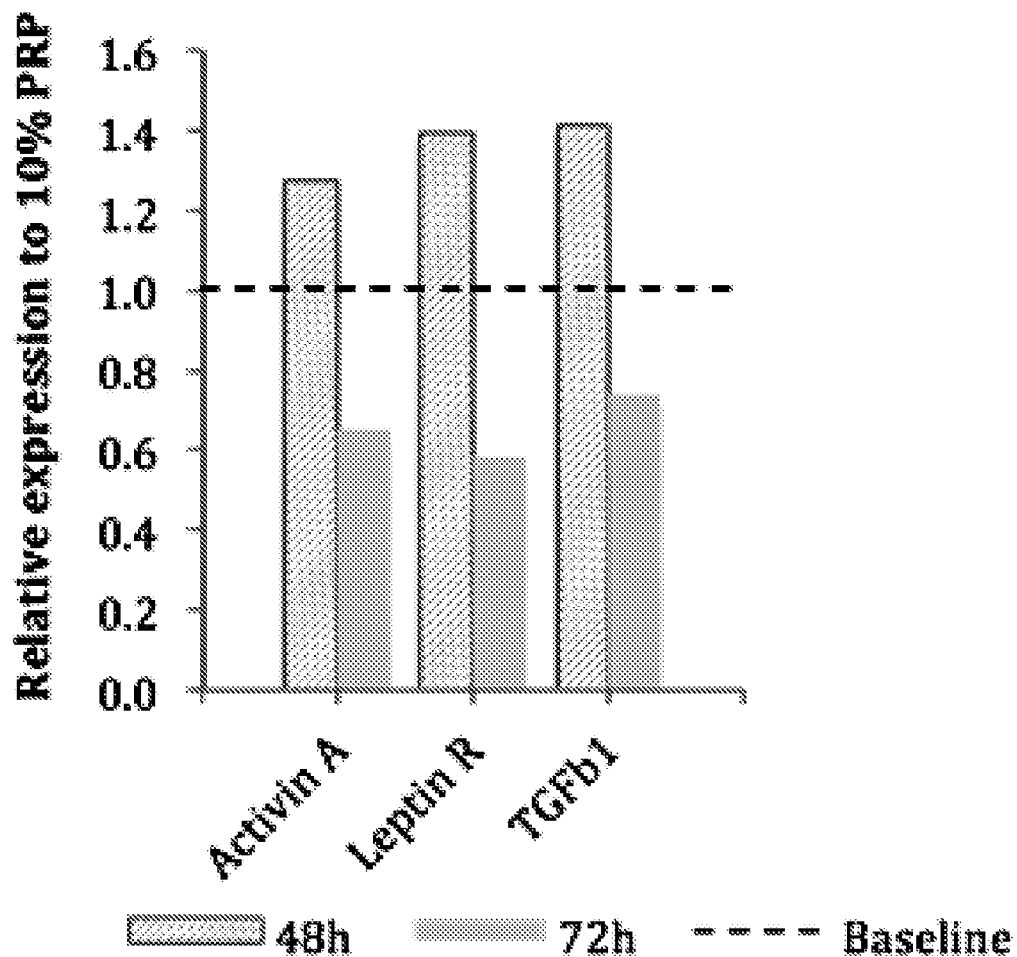

FIGS. 20-31 show an increase in the below named proteins (factors) from SR-hADSCs, 48 hours post incubation with 10% PRP alone (no IL-2 stimulation). Secretion levels are shown relative to the amount of the corresponding protein present at basal levels in the 10% PRP containing media, used for hADSC support. FIG. 20 shows the increase in secretion of Interleukin 9 (IL9) and Interleukin 18 binding protein alpha (IL18BPa). FIG. 21 shows the increase in secretion of Interleukin 1 receptor type II (IL1R2), Interleukin 2 receptor beta (IL-2Rb), Interleukin 2 receptor gamma (IL-2Rg), Interleukin 5 receptor alpha (IL5Ra), Interleukin 10 receptor beta (IL10Rb), Interleukin 18 receptor accessory protein (IL18Rb), and Interleukin 21 receptor (IL-21R). FIG. 22 shows the increase in secretion of Insulin-like growth factor 2 (IGF2), Transforming growth factor alpha (TGFα), Transforming growth factor beta 1/latency-associated peptide (LAP) (TGFβ1), and Transforming growth factor beta 2 (TGFb2). FIG. 23 shows the increase in secretion of Receptor tyrosine-protein kinase ErbB-3 (ErbB3), Fas ligand (Fas LG), Leukemia inhibitory factor (LIF), Prolactin (PRL) factor, platelet-derived growth factor receptor alpha (PDGFRα), platelet-derived growth factor receptor beta (PDGFRβ), Stem cell factor kit receptor (SCFR), and Sialic acid-binding Ig-like Lectin 5 (Siglec 5). FIG. 24 shows the increase in secretion of CXC chemokine ligand 16 (CXCL16). FIG. 25 shows the increase in secretion of activated leukocyte cell adhesion molecule (AL-CAM), E selectin (cell surface glycoprotein in immune-adhesion), Intercellular adhesion molecule 2 (ICAM2), L selectin (Leukocyte adhesion molecule), and Platelet endothelial cell adhesion molecule (PECAM 1). FIG. 26 shows the increase in secretion of Activin A (INHBA), Insulin-like growth factor 2 (IGF-2), and Leptin Receptor (LEPR). FIG. 27 shows the increase in secretion of Bone morphogenetic protein 5 (BMP5), Bone morphogenetic protein 7 (BMP7), Macrophage colony-stimulating factor 1 receptor (MCSFR), matrix metalloproteinase 1 (MMP1), matrix metalloproteinase 3 (MMP3), matrix metalloproteinase 9 (MMP9), and matrix metalloproteinase 13 (MMP13). FIG. 28 shows the increase in secretion of monocyte differentiation antigen (CD14), cell differentiation antigen (CD80), Cardiotrophin-1 (CT-1), and Leukemia inhibitory factor (LIF). FIG. 29 shows the increase in secretion of Endoglin (ENG). FIG. 30 shows the increase in secretion of Tyrosine kinase with immunoglobulin-like and EGF-like domains 1 (TIE-1) and Tyrosine kinase with immunoglobulin-like and EGF-like domains 2 (TIE-2). FIG. 31 shows the increase in secretion of Activin A (Inhibin beta A, INHBA), Leptin Receptor (Leptin R), and Transforming growth factor beta 1 (TGFβ1).

Figure 32:
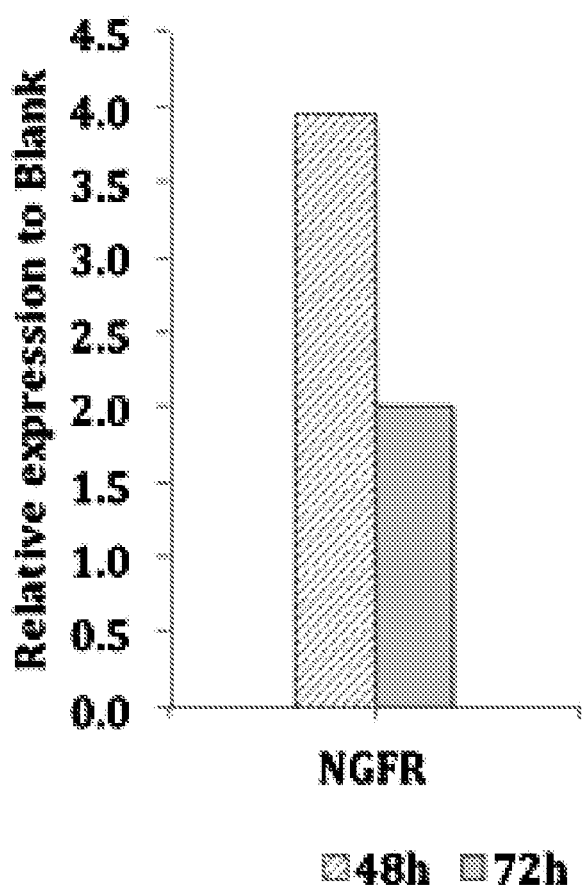

FIG. 32 shows the increase in secretion of Nerve growth factor receptor (NGFR) from SR-MSCs, 48 hours post incubation with 10% PRP alone (no IL-2 stimulation). NGFR was found to not be present in PRP.

Figure 33:
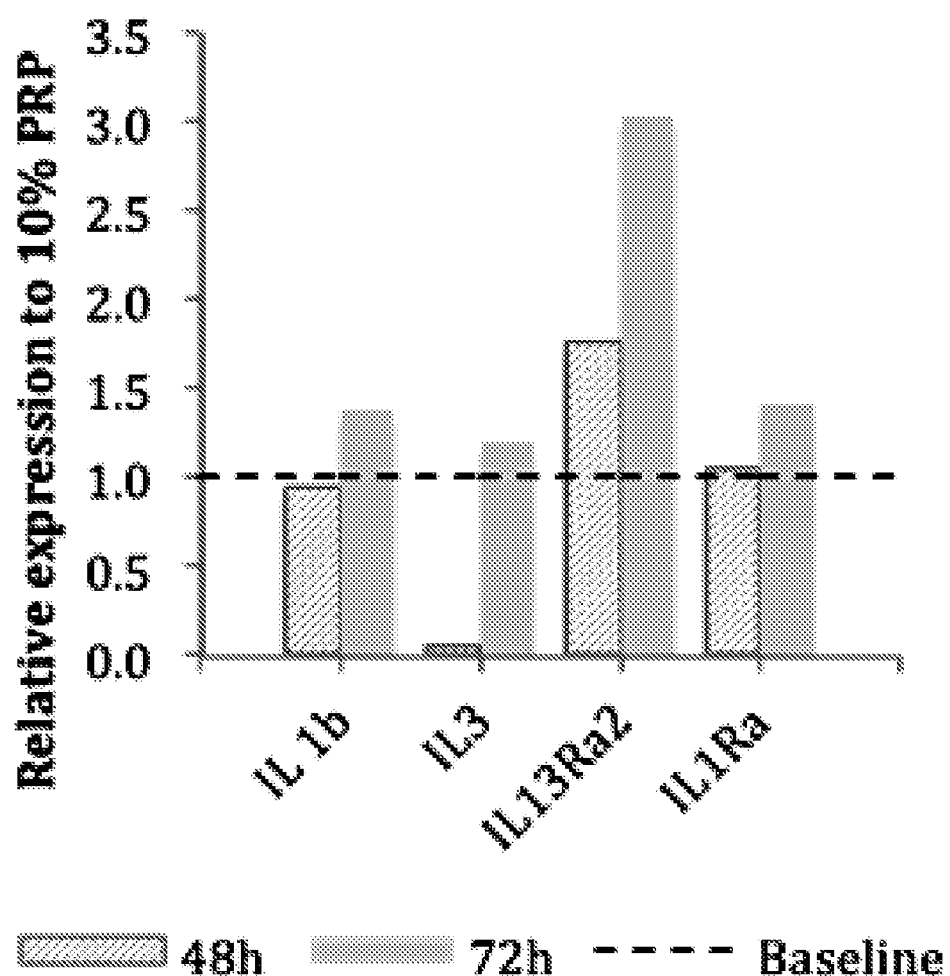
Figure 34:
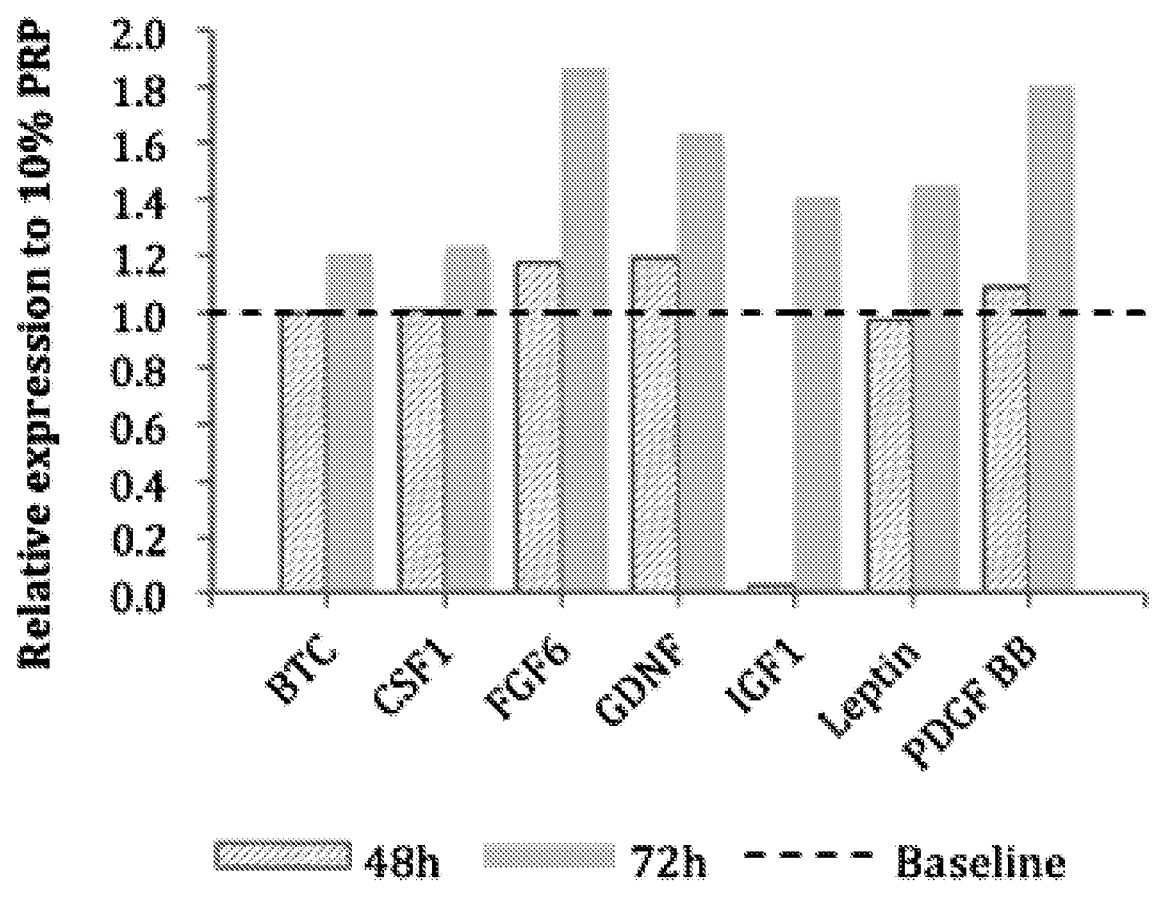
Figure 35:
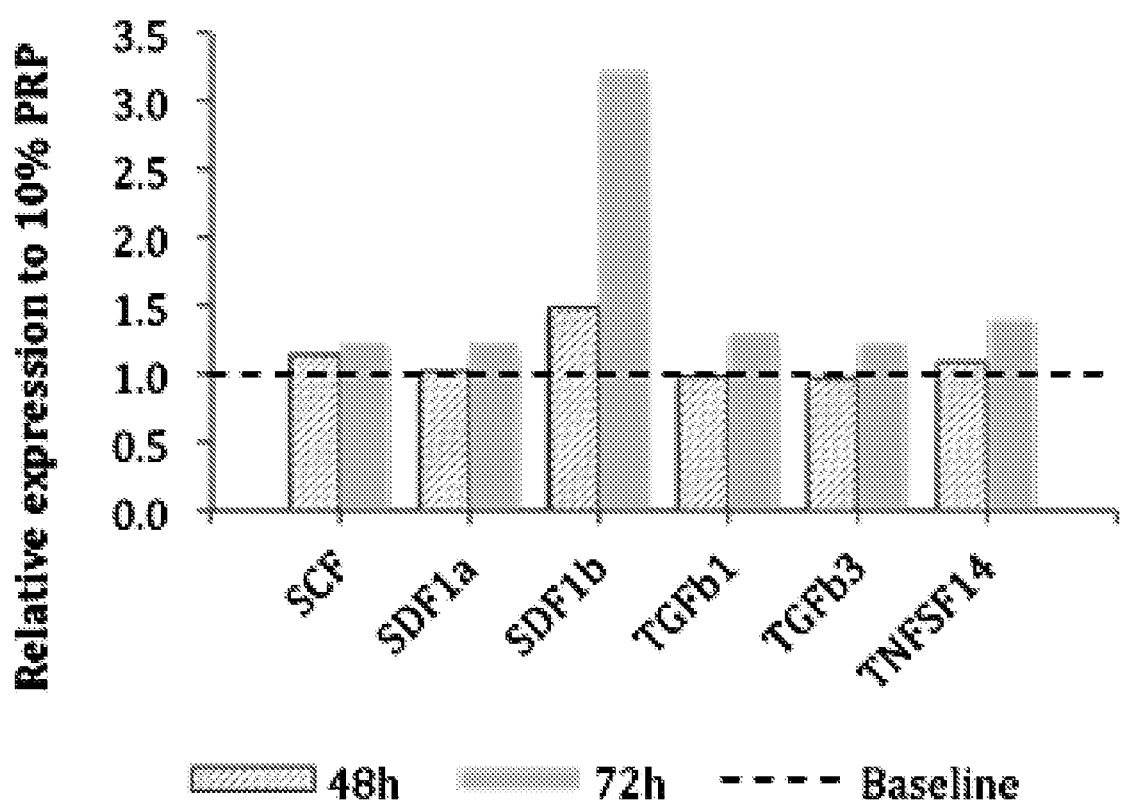
Figure 36:
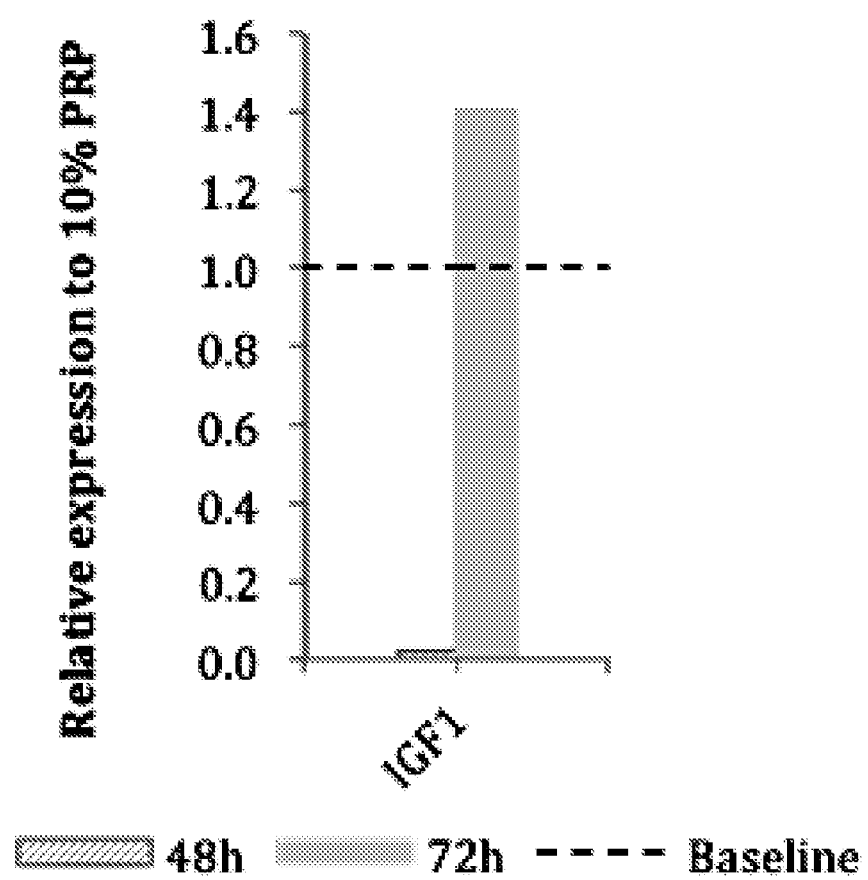
Figure 37:
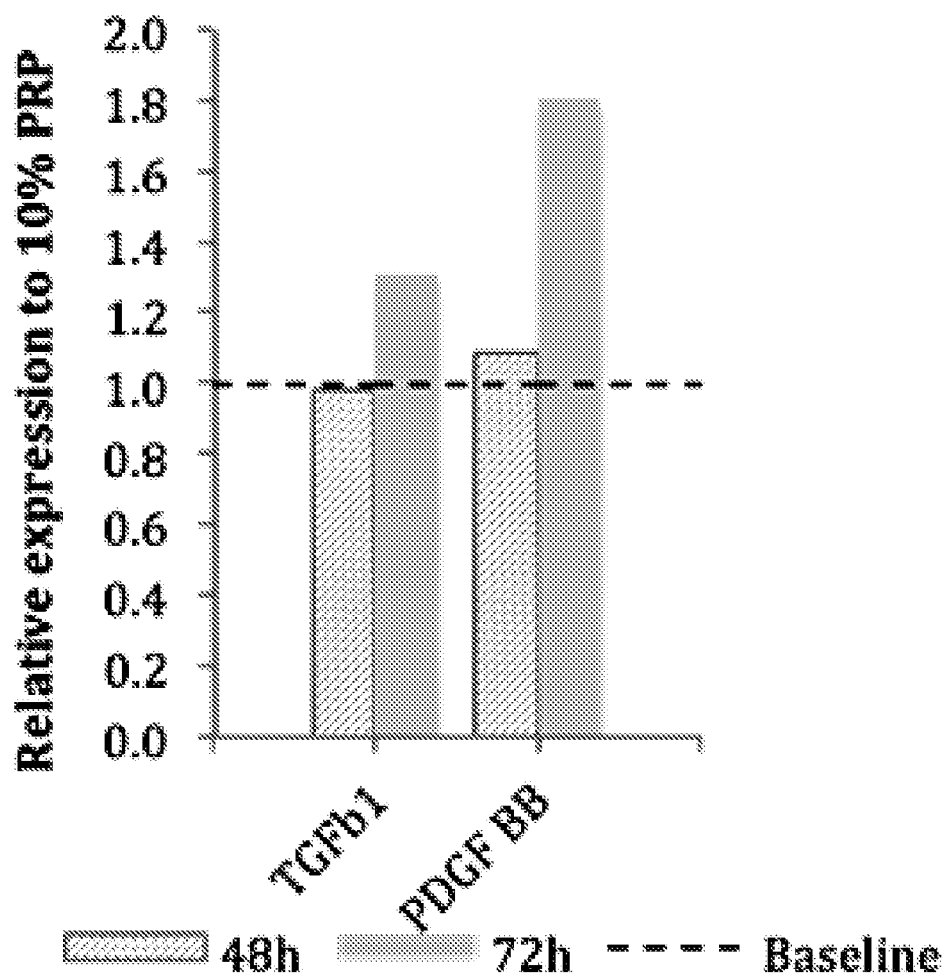
Figure 38:
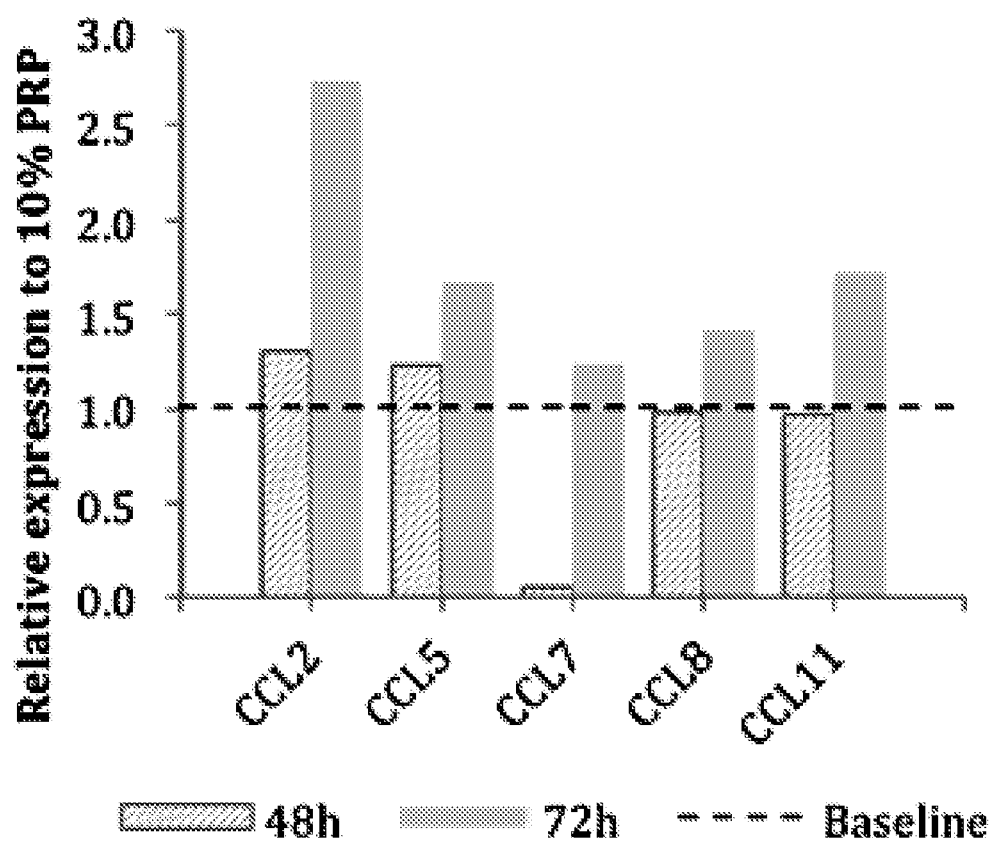
Figure 39:
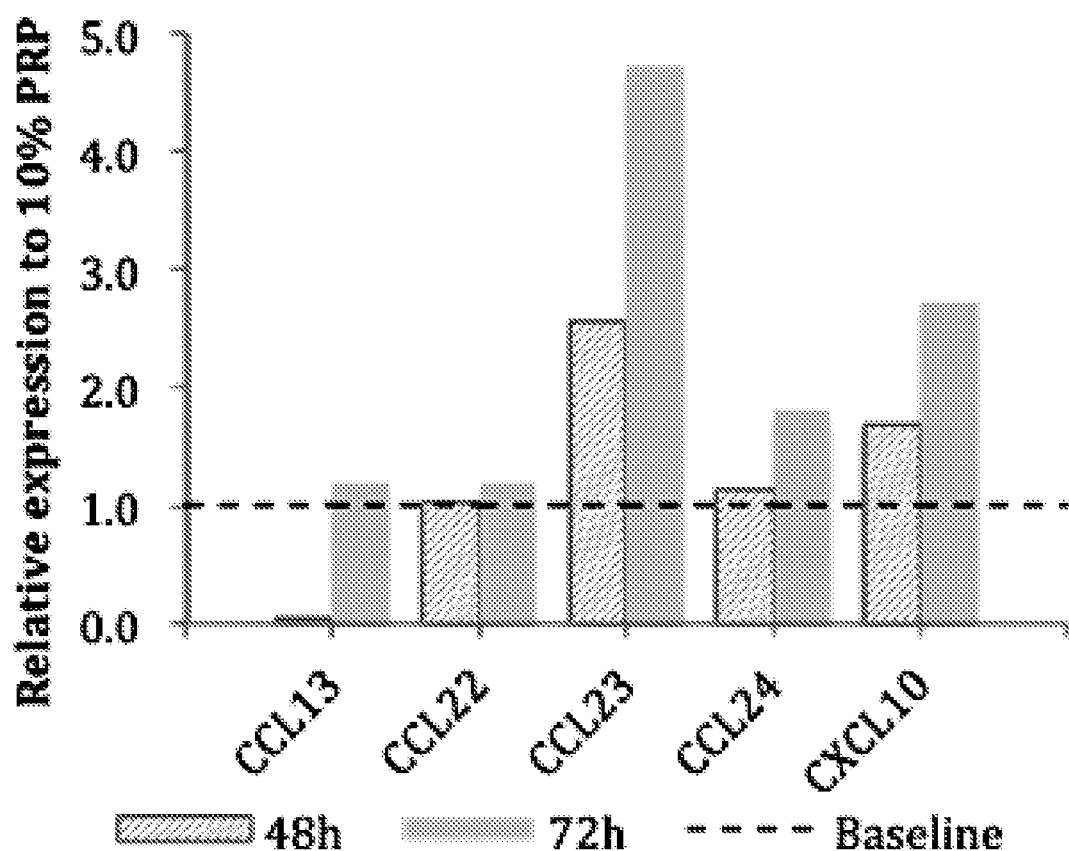

FIGS. 33-39 show the increase in secretion of the below named proteins (factors) from SR-hADSCs, 72 hours post incubation with 10% PRP alone (no IL-2 stimulation). Secretion levels are shown relative to the amount of the corresponding protein present at basal levels in the 10% PRP containing media, used for hADSC support. FIG. 33 shows the increase in secretion of Interleukin 1 beta (IL1β), Interleukin 3 (IL3), Interleukin-13 Receptor subunit alpha-2 (IL13Rα2), and Interleukin 1 receptor alpha (IL1Ra). FIG. 34 shows the increase in secretion of Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, and platelet-derived growth factor B beta (PDGF BB). FIG. 35 shows the increase in secretion of stem cell factor/c-kit ligand (SCF), Stromal Cell-Derived Factor-1 alpha (SDF1a), Stromal Cell-Derived Factor-1 beta (SDF1b), Transforming growth factor beta 1 (TGFβ1), Transforming growth factor beta 3 (TGFb3), and tumor necrosis factor superfamily member 14 (TNFSF14). FIG. 36 shows the increase in secretion of Insulin-like growth factor 1 (IGF1). FIG. 37 shows the increase in secretion of Transforming growth factor beta 1 (TGFβ1) and platelet-derived growth factor B beta (PDGF BB). FIG. 38 shows the increase in secretion of Chemokine (C—C motif) ligand 2 (CCL2), Chemokine (C—C motif) ligand 5 (CCL5), Chemokine (C—C motif) ligand 7 (CCL7), Chemokine (C—C motif) ligand 8 (CCL8), and Chemokine (C—C motif) ligand 11 (CCL11). FIG. 39 shows the increase in secretion of Chemokine (C—C motif) ligand 13 (CCL13), Chemokine (C—C motif) ligand 22 (CCL22), Chemokine (C—C motif) ligand 23 (CCL23), Chemokine (C—C motif) ligand 24 (CCL24), and CXC Chemokine ligand 10 (CXCL10).

Figure 40:
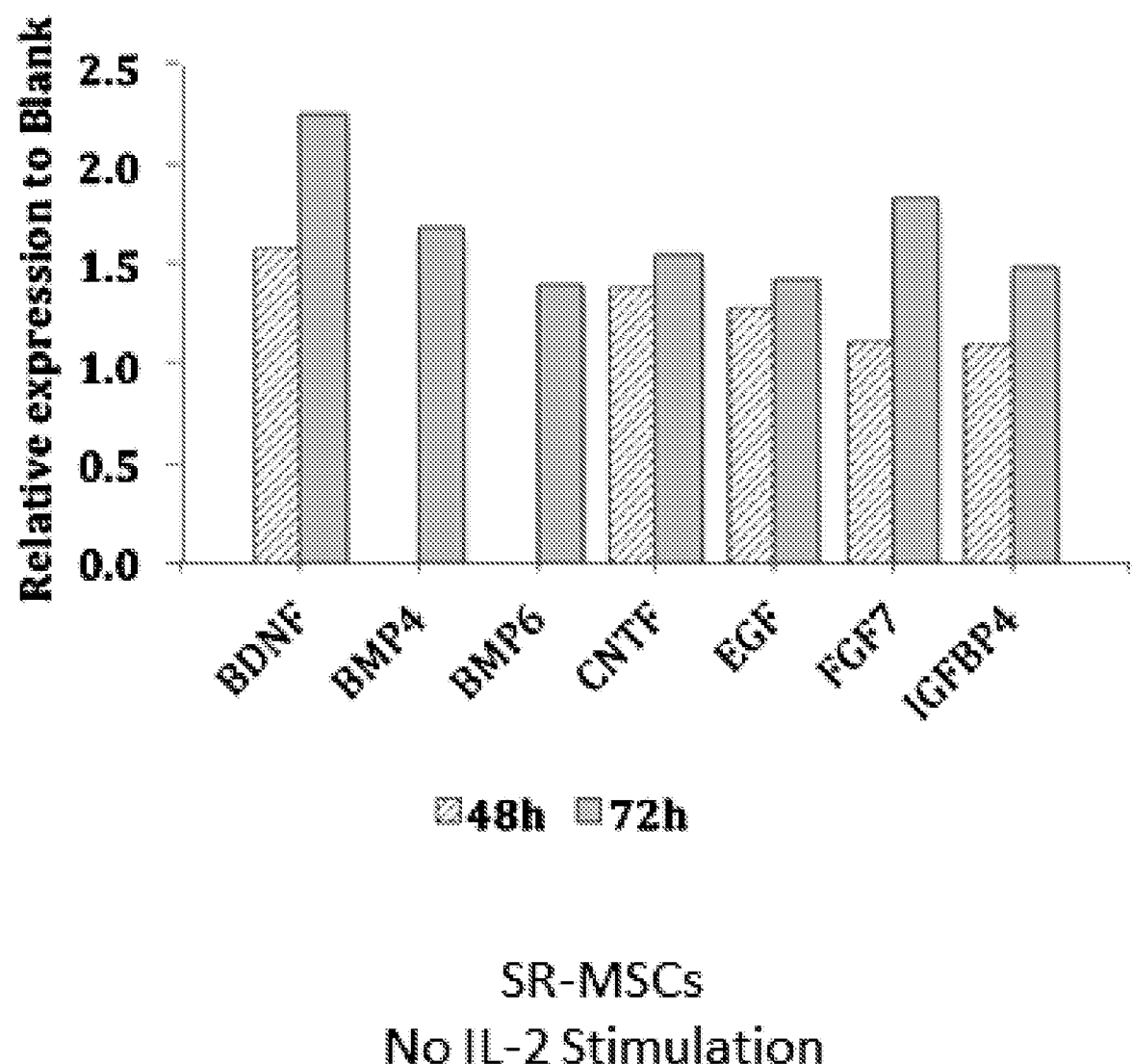
Figure 41:
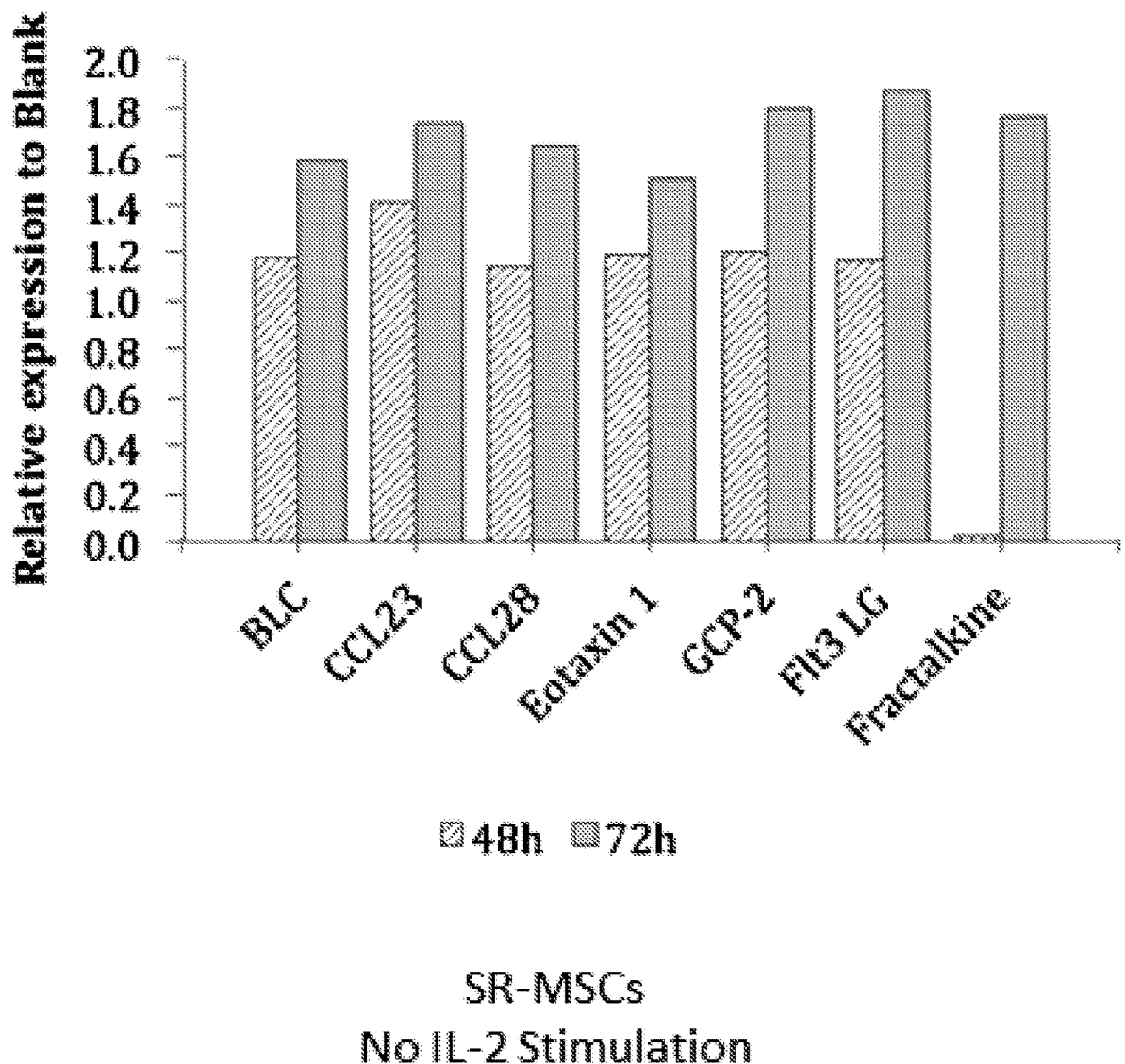
Figure 42:
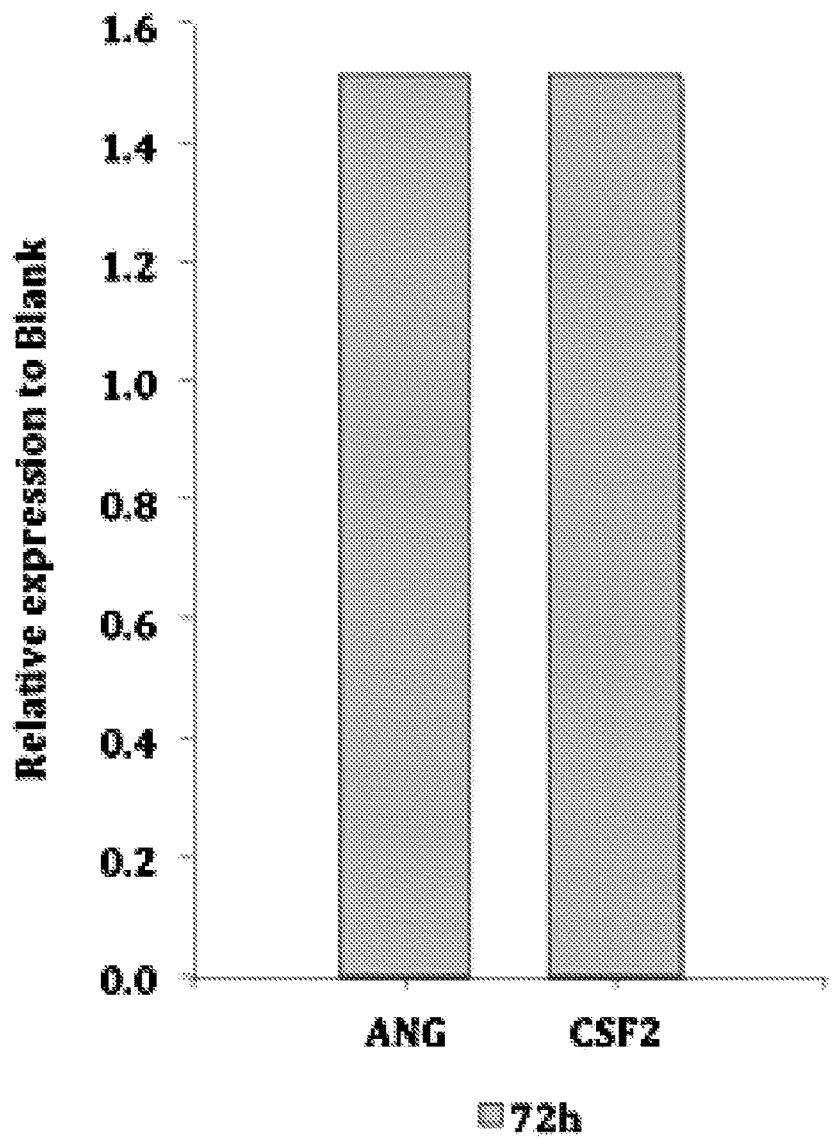

FIGS. 40-42 show the increase in secretion of the below named proteins (factors) from SR-hADSCs, 72 hours post incubation with 10% PRP alone (no IL-2 stimulation). These factors were found to not be present in PRP. FIG. 40 shows the increase in secretion of Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), and insulin-like growth factor-binding protein-4 (IGFBP4). FIG. 41 shows the increase in secretion of chemokine (C—X—C motif) ligand 13 (BLC), Chemokine (C—C motif) ligand 23 (CCL23), Chemokine (C—C motif) ligand 28 (CCL28), chemokine (C—C motif) ligand 11 (Eotaxin 1), Chemokine (C—X—C motif) ligand 6 (GCP-2), FLT3LG (Fms-Related Tyrosine Kinase 3 Ligand), and Fractalkine (CX3CL1). FIG. 42 shows the increase in secretion of Angiotensin (ANG) and colony stimulating factor 2 (CSF2).

Figure 43:
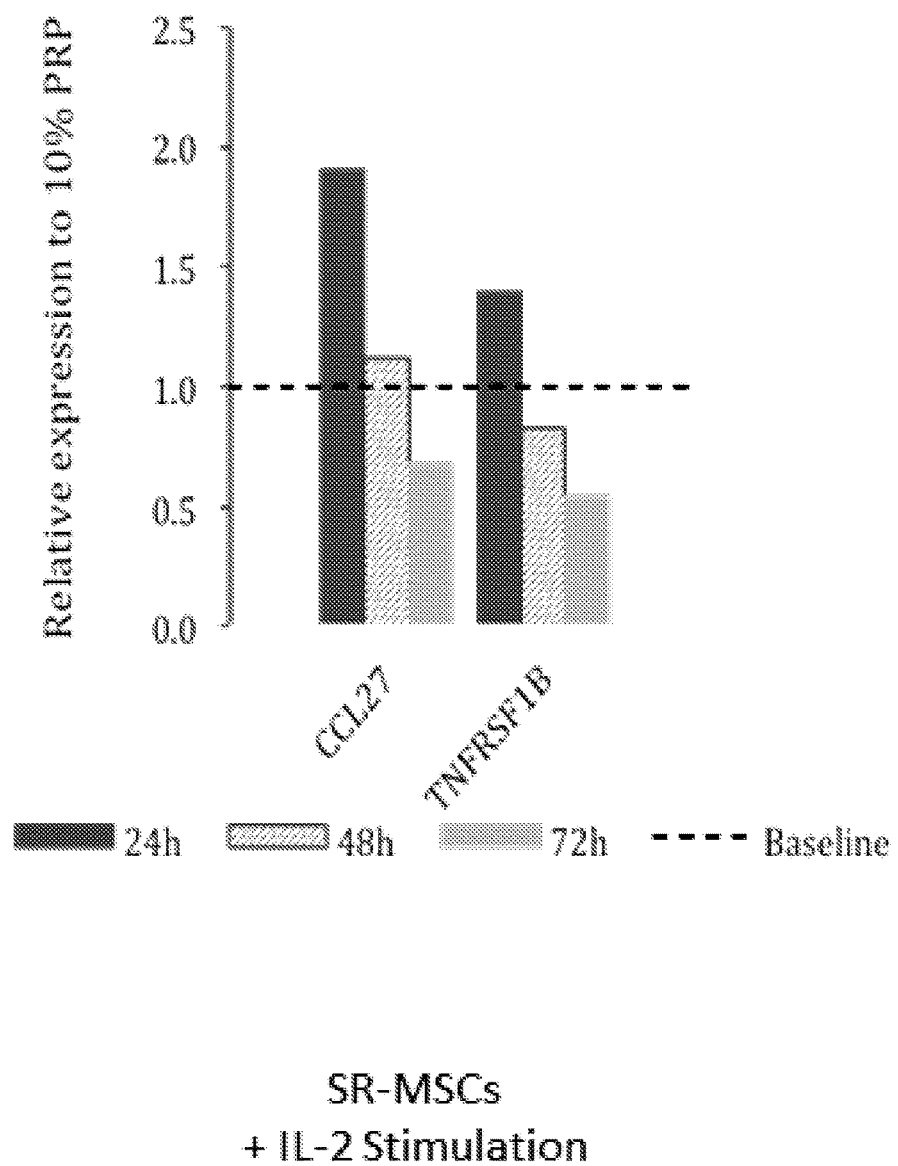

FIG. 43 shows the increase in secretion of Chemokine (C—C motif) ligand 27 (CCL27) and TNFRSF1B (Tumor Necrosis Factor Receptor Superfamily, Member 1B) from SR-hADSCs, 24 hours post stimulation with IL-2. Secretion levels are shown relative to the amount of the corresponding protein present at basal levels in the 10% PRP containing media, used for hADSC support.

Figure 44:
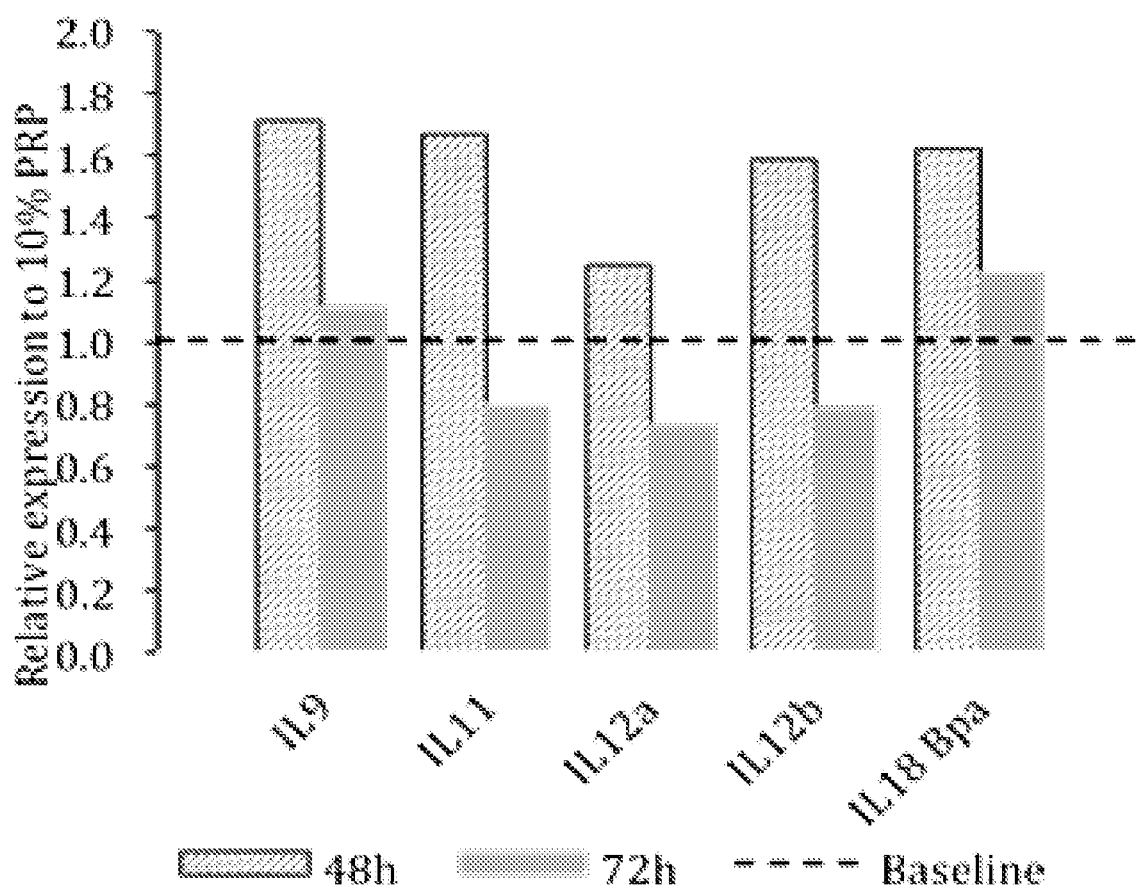
Figure 45:
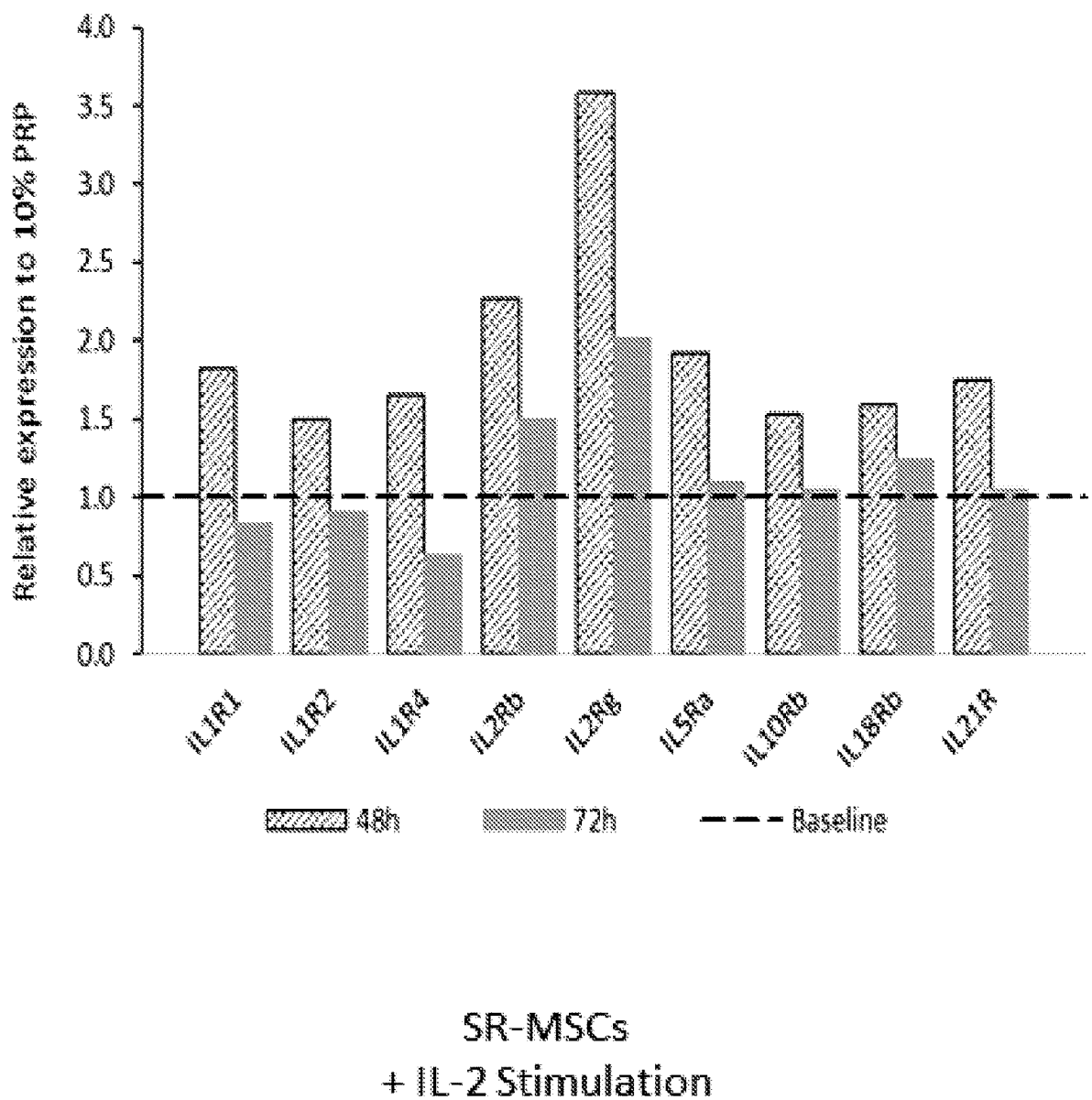
Figure 46:
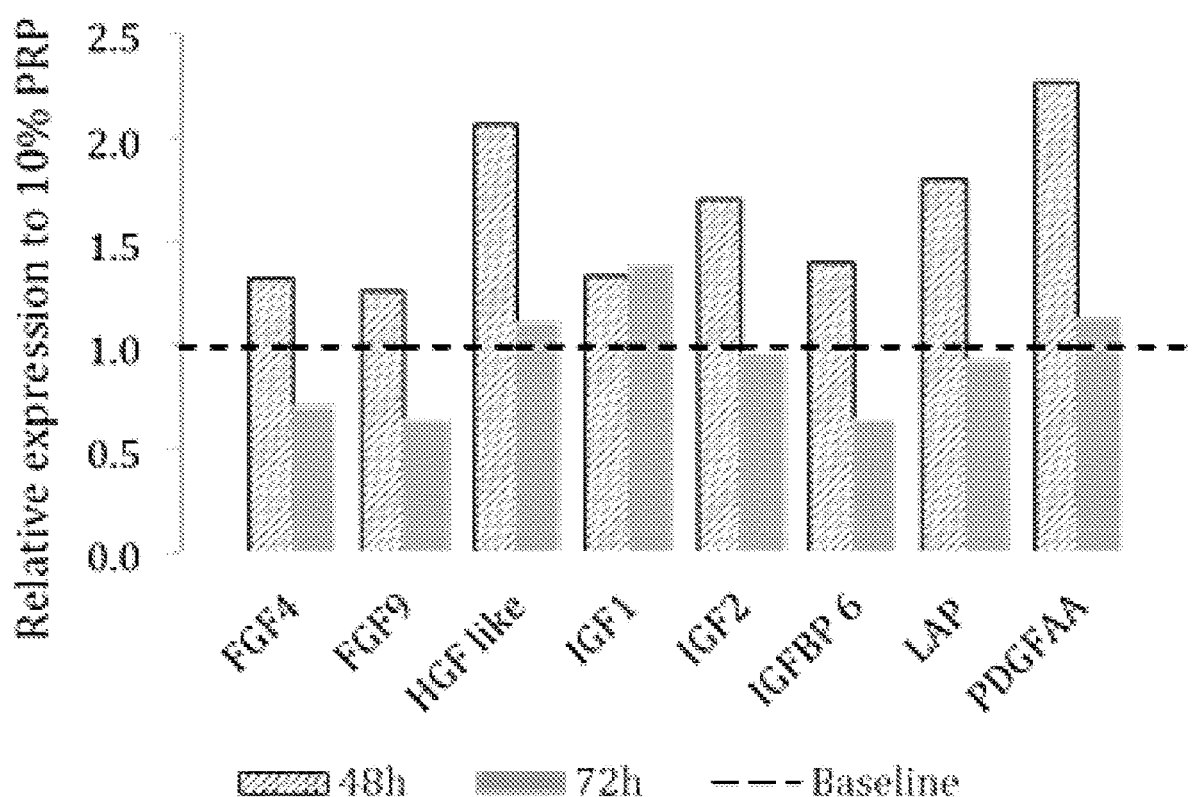
Figure 48:
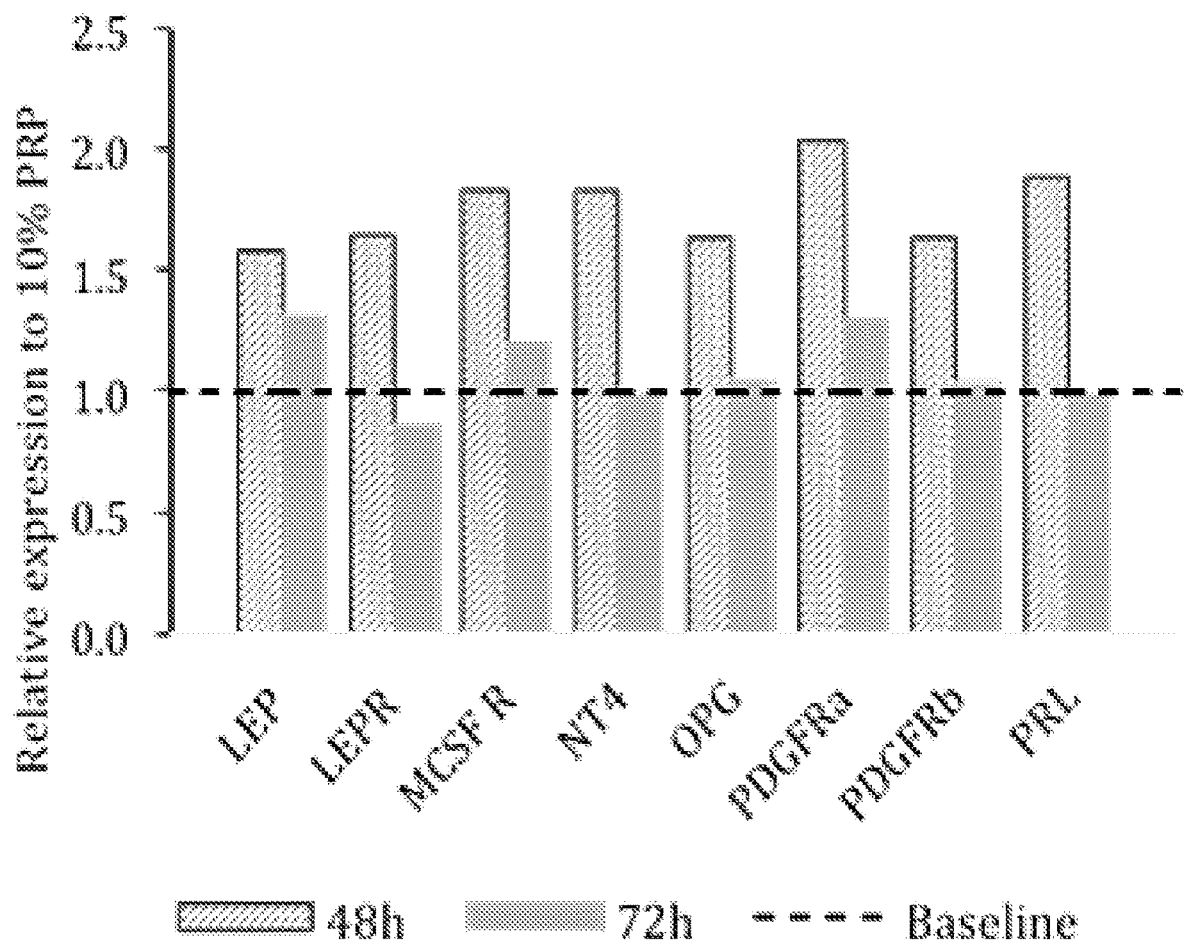
Figure 49:
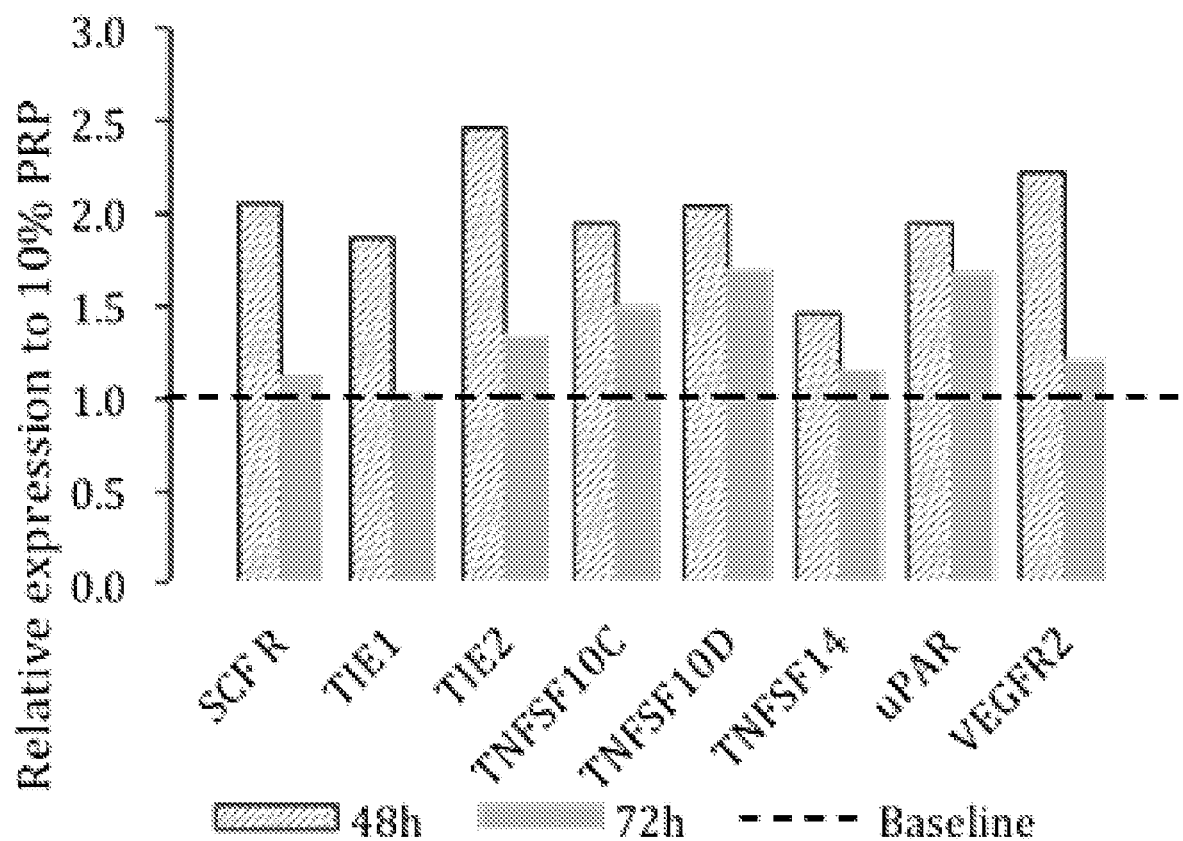
Figure 50:
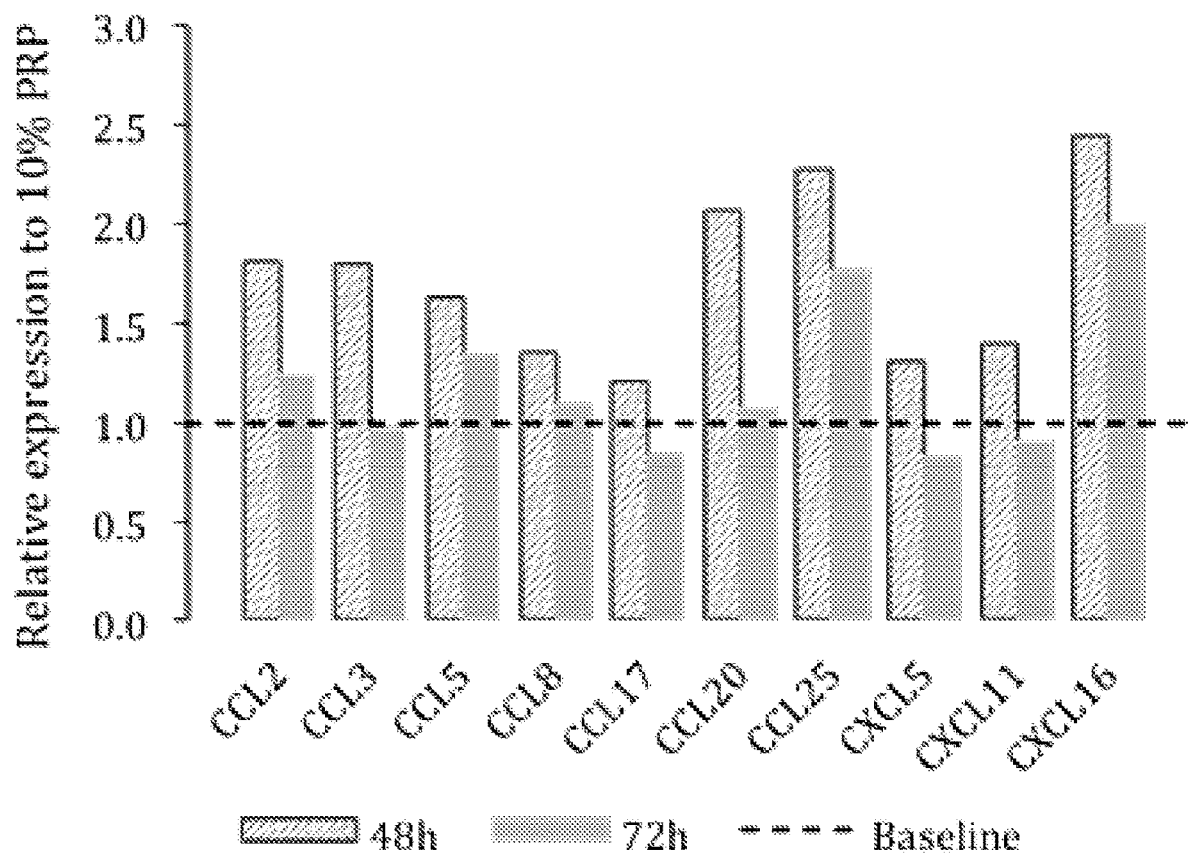

FIGS. 44-53 show the increase of the below named proteins (factors) from SR-hADSCs, 48 hours post stimulation with IL-2. Secretion levels are shown relative to the amount of the corresponding protein present at basal levels in the 10% PRP containing media, used for hADSC support. FIG. 44 shows the increase in secretion of Interleukin 9 (IL9), Interleukin 11 (IL-11), Interleukin 12 alpha (IL12a), Interleukin 12 beta (IL12b), and Interleukin 18 binding protein alpha (IL18BPa). FIG. 45 shows the increase in secretion of Interleukin 1 receptor type I (IL1R1), Interleukin 1 receptor type II (IL1R2), Interleukin 1 receptor type IV (IL1R4), Interleukin 2 receptor beta (IL-2Rb), Interleukin 2 receptor gamma (IL-2Rg), Interleukin 5 receptor alpha (IL5Ra) Interleukin 10 receptor beta (IL10Rb), Interleukin 18 receptor beta (IL18Rb), and Interleukin 21 receptor (IL-21R). FIG. 46 shows the increase in secretion of Fibroblast growth factor 4 (FGF4), FGF9, MSP alpha/HGF like factor (HGF like), Insulin-like growth factor 1 (IGF1), IGF2, insulin-like growth factor-binding protein-6 (IGFBP6), LAP (TGF beta family), and platelet derived growth factor A alpha (PDGFAA). FIG. 47 shows the increase in secretion of platelet derived growth factor A beta (PDGFAB), platelet derived growth factor B beta (PDGFBB), Stromal Cell-Derived Factor-1 alpha (SDF1a), Sialic acid-binding Ig-like Lectin 5 (Siglec 5), Transforming growth factor alpha (TGFα), Transforming growth factor beta 2 (TGFb2), Vascular endothelial growth factor (VEGF), and Vascular endothelial growth factor D (VEGFD). FIG. 47 also shows the increase in secretion of DR6, Dtk, EGFR, Endoglin, ErbB3, Fas, Fas LG, and IGF1 sr. FIG. 48 shows the increase in secretion of Leptin (LEP), Leptin Receptor (LEPR), Macrophage colony-stimulating factor 1 receptor (MCSFR), Neurotrophin 4 (NT4), Osteoprotegerin (OPG), platelet-derived growth factor receptor alpha (PDGFRa), platelet-derived growth factor receptor beta (PDGFRb), and Prolactin (PRL). FIG. 49 shows the increase in secretion of Stem cell factor receptor (SCFR), Angiopoietin 1 receptor (TIE-1), Angiopoietin 1 receptor (TIE-2), TNF superfamily member 10C (TNFSF10C), TNF superfamily member 10D (TNFSF10D), TNF superfamily member 14 (TNFSF14), urokinase plasminogen activator receptor (uPAR), and Vascular endothelial growth factor receptor-2 (VEGFR2). FIG.

Figure 51:
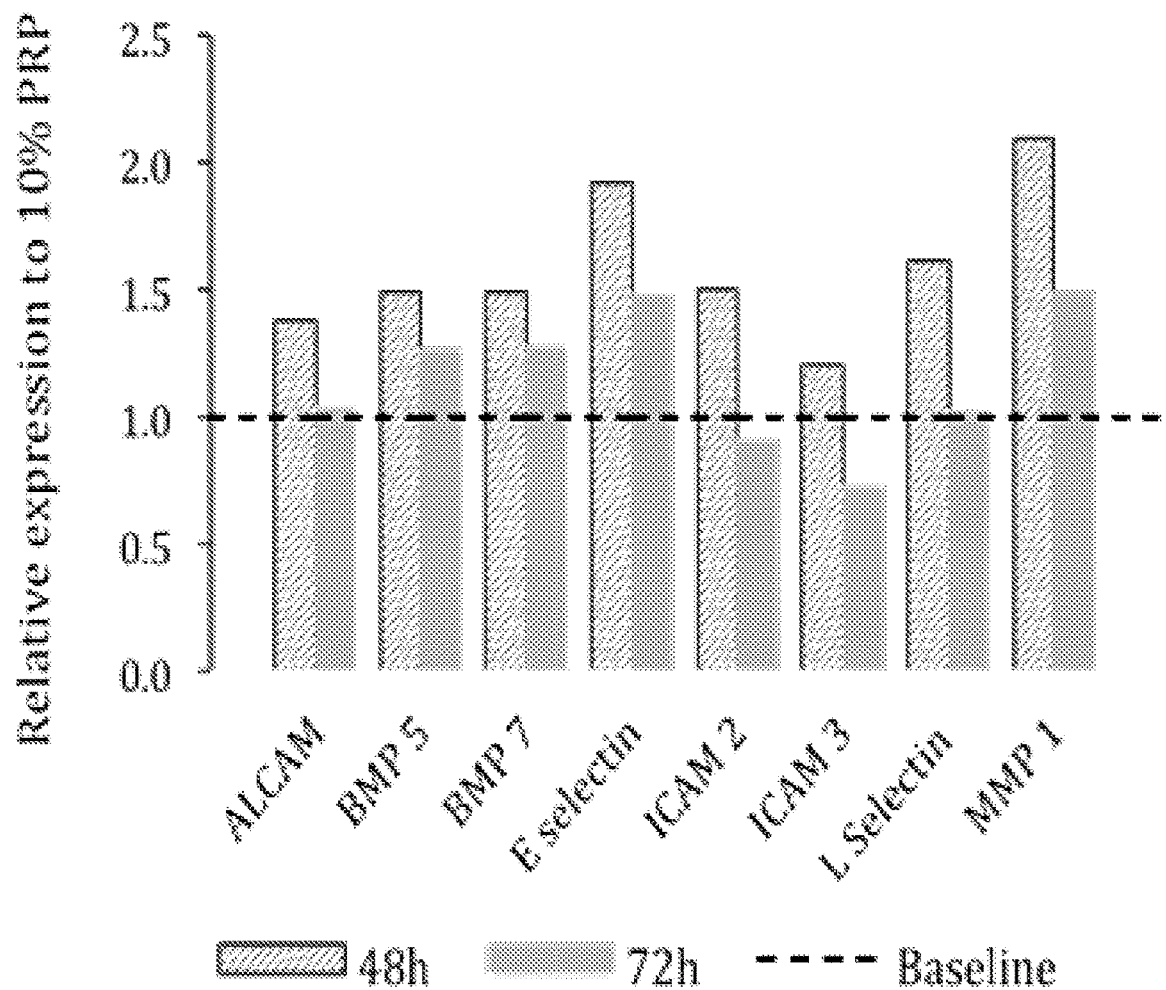
Figure 52:
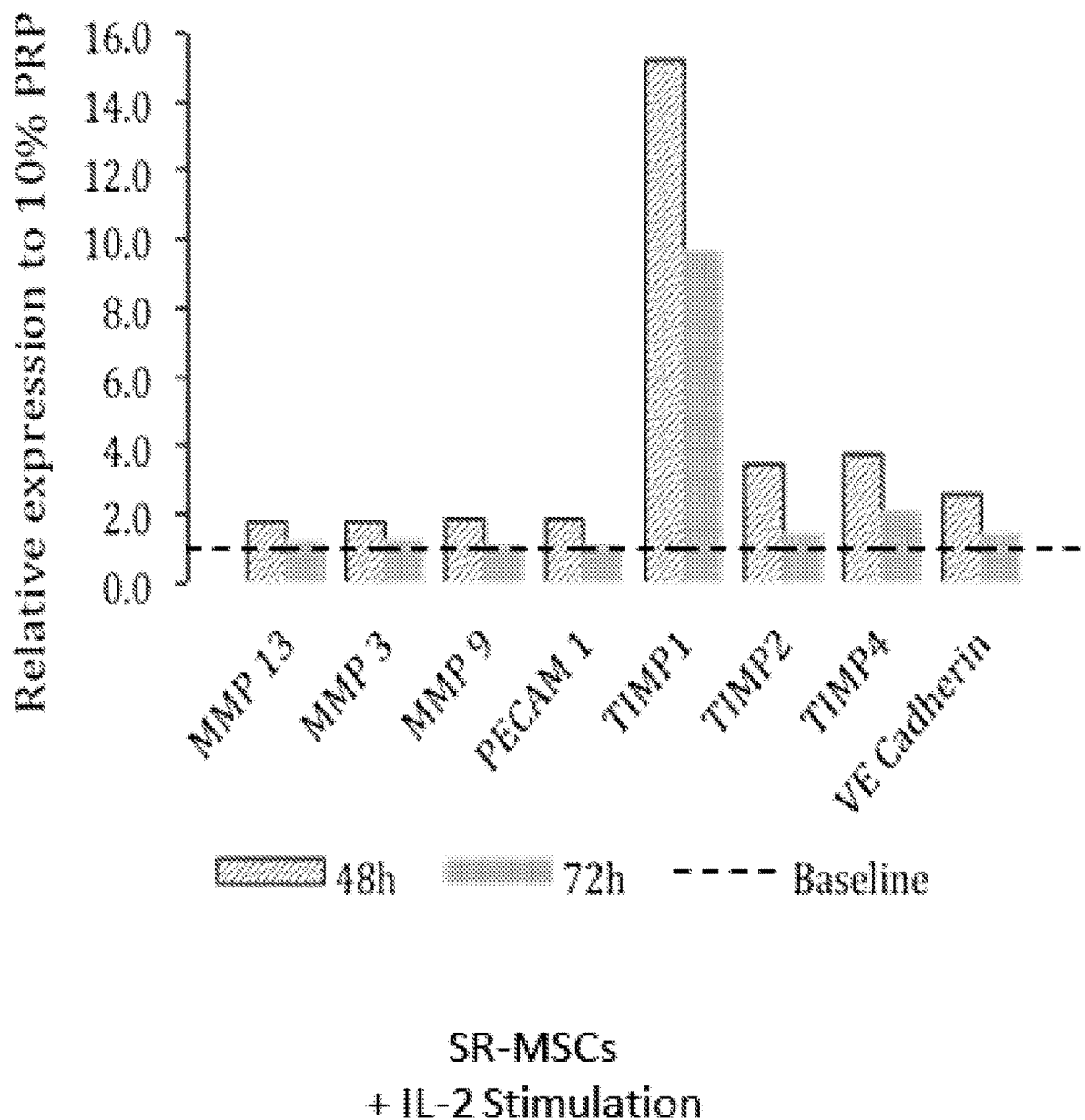
Figure 53:
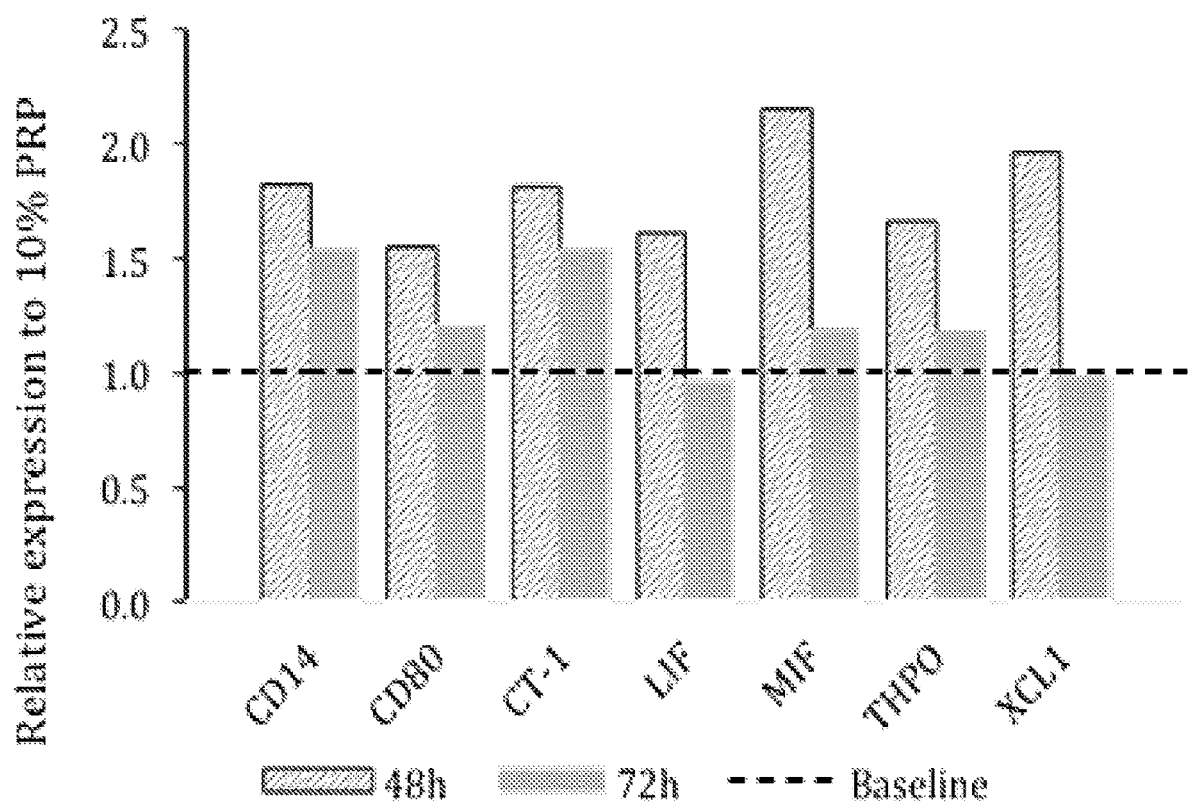

50 shows the increase in secretion of Chemokine (C—C motif) ligand 2 (CCL2), CCL3, CCL5, CCL8, CCL17, CCL20, CCL25, CXC chemokine ligand 5 (CXCL5), CXCL11, and CXCL16. FIG. 51 shows the increase in secretion of activated leukocyte cell adhesion molecule (ALCAM), Bone morphogenetic protein 5 (BMP5), BMP7, E selectin (endothelial cell adhesion molecule), Intercellular adhesion molecule 2 (ICAM2), ICAM3, L selectin (Leukocyte adhesion molecule), and matrix metalloproteinase 1 (MMP1). FIG. 52 shows the increase in secretion of matrix metalloproteinase 13 (MMP13), MMP3, MMP9, Platelet endothelial cell adhesion molecule (PECAM 1), Metalloproteinase inhibitors TIMP 1, TIMP 2, TIMP 4, and vascular epithelium (VE) Cadherin (calcium dependent cell adhesion protein). FIG. 53 shows the increase in secretion of monocyte differentiation antigen (CD14), cell differentiation antigen (CD80), Cardiotrophin-1 (CT-1), Leukemia inhibitory factor (LIF), Macrophage migration inhibitory factor (MIF), Thrombopoietin (THPO), and Lymphotactin (XCL1).

FIG. 54 shows the increase in secretion of Nerve growth factor receptor (NGFR) from SR-hADSCs, 24 or 48 hours post stimulation with IL-2. FIG. 54 also shows the increase in secretion of IL8 and TNFRSF1A. These factors in FIG. 54 were found to not be present in PRP.

Figure 55:
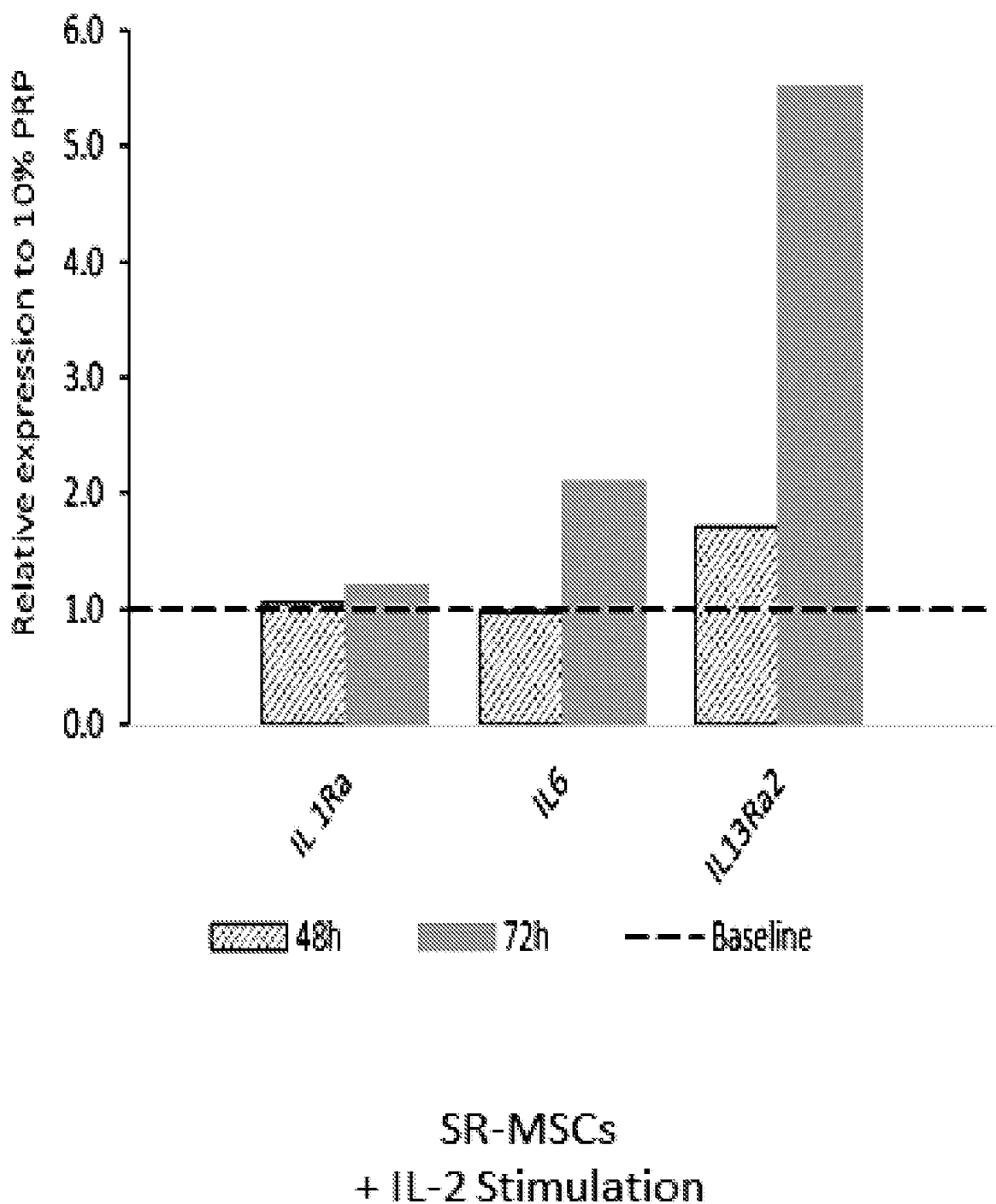
Figure 56:
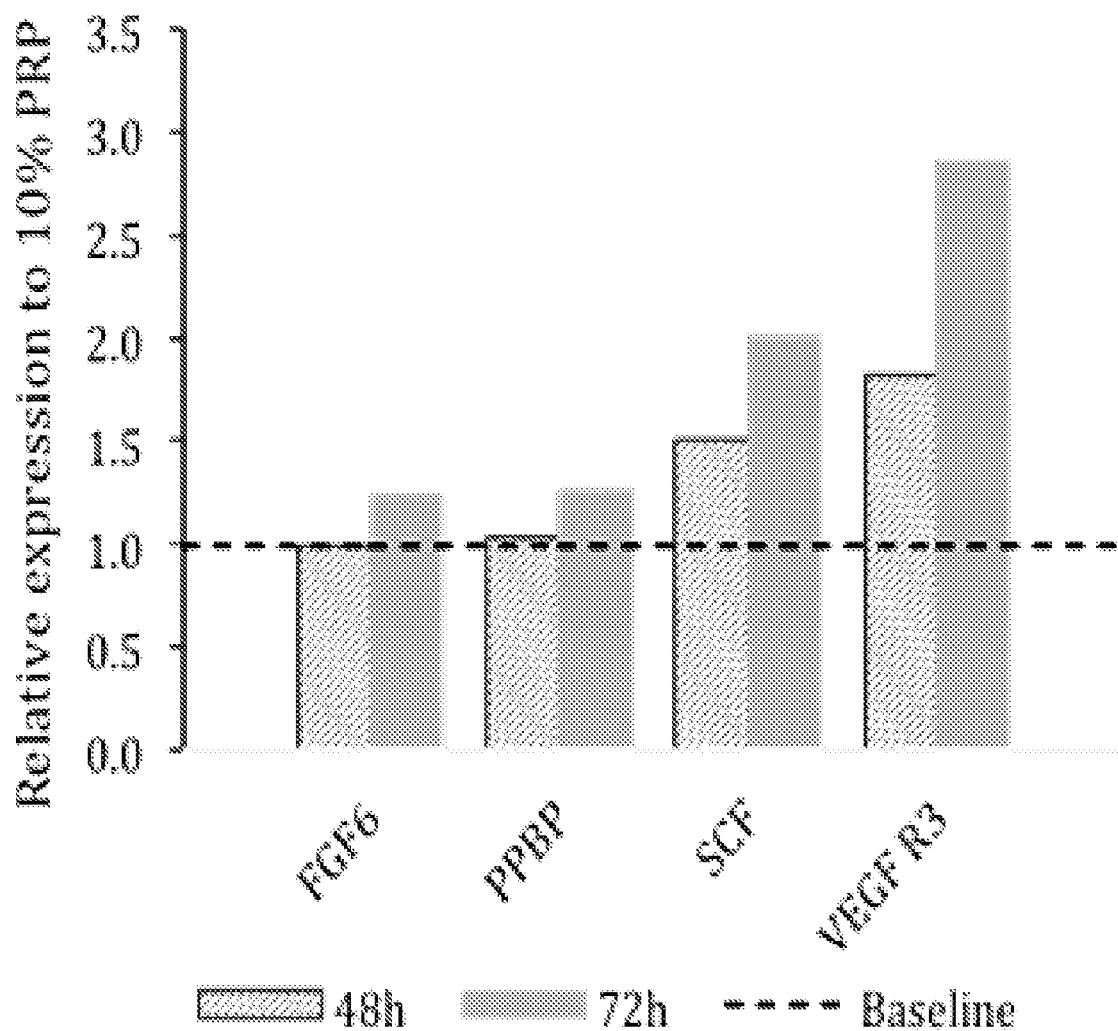
Figure 57:
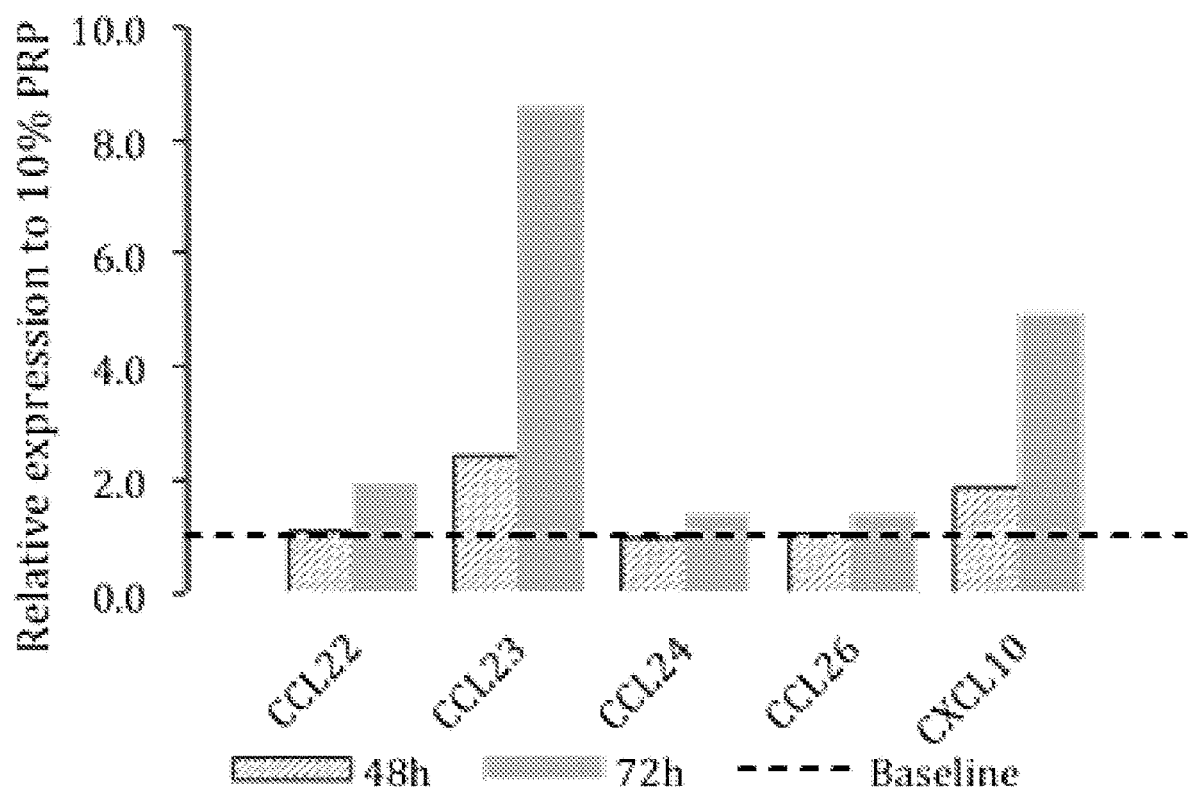

FIGS. 55-57 show the increase in the secretion of the below named proteins (factors) from SR-hADSCs, 72 hours post stimulation with IL-2. Secretion levels are shown relative to the amount of the corresponding protein present at basal levels in the 10% PRP containing media, used for hADSC support. FIG. 55 shows the increase in secretion of Interleukin 1 receptor alpha (IL1Ra), Interleukin 6 (IL6), and Interleukin-13 receptor subunit alpha-2 (IL13Ra2). FIG. 56 shows the increase in secretion of Fibroblast growth factor 6 (FGF6), pro-platelet basic protein (PPBP), stem cell factor (SCF), and Vascular endothelial growth factor receptor-3 (VEGFR3). FIG. 57 shows the increase in secretion of Chemokine (C—C motif) ligand 22 (CCL22), CCL23, CCL24, CCL26, and CXC chemokine ligand 10 (CXCL10).

Figure 58:
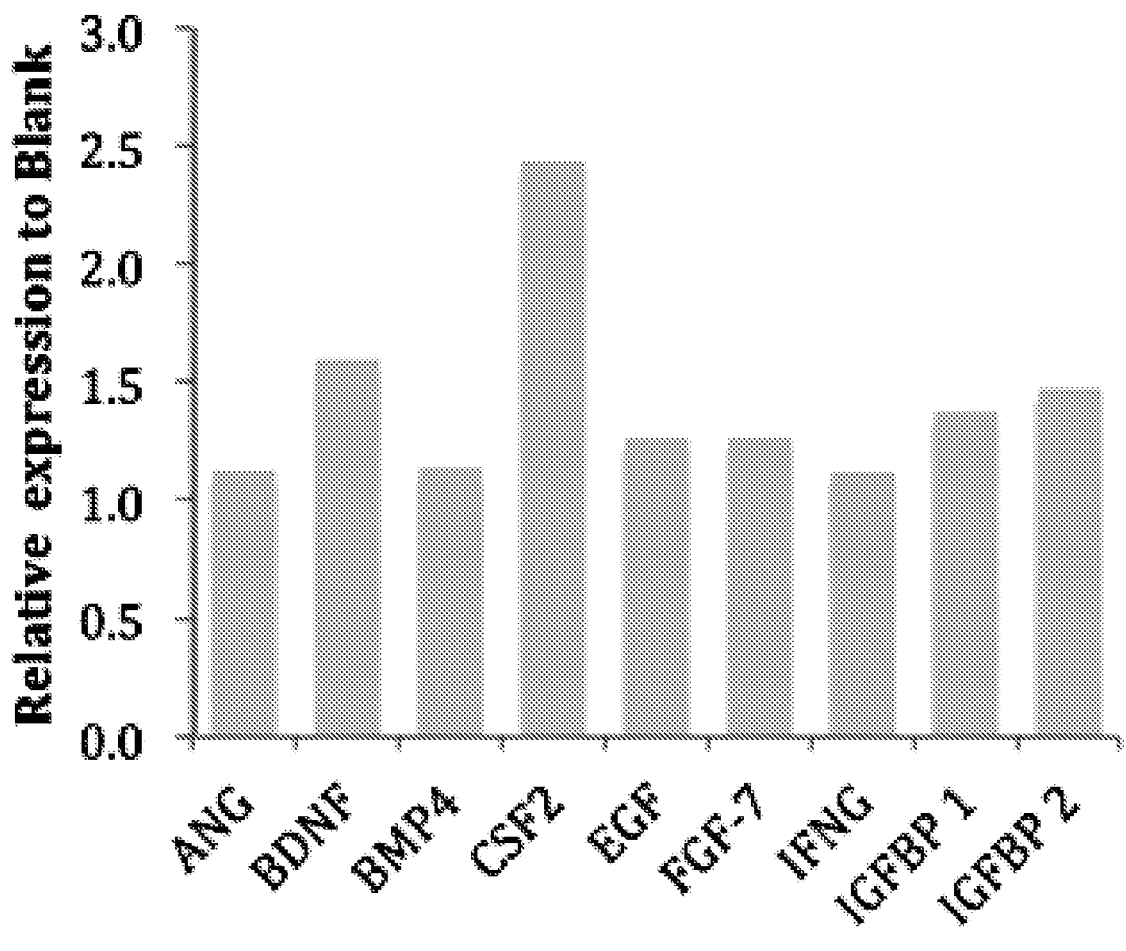

FIG. 58 shows the increase in secretion of Angiotensin (ANG), Brain-derived neurotrophic factor (BDNF), Bone morphogenetic protein 4 (BMP4), colony stimulating factor 2 (CSF2), Epidermal growth factor (EGF), Fibroblast growth factor 7 (FGF-7), Interferon gamma (IFNγ), insulin-like growth factor-binding protein-1 (IGFBP 1), and IGFBP 2 from SR-hADSCs, 72 hours post stimulation with IL-2. These factors were found to not be present in PRP.

Figure 59:
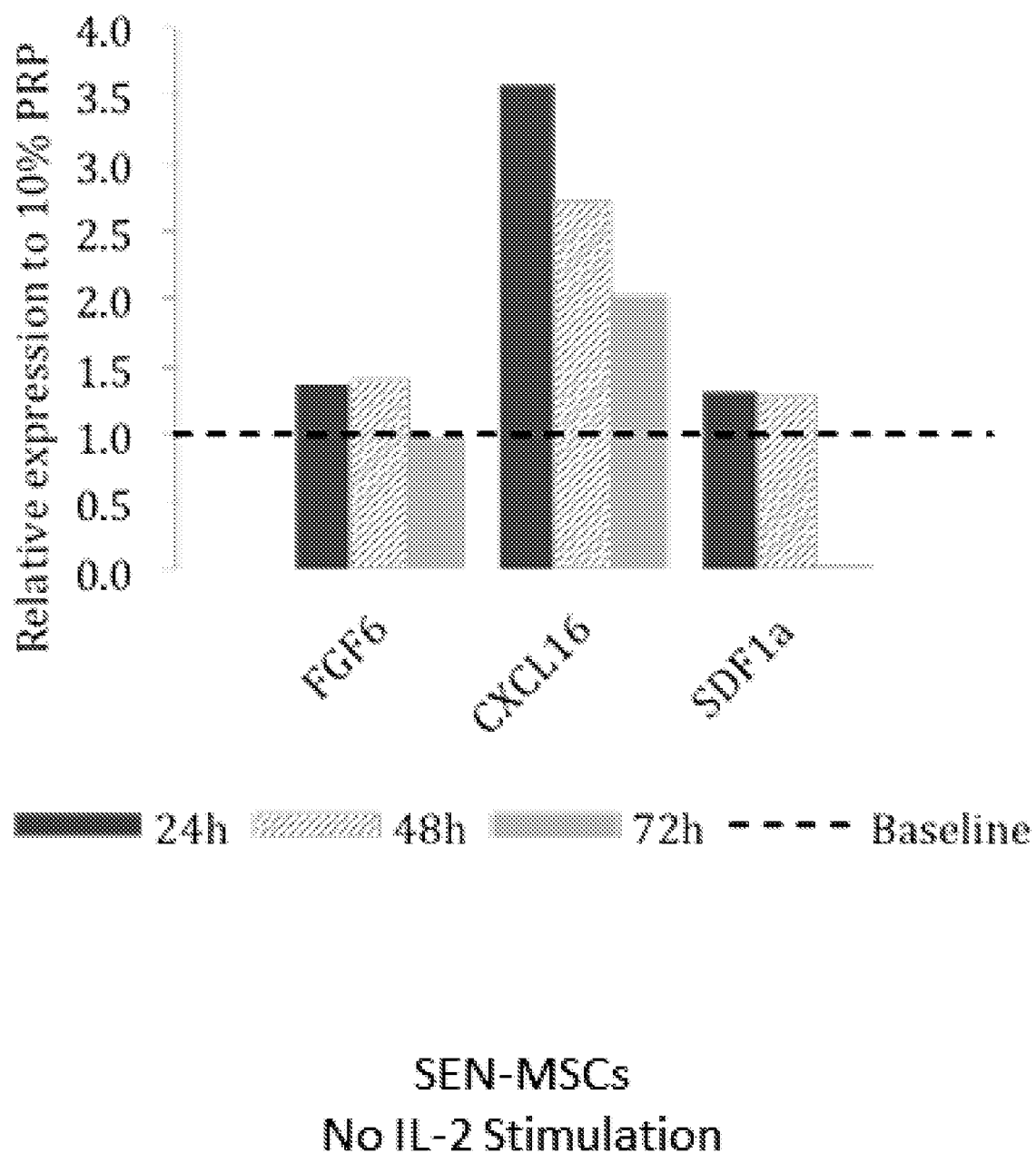

FIG. 59 shows the increase in secretion of Fibroblast growth factor 6 (FGF6), CXC chemokine ligand 16 (CXCL16), and Stromal Cell-Derived Factor-1 alpha (SDF1a) from SEN-hADSCs, 24 hours post incubation with 10% PRP alone (no IL-2 stimulation). Secretion levels are shown relative to the amount of the corresponding protein present at basal levels in the 10% PRP containing media, used for hADSC support.

Figure 60:
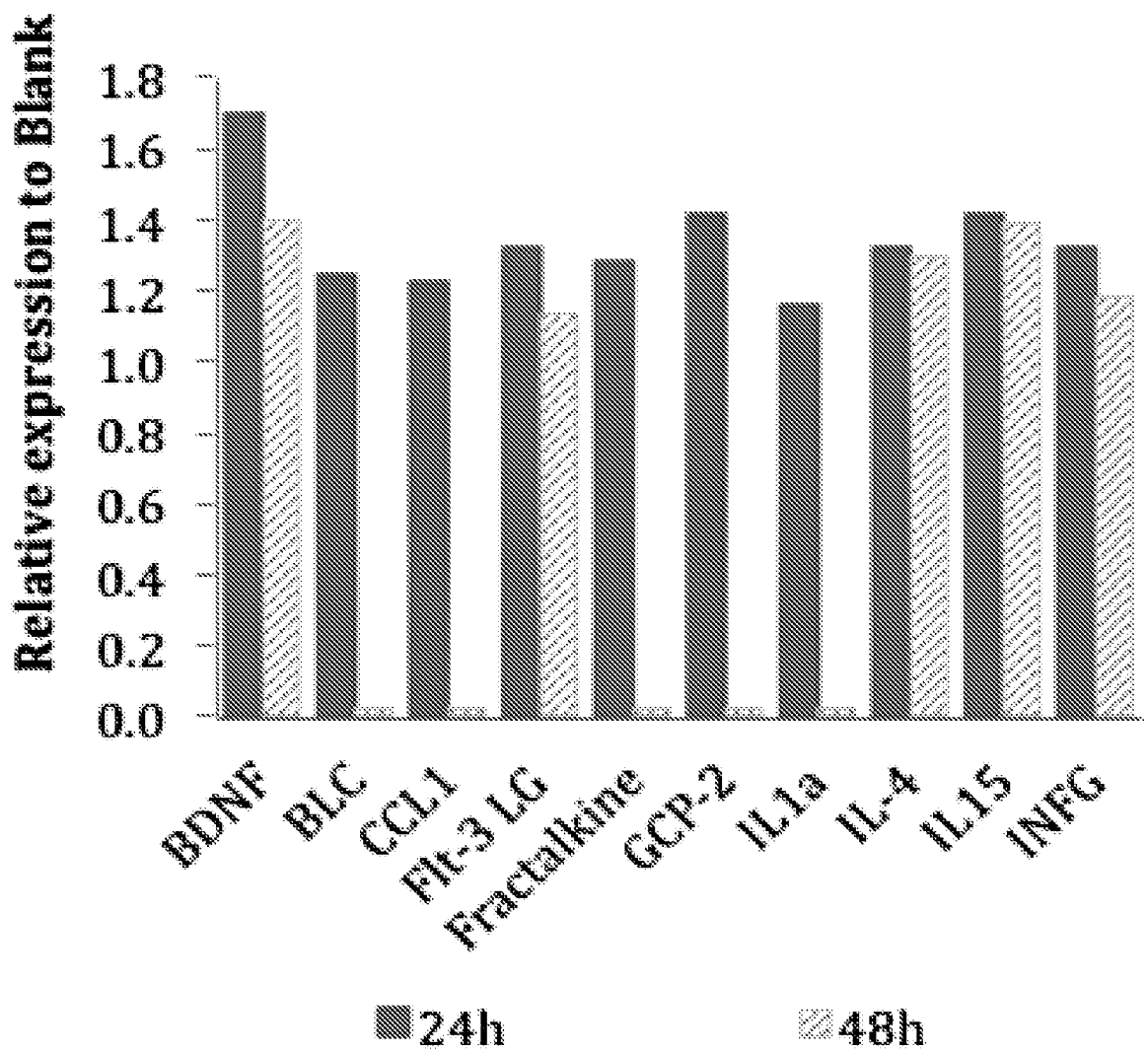

FIG. 60 shows the increase in secretion of Brain-derived neurotrophic factor (BDNF), B lymphocyte chemokine (CXCL13; BLC), Chemokine (C—C motif) ligand 1 (CCL1), Flt-3 LG (Fms-Related Tyrosine Kinase 3 Ligand), Fractalkine (T-cell chemokine CX3CL1), granulocyte chemotactic protein 2 (GCP-2)/CXCL6, Interleukin 1 alpha (IL1a), Interleukin 4 (IL4), IL15, and Interferon gamma (IFNγ) from SEN-hADSCs, 24 hours post incubation with 10% PRP alone (no IL-2 stimulation). These factors were found to not be present in PRP.

Figure 61:
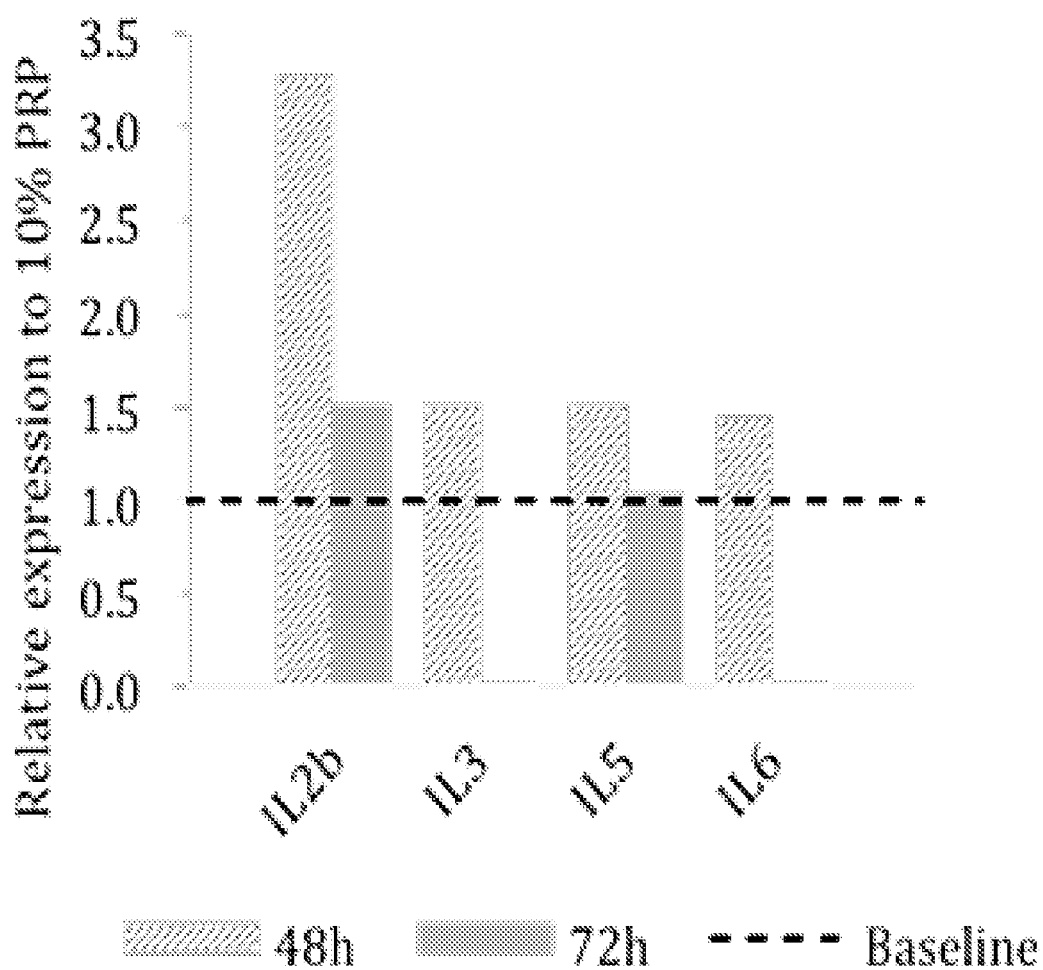
Figure 62:
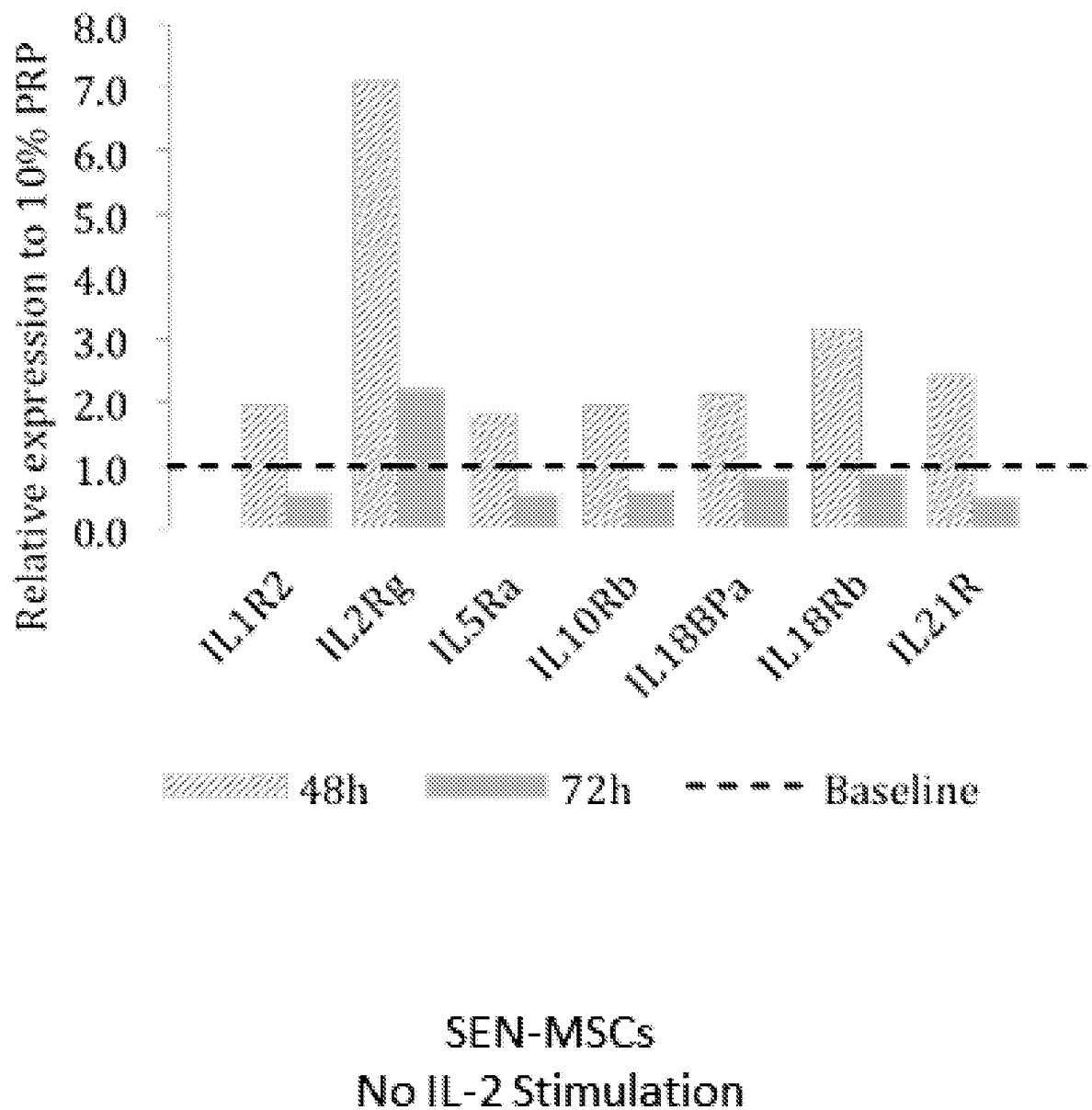
Figure 63:
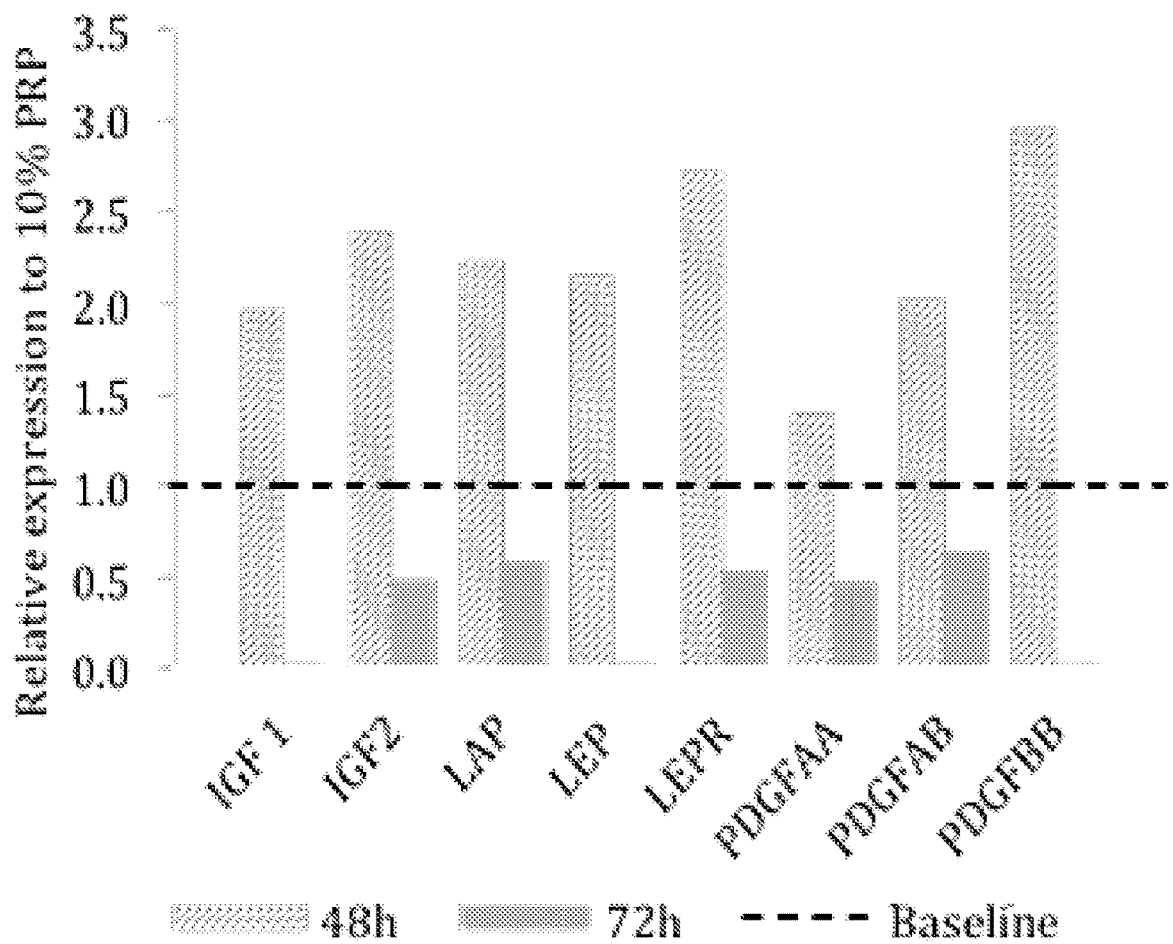
Figure 64:
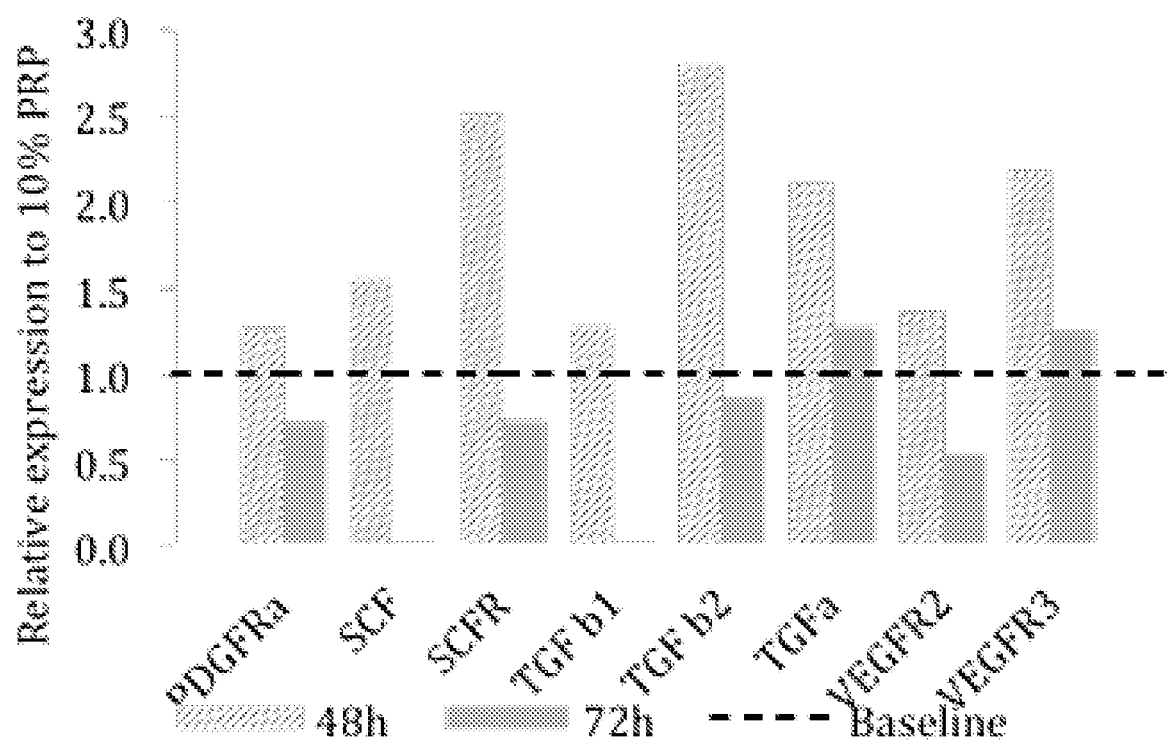
Figure 65:
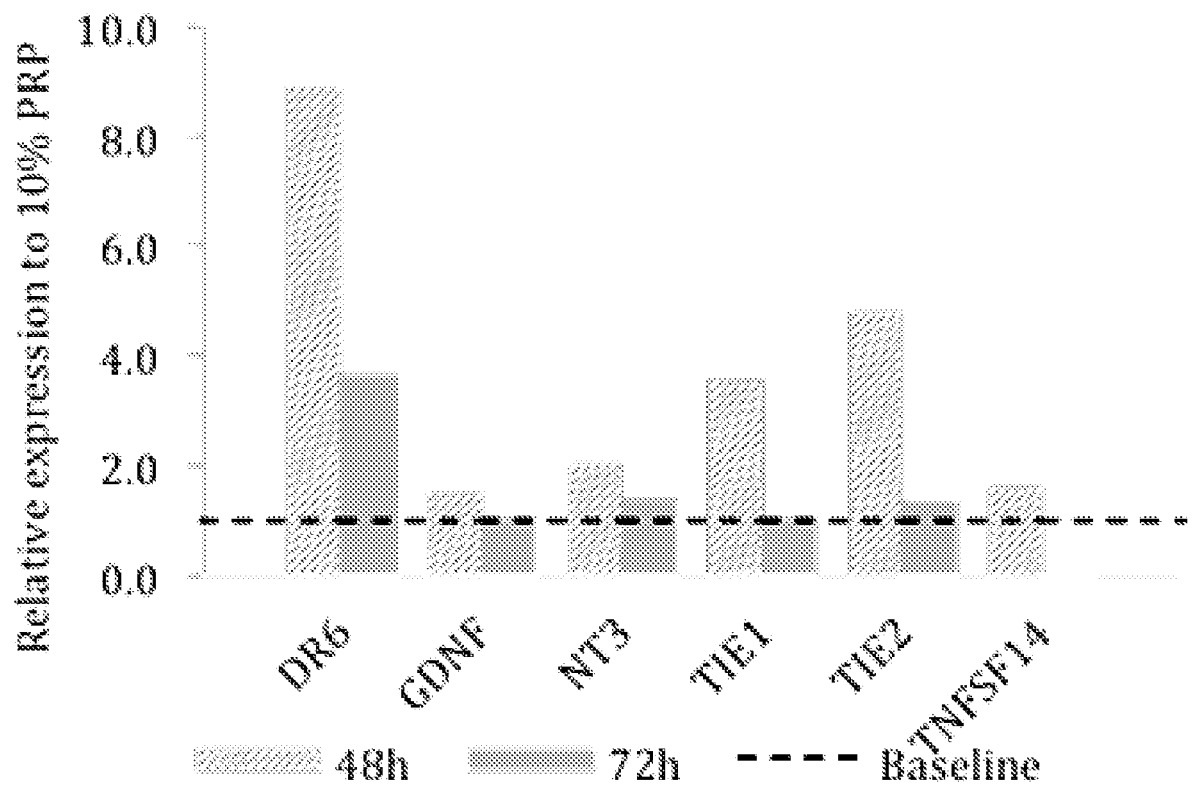
Figure 66:
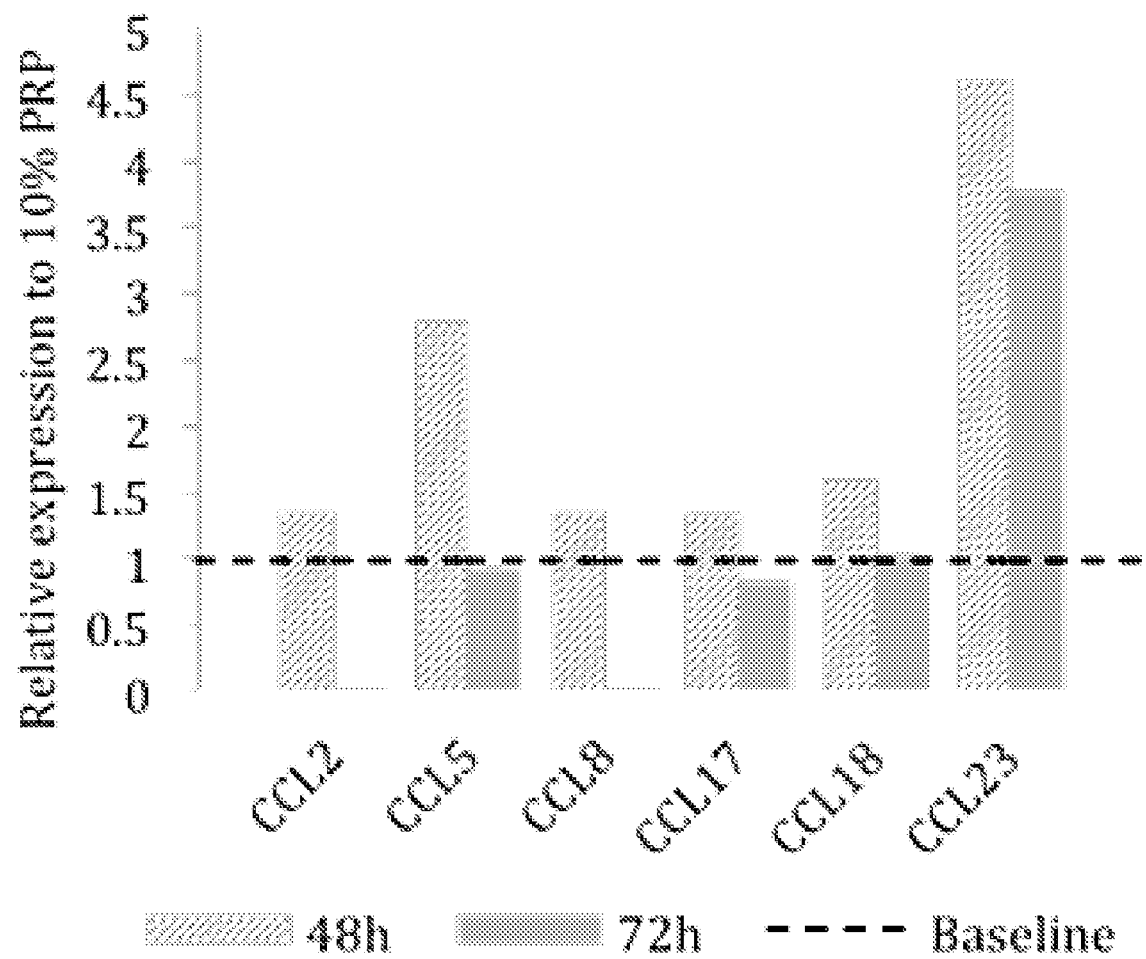
Figure 67:
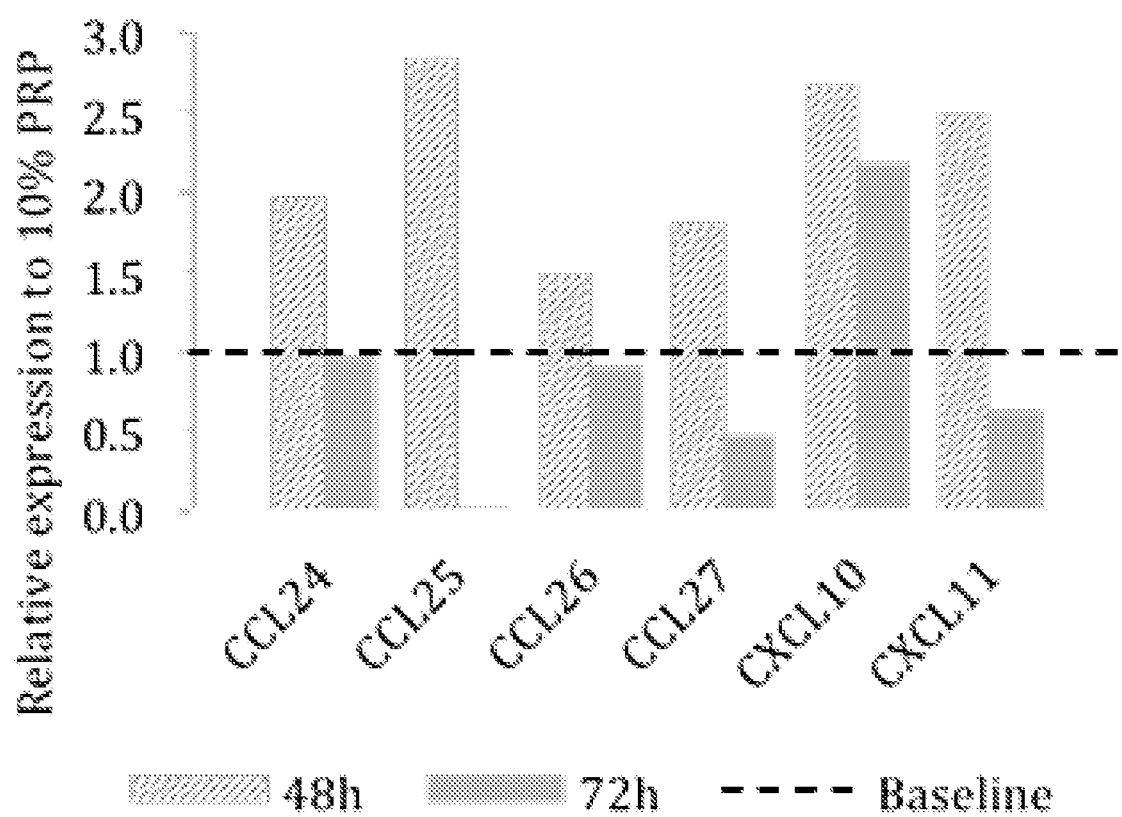
Figure 68:
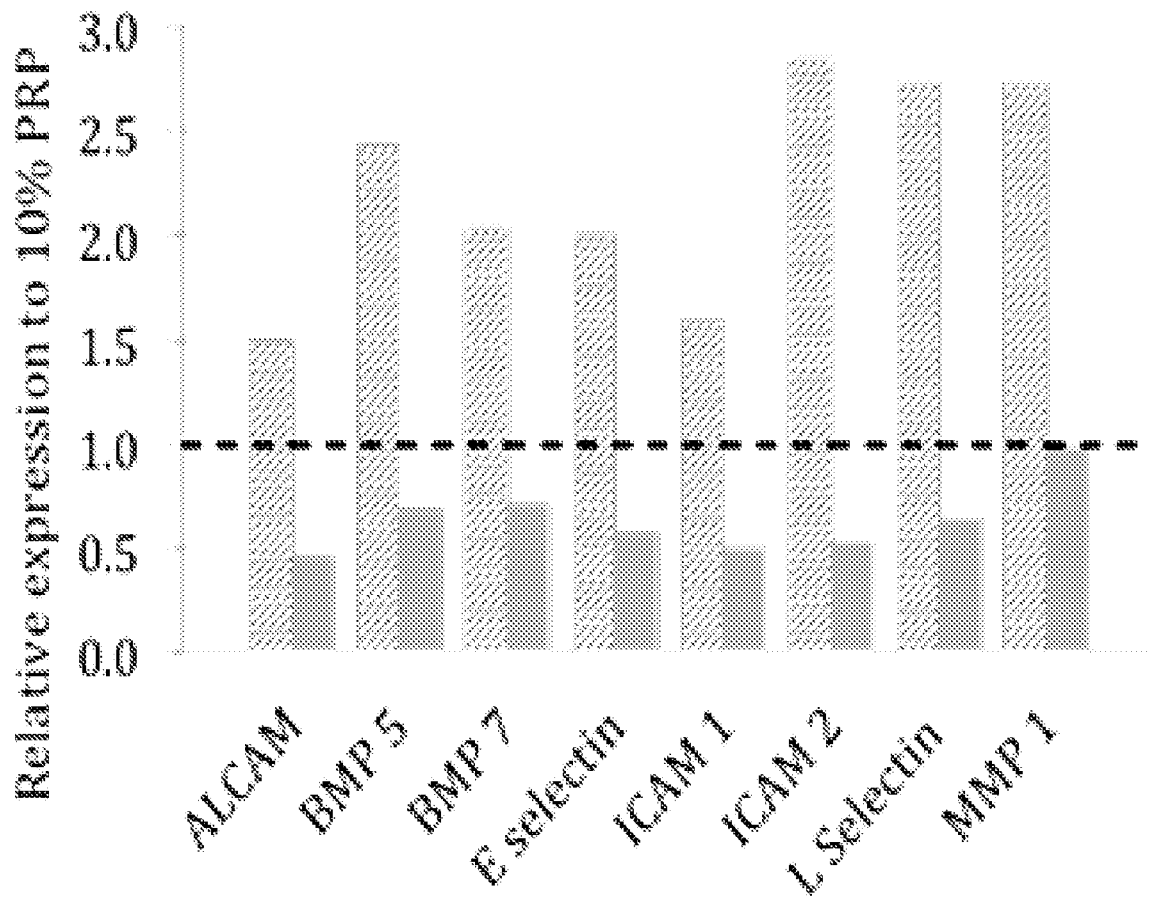
Figure 69:
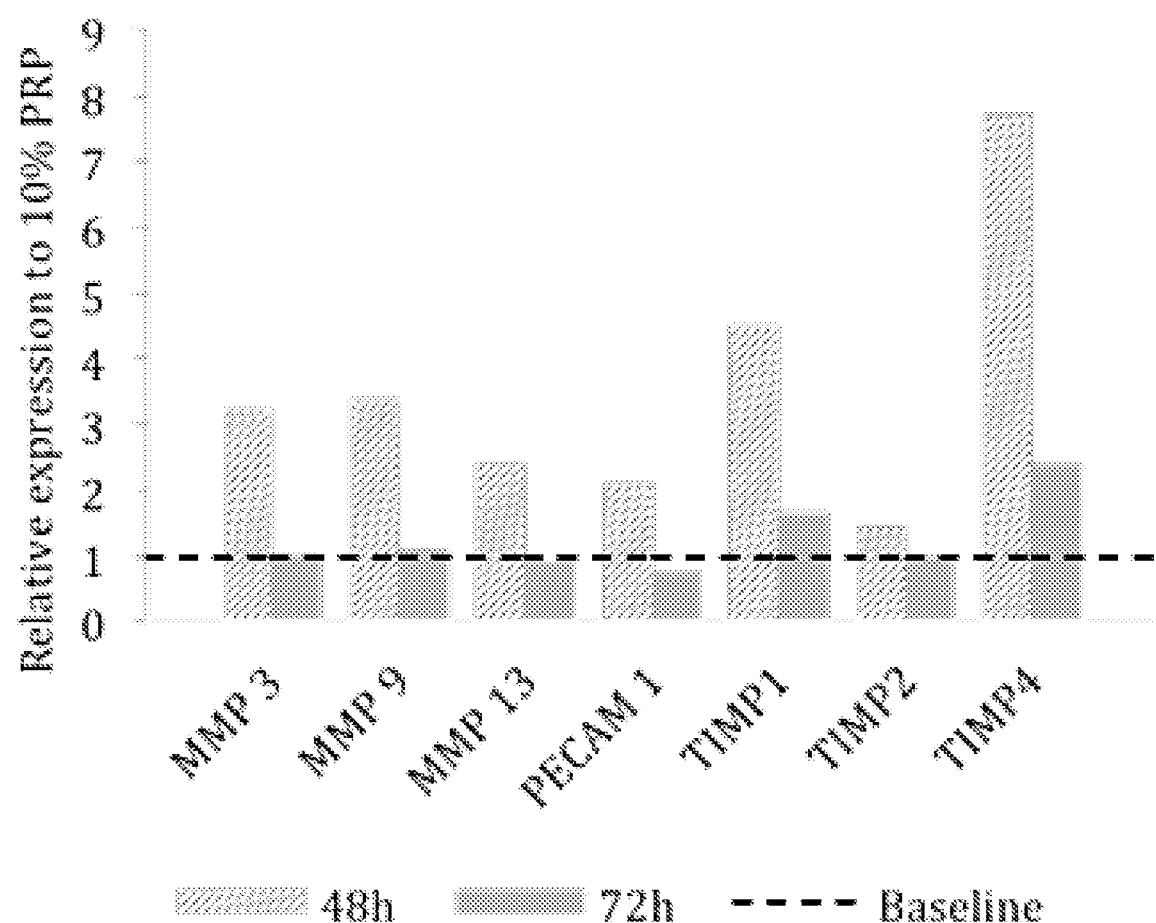
Figure 70:
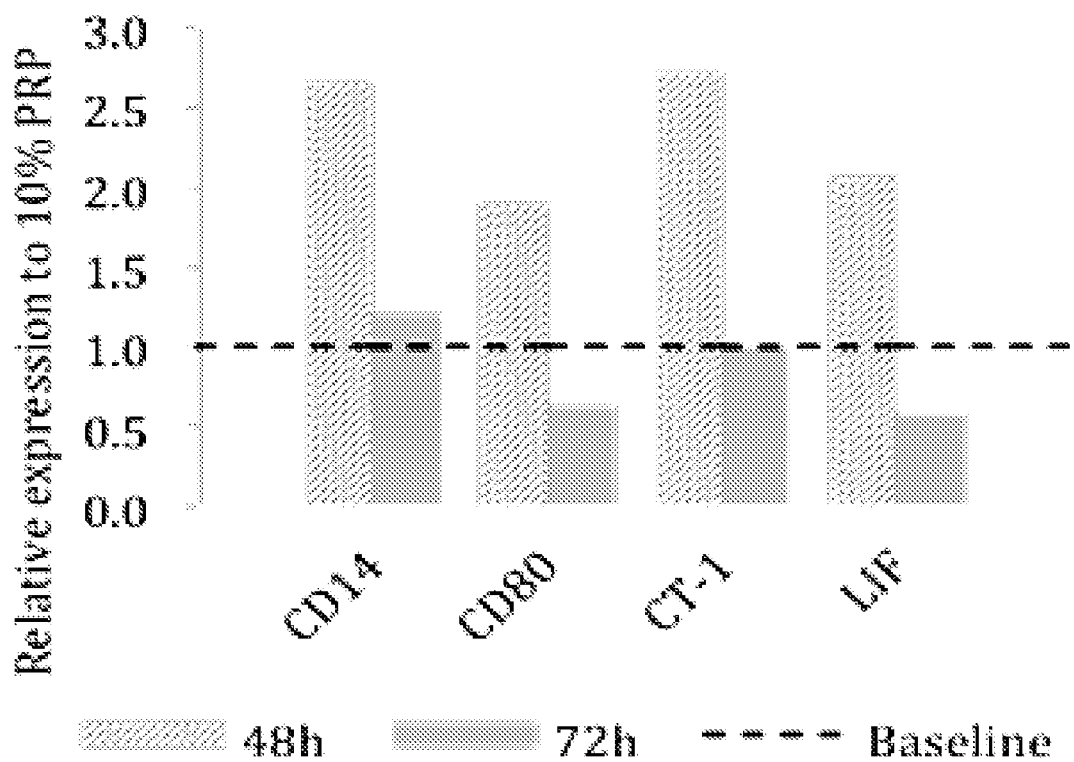

FIGS. 61-70 show the increase in the secretion of the below named proteins (factors) from SEN-hADSCs, 48 hours post incubation with 10% PRP alone (no IL-2 stimulation). Secretion levels are shown relative to the amount of the corresponding protein present at basal levels in the 10% PRP containing media, used for hADSC support. FIG. 61 shows the increase in secretion of Interleukin 2 beta (IL-2b), IL3, IL5, and IL6. FIG. 62 shows the increase in secretion of Interleukin 1 receptor type II (IL1R2), Interleukin 2 receptor gamma (IL-2Rg), Interleukin 5 receptor alpha (IL5Ra), Interleukin 10 receptor beta (IL10Rb), Interleukin 18 receptor binding protein alpha (IL18BPa), Interleukin 18 receptor beta (IL18Rb), and Interleukin 21 receptor (IL-21R). FIG. 63 shows the increase in secretion of Insulin-like growth factor 1 (IGF1), IGF2, LAP (TGF beta family), Leptin (LEP), Leptin Receptor (LEPR), platelet derived growth factor A alpha (PDGFAA), platelet derived growth factor A beta (PDGFAB), and platelet derived growth factor B beta (PDGFBB). FIG. 64 shows the increase in secretion of platelet-derived growth factor receptor alpha (PDGFRa), Stem cell factor (SCF), Stem cell factor receptor (SCFR), Transforming growth factor beta 1 (TGF b1), Transforming growth factor beta 2 (TGF b2), Transforming growth factor alpha (TGFα), Vascular endothelial growth factor receptor-2 (VEGFR2), and VEGFR3. FIG. 65 shows the increase in secretion of Death receptor 6 (DR6; TNF receptor superfamily member 21), Glial cell line-derived neurotrophic factor (GDNF), Neurotrophin 3 (NT3), Tyrosine kinase with immunoglobulin-like and EGF-like domains 1 (TIE-1), TIE-2, and TNF superfamily member 14 (TNFSF14). FIG. 66 shows the increase in secretion of Chemokine (C—C motif) ligand 2 (CCL2), CCL5, CCL8, CCL17, CCL18, and CCL23. FIG. 67 shows the increase in secretion of Chemokine (C—C motif) ligand 24 (CCL24), CCL25, CCL26, CCL27, CXC Chemokine ligand 10 (CXCL10), and CXCL11. FIG. 68 shows the increase in secretion of activated leukocyte cell adhesion molecule (ALCAM), Bone morphogenetic protein 5 (BMP5), BMP7, E selectin (endothelial cell adhesion molecule), Intercellular adhesion molecule 1 (ICAM1), ICAM2, L selectin (Leukocyte adhesion molecule), and matrix metalloproteinase 1 (MMP1). FIG. 69 shows the increase in secretion of matrix metalloproteinase 3 (MMP3), MMP9, MMP13, Platelet endothelial cell adhesion molecule (PECAM 1), Metalloproteinase inhibitors TIMP 1, TIMP 2, and TIMP 4. FIG. 70 shows the increase in secretion of monocyte differentiation antigen (CD14), monocyte differentiation antigen (CD80), Cardiotrophin-1 (CT-1), and Leukemia inhibitory factor (LIF).

Figure 71:
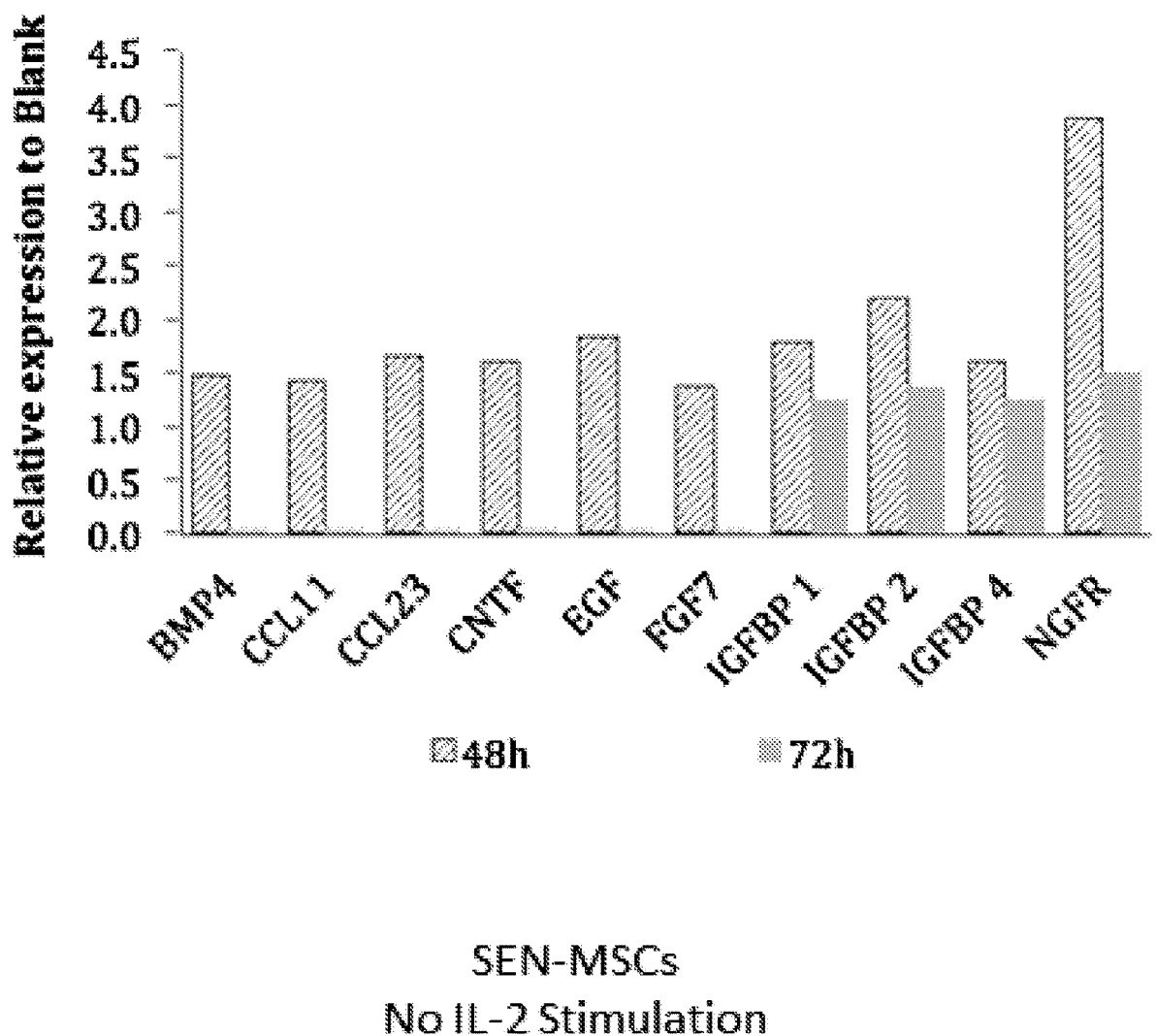
Figure 72:
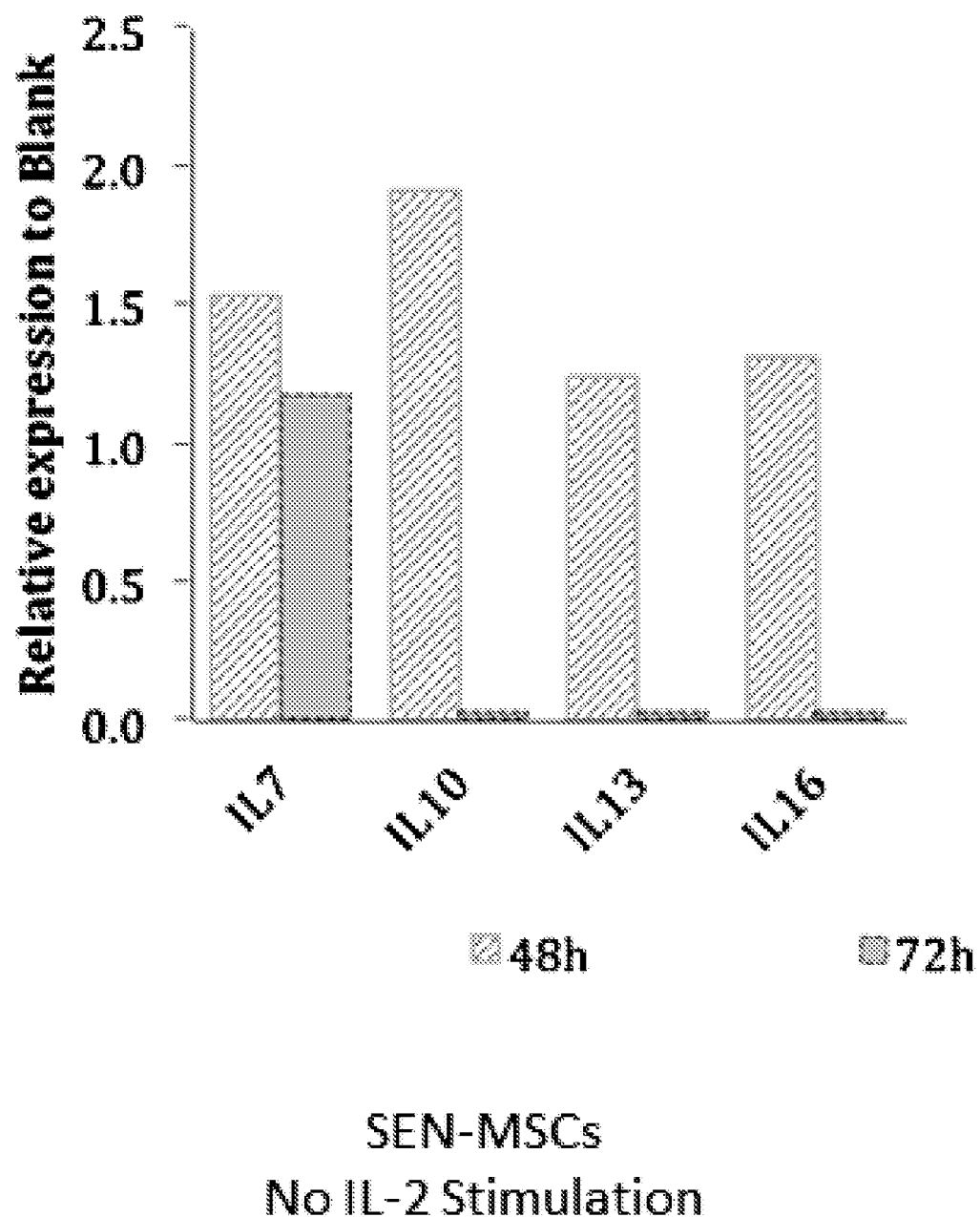

FIGS. 71-72 show the increase in the secretion of the below named proteins (factors) from SEN-hADSCs, 48 hours post incubation with 10% PRP alone (no IL-2 stimulation). These factors were found to not be present in PRP. FIG. 71 shows the increase in secretion of Bone morphogenetic protein 4 (BMP4), Chemokine (C—C motif) ligand 11 (CCL11), CCL23, Ciliary neurotrophic factor (CNTF), Epidermal growth factor (EGF), Fibroblast growth factor 7 (FGF7), insulin-like growth factor-binding protein-1 (IGFBP1), IGFBP2, IGFBP4, and Nerve growth factor receptor (NGFR). FIG. 72 shows the increase in secretion of Interleukin 7 (IL7), IL10, IL13, and IL-16.

Figure 73:
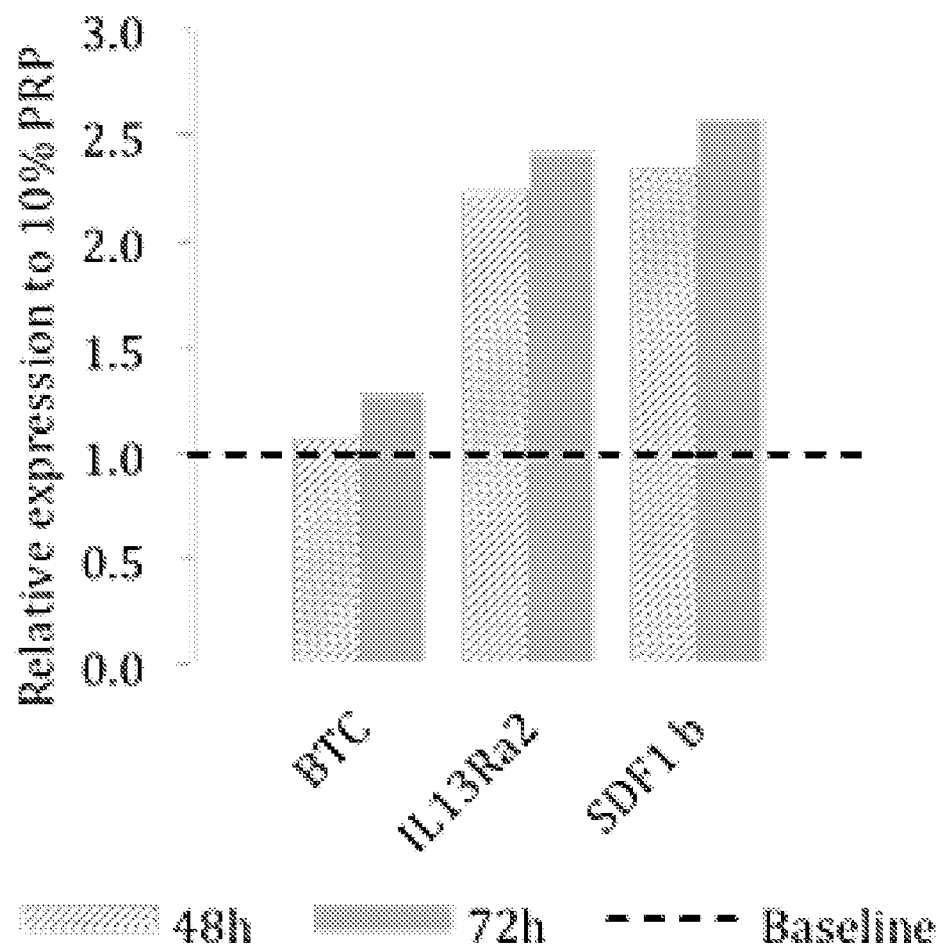

FIG. 73 shows the increase in secretion of Probetacellulin (BTC), Interleukin-13 receptor subunit alpha-2 (IL13Ra2), and Stromal Cell-Derived Factor-1 beta (SDF1b) from SEN-hADSCs, 72 hours post incubation with 10% PRP alone (no IL-2 stimulation). Secretion levels are shown relative to the amount of the corresponding protein present at basal levels in the 10% PRP containing media, used for hADSC support.

Figure 74:
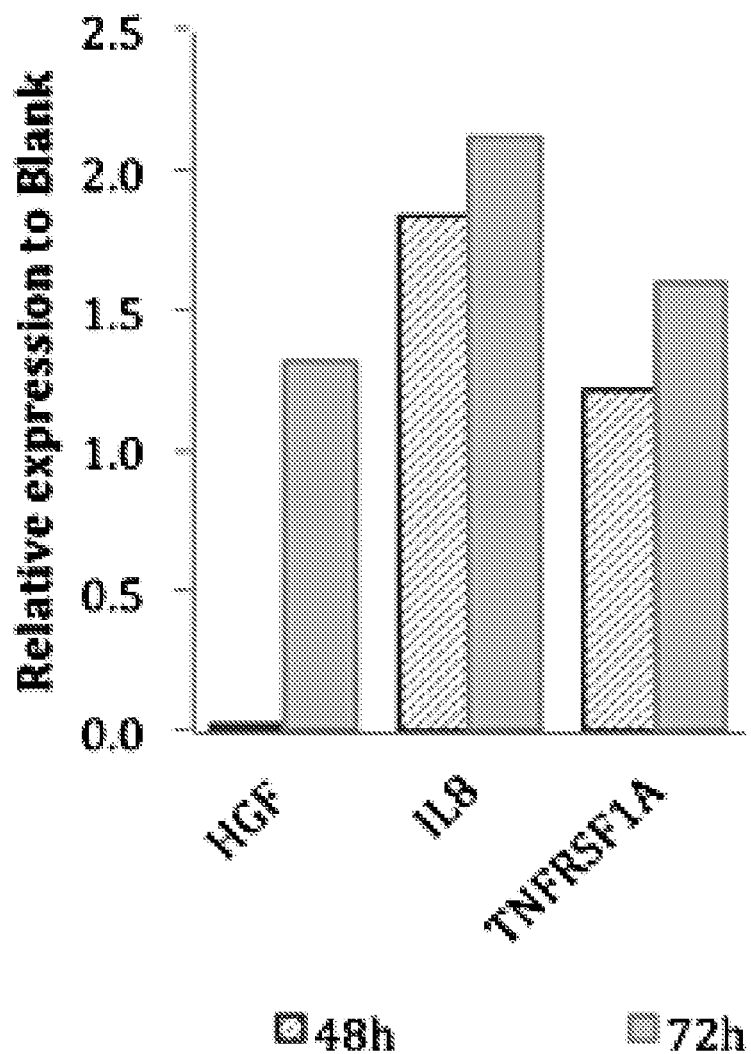

FIG. 74 shows the increase in secretion of Hepatocyte growth factor (HGF), Interleukin 8 (IL8), and TNFRSF1A (Tumor Necrosis Factor Receptor Superfamily, member 1A)

from SEN-hADSCs, 72 hours post incubation with 10% PRP alone (no IL-2 stimulation). These factors were found to not be present in PRP.

Figure 75:
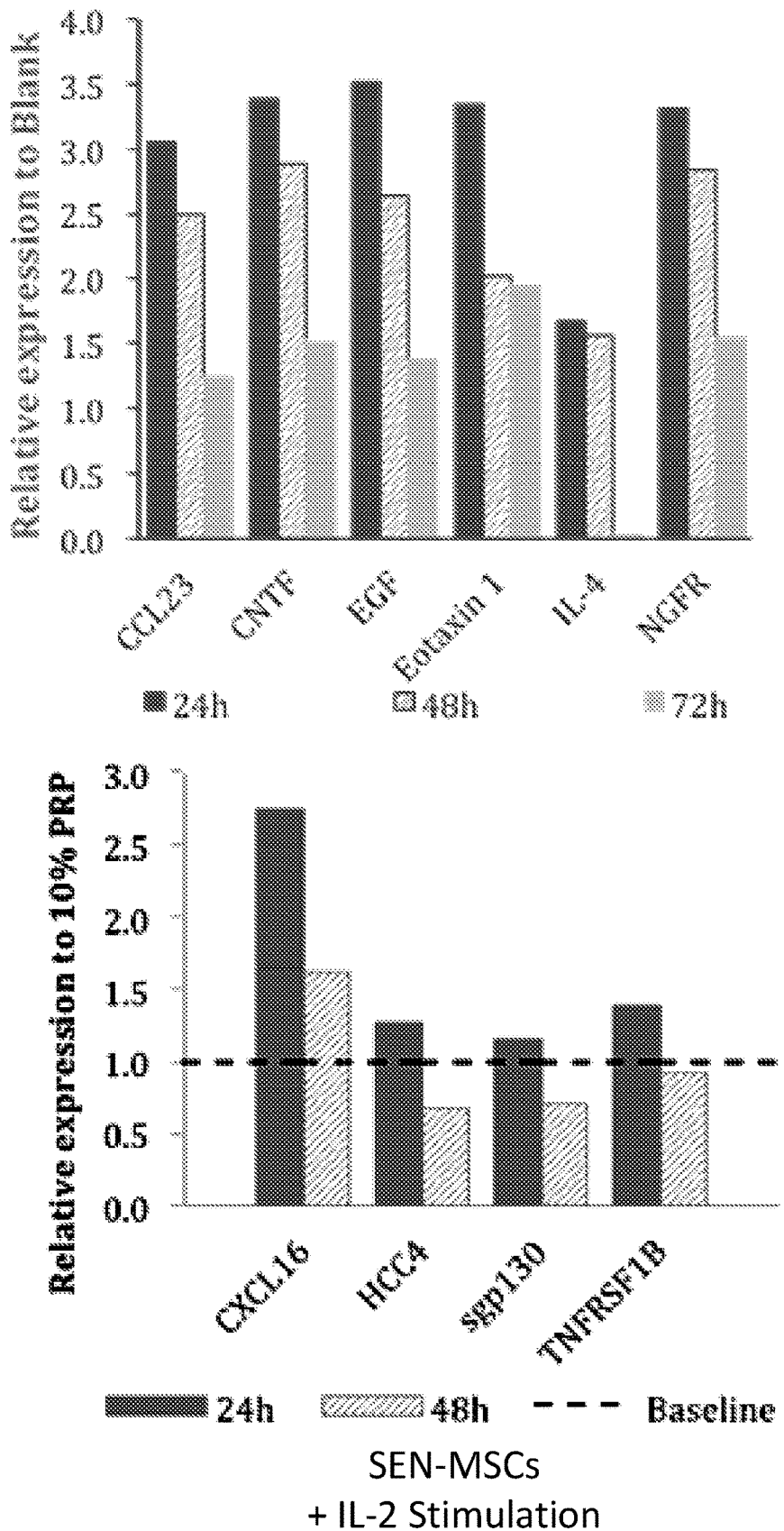

FIG. 75 shows the increase in secretion of Chemokine (C—C motif) ligand 23 (CCL23), Ciliary neurotrophic factor (CNTF), Epidermal growth factor (EGF), CCL11 (Eotaxin 1), IL4, and Nerve growth factor receptor (NGFR) from SEN-hADSCs, 24 hours post stimulation with IL-2. These factors were found to not be present in PRP.

FIG. 75 also shows the increase in secretion of CXCL16, HCC4, sgp130, and TNFRSF1B at 24h post IL-2 stimulation. Secretion levels are shown relative to the amount of the corresponding protein present at basal levels in the 10% PRP containing media.

Figure 76:
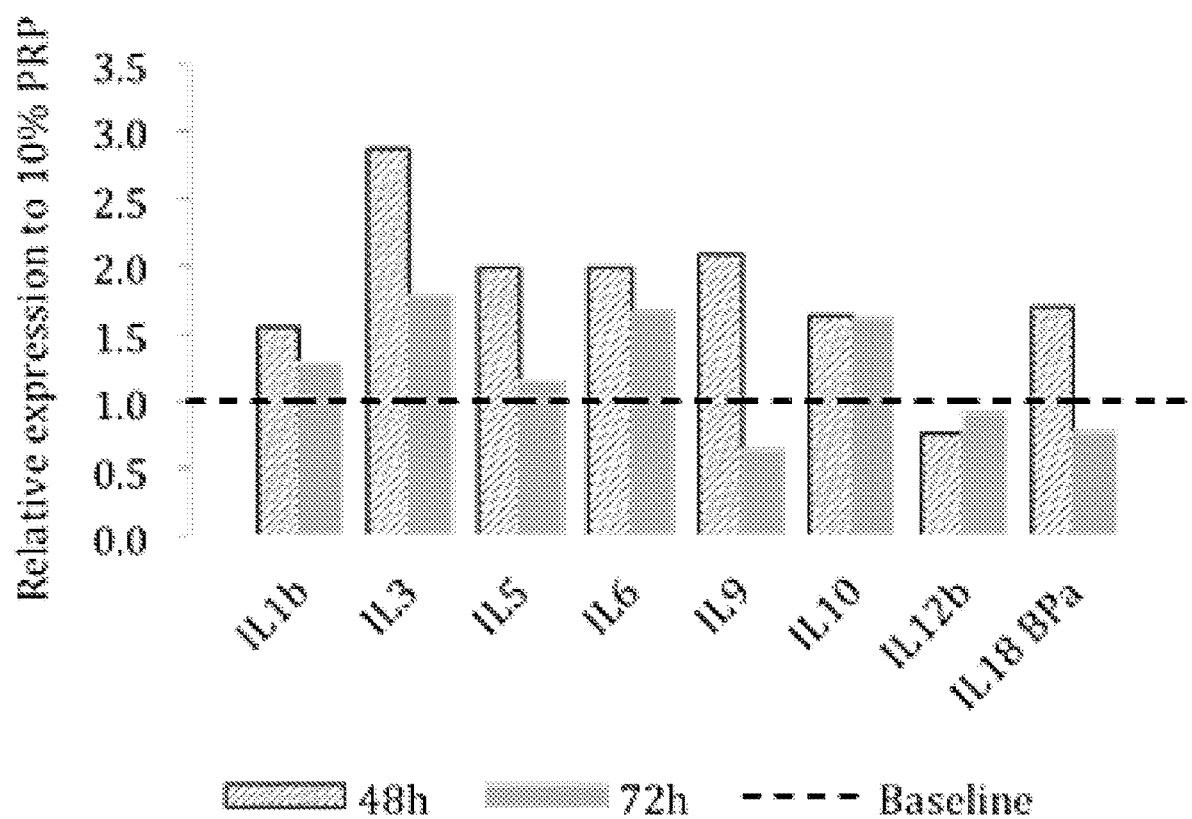
Figure 77:
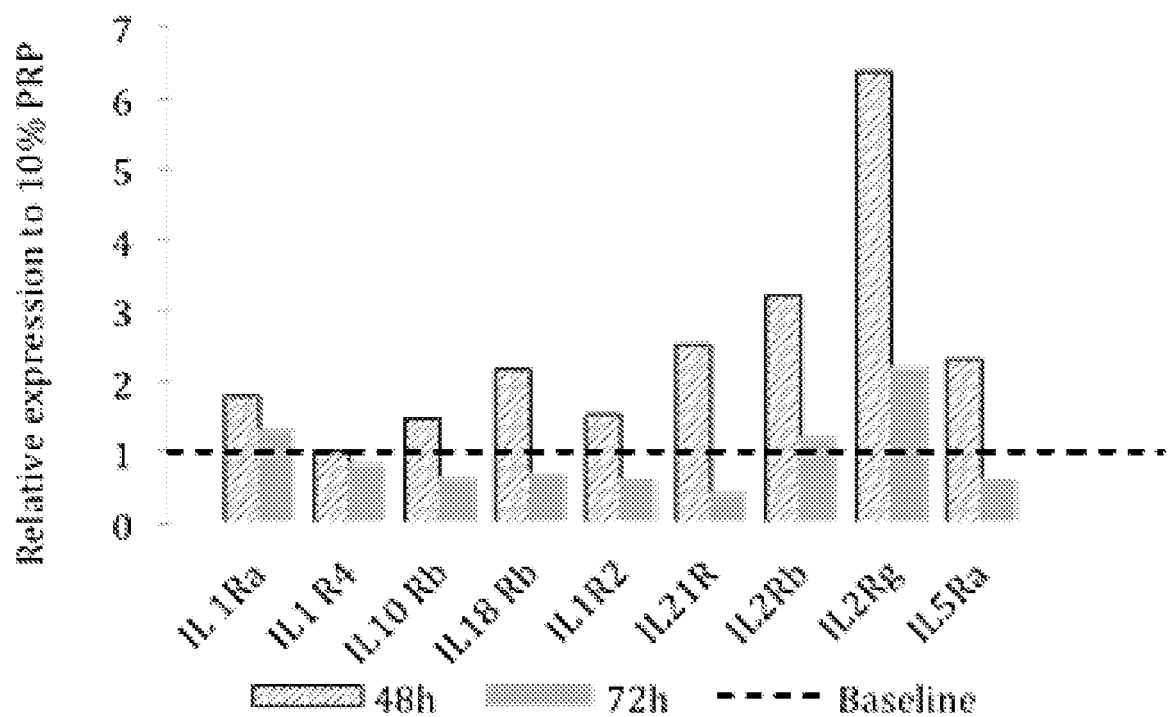
Figure 78:
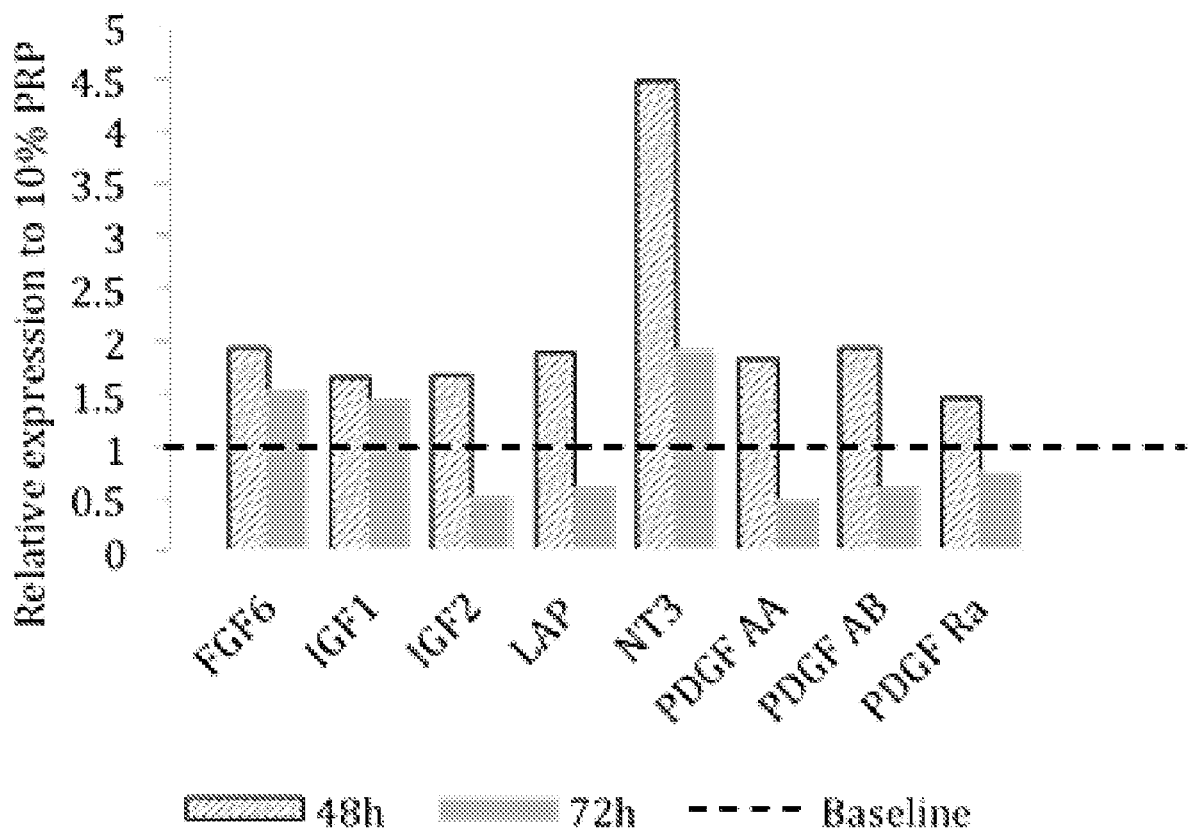
Figure 79:
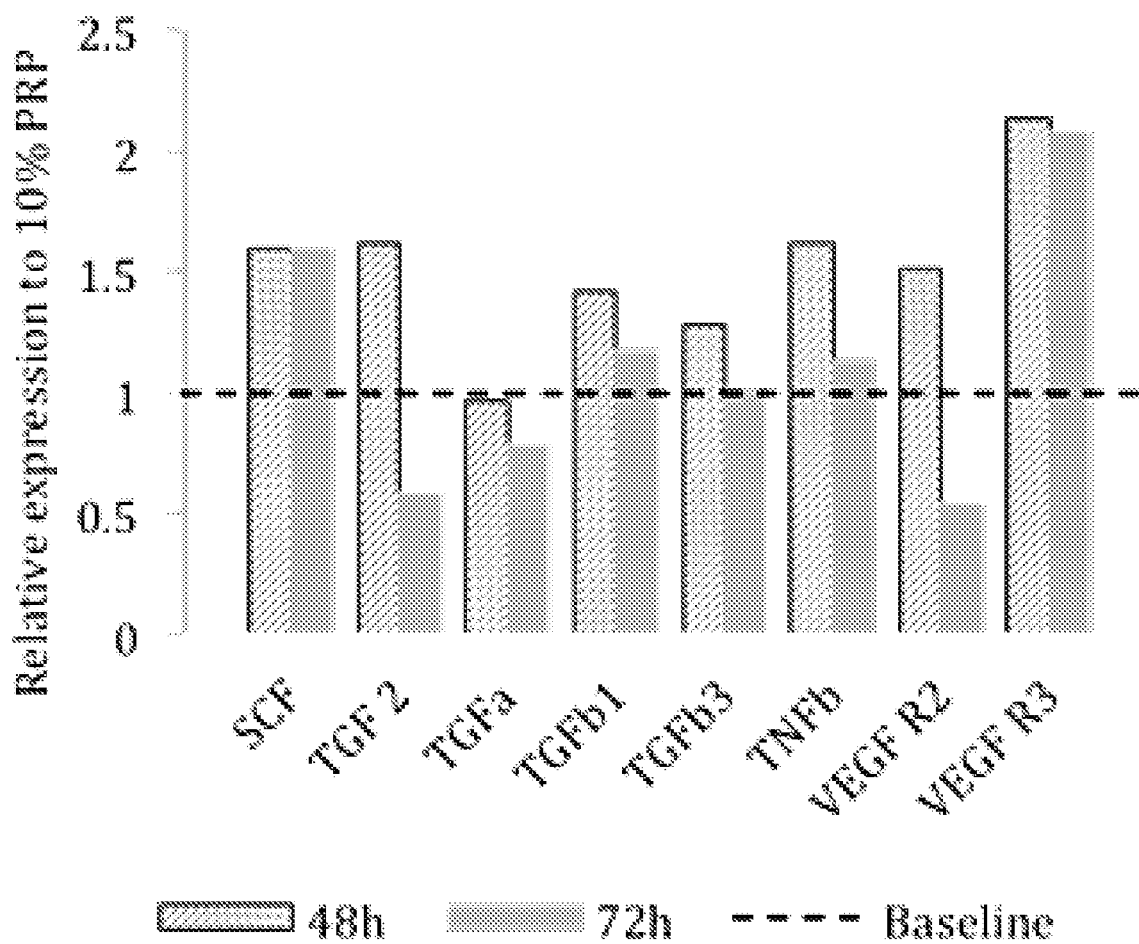
Figure 80:
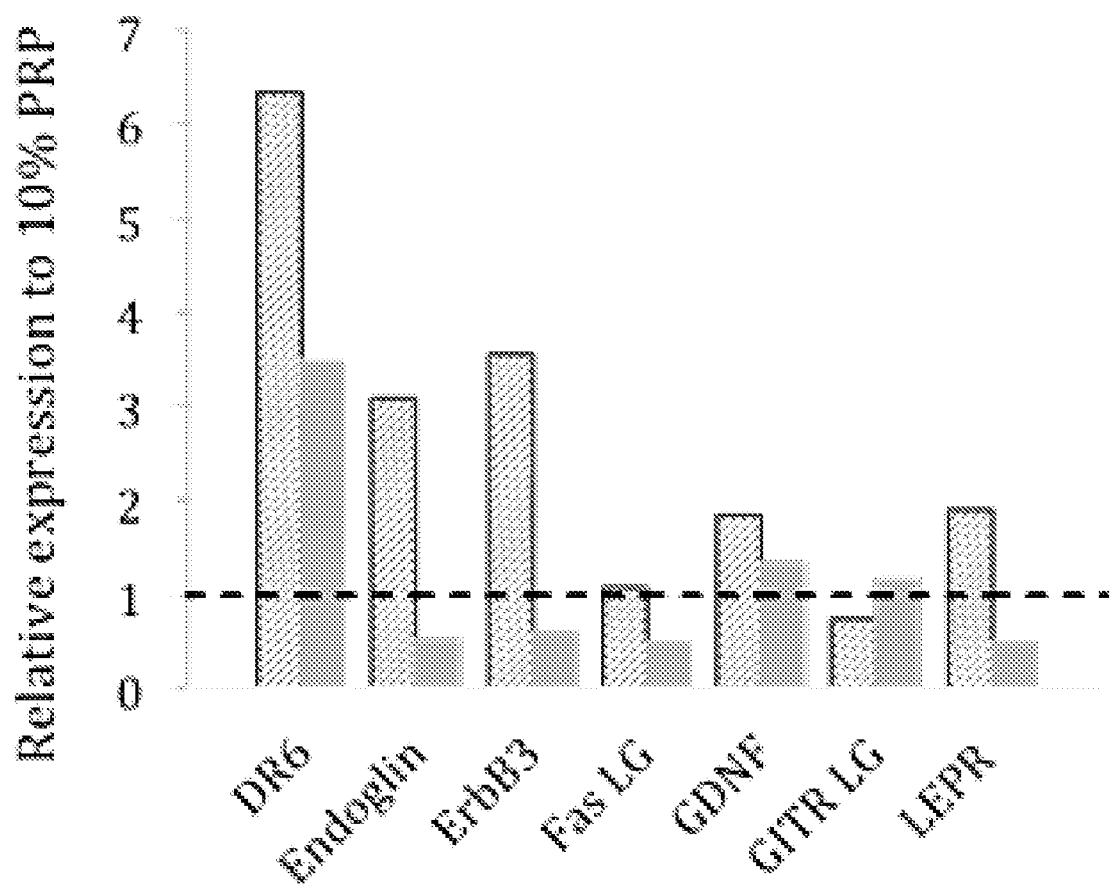
Figure 81:
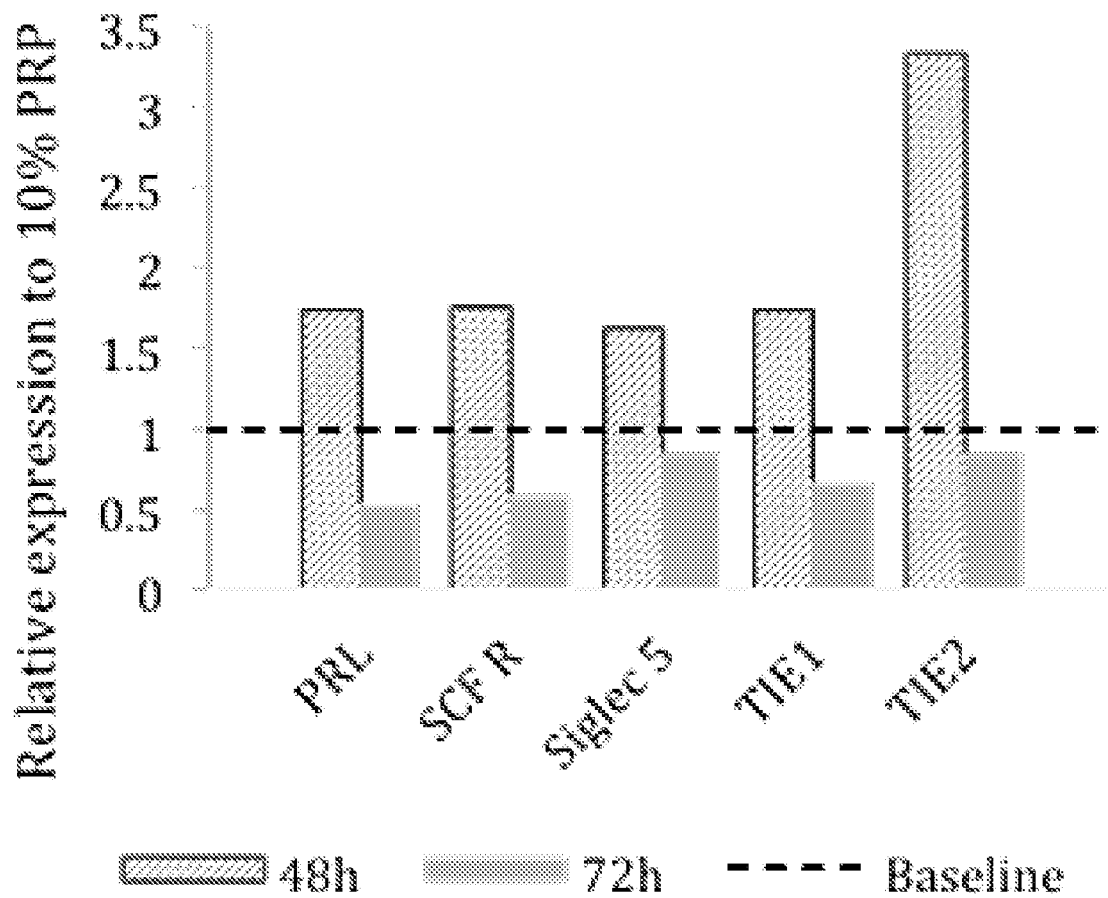
Figure 82:
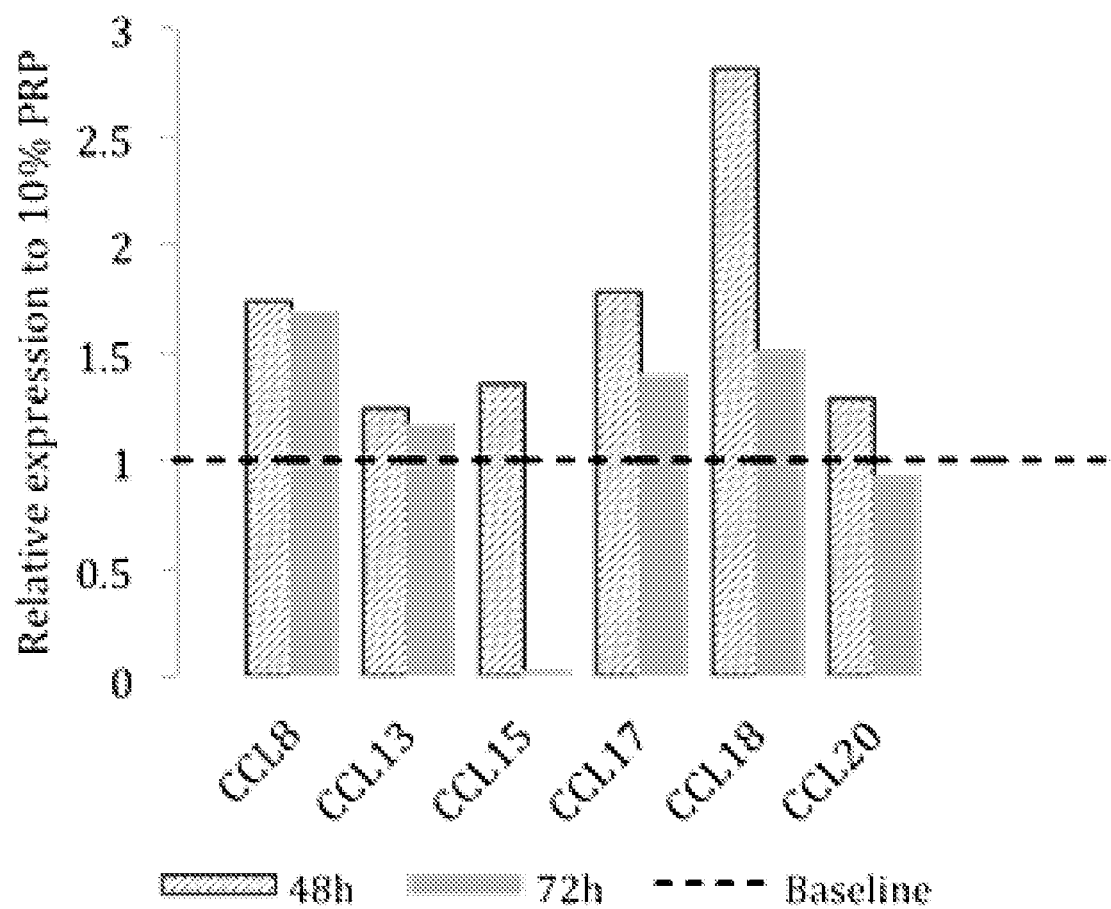
Figure 83:
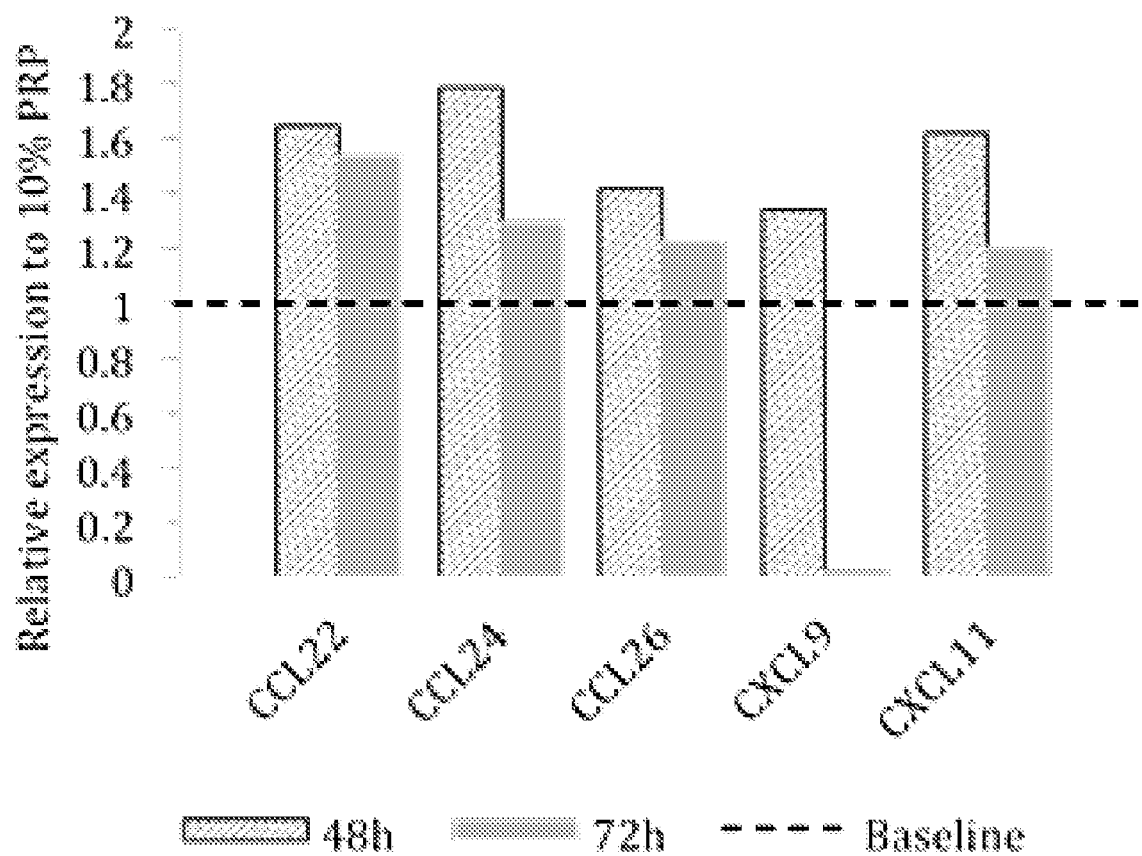
Figure 84:
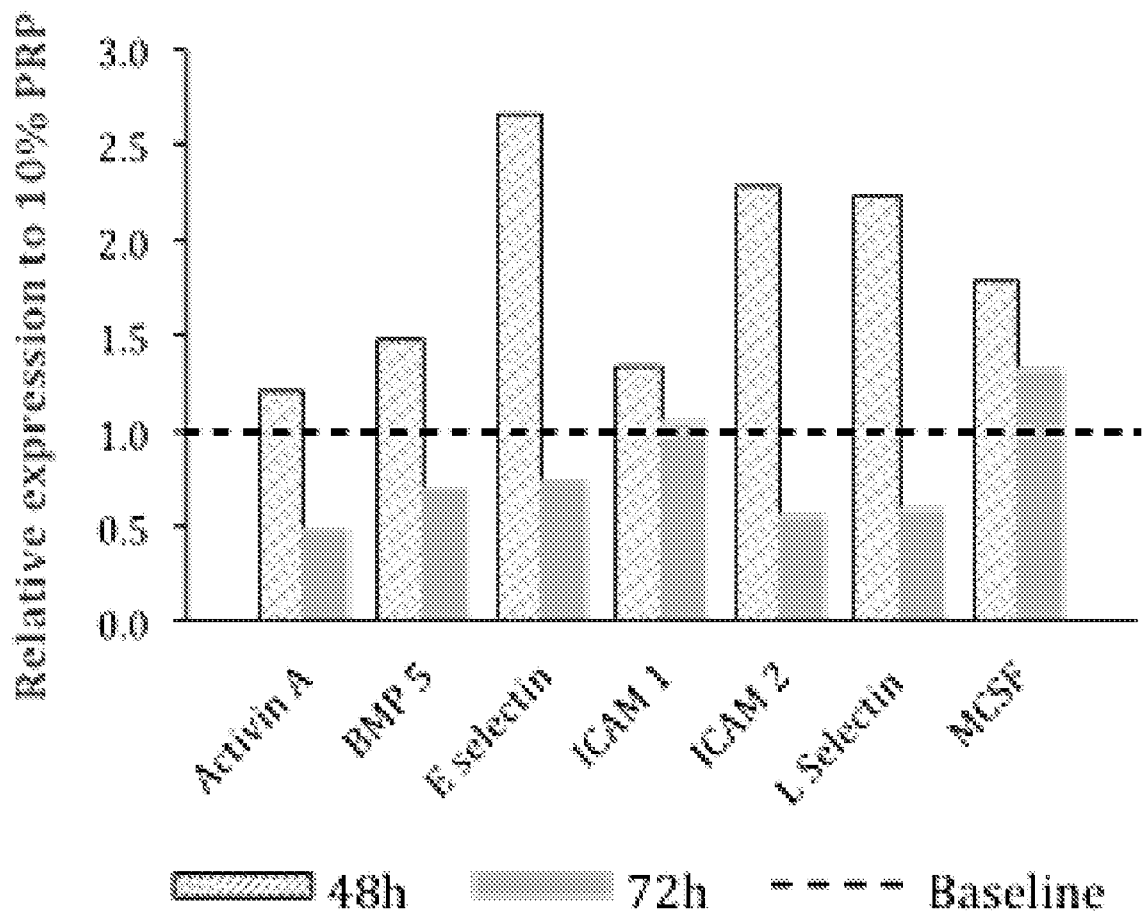
Figure 85:
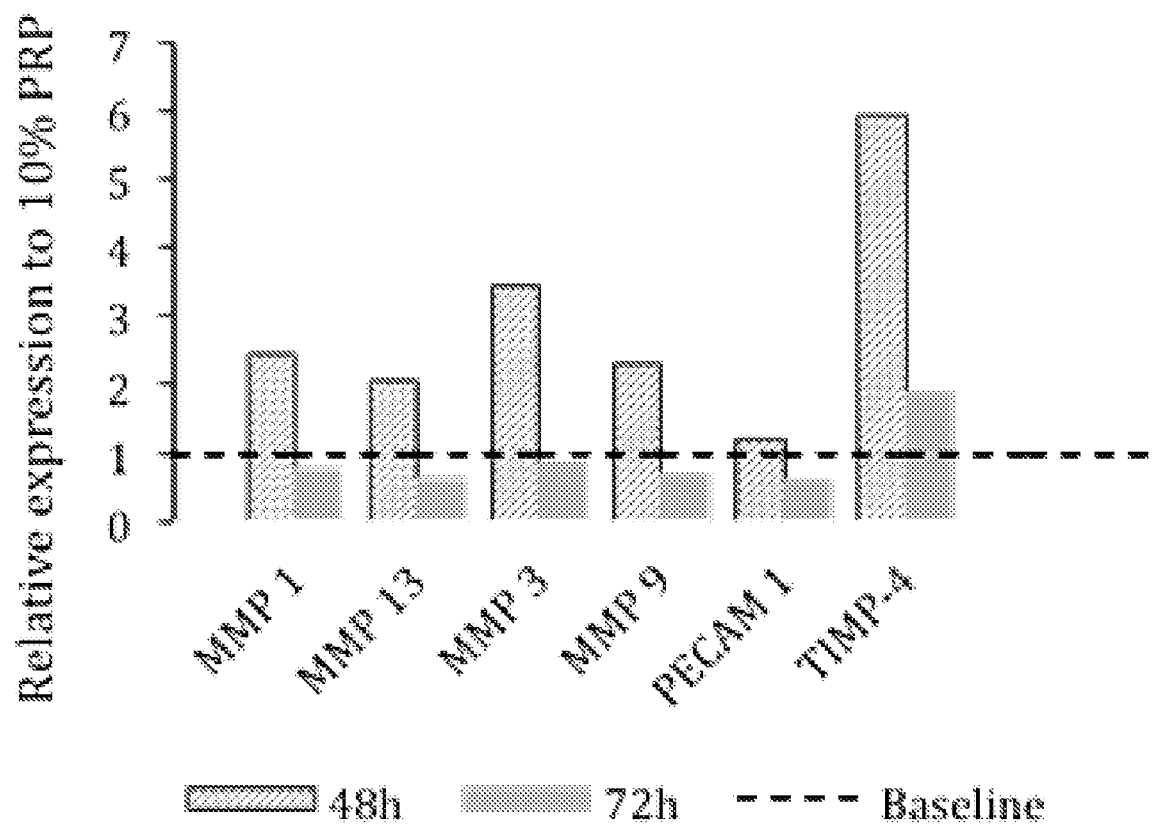
Figure 86:
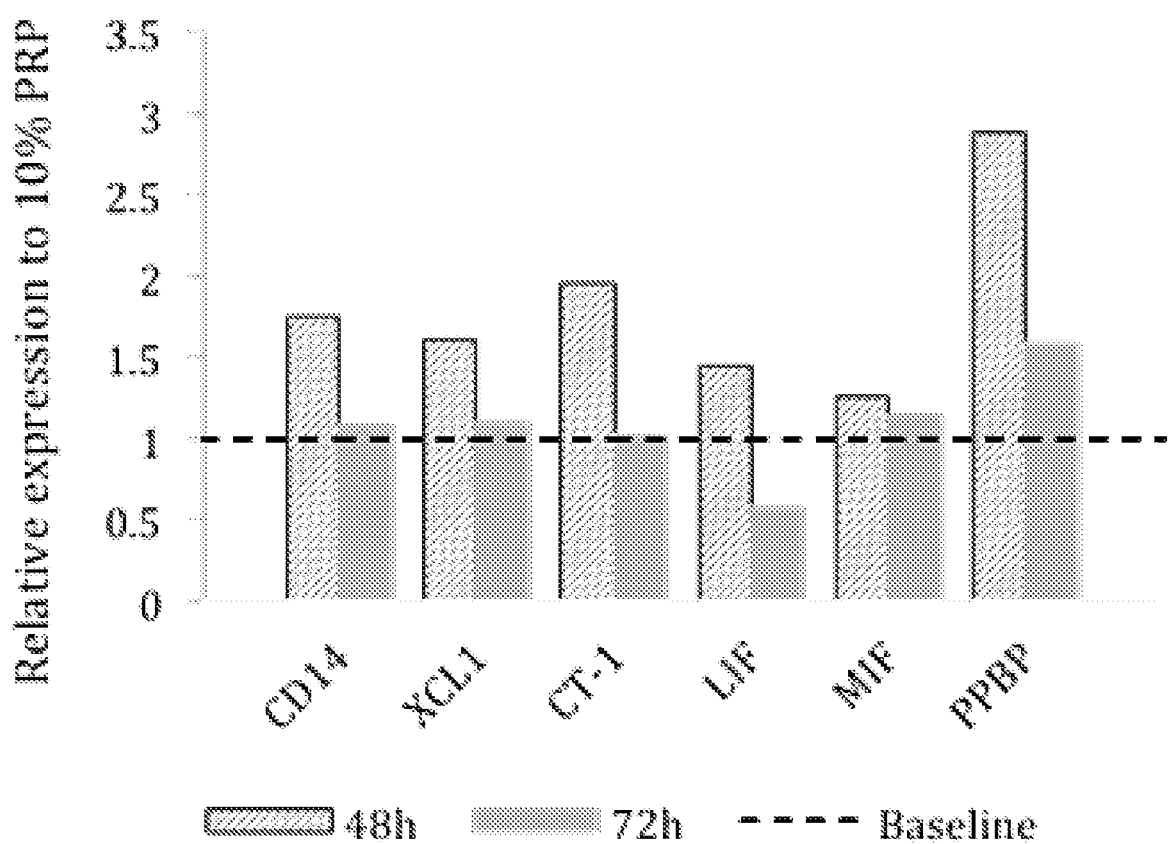

FIGS. 76-86 show the increase in the secretion of the below named proteins (factors) from SEN-hADSCs, 48 hours post stimulation with IL-2. Secretion levels are shown relative to the amount of the corresponding protein present at basal levels in the 10% PRP containing media, used for hADSC support. FIG. 76 shows the increase in secretion of Interleukin 1 beta (IL1β), IL3, IL5, IL6, IL9, IL10, IL12b, and Interleukin 18 binding protein alpha (IL18BPa). FIG. 77 shows the increase in secretion of Interleukin 1 receptor alpha (IL1Ra), IL1R4, IL10Rb, IL18Rb, IL1R2, IL-21R, IL-2Rβ, IL-2Rγ, and IL5Ra. FIG. 78 shows the increase in secretion of Fibroblast growth factor 6 (FGF6), insulin-like growth factors IGF1 and IGF2, LAP (TGF beta family), Neurotrophin 3 (NT3), platelet derived growth factor A alpha (PDGFAA), platelet derived growth factor A beta (PDGFAB), and platelet-derived growth factor receptor alpha (PDGFRa). FIG. 79 shows the increase in secretion of Stem cell factor (SCF), Transforming growth factor 2 (TGF2), TGFα, TGFβ1, TGFb3, Tumor necrosis factor beta (TNFb), Vascular endothelial growth factor receptor-2 (VEGF R2), and VEGF R3. FIG. 80 shows the increase in secretion of DR6 (TNF receptor superfamily member 21), Endoglin (ENG), Receptor tyrosine-protein kinase erbB-3 (ErbB3), Fas ligand (Fas LG), Glial cell line-derived neurotrophic factor (GDNF), GITR ligand (GITR LG), and Leptin receptor (LEPR). FIG. 81 shows the increase in secretion of Prolactin (PRL), Stem cell factor receptor (SCFR), Sialic acid-binding Ig-like Lectin 5 (Siglec 5), Angiopoietin 1 receptor (TIE-1), and Angiopoietin 1 receptor (TIE-2). FIG. 82 shows the increase in secretion of Chemokine (C—C motif) ligand 8 (CCL8), CCL13, CCL15, CCL17, CCL18, and CCL20. FIG. 83 shows the increase in secretion of Chemokine (C—C motif) ligand 22 (CCL22), CCL24, CCL26, CXC chemokine ligand 9 (CXCL9), and CXCL11. FIG. 84 shows the increase in secretion of Activin A (INHBA), Bone morphogenetic protein 5 (BMP5), E selectin (endothelial cell adhesion molecule), Intercellular adhesion molecule 1 (ICAM 1), ICAM 2, L selectin (Leukocyte adhesion molecule), and Macrophage colony-stimulating factor (MCSF). FIG. 85 shows the increase in secretion of matrix metalloproteinase 1 (MMP1), MMP13, MMP3, MMP9, Platelet endothelial cell adhesion molecule (PECAM 1), and Metalloproteinase inhibitor 4 (TIMP-4). FIG. 86 shows the increase in secretion of monocyte differentiation antigen (CD14), Lymphotactin (XCL1), Cardiotrophin-1 (CT-1), Leukemia inhibitory factor (LIF), Macrophage Migration Inhibitory Factor (MIF), and pro-platelet basic protein (PPBP).

Figure 87:
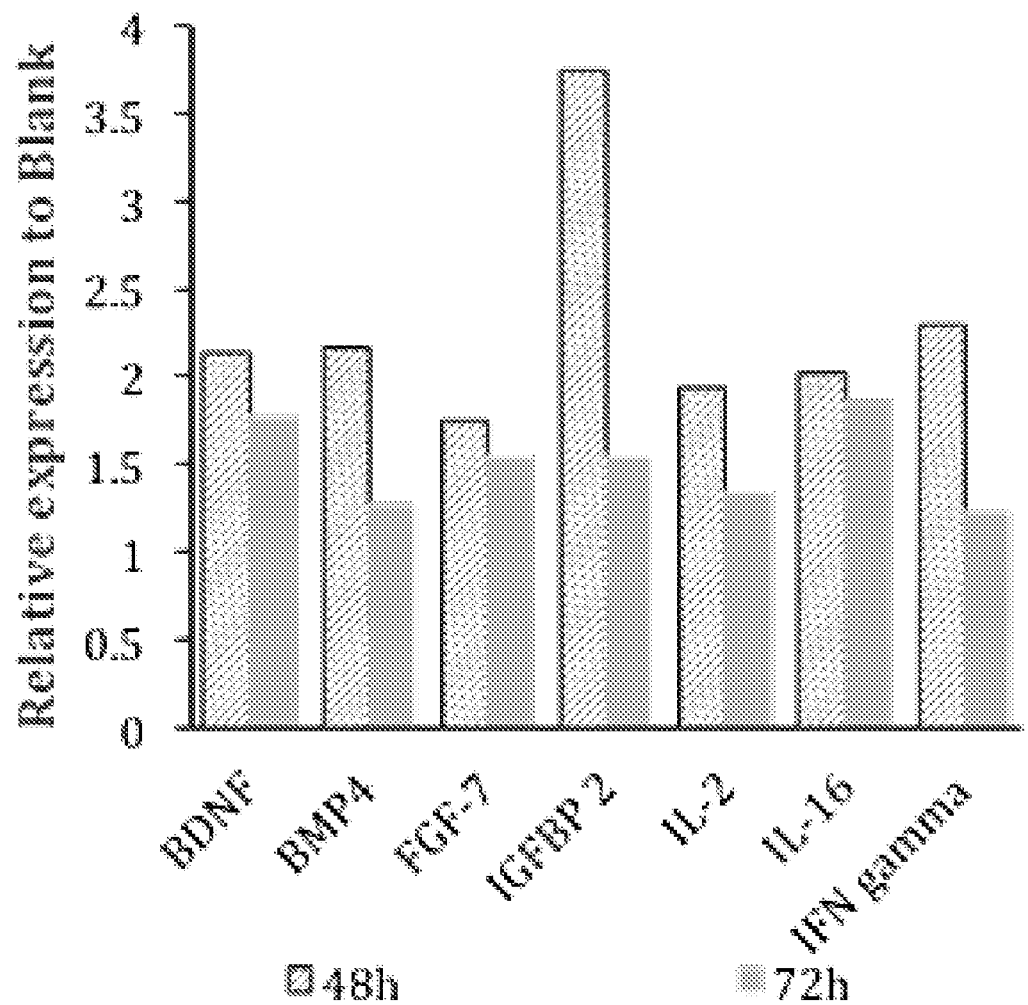

FIG. 87 shows the increase in secretion of Brain-derived neurotrophic factor (BDNF), Bone morphogenetic protein 4 (BMP4), Fibroblast growth factor 7 (FGF7), insulin-like growth factor-binding protein-2 (IGFBP2), IL-2, IL-16, and Interferon gamma (INF gamma) from SEN-hADSCs, 48 hours post stimulation with IL-2. These factors were found to not be present in PRP.

Figure 88:
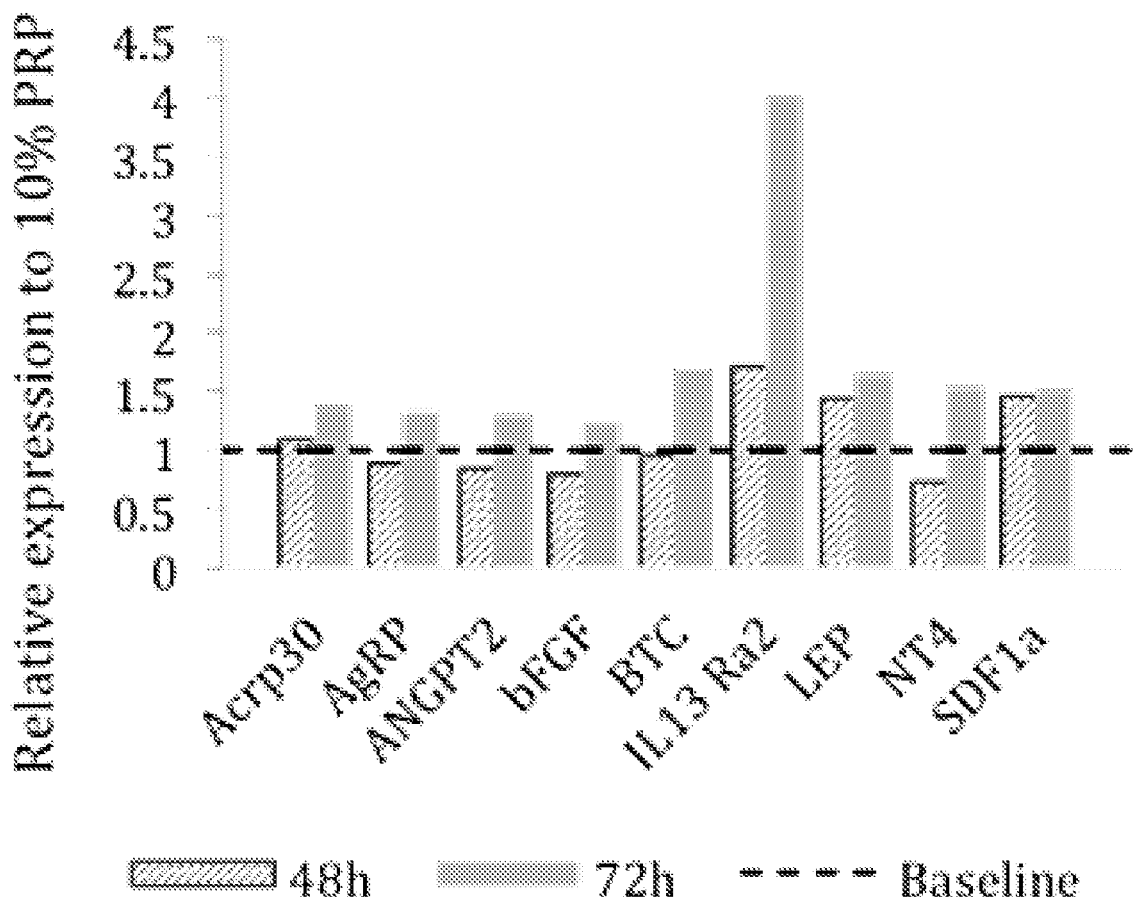
Figure 89:
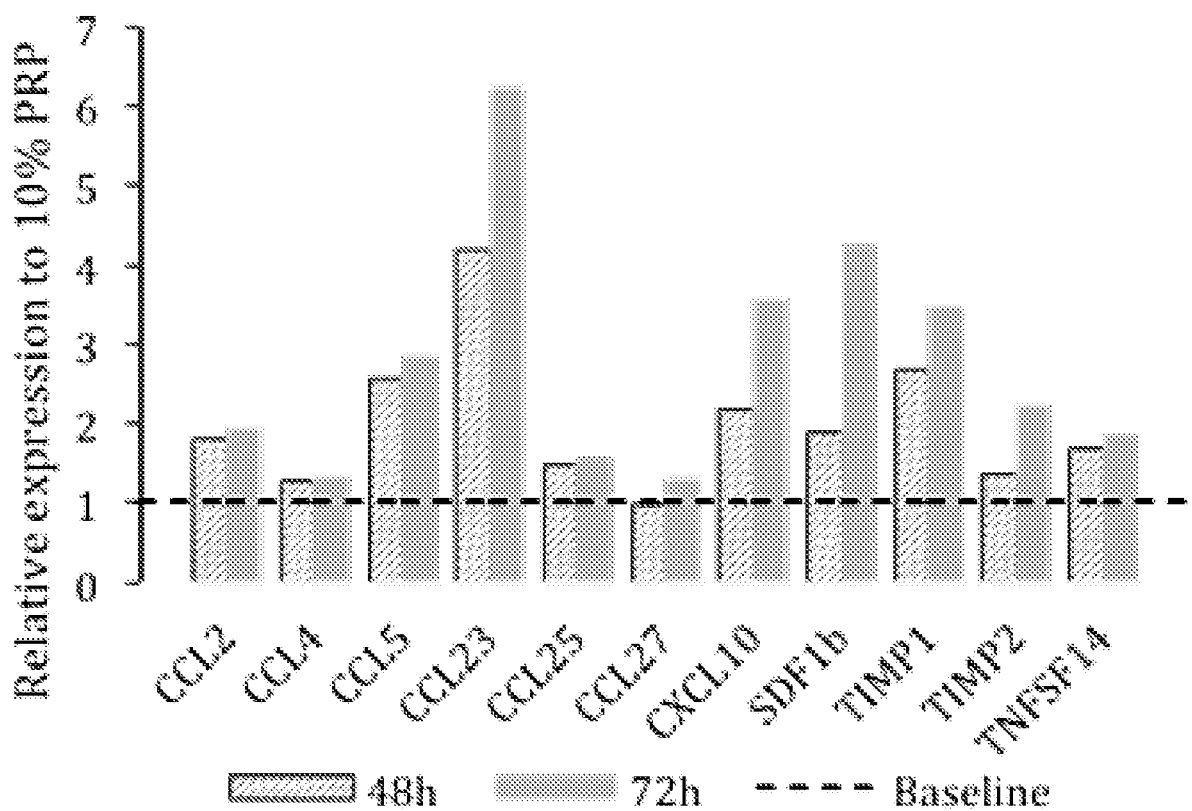

FIGS. 88-89 show the increase in secretion of the below named proteins (factors) from SEN-hADSCs, 72 hours post stimulation with IL-2. Secretion levels are shown relative to the amount of the corresponding protein present at basal levels in the 10% PRP containing media, used for hADSC support. FIG. 88 shows the increase in secretion of Adiponectin (Acrp30), Agouti-related protein (AgRP), ANGPT2 (Angiopoietin 2), basic-Fibroblast Growth Factor (bFGF), Probetacellulin (BTC), Interleukin-13 receptor subunit alpha-2 (IL13Ra2), Leptin (LEP), Neurotrophin 4 (NT4), and Stromal Cell-Derived Factor-1 alpha (SDF1a). FIG. 89 shows the increase in secretion of Chemokine (C—C motif) ligand 2 (CCL2), CCL4, CCL5, CCL23, CCL25, CCL27, CXC Chemokine ligand 10 (CXCL10), Stromal Cell-Derived Factor-1 beta (SDF1b), Metalloproteinase inhibitors 1 (TIMP1), TIMP2, and tumor necrosis factor superfamily member 14 (TNFSF14).

Figure 90:
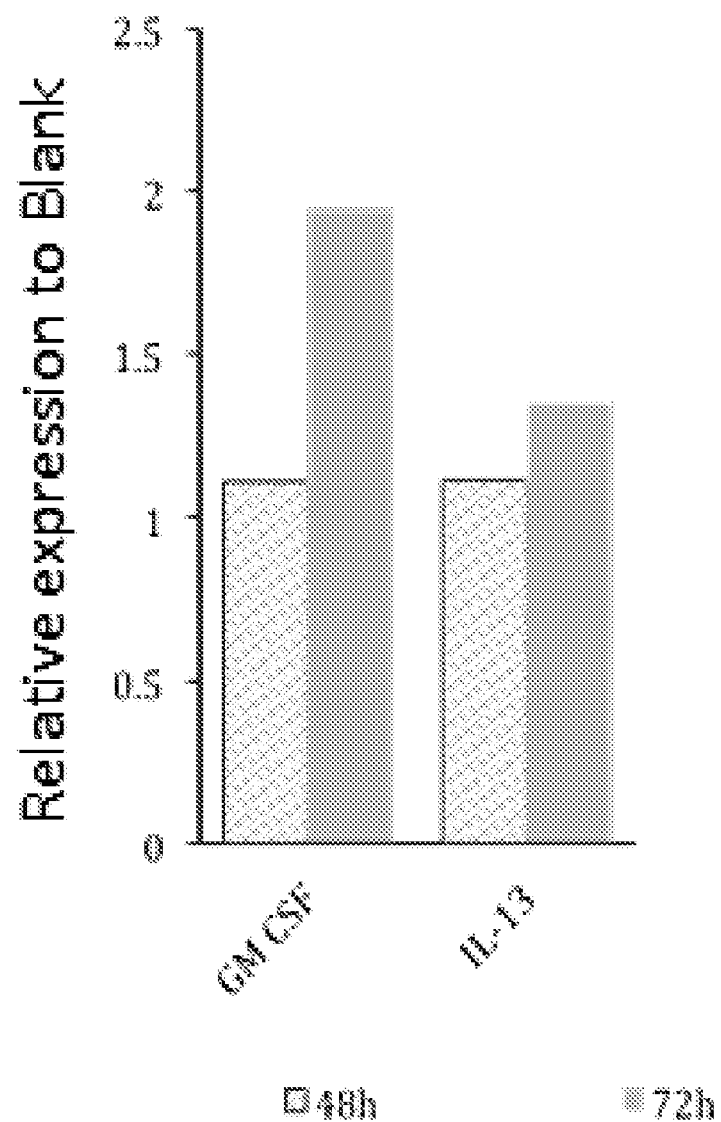

FIG. 90 shows the increase in secretion of Granulocyte-macrophage colony-stimulating factor (GM-CSF) and IL13 from SEN-hADSCs, 72 hours post stimulation with IL-2. These factors were found to not be present in PRP.

Lengthy table referenced here

US12138282-20241112-T00001

Please refer to the end of the specification for access instructions.

Lengthy table referenced here

US12138282-20241112-T00002

Please refer to the end of the specification for access instructions.

Lengthy table referenced here

US12138282-20241112-T00003

Please refer to the end of the specification for access instructions.

Lengthy table referenced here

US12138282-20241112-T00004

Please refer to the end of the specification for access instructions.

Lengthy table referenced here

US12138282-20241112-T00005

Please refer to the end of the specification for access instructions.

From the foregoing it will be appreciated that, although specific variations of the invention have been described herein for purposes of illustration, various modifications may be made without deviating from the spirit and scope of the invention. Accordingly, the invention is not limited except as by the appended claims.

LENGTHY TABLES

The patent contains a lengthy table section. A copy of the table is available in electronic form from the USPTO web site (https://seqdata.uspto.gov/?pageRequest=docDetail&DocID=US12138282B2). An electronic copy of the table will also be available from the USPTO upon request and payment of the fee set forth in 37 CFR 1.19(b)(3).

What is claimed is:

1. A method of selecting and treating an individual for cancer with an IL-2-based therapy, wherein the cancer is melanoma or renal cell carcinoma, the method comprising:
   (a) measuring the expression levels of at least three biomarkers selected from a panel of biomarkers in a sample from an individual, wherein either (1) the individual has received at least one dose of an IL-2-based therapy or (2) the sample is combined with IL-2 in vitro, wherein the sample comprises mesenchymal stem cells (MSCs), wherein the biomarkers are indicative of cellular senescence of the cells in the sample, and wherein the panel of biomarkers comprises FGF1, FGF11, FGF14, IL-32, IL-6, IL1RN, IL-20RB, IL-21R, PLAU, PLEKHA6, CTSB, FERMT1, CRMP1, VEGFB, VEGFA, and PLEKHA1;
   (b) comparing the levels of the biomarkers to reference levels to query the senescence status of the MSCs, wherein a decrease or no change in the levels compared to the reference levels indicates that the individual may not experience an adverse event associated with the IL-2-based therapy, wherein the adverse event is one or more of an increased risk of tumorigenesis and an increased risk of metastasis;
   (c) selecting the individual for treating using the comparison of step (b), wherein the sample from the individual shows a decrease or no change in the levels compared to the reference levels indicating that the individual may not experience an adverse event associated with the IL-2-based therapy; and
   (d) administering an effective amount of the IL-2-based therapy to the selected individual.

2. The method of claim 1, wherein the individual has received at least one dose of an IL-2-based therapy.

3. The method of claim 2, wherein the individual has received the IL-2-based therapy for the treatment of the cancer.

4. The method of claim 1, wherein the sample has been obtained from the individual 24, 48, or 72 hours after having received the IL-2-based therapy.

5. The method of claim 1, wherein the sample is combined with IL-2 in vitro.

6. The method of claim 5, wherein the sample is combined with IL-2 for about 24 hours.

7. The method of claim 5, wherein the expression levels are measured 24, 48, or 72 hours following the removal of IL-2 from the sample in vitro.

8. The method of claim 1, wherein the method comprises measuring the expression levels of four biomarkers from the panel of biomarkers.

9. The method of claim 1, wherein the method comprises measuring protein levels of the biomarkers.

10. The method of claim 1, wherein the method comprises measuring RNA levels of the biomarkers.

11. The method of claim 1, wherein the cancer is melanoma.

12. The method of claim 1, wherein the cancer is renal cell carcinoma.

* * * * *

```
                            SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
ctgccactcg gaacacaac                                                      19

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
tggtccactg gctgcatt                                                       18

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
actcgagagc caacatctcc                                                     20

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
tccgaggatc aggttgcag                                                      19

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
tggatgggca gaaacgcta                                                      19

<210> SEQ ID NO 6
<211> LENGTH: 20
```

```
<212> TYPE: DNA
<213> ORGANISM: Artificial Sequence
<220> FEATURE:
<223> OTHER INFORMATION: Synthetic Construct

<400> SEQUENCE: 6
ggcttccaat gcaaacagga                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
acgcaggaca cagagaatga                                              20

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
ctgggcaaac tgagcttgg                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
acacagctcc agaacacgt                                               19

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
tgttggcttc tcggaccaa                                               19

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ggaggagggc agaatcatca                                              20

<210> SEQ ID NO 12
<211> LENGTH: 19
```

```
<212> TYPE: DNA
<213> ORGANISM: Artificial Sequence
<220> FEATURE:
<223> OTHER INFORMATION: Synthetic Construct

<400> SEQUENCE: 12
atcaggggca cacaggatg                                                    19
```